US006930185B2

United States Patent
Ishihara et al.

(10) Patent No.: US 6,930,185 B2
(45) Date of Patent: Aug. 16, 2005

(54) MELANIN-CONCENTRATING HORMONE ANTAGONIST

(75) Inventors: Yuji Ishihara, Itami (JP); Nobuhiro Suzuki, Minoo (JP); Shiro Takekawa, Nishinomiya (JP)

(73) Assignee: Takeda Chemical Industries, Ltd., Osaka (JP)

( * ) Notice: Subject to any disclaimer, the term of this patent is extended or adjusted under 35 U.S.C. 154(b) by 177 days.

(21) Appl. No.: 10/258,492

(22) PCT Filed: Apr. 26, 2001

(86) PCT No.: PCT/JP01/03614

§ 371 (c)(1),
(2), (4) Date: Oct. 24, 2002

(87) PCT Pub. No.: WO01/82925

PCT Pub. Date: Nov. 8, 2001

(65) Prior Publication Data

US 2004/0077628 A1 Apr. 22, 2004

(30) Foreign Application Priority Data

Apr. 28, 2000 (JP) ......................................... 2000-134295
Dec. 13, 2000 (JP) ......................................... 2000-384897

(51) Int. Cl.[7] ..................... A61K 31/47; C07D 215/16; C07D 215/38
(52) U.S. Cl. ..................... 546/153; 546/162; 546/163; 546/169; 514/311; 514/312; 514/313
(58) Field of Search ................................ 514/311, 312, 514/313; 546/153, 162, 163, 169

(56) References Cited

FOREIGN PATENT DOCUMENTS

| DE | 2502588 | 7/1976 |
|---|---|---|
| EP | 0533266 | 3/1993 |
| JP | 7-179407 | 7/1995 |
| WO | WO 95/32967 | * 12/1995 |
| WO | WO 98/15274 | 4/1998 |
| WO | WO 98/38156 | * 9/1998 |
| WO | WO 98/46590 | 10/1998 |
| WO | WO 99/52875 | * 10/1999 |
| WO | WO 00/23437 | 4/2000 |
| WO | WO 00/31021 | * 6/2000 |
| WO | WO 00/40725 | * 7/2000 |
| WO | WO 01/21577 | * 3/2001 |

OTHER PUBLICATIONS

Chambers, et al. "Melanin–concentrating hormone is the cognate ligand for the orphan G–protein–coupled receptor SLC–1" NATURE 400(6741): 261–265 (1999).
Saito, et al. "Molecular characterization of the melanin–concentrating–hormone receptor" NATURE 400(6741): 265–269(1999).
Oakes, et al. "Polyazanaphtalenes. Part VII. Some Derivatives of Quinazoline and 1,3,5–Triazanaphtalene" J. Chem Soc. 4678–4685 (1962).
Werbel, et al. "Synthesis and Antimalarial Activity of a Series of 2,4–Diamino–6[{N–alkylanilino)methyl]quinazolines [1,2]" J. Heterocylic Chem. 24(2): 345–349(1987).

* cited by examiner

Primary Examiner—D. Margaret Seaman
(74) Attorney, Agent, or Firm—Elaine M. Ramesh; Mark Chao

(57) ABSTRACT

A melanin-concentrating hormone antagonist comprising a compound of the formula (I):

$$Ar^1 - X - Ar - Y - N \begin{pmatrix} R^1 \\ R^2 \end{pmatrix}$$

(I)

wherein $Ar^1$ is a cyclic group which may be substituted; X and Y are the same or different and are a spacer having a main chain of 1 to 6 atoms; Ar is a condensed polycyclic aromatic ring which may be substituted; $R^1$ and $R^2$ are the same or different and are hydrogen atom or a hydrocarbon group which may be substituted; or $R^1$ and $R^2$, together with the adjacent nitrogen atom, may form a nitrogen-containing heterocyclic ring which may be substituted; or $R^2$, together with the adjacent nitrogen atom and Y, may form a nitrogen-containing heterocyclic ring which may be substituted; or $R^2$, together with the adjacent nitrogen atom, Y and Ar, may form a condensed ring; or a salt thereof is useful as an agent for preventing or treating obesity, etc.

13 Claims, No Drawings

SEQUENCE LISTING

<160> NUMBER OF SEQ ID NOS: 16

<210> SEQ ID NO 1
<211> LENGTH: 32
<212> TYPE: DNA
<213> ORGANISM: Artificial Sequence
<220> FEATURE:
<223> OTHER INFORMATION: primer

<400> SEQUENCE: 1
gtcgacatgg atctgcaaac ctcgttgctg tg                          32

<210> SEQ ID NO 2
<211> LENGTH: 32
<212> TYPE: DNA
<213> ORGANISM: Artificial Sequence
<220> FEATURE:
<223> OTHER INFORMATION: primer

<400> SEQUENCE: 2
actagttcag gtgcctttgc tttctgtcct ct                          32

<210> SEQ ID NO 3
<211> LENGTH: 353
<212> TYPE: PRT
<213> ORGANISM: Rat

<400> SEQUENCE: 3

```
Met Asp Leu Gln Thr Ser Leu Leu Ser Thr Gly Pro Asn Ala Ser Asn
1               5                   10                  15

Ile Ser Asp Gly Gln Asp Asn Leu Thr Leu Pro Gly Ser Pro Pro Arg
            20                  25                  30

Thr Gly Ser Val Ser Tyr Ile Asn Ile Ile Met Pro Ser Val Phe Gly
        35                  40                  45

Thr Ile Cys Leu Leu Gly Ile Val Gly Asn Ser Thr Val Ile Phe Ala
    50                  55                  60

Val Val Lys Lys Ser Lys Leu His Trp Cys Ser Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125

Thr Ser Thr Tyr Ile Leu Thr Ala Met Thr Ile Asp Arg Tyr Leu Ala
    130                 135                 140

Thr Val His Pro Ile Ser Ser Thr Lys Phe Arg Lys Pro Ser Met Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
        195                 200                 205

Thr Leu Tyr Gln Phe Phe Leu Ala Phe Ala Leu Pro Phe Val Val Ile
    210                 215                 220

Thr Ala Ala Tyr Val Lys Ile Leu Gln Arg Met Thr Ser Ser Val Ala
```

```
                225                 230                 235                 240
Pro Ala Ser Gln Arg Ser Ile Arg Leu Arg Thr Lys Arg Val Thr Arg
                    245                 250                 255
Thr Ala Ile Ala Ile Cys Leu Val Phe Phe Val Cys Trp Ala Pro Tyr
                260                 265                 270
Tyr Val Leu Gln Leu Thr Gln Leu Ser Ile Ser Arg Pro Thr Leu Thr
                275                 280                 285
Phe Val Tyr Leu Tyr Asn Ala Ala Ile Ser Leu Gly Tyr Ala Asn Ser
            290                 295                 300
Cys Leu Asn Pro Phe Val Tyr Ile Val Leu Cys Glu Thr Phe Arg Lys
305                 310                 315                 320
Arg Leu Val Leu Ser Val Lys Pro Ala Ala Gln Gly Gln Leu Arg Thr
                    325                 330                 335
Val Ser Asn Ala Gln Thr Ala Asp Glu Glu Arg Thr Glu Ser Lys Gly
                340                 345                 350
Thr
```

<210> SEQ ID NO 4
<211> LENGTH: 1074
<212> TYPE: DNA
<213> ORGANISM: Rat

<400> SEQUENCE: 4

```
gtcgacatgg atctgcaaac ctcgttgctg tccactggcc ccaatgccag caacatctcc      60
gatggccagg ataatctcac attgccgggg tcacctcctc gcacagggag tgtctcctac     120
atcaacatca ttatgccttc cgtgtttggt accatctgtc tcctgggcat cgtgggaaac     180
tccacggtca tctttgctgt ggtgaagaag tccaagctac actggtgcag caacgtcccc     240
gacatcttca tcatcaacct ctctgtggtg gatctgctct tcctgctggg catgcctttc     300
atgatccacc agctcatggg gaacggcgtc tggcactttg gggaaaccat gtgcacccttc     360
atcacagcca tggacgccaa cagtcagttc actagcacct acatcctgac tgccatgacc     420
attgaccgct acttggccac cgtccacccc atctcctcca ccaagttccg gaagccctcc     480
atggccaccc tggtgatctg cctcctgtgg gcgctctcct tcatcagtat caccccctgtg    540
tggctctacg ccaggctcat tcccttccca gggggtgctg tgggctgtgg catccgcctg     600
ccaaacccgg acactgacct ctactggttc actctgtacc agttttttcct ggccttttgcc   660
cttccgtttg tggtcattac cgccgcatac gtgaaaatac tacagcgcat gacgtcttcg     720
gtggccccag cctcccaacg cagcatccgg cttcggacaa agagggtgac ccgcacggcc     780
attgccatct gtctggtctt ctttgtgtgc tgggcaccct actatgtgct gcagctgacc     840
cagctgtcca tcagccgccc gaccctcacg tttgtctact gtacaacgc ggccatcagc      900
ttgggctatg ctaacagctg cctgaacccc tttgtgtaca tagtgctctg tgagaccttt     960
cgaaaacgct tggtgttgtc agtgaagcct gcagcccagg gcagctccg cacggtcagc     1020
aacgctcaga cagctgatga ggagaggaca gaaagcaaag gcacctgaac tagt           1074
```

<210> SEQ ID NO 5
<211> LENGTH: 262
<212> TYPE: RNA
<213> ORGANISM: Rat

<400> SEQUENCE: 5

```
gcgaauuggg uaccgggccc ccccucgagg ucgacgguau cgauaagcuu gauaucgaau      60
```

-continued

| | |
|---|---|
| uccugcagcc cggggauccc gcccacuagu ucaggugccu uugcuuucug uccucuccuc | 120 |
| aucagcuguc ugagcguugc ugaccgugcg gagcugcccc ugggcugcag gcuucacuga | 180 |
| caacaccaag cguuuucgaa aggucucaca gagcacuaug uacacaaagg gguucaggca | 240 |
| gcuguuagca uagcccaagc ug | 262 |

<210> SEQ ID NO 6
<211> LENGTH: 18
<212> TYPE: DNA
<213> ORGANISM: Artificial Sequence
<220> FEATURE:
<223> OTHER INFORMATION: primer

<400> SEQUENCE: 6

| | |
|---|---|
| caacagctgc ctcaaccc | 18 |

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7

| | |
|---|---|
| cctggtgatc tgcctcct | 18 |

<210> SEQ ID NO 8
<211> LENGTH: 1275
<212> TYPE: DNA
<213> ORGANISM: Human

<400> SEQUENCE: 8

| | |
|---|---|
| taggtgatgt cagtgggagc catgaagaag ggagtgggga gggcagttgg gcttggaggc | 60 |
| ggcagcggct gccaggctac ggaggaagac ccccttccca actgcgggc ttgcgctccg | 120 |
| ggacaaggtg gcaggcgctg gaggctgccg cagcctgcgt gggtggaggg gagctcagct | 180 |
| cggttgtggg agcaggcgac cggcactggc tggatggacc tggaagcctc gctgctgccc | 240 |
| actggtccca acgccagcaa cacctctgat ggccccgata acctcacttc ggcaggatca | 300 |
| cctcctcgca cggggagcat ctcctacatc aacatcatca tgccttcggt gttcggcacc | 360 |
| atctgcctcc tgggcatcat cgggaactcc acggtcatct tcgcggtcgt gaagaagtcc | 420 |
| aagctgcact ggtgcaacaa cgtccccgac atcttcatca tcaacctctc ggtagtagat | 480 |
| ctcctctttc tcctgggcat gccccttcatg atccaccagc tcatgggcaa tgggggtgtgg | 540 |
| cactttgggg agaccatgtg caccctcatc acggccatgg atgccaatag tcagttcacc | 600 |
| agcacctaca tcctgaccgc catggccatt gaccgctacc tggccactgt ccaccccatc | 660 |
| tcttccacga agttccggaa gccctctgtg gccaccctgg tgatctgcct cctgtgggcc | 720 |
| ctctccttca tcagcatcac ccctgtgtgg ctgtatgcca gactcatccc cttcccagga | 780 |
| ggtgcagtgg gctgcggcat acgcctgccc aacccagaca ctgacctcta ctggttcacc | 840 |
| ctgtaccagt ttttcctggc cttgccctg ccttttgtgg tcatcacagc cgcatacgtg | 900 |
| aggatcctgc agcgcatgac gtcctcagtg gccccgcct cccagcgcag catccggctg | 960 |
| cggacaaaga gggtgaccc cacagccatc gccatctgtc tggtcttctt tgtgtgctgg | 1020 |
| gcaccctact atgtgctaca gctgaccag ttgtccatca gccgcccgac cctcacctt | 1080 |
| gtctacttat acaatgcggc catcagcttg ggctatgcca acagctgcct caacccctt | 1140 |
| gtgtacatcg tgctctgtga gacgttccgc aaacgcttgg tcctgtcggt gaagcctgca | 1200 |

```
gcccagggc agcttcgcgc tgtcagcaac gctcagacgg ctgacgagga gaggacagaa    1260
agcaaaggca cctga                                                     1275
```

<210> SEQ ID NO 9
<211> LENGTH: 422
<212> TYPE: PRT
<213> ORGANISM: Human

<400> SEQUENCE: 9

```
Met Ser Val Gly Ala MeT Lys Lys Gly Val Gly Arg Ala Val Gly Leu
1               5                   10                  15

Gly Gly Gly Ser Gly Cys Gln Ala Thr Glu Glu Asp Pro Leu Pro Asn
            20                  25                  30

Cys Gly Ala Cys Ala Pro Gly Gln Gly Gly Arg Arg Trp Arg Leu Pro
        35                  40                  45

Gln Pro Ala Trp Val Glu Gly Ser Ser Ala Arg Leu Trp Glu Gln Ala
    50                  55                  60

Thr Gly Thr Gly Trp MeT Asp Leu Glu Ala Ser Leu Leu Pro Thr Gly
65                  70                  75                  80

Pro Asn Ala Ser Asn Thr Ser Asp Gly Pro Asp Asn Leu Thr Ser Ala
                85                  90                  95

Gly Ser Pro Pro Arg Thr Gly Ser Ile Ser Tyr Ile Asn Ile Ile MeT
            100                 105                 110

Pro Ser Val Phe Gly Thr Ile Cys Leu Leu Gly Ile Ile Gly Asn Ser
        115                 120                 125

Thr Val Ile Phe Ala Val Val Lys Lys Ser Lys Leu His Trp Cys Asn
    130                 135                 140

Asn Val Pro Asp Ile Phe Ile Ile Asn Leu Ser Val Val Asp Leu Leu
145                 150                 155                 160

Phe Leu Leu Gly MeT Pro Phe MeT Ile His Gln Leu MeT Gly Asn Gly
                165                 170                 175

Val Trp His Phe Gly Glu Thr MeT Cys Thr Leu Ile Thr Ala MeT Asp
            180                 185                 190

Ala Asn Ser Gln Phe Thr Ser Thr Tyr Ile Leu Thr Ala MeT Ala Ile
        195                 200                 205

Asp Arg Tyr Leu Ala Thr Val His Pro Ile Ser Ser Thr Lys Phe Arg
    210                 215                 220

Lys Pro Ser Val Ala Thr Leu Val Ile Cys Leu Leu Trp Ala Leu Ser
225                 230                 235                 240

Phe Ile Ser Ile Thr Pro Val Trp Leu Tyr Ala Arg Leu Ile Pro Phe
                245                 250                 255

Pro Gly Gly Ala Val Gly Cys Gly Ile Arg Leu Pro Asn Pro Asp Thr
            260                 265                 270

Asp Leu Tyr Trp Phe Thr Leu Tyr Gln Phe Phe Leu Ala Phe Ala Leu
        275                 280                 285

Pro Phe Val Val Ile Thr Ala Ala Tyr Val Arg Ile Leu Gln Arg MeT
    290                 295                 300

Thr Ser Ser Val Ala Pro Ala Ser Gln Arg Ser Ile Arg Leu Arg Thr
305                 310                 315                 320

Lys Arg Val Thr Arg Thr Ala Ile Ala Ile Cys Leu Val Phe Phe Val
                325                 330                 335

Cys Trp Ala Pro Tyr Tyr Val Leu Gln Leu Thr Gln Leu Ser Ile Ser
            340                 345                 350
```

```
Arg Pro Thr Leu Thr Phe Val Tyr Leu Tyr Asn Ala Ala Ile Ser Leu
        355                 360                 365
Gly Tyr Ala Asn Ser Cys Leu Asn Pro Phe Val Tyr Ile Val Leu Cys
    370                 375                 380
Glu Thr Phe Arg Lys Arg Leu Val Leu Ser Val Lys Pro Ala Ala Gln
385                 390                 395                 400
Gly Gln Leu Arg Ala Val Ser Asn Ala Gln Thr Ala Asp Glu Glu Arg
            405                 410                 415
Thr Glu Ser Lys Gly Thr
            420

<210> SEQ ID NO 10
<211> LENGTH: 31
<212> TYPE: DNA
<213> ORGANISM: Artificial Sequence
<220> FEATURE:
<223> OTHER INFORMATION: primer

<400> SEQUENCE: 10
gtcgacatgg acctggaagc ctcgctgctg c                              31

<210> SEQ ID NO 11
<211> LENGTH: 31
<212> TYPE: DNA
<213> ORGANISM: Artificial Sequence
<220> FEATURE:
<223> OTHER INFORMATION: primer

<400> SEQUENCE: 11
actagttcag gtgcctttgc tttctgtcct c                              31

<210> SEQ ID NO 12
<211> LENGTH: 33
<212> TYPE: DNA
<213> ORGANISM: Artificial Sequence
<220> FEATURE:
<223> OTHER INFORMATION: primer

<400> SEQUENCE: 12
agtcgacatg tcagtgggag ccatgaagaa ggg                            33

<210> SEQ ID NO 13
<211> LENGTH: 33
<212> TYPE: DNA
<213> ORGANISM: Artificial Sequence
<220> FEATURE:
<223> OTHER INFORMATION: primer

<400> SEQUENCE: 13
aactagttca ggtgcctttg ctttctgtcc tct                            33

<210> SEQ ID NO 14
<211> LENGTH: 1074
<212> TYPE: DNA
<213> ORGANISM: Human

<400> SEQUENCE: 14
gtcgacatgg acctggaagc ctcgctgctg cccactggtc ccaacgccag caacacctct    60
gatggccccg ataacctcac ttcggcagga tcacctcctc gcacgggag catctcctac   120 atcaacatca tcatgcctte ggtgttcggc accatctgcc tcctgggcat catcgggaac   180
tccacggtca tcttcgcggt cgtgaagaag tccaagctgc actggtgcaa caacgtcccc   240
```

-continued

```
gacatcttca tcatcaacct ctcggtagta gatctcctct ttctcctggg catgcccttc    300
atgatccacc agctcatggg caatggggtg tggcactttg gggagaccat gtgcaccctc    360
atcacggcca tggatgccaa tagtcagttc accagcacct catcctgac cgccatggcc     420
attgaccgct acctggccac tgtccacccc atctcttcca cgaagttccg gaagccctct    480
gtggccaccc tggtgatctg cctcctgtgg cccctctcct tcatcagcat cacccctgtg    540
tggctgtatg ccagactcat ccccttccca ggaggtgcag tgggctgcgg catacgcctg    600
cccaacccag acactgacct ctactggttc accctgtacc agttttttcct ggcctttgcc   660
ctgccttttg tggtcatcac agccgcatac gtgaggatcc tgcagcgcat gacgtcctca    720
gtggcccccg cctcccagcg cagcatccgg ctgcggacaa gagggtgac ccgcacagcc     780
atcgccatct gtctggtctt ctttgtgtgc tgggcaccct actatgtgct acagctgacc    840
cagttgtcca tcagccgccc gaccctcacc tttgtctact tatacaatgc ggccatcagc   900
ttgggctatg ccaacagctg cctcaacccc tttgtgtaca tcgtgctctg tgagacgttc    960
cgcaaacgct tggtcctgtc ggtgaagcct gcagcccagg ggcagcttcg cgctgtcagc  1020
aacgctcaga cggctgacga ggagaggaca gaaagcaaag gcacctgaac tagt           1074
```

<210> SEQ ID NO 15
<211> LENGTH: 1283
<212> TYPE: DNA
<213> ORGANISM: Human

<400> SEQUENCE: 15

```
agtcgacatg tcagtgggag ccatgaagaa gggagtgggg agggcagttg ggcttggagg     60
cggcagcggc tgccaggcta cggaggaaga cccccttccc aactgcgggg cttgcgctcc   120
gggacaaggt ggcaggcgct ggaggctgcc gcagcctgcg tgggtggagg ggagctcagc   180
tcggttgtgg gagcaggcga ccggcactgg ctggatggac ctggaagcct cgctgctgcc   240
cactggtccc aacgccagca acacctctga tggccccgat aacctcactt cggcaggatc   300
acctcctcgc acggggagca tctcctacat caacatcatc atgccttcgg tgttcggcac   360
catctgcctc ctgggcatca tcgggaactc cacggtcatc ttcgcggtcg tgaagaagtc   420
caagctgcac tggtgcaaca acgtccccga catcttcatc atcaacctct cggtagtaga   480
tctcctcttt ctcctgggca tgcccttcat gatccaccag ctcatgggca atgggtgtg    540
gcactttggg gagaccatgt gcaccctcat cacggccatg gatgccaata gtcagttcac   600
cagcacctac atcctgaccg ccatggccat tgaccgctac ctggccactg tccacccat    660
ctcttccacg aagttccgga agccctctgt ggccaccctg gtgatctgcc tcctgtgggc   720
cctctccttc atcagcatca cccctgtgtg gctgtatgcc agactcatcc ccttcccagg   780
aggtgcagtg ggctgcggca tacgcctgcc caacccagac actgacctct actggttcac   840
cctgtaccag ttttttcctgg cctttgccct gccttttgtg gtcatcacag ccgcatacgt   900
gaggatcctg cagcgcatga cgtcctcagt ggcccccgcc tcccagcgca gcatccggct   960
gcggacaaag agggtgaccc gcacagccat cgccatctgt ctggtcttct ttgtgtgctg  1020
ggcaccctac tatgtgctac agctgaccca gttgtccatc agccgcccga ccctcacctt  1080
tgtctactta tacaatgcgg ccatcagctt gggctatgcc aacagctgcc tcaacccctt  1140
tgtgtacatc gtgctctgtg agacgttccg caaacgcttg gtcctgtcgg tgaagcctgc  1200
agcccagggg cagcttcgcg ctgtcagcaa cgctcagacg gctgacgagg agaggacaga  1260
aagcaaaggc acctgaacta gtt                                          1283
```

```
<210> SEQ ID NO 16
<211> LENGTH: 420
<212> TYPE: RNA
<213> ORGANISM: Human

<400> SEQUENCE: 16
caaaagcugg agcuccaccg cgguggcggc cgcucuagcc cacuaguuca ggugccuuug      60
cuuucugucc ucuccucguc agccgucuga gcguugcuga cagcgcgaag cugccccugg     120
gcugcaggcu ucaccgacag gaccaagcgu uugcggaacg ucucacagag cacgauguac     180
acaaaggggu ugaggcagcu guuggcauag cccaagcuga uggccgcauu guauaaguag     240
acaaagguga gggucgggcg gcugauggac aacuggguca gcuguagcac auaguagggu     300
gcccagcaca caaagaagac cagacagaug gcgauggcug ugcggucac ccucuuuguc      360 cgcagccgga ugcugcgcug ggaggcgggg gccacugagg acgucaugcg cugcaggauc     420
```

MELANIN-CONCENTRATING HORMONE ANTAGONIST

This application is the National Phase filing of International Patent Application No. PCT/JP01/03614, filed Apr. 26, 2001.

TECHNICAL FIELD

The present invention relates to a melanin-concentrating hormone antagonist which is useful as an agent for preventing or treating obesity, etc.

BACKGROUND ART

Feeding behavior is an essential action for many living beings including humans. Therefore, if irregularities in feeding behavior occur, disorders, often connected to diseases, will occur in normal life-maintaining activities. Accompanying recent changes of our dietary environment, obesity is now becoming a social problem. In addition, not only is obesity a serious risk factor for life-style diseases such as diabetes, hypertension, and arteriosclerosis; it is also widely known that increased body weight places excessive burdens on joints such as knee joints, causing arthritis and pain. The "diet boom," etc. show that there is a potentially great percentage of the population hoping to reduce body weight; on the other hand, many cases of feeding problems such as overeating, occurring due to causes such as hereditary neurosis or neurosis due to stress, have been reported.

Therefore, research on and development of agents for preventing or treating obesity, or agents for inhibiting eating, have been vigorously done for a long time. The centrally acting anorectic drug, Mazindol, is now being marketed.

Many appetite control factors such as leptin, have recently been discovered, and the development of anti-obesity agents or anorectic agents which will regulate the functions of these appetite control factors is progressing. In particular, it is known that melanin-concentrating hormone (hereinafter also abbreviated as "MCH") originates in the hypothalamus and has orexigenic action. In addition, it has been reported that even though the daily behavior of MCH knock-out mice was normal, the amount of feeding by MCH knock-out mice was significantly reduced and their body weights were lighter than those of normal mice [Nature, Vol. 396, p.670, 1998]. This indicates that, if a MCH antagonist was produced, it can be expected to be an excellent anorectic agent or anti-obesity agent; but at present there are no known compound, especially non-peptide type compounds, which possess MCH antagonistic actions.

On the other hand, the following compounds are known as amine derivatives.

1) WO98/38156 describes a compound of the formula:

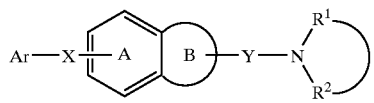

wherein Ar is an optionally substituted ring assembly aromatic group or an optionally substituted condensed aromatic group; X is a bond, etc.; Y is an optionally substituted bivalent $C_{1-6}$ aliphatic hydrocarbon group which may have an intervening oxygen atom or sulfur atom; $R^1$ and $R^2$ are independently hydrogen atom or an optionally substituted lower alkyl, or $R^1$ and $R^2$, together with the adjacent nitrogen atom, form an optionally substituted nitrogen-containing heterocyclic ring; Ring A is a benzene ring which may have further substituents in addition to the groups of the formula: —X—Ar where each symbol is as defined above; Ring B is a 4- to 8-membered ring which may have further substituents in addition to the group of the formula: —Y—NR$^1$R$^2$ where each symbol is as defined above; with the proviso that, when the condensed ring formed by ring A and ring B is an indole ring, the group of the formula: —X—Ar, where each symbol is as defined above is substituted at the 4-, 6-, or 7-position on the indole ring; or its salt, which has an action of inhibiting the production and secretion of β-amyloid protein.

2) WO95/32967 describes compound of the formula:

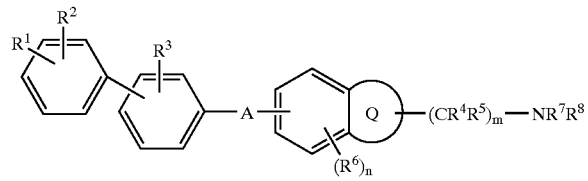

wherein A is CONR, in which R is hydrogen or $C_{1-6}$ alkyl; Q is an optionally substituted 5- to 7-membered heterocyclic ring containing 1 to 3 hetero atoms selected from oxygen, nitrogen or sulfur; $R^1$ is hydrogen, halogen, etc.; $R^2$ and $R^3$ are independently hydrogen, halogen, etc.; $R_4$ and $R_5$ are independently hydrogen or $C_{1-6}$ alkyl; $R^6$ is halogen, hydroxy, etc.; $R_7$ and $R_8$ are independently hydrogen, $C_{1-6}$ alkyls, etc.; m is 0 to 4; n is 0, 1 or 2; or its salt, which has 5HT1D antagonist activity and can be expected to ameliorate anorexia.

3) WO98/15274 describes a compound of the formula:

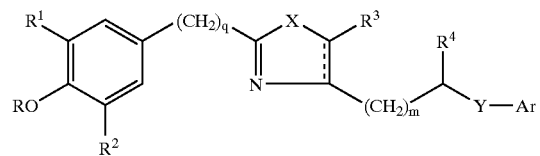

wherein Ar is phenyl, etc.; X is —O— or —S—; Y is CR$^5$R$^{5'}$— where R$^{5'}$ is H and R$^5$ is —H, etc.; Z is —CH$_2$— or —N—; R is H or —(C1–C6) alkyl; $R^1$ and $R^2$ are independently —(C1–C6) alkyl, etc.; $R^3$ is H etc.; $R^4$ is hydrogen, etc.; m is an integer of 0 to 2; q is 0 or 1; n is an integer of 0 to 4; p is an integer of 1 to 6; t is an integer of 1 to 4; which has an anti-oxidant activity and can be expected to ameliorate Alzheimer's disease.

4) EP533266 describes a compound of the formula:

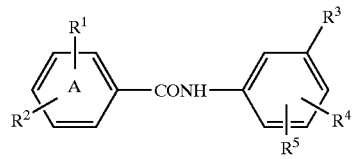

wherein $R^1$ is halogen, etc.; $R^2$ is phenyl optionally substituted by 1 or 2 substituents selected from halogen, etc.; $R^3$ is

$R^4$ and $R^5$ are independently hydrogen, halogen, etc.; $R^{11}$ is hydrogen or $C_{1-6}$ alkyl; which has 5HT1D antagonist activity, and can be expected to ameliorate anorexia.

5) DE2502588 describes a compound of the formula:

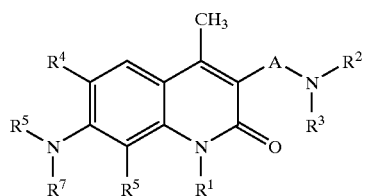

wherein $R^1$ is hydrogen, or lower alkyl such as Me, Et, etc.; $NR^2R^3$ is $NH_2$, a primary amine such as NHMe, etc., a secondary amine such as $NEt_2$, $NBu_2$, etc., or a cyclic amine such as pyrrolidinyl, piperidinyl, morpholinyl, etc.; $R^4$ and $R^5$ are hydrogen, lower alkyl such as Me, etc., lower alkoxy such as OMe, etc., or halogen; $R^6$ is hydrogen, or lower alkyl such as Me, Et, etc.; $R^7$ is H, lower alkyl such as Me, Et, etc., $COR^8$ ($R^8$ is alkoxy, aryloxy, $NR^9R^{10}$ ($NR^9R^{10}$ is NH2, an optionally substituted primary amine such as NHMe, etc., secondary amine such as $NEt_2$, $NBu_2$, etc., or a cyclic amine such as pyrrolidinyl, piperidinyl, morpholinyl, etc.)); A is an alkyl chain such as $-CH_2-$, $-CH_2CH_2-$, etc., which can be expected to ameliorate hypertrophy of the small intestine.

6) J. Chem. Soc., 4678 (1962) or J. Heterocycl. Chem., 24, 345 (1987) describes a compound of the formula:

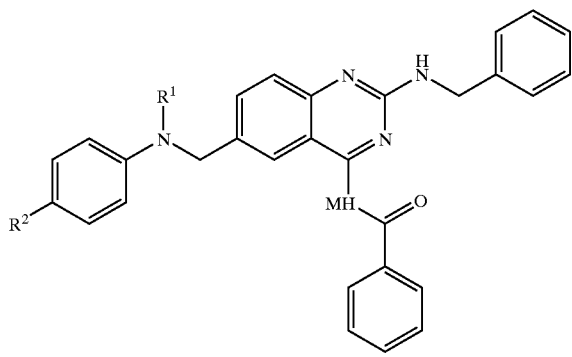

wherein $R^1$ is hydrogen, or alkyl such as Me, Et, etc.; $R^2$ is hydrogen, halogen or a carboxylic acid ester, which has folic acid antagonistic activity.

There has been great desire for the development of a melanin-concentrating hormone antagonist which is useful as an agent for preventing or treating obesity, excellent in oral absorbency, and safe.

DISCLOSURE OF INVENTION

As a result of intensive studies of compounds with a MCH antagonistic action, the present inventors found that a derivative which is obtained by introducing a group of the formula: $Ar^1-X-$ where each symbol is as defined hereafter, into a compound of the formula:

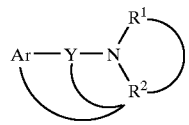

wherein each symbol is as defined hereinafter, had an excellent MCH antagonistic actions, to complete the present invention.

Namely, the present invention relates to:

1) A melanin-concentrating hormone antagonist which comprises a compound of the formula:

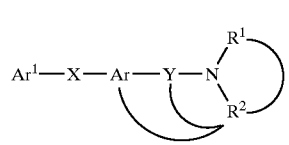

(I)

wherein $Ar^1$ is a cyclic group which may be substituted; X and Y are the same or different and are a spacer having a main chain of 1 to 6 atoms;

Ar is a condensed polycyclic aromatic ring which may be substituted;

$R^1$ and $R^2$ are the same or different and are hydrogen atom or a hydrocarbon group which may be substituted; or $R^1$ and $R^2$, together with the adjacent nitrogen atom, may form a nitrogen-containing heterocyclic ring which may be substituted; or $R^2$, together with the adjacent nitrogen atom and Y, may form a nitrogen-containing heterocyclic ring which may be substituted; or $R^2$, together with the adjacent nitrogen atom, Y and Ar, may form a nitrogen-containing condensed ring which may be substituted; or a salt thereof;

2) The antagonist according to the above 1), wherein $R^1$ and $R^2$ are the same or different and are hydrogen atom or a hydrocarbon group which may be substituted; or $R^1$ and $R^2$, together with the adjacent nitrogen atom, form a nitrogen-containing heterocyclic ring which may be substituted; or $R^2$, together with the adjacent nitrogen atom and Y, form a nitrogen-containing heterocyclic ring which may be substituted;

3) The antagonist according to the above 1) which is an agent for preventing or treating diseases caused by melanin-concentrating hormone;

4) The antagonist according to the above 1) which is an agent for preventing or treating obesity;

5) A compound of the formula:

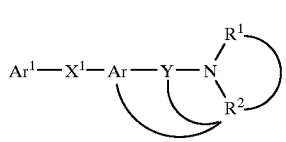

(I')

wherein $Ar^1$ is a cyclic group which may be substituted; $X^1$ is $CONR^8$, $NR^8CO$ (wherein $R^8$ is hydrogen atom, optionally halogenated $C_{1-6}$ alkyl, optionally halogenated $C_{1-6}$ alkyl-carbonyl or optionally halogenated $C_{1-6}$ alkylsulfonyl), OCO or COO;

Y is a spacer having a main chain of 1 to 6 atoms;

Ar is a condensed polycyclic aromatic ring which may be substituted;

$R^1$ and $R^2$ are the same or different and are hydrogen atom or a hydrocarbon group which may be substituted; or $R^1$ and R², together with the adjacent nitrogen atom, may form a nitrogen-containing heterocyclic ring which may be substituted; or R², together with the adjacent nitrogen atom and Y, may form a nitrogen-containing heterocyclic ring which may be substituted; or R², together with the adjacent nitrogen atom, Y and Ar, may form a nitrogen-containing condensed ring which may be substituted;

provided that, when $X^1$ is CONR (wherein R is hydrogen atom or $C_{1-6}$ alkyl), Ar is not indole or benzoxazole which may have one or two halogen, hydroxy, $C_{1-6}$ alkyl or $C_{1-6}$ alkoxy; when $X^1$ is CONH, Ar is not 4-methyl-2-quinolone which may have a substituent selected from the group consisting of alkyl, alkoxy and halogen, or is not 2-benzoylamino-quinazoline; and, when $X^1$ is COO, $Ar^1$ is not an aromatic group which may be substituted; or a salt thereof;

6) The compound according to the above 5), wherein $X^1$ is $CONR^8$ or $NR^8CO$ (wherein $R^8$ is hydrogen atom, optionally halogenated $C_{1-6}$ alkyl, optionally halogenated $C_{1-6}$ alkyl-carbonyl or optionally halogenated $C_{1-6}$ alkylsulfonyl); and $R^1$ and $R^2$ are the same or different and are hydrogen atom or a hydrocarbon group which may be substituted; or $R^1$ and $R^2$, together with the adjacent nitrogen atom, may form a nitrogen-containing heterocyclic ring which may be substituted; or $R^2$, together with the adjacent nitrogen atom and Y, may form a nitrogen-containing heterocyclic ring which may be substituted;

7) The compound according to the above 5), wherein the cyclic group represented by $Ar^1$ is an aromatic group;

8) The compound according to the above 7), wherein the aromatic group is formed by removing an optional one hydrogen atom from an aromatic ring assembly formed by 2 or 3 members selected from $C_{6-14}$ monocyclic or condensed polycyclic aromatic hydrocarbon and 5- to 10-membered aromatic heterocyclic ring;

9) The compound according to the above 5), wherein $Ar^1$ is phenyl, biphenylyl or phenyl-pyridyl, each of which may be substituted with 1 to 3 substituents selected from halogen, optionally halogenated $C_{1-6}$ alkyl and optionally halogenated $C_{1-6}$ alkoxy;

10) The compound according to the above 5), wherein $Ar^1$ is piperidinyl which may be substituted with $C_{6-14}$ aryl which may be substituted;

11) The compound according to the above 5), wherein $X^1$ is CONH or COO;

12) The compound according to the above 5), wherein the condensed polycyclic aromatic ring represented by Ar is a condensed polycyclic aromatic hydrocarbon having 9 to 14 carbon atoms;

13) The compound according to the above 4), wherein the condensed polycyclic aromatic ring represented by Ar is a 10-membered condensed polycyclic aromatic heterocyclic ring;

14) The compound according to the above 5), wherein the condensed polycyclic aromatic ring represented by Ar is quinoline or naphthalene;

15) The compound according to the above 5), wherein $X^1$ is $CONR^8$ or $NR^8CO$ (wherein $R^8$ is hydrogen atom, optionally halogenated $C_{1-6}$ alkyl, optionally halogenated $C_{1-6}$ alkyl-carbonyl or optionally halogenated $C_{1-6}$ alkylsulfonyl), and Ar is quinoline or naphthalene;

16) The compound according to the above 4), wherein the "spacer having a main chain of 1 to 6 atoms" represented by Y is a bivalent group consisting of 1 to 3 species selected from —O—, —S—, —CO—, —SO—, —SO₂—, —NR⁸— ($R^8$ is hydrogen atom, optionally halogenated $C_{1-6}$ alkyl, optionally halogenated $C_{1-6}$ alkyl-carbonyl, optionally halogenated $C_{1-6}$ alkylsulfonyl), and an optionally halogenated bivalent $C_{1-6}$ non-cyclic hydrocarbon group;

17) The compound according to the above 5), wherein Y is $C_{1-3}$ alkylene;

18) The compound according to the above 4), wherein $R^1$ and $R^2$, together with the adjacent nitrogen atom, form a nitrogen-containing heterocyclic ring which may be substituted;

19) The compound according to the above 18), wherein the nitrogen-containing heterocyclic ring is morpholine, piperidine, piperazine, pyrrolidine, 1,3-thiazolidine, 1H-imidazole, 4,5-dihydro-1H-imidazole, 2,3-dihydroindole, 1,2,3,4-tetrahydroquinoline or 1,2,3,4-tetrahydroisoquinoline;

20) A pharmaceutical composition comprising the compound according to the above 5), or a salt thereof.

21) A prodrug of the compound according to the above 5).

22) The compound according to the above 5) which is:
4'-chloro-N-[6-[(N,N-dimethylamino)methyl]-2-naphthyl][1,1'-biphenyl]-4-carboxamide;
4'-chloro-N-[6-(1-pyrrolidinylmethyl)-2-naphthyl][1,1'-biphenyl]-4-carboxamide;
4'-fluoro-N-[2-(1-pyrrolidinylmethyl)-6-quinolinyl][1,1'-biphenyl]-4-carboxamide;
4'-fluoro-N-[2-(1-piperidinylmethyl)-6-quinolinyl][1,1'-biphenyl]-4-carboxamide;
4'-chloro-N-[2-[(2-methyl-4,5-dihydro-1H-imidazol-1-yl)methyl]-6-quinolinyl][1,1 '-biphenyl]-4-carboxamide;
4'-chloro-N-[2-[(2,2,6,6-tetramethyl-1-piperidinyl)methyl]-6-quinolinyl][1,1'-biphenyl]-4-carboxamide;
4-(4-chlorophenyl)-N-[2-(1-pyrrolidinylmethyl)-6-quinolinyl]-1-piperidinecarboxamide;
N-[2-(1-pyrrolidinylmethyl)-6-quinolinyl][1,1'-biphenyl]-4-carboxamide;
6-(4-methylphenyl)-N-[2-(1-pyrrolidinylmethyl)-6-quinolinyl]nicotinamide;
4-(4-methoxyphenyl)-N-[6-(1-pyrrolidinylmethyl)-2-naphthyl]-1-piperidinecarboxamide;
6-(4-methoxyphenyl)-N-[6-(1-pyrrolidinylmethyl)-2-naphthyl]nicotinamide;
6-(4-methylphenyl)-N-[6-(1-pyrrolidinylmethyl)-2-naphthyl]nicotinamide;
or a salt thereof;

23) A process for producing a compound of the formula (I'), or a salt thereof, which comprises reacting a compound of the formula:

$$Ar^1\text{—H} \qquad (XII)$$

wherein $Ar^1$ is as defined in the above 5), or a salt thereof with a compound of the formula:

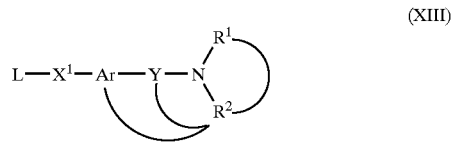

(XIII)

wherein L is a leaving group and the other symbols are as defined in the above 5), or a salt thereof;

24) The antagonist according to the above 1) which is an anorectic agent;

25) A pharmaceutical which comprises the melanin-concentrating hormone antagonist according to the above 1) in combination with at least one species selected from the group consisting of an agent for treating diabetes, an agent for treating hypertension and an agent for treating arteriosclerosis;

26) A method for preventing or treating diseases caused by a melanin-concentrating hormone in a mammal in need thereof, which comprises administering to said mammal an effective amount of the compound represented by the formula (I), or a salt thereof;

27) A method for preventing or treating obesity in a mammal in need thereof, which comprises administering to said mammal an effective amount of the compound represented by the formula (I), or a salt thereof;

28) Use of the compound represented by the formula (I), or a salt thereof for the manufacture of a pharmaceutical preparation for preventing or treating diseases caused by a melanin-concentrating hormone;

29) Use of the compound of the formula (I) or a salt thereof for the manufacture of a pharmaceutical preparation for preventing or treating obesity; and the like.

Examples of the "cyclic group" in the "cyclic group which may be substituted" represented by $Ar^1$ include aromatic groups, non-aromatic cyclic hydrocarbon groups, non-aromatic heterocyclic groups and the like.

Here, examples of the "aromatic groups" include monocyclic aromatic groups, condensed aromatic groups, ring assembly aromatic groups and the like.

Examples of the condensed monocyclic aromatic groups include univalent groups which can be formed by removing an optional one hydrogen atom from a monocyclic aromatic ring. Example of the "monocyclic aromatic ring" include a benzene ring and a 5- or 6-membered aromatic heterocyclic ring.

Examples of the "5- or 6-membered aromatic heterocyclic ring" include a 5- or 6-membered aromatic heterocyclic ring containing one or more (for example, 1 to 3) hetero atoms selected from nitrogen, sulfur and oxygen atoms in addition to carbon atoms, and the like. Specifically, thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, furazan, etc., can be mentioned.

Specific examples of the "monocyclic aromatic groups" include phenyl, 2- or 3-thienyl, 2-, 3-, or -4-pyridyl, 2- or 3-furyl, 2-, 4- or 5-thiazolyl, 2-, 4- or 5-oxazolyl, 1-, 3- or 4-pyrazolyl, 2-pyrazinyl, 2-, 4- or 5-pyrimidinyl, 1-, 2- or 3-pyrrolyl, 1-, 2- or 4-imidazolyl, 3- or. 4-pyridazinyl, 3-isothiazolyl, 3-isoxazolyl, 1,2,4-oxadiazol-5-yl, 1,2,4-oxadiazol-3-yl, etc.

The "condensed aromatic groups" mean a univalent group that can be formed by removing an optional one hydrogen atom from condensed polycyclic (preferably bicyclic to tetracyclic, more preferably bicyclic or tricyclic) aromatic rings, etc.

Examples of the "condensed aromatic groups" include condensed polycyclic aromatic hydrocarbons, condensed polycyclic aromatic heterocyclic rings, etc.

Examples of the "condensed polycyclic aromatic hydrocarbons" include $C_{9-14}$ condensed polycyclic (bicyclic or tricyclic) aromatic hydrocarbons (e.g. naphthalene, indene, fluorene, anthracene, etc.), etc.

Examples of the "condensed polycyclic aromatic heterocyclic rings" include 9- to 14-membered, preferably, 9- or 10-membered, condensed polycyclic aromatic heterocyclic rings containing one or more (for example, 1 to 4) hetero atoms selected from nitrogen, sulfur and oxygen atoms in addition to carbon atoms, and the like. The "condensed polycyclic aromatic heterocyclic rings" is preferably 10-membered condensed polycyclic aromatic heterocyclic ring. Specific examples of the "condensed polycyclic aromatic heterocyclic rings" include benzofuran, benzimidazole, benzoxazole, benzothiazole, benzisothiazole, naphtho[2,3-b]thiophene, isoquinoline, quinoline, indole, quinoxaline, phenanthridine, phenothiadine, phenoxazine, phthalazine, naphthyridine, quinazoline, cinnoline, carbazole, β-carboline, acridine, phenazine, phthalimide, thioxanthene, etc.

Specific examples of the "condensed aromatic groups" include 1-naphthyl; 2-naphthyl; 2-, 3-, 4-, 5- or 8-quinolyl; 1-, 3-, 4-, 5-, 6-, 7- or 8-isoquinolyl; 1-, 2-, 3-, 4-, 5-, 6- or 7-indolyl; 1-, 2-, 4- or 5-isoindolyl; 1-, 5- or 6-phthalazinyl; 2-, 3- or 5-quinoxalinyl; 2-, 3-, 4-, 5- or 6-benzofuranyl; 2-, 4-, 5- or 6-benzothiazolyl; 1-, 2-, 4-, 5- or 6-benzimidazolyl; etc.

The "ring assembly aromatic group" means a group formed by removing an optional one hydrogen atom from an aromatic ring assembly in which 2 or more (preferably 2 or 3) aromatic rings are directly bonded by single bonds, and in which the number of bonds which directly bond the rings, is less by one than the number of ring systems.

Examples of the aromatic ring assembly include an aromatic ring assemblies formed by 0.2 or 3 (preferably 2) species selected from $C_{6-14}$ monocyclic or condensed polycyclic aromatic hydrocarbons (e.g. benzene and naphthalene) and 5- to 10-membered (preferably 5- or 6-membered) aromatic heterocyclic rings, etc.

Preferred example of the aromatic ring assemblies include aromatic ring assembles comprising 2 or 3 aromatic rings selected from benzene, naphthalene, pyridine, pyrimidine, thiophene, furan, thiazole, isothiazole, oxazole, isoxazole, 1,2,4-oxadiazole, 1,3,4-oxadiazole, 1,2,4-thiadiazole, 1,3,4-thiadiazole, quinoline, isoquinoline, indole, benzothiophene, benzoxazole, benzothiazole and benzofuran.

Specific examples of the "ring assembly aromatic groups" include 2-, 3- or 4-biphenylyl; 3-(1-naphthyl)-1,2,4-oxadiazol-5-yl; 3-(2-naphthyl)-1,2,4-oxadiazol-5-yl; 3-(2-benzofuranyl)-1,2,4-oxadiazol-5-yl; 3-phenyl-1,2,4-oxadiazol-5-yl; 3-(2-benzoxazolyl)-1,2,4-oxadiazol-5-yl; 3-(3-indolyl)-1,2,4-oxadiazol-5-yl; 3-(2-indolyl)-1,2,4-oxadiazol-5-yl; 4-phenylthiazol-2-yl; 4-(2-benzofuranyl)thiazol-2-yl; 4-phenyl-1,3-oxazol-5-yl; 5-phenyl-isothiazol-4-yl; 5-phenyloxazol-2-yl; 4-(2-thienyl)phenyl; 4-(3-thienyl)phenyl; 3-(3-pyridyl)phenyl; 4-(3-pyridyl)phenyl; 6-phenyl-3-pyridyl; 5-phenyl-1,3,4-oxadiazol-2-yl; 4-(2-naphthyl)phenyl; 4-(2-benzofuranyl)phenyl; 4,4'-terphenyl; 5-phenyl-2-pyridyl; 2-phenyl-5-pyrimidinyl; 4-(4-pyridyl)phenyl; 2-phenyl-1,3-oxazol-5-yl; 2,4-diphenyl-1,3-oxazol-5-yl; 3-phenyl-isoxazol-5-yl; 5-phenyl-2-furyl; 4-(2-furyl)phenyl; etc.

Preferred groups among the above "aromatic groups" are "a group formed by removing an optional one hydrogen atom from an aromatic ring assembly formed by 2 or 3 members selected from a $C_{6-14}$ monocyclic or condensed polycyclic aromatic hydrocarbon and 5- to 10-membered aromatic heterocyclic ring (preferably, 2-, 3- or 4-biphenylyl; 6-phenyl-3-pyridyl, 5-phenyl-2-pyridyl, etc.)".

Examples of the "non-aromatic cyclic hydrocarbon groups" include $C_{3-8}$ cycloalkyl, $C_{3-8}$ cycloalkenyl, etc.

Here, specific examples of the $C_{3-7}$ cycloalkyl include cyclopropyl, cyclobutyl, cyclopentyl, cyclohexyl, cycloheptyl, cyclooctyl. etc.

Specific examples of the $C_{3-8}$ cycloalkenyl include cyclopropenyl, cyclobutenyl, cyclopentenyl, cyclohexenyl, cycloheptenyl, cyclooctenyl, etc.

Among the above "non-aromatic cyclic hydrocarbon groups", $C_{3-8}$ cycloalkyl is preferred, and cyclohexyl is particularly preferred.

Examples of "non-aromatic heterocyclic groups" include monocyclic non-aromatic heterocyclic groups, condensed polycyclic non-aromatic heterocyclic groups, and the like.

Examples of the "imonocyclic non-aromatic heterocyclic groups" include univalent groups formed by removing an optional one hydrogen atom from monocyclic non-aromatic heterocyclic ring. Examples of the "imonocyclic non-aromatic heterocyclic groups" include 5- to 8-membered monocyclic non-aromatic heterocyclic groups containing one or more (e.g. 1 to 3) hetero atoms selected from nitrogen, sulfur and oxygen atoms in addition to carbon atoms. Specifically, tetrahydrothiophene, tetrahydrofuran, pyrrolidine, imidazoline, imidazolidine, pyrazoline, pyrazolidine, tetrahydrothiazole, tetrahydroisothiazole, tetrahydrooxazole, tetrahydroisoxazole, piperidine, tetrahydropyridine, dihydropyridine, piperazine, morpholine, thiomorpholine, tetrahydropyrimidine, tetrahydropyridazine, hexamethyleneimine, 1,3-dioxane, 1,4-dioxane, etc. can be mentioned.

The "condensed polycyclic non-aromatic heterocyclic group" means a univalent group formed by removing an optional one hydrogen atom from a condensed polycyclic (preferably bicyclic to tetracyclic, more preferably bicyclic or tricyclic) non-aromatic heterocyclic ring. Examples of the "condensed polycyclic non-aromatic heterocyclic ring" include 9- to 14-membered, preferably 9- or 10-membered condensed polycyclic non-aromatic heterocyclic rings which contain one or more (e.g. 1 to 4) hetero atoms selected from nitrogen, sulfur and oxygen atoms in addition to carbon atoms. Specifically, dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, indoline, isoindoline, tetrahydroquinoxaline, tetrahydrophenanthridine, hexahydrophenothiadine, hexahydrophenoxazine, tetrahydrophthaladine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxantene, etc., can be mentioned.

Among the above "non-aromatic heterocyclic groups", "5- to 8-membered monocyclic non-aromatic heterocyclic groups (preferably piperidinyl (piperidino); piperazinyl; pyrrolidinyl; 1,3-dioxanyl; etc. are preferred.

The "cyclic group" represented by $Ar^1$ is preferably monocyclic aromatic groups (preferably phenyl), ring assembly aromatic groups (preferably biphenylyl, phenylpyridyl), 5- to 8-membered monocyclic non-aromatic heterocyclic groups (preferably piperidinyl (piperidino), 1,3-dioxane), etc.

Examples of the "substituent" in the "cyclic group which may be substituted" represented by $Ar^1$ include oxo, halogen atoms (e.g. fluorine, chlorine, bromine, iodine, etc.), $C_{1-3}$ alkylenedioxy (e.g. methylenedioxy, ethylenedioxy, etc.), nitro, cyano, optionally halogenated $C_{1-6}$ alkyl, hydroxy-$C_{1-6}$ alkyl, $C_{6-14}$ aryloxy-$C_{1-6}$ alkyl (e.g. phenoxymethyl, etc.), $C_{1-6}$ alkyl-$C_{6-14}$ aryl-$C_{2-6}$ alkenyl (e.g. methylphenylethenyl, etc.), optionally halogenated $C_{3-6}$ cycloalkyl, optionally halogenated $C_{1-6}$ alkoxy, optionally halogenated $C_{1-6}$ alkylthio, $C_{7-19}$ aralkyl which may be substituted, hydroxy, $C_{6-14}$ aryloxy which may be substituted, $C_{7-19}$ aralkyloxy which may be substituted, $C_{6-14}$ aryl-carbamoyl which may be substituted, amino, amino-$C_{1-6}$ alkyl (e.g. aminomethyl, aminoethyl, aminopropyl, aminobutyl, etc.), mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, dipropylamino, dibutylamino, ethylmethylamino, etc.), mono-$C_{1-6}$ alkylamino-$C_{1-6}$ alkyl (e.g. methylaminomethyl, ethylaminomethyl, propylaminomethyl, isopropylaminoethyl, butylaminoethyl, etc.), di-$C_{1-6}$ alkylamino-$C_{1-6}$ alkyl (e.g. dimethylaminomethyl, diethylaminomethyl, dipropylaminomethyl, diisopropylaminoethyl, dibutylaminoethyl, etc.), 5- to 7-membered saturated cyclic amino which may be substituted, 5- to 7-membered non-aromatic heterocyclic groups which may be substituted, acyl, acylamino, acyloxy, etc.

The "cyclic group" represented by $Ar^1$ may have 1 to 5, preferably 1 to 3, of the above-mentioned substituents at a substitutable position on the cyclic group. When the number of substituents is 2 or more, each substituents can be the same or different.

Also, when the "cyclic group" represented by $Ar^1$ is a non-aromatic cyclic hydrocarbon group or a non-aromatic heterocyclic group, the "cyclic group" may have as its substituent(s), $C_{6-14}$ aryl which may be substituted, 5- to 10-membered aromatic heterocyclic groups which may be substituted, etc.

Here, the groups exemplified as the "substituent" in the "5- to 7-membered saturated cyclic amino which may be substituted" mentioned hereinafter, can be mentioned as "$C_{6-14}$ aryl which may be substituted" and "5- to 10-membered aromatic heterocyclic groups which may be substituted". The number of substituents is, for example, 1 to 3. When the number of substituents is 2 or more, each substituents can be the same or different.

Specific examples of the above "optionally halogenated $C_{1-6}$ alkyl" include $C_{1-6}$ alkyl (e.g. methyl, ethyl, propyl, isopropyl, butyl, isobutyl, sec-butyl, tert-butyl, pentyl, hexyl, etc.) which may have 1 to 5, preferably 1 to 3, halogen atoms (e.g. fluorine, chlorine, bromine, iodine, etc.). Specific examples include methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.

The $C_{1-6}$ alkyl in the above "optionally halogenated $C_{1-6}$ alkyl" can be mentioned as the $C_{1-6}$ alkyl in the above "hydroxy-$C_{1-6}$ alkyl".

Examples of the above "optionally halogenated $C_{3-6}$ cycloalkyl" include $C_{3-6}$ cycloalkyl (e.g. cyclopropyl, cyclobutyl, cyclopentyl, cyclohexyl, etc.) which may have 1 to 5, preferably 1 to 3, halogen atoms (e.g. fluorine, chlorine, bromine, iodine, etc.). Specific examples include cyclopropyl, cyclobutyl, cyclopentyl, cyclohexyl, 4,4-dichlorocyclohexyl, 2,2,3,3-tetrafluorocyclopentyl, 4-chlorocyclohexyl, etc.

Examples of the above "optionally halogenated $C_{1-6}$ alkoxy" include $C_{1-6}$ alkoxy (e.g. methoxy, ethoxy, propoxy, butoxy, pentyloxy, etc.) which may have 1 to 5, preferably 1 to 3, halogen atoms (e.g. fluorine, chlorine, bromine, iodine, etc.). Specific examples include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.

Examples of the above "optionally halogenated $C_{1-6}$ alkylthio" include $C_{1-6}$ alkylthio (e.g. methylthio, ethylthio, propylthio, isopropylthio, butylthio, sec-butylthio, tert-butylthio, etc.) which may have 1 to 5, preferably 1 to 3, halogen atoms (e.g. fluorine, chlorine, bromine, iodine, etc.).

Specific examples include methylthio, difluoromethylthio, trifluoromethylthio, ethylthio, propylthio, isopropylthio, butylthio, 4,4,4-trifluorobutylthio, pentylthio, hexylthio, etc.

Examples of the "$C_{7-19}$ aralkyl" in the above "$C_{7-19}$ aralkyl which may be substituted" include benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl, etc. Benzyl is particularly preferred.

Examples of the "substituent" in the above "$C_{7-19}$ aralkyl which may be substituted" include halogen atom (e.g. fluorine, chlorine, bromine, iodine, etc.), $C_{1-3}$ alkylenedioxy (e.g. methylenedioxy, ethylenedioxy, etc.) nitro, cyano, optionally halogenated $C_{1-6}$ alkyl, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, dipropylamino, dibutylamino, ethylmethylamino, etc.), amino-$C_{1-6}$ alkyl (e.g. aminomethyl, aminoethyl, aminopropyl, aminobutyl, etc.), mono-$C_{1-6}$ alkylamino-$C_{1-6}$ alkyl (e.g. methylaminomethyl, ethylaminomethyl, propylaminomethyl, isopropylaminoethyl, butylaminoethyl, etc.), di-$C_{1-6}$ alkylamino-$C_{1-6}$ alkyl (e.g. dimethylaminomethyl, diethylaminomethyl, dipropylaminomethyl, diisopropylaminoethyl, dibutylaminoethyl, etc.), formyl, carboxy, carbamoyl, thiocarbamoyl, optionally halogenated $C_{1-6}$ alkyl-carbonyl, $C_{1-6}$ alkoxy-carbonyl (e.g., methoxycarbonyl, ethoxycarbonyl, propoxycarbonyl, tert-butoxycarbonyl, etc.), mono-$C_{1-6}$ alkyl-carbamoyl (e.g., methylcarbamoyl, ethylcarbamoyl, etc.), di-$C_{1-6}$ alkyl-carbamoyl (e.g. dimethylcarbamoyl, diethylcarbamoyl, ethylmethylcarbamoyl, etc.), optionally halogenated $C_{1-6}$ alkylsulfonyl, formylamino, optionally halogenated $C_{1-6}$ alkyl-carboxamide, $C_{1-6}$ alkoxy-carboxamide (e.g. methoxycarboxamide, ethoxycarboxamide, prpoxycarboxamide, butoxycarboxamide, etc.), $C_{1-6}$ alkyl-sulfonylamino (e.g. methylsulfonylamino, ethylsulfonylamino, etc.), $C_{1-6}$ alkyl-carbonyloxy (e.g. acetoxy, propanoyloxy, etc.), $C_{1-6}$ alkoxy-carbonyloxy (e.g. methoxycarbonyloxy, ethoxycarbonyloxy, propoxycarbonyloxy, butoxycarbonyloxy, etc.), mono-$C_{1-6}$ alkyl-carbamoyloxy (e.g. methylcarbamoyloxy, ethylcarbamoyloxy, etc.), di-$C_{1-6}$ alkyl-carbamoyloxy (e.g. dimethylcarbamoyloxy, diethylcarbamoyloxy, etc.), etc. The number of substituents is, for example, 1 to 5, preferably 1 to 3. When the number of substituents is 2 or more, each substituents can be the same or different.

As the "optionally halogenated $C_{1-6}$ alkyl", "optionally halogenated $C_{3-6}$ cycloalkyl", "optionally halogenated $C_{1-6}$ alkoxy" and "optionally halogenated $C_{1-6}$ alkylthio", those exemplified as the "substituents" in the above "cyclic group which may be substituted" can be used, respectively.

Examples of the above "optionally halogenated $C_{1-6}$ alkyl-carbonyl" include $C_{1-6}$ alkyl-carbonyl (e.g. acetyl, propanoyl, butanoyl, pentanoyl, hexanoyl, etc.) which may have 1 to 5, preferably 1 to 3, halogen atoms (e.g., fluorine, chlorine, bromine, iodine, etc.), etc. Specific examples include acetyl, monochloroacetyl, trifluoroacetyl, trichloroacetyl, propanoyl, butanoyl, pentanoyl, hexanoyl, etc.

Examples of the above "optionally halogenated $C_{1-6}$ alkylsulfonyl" include $C_{1-6}$ alkylsulfonyl (e.g. methylsulfonyl, ethylsulfonyl, propylsulfonyl, isopropylsulfonyl, butylsulfonyl, sec-butylsulfonyl, tert-butylsulfonyl, etc.) which may have 1 to 5, preferably 1 to 3, halogen atoms (e.g., fluorine, chlorine, bromine, iodine, etc.), etc. Specific examples include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl, hexylsulfonyl, etc.

Examples of the above "optionally halogenated $C_{1-6}$ alkyl-carboxamide" include $C_{1-6}$ alkyl-carboxamide (e.g. acetamide, propanamide, butanamide, etc.) which may have 1 to 5, preferably 1 to 3, halogen atoms (e.g. fluorine, chlorine, bromine, iodine, etc.), etc. Specific examples include acetamide, trifluoroacetamide, propanamide, butanamide, etc.

Examples of the "$C_{6-14}$ aryloxy" in the above "$C_{6-14}$ aryloxy which may be substituted" include phenyloxy, 1-naphthyloxy, 2-naphthyloxy, etc.

Examples of the "$C_{7-19}$ aralkyloxy" in the above "$C_{7-19}$ aralkyloxy which may be substituted" include benzyloxy, phenethyloxy, diphenylmethyloxy, triphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy, etc.

Examples of the "$C_{6-14}$ aryl-carbamoyl" in the above "$C_{6-14}$ aryl-carbamoyl which may be substituted" include phenylcarbamoyl, 1-naphthylcarbamoyl, 2-naphthylcarbamoyl, etc.

As the "substituents" in the "$C_{6-14}$ aryloxy which may be substituted", "$C_{7-19}$ aralkyloxy which may be substituted" and "$C_{6-14}$ aryl-carbamoyl which may be substituted", those exemplified for the "substituents" in the above "$C_{7-19}$ aralkyl which may be substituted" can be used. The number of substituents is, for example, 1 to 5, preferably 1 to 3. When the number of substituents is 2 or more, each substituents can be the same or different.

Examples of the "5- to 7-membered saturated cyclic amino" in the above "5- to 7-membered saturated cyclic amino which may be substituted" include morpholino, thiomorpholino, piperazin-1-yl, piperidino, pirrolidin-1-yl, etc. The "5- to 7-membered saturated cyclic amino" can be condensed with a benzene ring.

Examples of the "substituent" in the "5- to 7-membered saturated cyclic amino which may be substituted" include oxo, optionally halogenated $C_{1-6}$ alkyl, optionally halogenated $C_{1-6}$ alkyl-carbonyl, optionally halogenated $C_{1-6}$ alkylsulfonyl, $C_{6-14}$ aryl which may be substituted, $C_{7-19}$ aralkyl which may be substituted, $C_{6-14}$ aryl-carbonyl which may be substituted, 5- to 10-membered aromatic heterocyclic group which may be substituted, $C_{1-6}$ alkoxy-$C_{1-6}$ alkyl (e.g., methoxymethyl, ethoxymethyl), $C_{1-6}$ alkoxy-carbonyl (e.g. methoxycarbonyl, ethoxycarbonyl, propoxycarbonyl, tert-butoxycarbonyl), etc. The number of substituents is, for example, 1 to 5, preferably 1 to 3. When the number of substituents is 2 or more, each substituents can be the same or different.

Here, as the "optionally halogenated $C_{1-6}$ alkyl" and "$C_{7-19}$ aralkyl which may be substituted", those exemplified as the "substituents" in the above "cyclic group which may be substituted" can be used, respectively.

As the "optionally halogenated $C_{1-6}$ alkyl-carbonyl" and "optionally halogenated $C_{1-6}$ alkylsulfonyl", those exemplified for the "substituents" in the above "$C_{7-9}$ aralkyl which may be substituted" can be used.

Examples of the "$C_{6-14}$ aryl" in the "$C_{6-14}$ aryl which may be substituted" include phenyl, 1-naphthyl, 2-naphthyl, 2-indenyl, 2-anthryl, etc. Phenyl is especially preferable.

As the "substituents" in the "$C_{6-14}$ aryl which may be substituted", those exemplified as the "substituents" in the above "C<sub>7-19</sub> aralkyl which may be substituted" can be used. The number of substituents is, for example, 1 to 5, preferably 1 to 3. When the number of substituents is 2 or more, each substituents can be the same or different.

Examples of the "$C_{6-14}$ aryl-carbonyl" in the "$C_{6-14}$ aryl-carbonyl which may be substituted" include benzoyl, 1-naphthoyl, 2-naphthoyl, etc.

As the "substituents" in the "$C_{6-14}$ aryl-carbonyl which may be substituted", those exemplified as "substituents" in the above "$C_{7-19}$ aralkyl which may be substituted" can be used. The number of substituents is, for example, 1 to 5, preferably 1 to 3. When the number of substituents is 2 or more, each substituents can be the same or different.

Examples of the "5- to 10-membered aromatic heterocyclic groups" in the "5- to 10-membered aromatic heterocyclic groups which may be substituted" include 5- to 10-membered (monocyclic or bicyclic) aromatic heterocyclic groups containing 1 or 2 kinds of, preferably 1 to 4 hetero atoms selected from nitrogen, sulfur and oxygen atom in addition to carbon atoms. Specific examples include 2- or 3-thienyl; 2-, 3- or 4-pyridyl; 2- or 3-furyl; 2-, 4- or 5-thiazolyl; 2-, 4- or 5-oxazolyl; 1-, 3- or 4-pyrazolyl; 2-pyrazinyl; 2-, 4- or 5-pyrimidinyl; 1-, 2- or 3-pyrrolyl; 1-, 2- or 4-imidazolyl; 3- or 4-pyridazinyl; 3-isothiazolyl; 3-isoxazolyl; 1,2,4-oxadiazol-5-yl; 1,2,4-oxadiazol-3-yl; 2-, 3-, 4-, 5- or 8-quinolyl; 1-, 3-, 4-, 5-, 6-, 7- or 8-isoquinolyl; 1-, 2-, 3-, 4-, 5-, 6- or 7-indolyl; 1-, 2-, 4- or 5-isoindolyl; 1-, 5- or 6-phthalazinyl; 2-, 3- or 5-quinoxalinyl; 2-, 3-, 4-, 5- or 6-benzofuranyl; 2-, 4-, 5- or 6-benzothiazolyl; 1-, 2-, 4-, 5- or 6-benzimidazolyl, etc.

Examples of the "substituents" in the "5- to 10-membered aromatic heterocyclic groups which may be substituted" include halogen atom (e.g. fluorine, chlorine, bromine and iodine, etc.), $C_{1-3}$ alkylenedioxy (e.g. methylenedioxy, ethylenedioxy, etc.), nitro, cyano, optionally halogenated $C_{1-6}$ alkyl, $C_{6-14}$ aryloxy-$C_{1-6}$ alkyl (e.g. phenoxymethyl, etc.), $C_{1-6}$ alkyl-$C_{6-14}$ aryl-$C_{2-6}$ alkenyl (e.g. methylphenylethenyl, etc.), optionally halogenated $C_{3-6}$ cycloalkyl, optionally halogenated $C_{1-6}$ alkoxy, optionally halogenated $C_{1-6}$ alkylthio, $C_{7-19}$ aralkyl which may be substituted, hydroxy, $C_{6-14}$ aryloxy which may be substituted, $C_{7-19}$ aralkyloxy which may be substituted, amino, amino-$C_{1-6}$ alkyl (e.g. aminomethyl, aminoethyl, aminopropyl, aminobutyl, etc.), mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, dipropylamino, dibutylamino, ethylmethylamino, etc.), mono-$C_{1-6}$ alkylamino-$C_{1-6}$ alkyl (e.g. methylaminomethyl, ethylaminomethyl, propylaminomethyl, isopropylaminoethyl, butylaminoethyl, etc.), di-$C_{1-6}$ alkylamino-$C_{1-6}$ alkyl (e.g. dimethylaminomethyl, diethylaminomethyl, dipropylaminomethyl, diisopropylaminoethyl, dibutylaminoethyl, etc.), 5- to 7-membered saturated cyclic amino, acyl, acylamino, acyloxy, etc. The number of substituents is, for example, 1 to 5, preferably 1 to 3. When the number of substituents is 2 or more, each substituents can be the same or different.

Here, as the "optionally halogenated $C_{1-6}$ alkyl", "optionally halogenated $C_{3-6}$ cycloalkyl", "optionally halogenated $C_{1-6}$ alkoxy", "optionally halogenated $C_{1-6}$ alkylthio", "$C_{7-19}$ aralkyl which may be substituted", "$C_{6-14}$ aryloxy which may be substituted", "$C_{7-19}$ aralkyloxy which may be substituted", those exemplified as the "substituents" in the above "cyclic group which may be substituted" can be used, respectively.

As the "5- to 7-membered saturated cyclic amino", those exemplified as "5- to 7-membered saturated cyclic amino" regarding "5- to 7-membered saturated cyclic amino which may be substituted" which is the "substituent" in the above "cyclic group which may be substituted" can be used.

Examples of the above "acyl" include acyl of the formulas: —CO—R³, —CO—OR³, —CO—NR³R⁴, —CS—NR³R⁴, —SO₂—R³ᵃ, —SO—R³ᵃ, —PO(—OR³)—OR⁴ or —PO₂—R³ᵃ wherein R³ is (i) hydrogen atom, (ii) a hydrocarbon group which may be substituted, or (iii) a heterocyclic group which may be substituted; R³ᵃ is (i) a hydrocarbon group which may be substituted, or (ii) a heterocyclic group which may be substituted; R⁴ is hydrogen atom or $C_{1-6}$ alkyl; R³ and R⁴, together with the adjacent nitrogen atom, may form a nitrogen-containing heterocyclic ring which may be substituted, and the like.

Examples of the "hydrocarbon group" in "hydrocarbon group which may be substituted" represented by R³ or R³ᵃ include straight-chain or cyclic hydrocarbon groups (e.g. alkyl, alkenyl, alkynyl, cycloalkyl, aryl, aralkyl, etc.), etc. Among these, $C_{1-19}$ straight-chain or cyclic hydrocarbon groups as shown below are preferred.

a) $C_{1-6}$ alkyl (e.g. methyl, ethyl, propyl, isopropyl, butyl, isobutyl, sec-butyl, tert-butyl, pentyl, hexyl, etc.);
b) $C_{2-6}$ alkenyl (e.g., vinyl, allyl, isopropenyl, 2-butenyl, etc.);
c) $C_{2-6}$ alkynyl (e.g. ethynyl., propargyl, 2-butynyl, etc.);
d) $C_{3-6}$ cycloalkyl (e.g. cyclopropyl, cyclobutyl, cyclopentyl, cyclohexyl, etc.); the $C_{3-6}$ cycloalkyl may be condensed with one benzene ring;
e) $C_{6-14}$ aryl (e.g. phenyl, 1-naphthyl, 2-naphthyl, 2-indenyl, 2-anthryl, etc.), preferably phenyl;
f) $C_{7-19}$ aralkyl (e.g. benzyl, phenethyl, diphenylmethyl, triphenylmethyl, 1-naphthylmethyl, 2-naphthylmethyl, 2,2-diphenylethyl, 3-phenylpropyl, 4-phenylbutyl, 5-phenylpentyl, etc.), preferably benzyl.

The "hydrocarbon groups" are preferably $C_{1-6}$ alkyl, $C_{6-14}$ aryl, $C_{7-19}$ aralkyl, etc.

Examples of the "substituent" in the "hydrocarbon groups which may be substituted" include halogen atom (e.g. fluorine, chlorine, bromine, iodine, etc.), $C_{1-3}$ alkylenedioxy (e.g. methylenedioxy, ethylenedioxy, etc.), nitro, cyano, optionally halogenated $C_{1-6}$ alkoxy, optionally halogenated $C_{1-6}$ alkylthio, hydroxy, amino, mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, dipropylamino, dibutylamino, ethylmethylamino, etc.), formyl, carboxy, carbamoyl, thiocarbamoyl, optionally halogenated $C_{1-6}$ alkyl-carbonyl, $C_{1-6}$ alkoxy-carbonyl (e.g., methoxycarbonyl, ethoxycarbonyl, propoxycarbonyl, tert-butoxycarbonyl, etc.), 5- to 10-membered aromatic heterocyclic groups which may be substituted, $C_{6-14}$ aryl-carbonyl which may be substituted, $C_{6-14}$ aryloxy-carbonyl which may be substituted, $C_{7-19}$ aralkyloxy-carbonyl which may be substituted, 5- to 6-membered heterocyclic ring-carbonyl which may be substituted, mono-$C_{1-6}$ alkyl-carbamoyl (e.g. methylcarbamoyl, ethylcarbamoyl, etc.), di-$C_{1-6}$ alkyl-carbamoyl (e.g. dimethylcarbamoyl, diethylcarbamoyl, ethylmethylcarbamoyl, etc.), $C_{6-14}$ aryl-carbamoyl which may be substituted, 5- to 6-membered heterocyclic ring-carbamoyl which may be substituted, optionally halogenated $C_{1-6}$ alkylsulfonyl, $C_{6-14}$ arylsulfonyl which may be substituted, formylamino, $C_{1-6}$ alkyl-carbonyloxy (e.g. acetoxy, propanoyloxy, etc.), $C_{6-14}$ aryl-carbonyloxy which may be substituted, $C_{1-6}$ alkoxy-carbonyloxy (e.g. methoxycarbonyloxy, ethoxycarbonyloxy, propoxycarbonyloxy, butoxycarbonyloxy, etc.), mono-$C_{1-6}$ alkyl-carbamoyloxy (e.g. methylcarbamoyloxy, ethylcarbamoyloxy, etc.), di-$C_{1-6}$ alkyl-carbamoyloxy (e.g. dimethylcarbamoyloxy, diethylcarbamoyloxy, etc.), $C_{6-14}$ aryl-carbamoyloxy which may be substituted, nicotinoyloxy, etc. The number of substituents is, for example, 1 to 5, preferably 1 to 3. When the number of substituents is 2 or more, each substituents can be the same or different.

Here, as the "optionally halogenated $C_{1-6}$ alkoxy", "optionally halogenated $C_{1-6}$ alkylthio" and "$C_{6-14}$ arylcarbamoyl which may be substituted", those exemplified as the "substituent" in the above "cyclic group which may be substituted" can be used, respectively.

As the "optionally halogenated $C_{1-6}$ alkyl-carbonyl" and "optionally halogenated $C_{1-6}$ alkylsulfonyl", those exemplified as the "substituent" in the above "$C_{7-19}$ aralkyl which may be substituted" can be used, respectively.

As the above "5- to 10-membered aromatic heterocyclic groups which may be substituted" and "$C_{6-14}$ aryl-carbonyl which may be substituted", those exemplified as the "substituent" in the above "5- to 7-membered saturated cyclic amino which may be substituted" can be used, respectively.

Examples of the "$C_{6-14}$ aryloxy-carbonyl" in the "$C_{6-14}$ aryloxy-carbonyl which may be substituted" include phenyloxycarbonyl, 1-naphthyloxycarbonyl, 2-naphthyloxycarbonyl, etc.

Examples of the "$C_{7-19}$ aralkyloxy-carbonyl" in the "$C_{7-19}$ aralkyloxy-carbonyl which may be substituted" include benzyloxycarbonyl, phenethyloxycarbonyl, diphenylmethyloxycarbonyl, triphenylmethyloxycarbonyl, 1-naphthylmethyloxycarbonyl, 2-naphthylmethyloxycarbonyl, 2,2-diphenylethyloxycarbonyl, 3-phenylpropyloxycarbonyl, 4-phenylbutyloxycarbonyl, 5-phenylpentyloxycarbonyl, etc.

Examples of the "5- to 6-membered heterocyclic ring-carbonyl" in the above "5- to 6-membered heterocyclic ring-carbonyl which may be substituted" include nicotinoyl, isonicotinoyl, 2-thenoyl, 3-thenoyl, 2-furoyl, 3-furoyl, morpholinocarbonyl, piperidinocarbonyl, pyrrolidin-1-ylcarbonyl, etc.

Examples of the "5- to 6-membered heterocyclic ring-carbamoyl", in the above "5- to 6-membered heterocyclic ring-carbamoyl which may be substituted" include morpholinocarbamoyl, piperidinocarbamoyl, 2-pyridylcarbamoyl, 3-pyridylcarbamoyl, 4-pyridylcarbamoyl, 2-thienylcarbamoyl, 3-thienylcarbamoyl, etc.

Examples of the "$C_{6-14}$ arylsulfonyl" in the above "$C_{6-14}$ arylsulfonyl which may be substituted" include phenylsulfonyl, 1-naphthylsulfonyl, 2-naphthylsulfonyl, etc.

Examples of the "$C_{6-14}$ aryl-carbonyloxy" in the above "$C_{6-14}$ aryl-carbonyloxy which may be substituted" include benzoyloxy, 1-naphthoyloxy, 2-naphthoyloxy, etc.

Examples of the "$C_{6-14}$ aryl-carbamoyloxy" in the above "$C_{6-14}$ aryl-carbamoyloxy which may be substituted" include phenylcarbamoyloxy, naphthylcarbamoyloxy, etc.

As the "substituents" in the above "$C_{6-14}$ aryloxy-carbonyl which may be substituted", "$C_{7-19}$ aralkyloxy-carbonyl which may be substituted", "5- to 6-membered heterocyclic ring-carbonyl which may be substituted", "5- to 6-membered heterocyclic ring-carbamoyl which may be substituted", "$C_{6-14}$ arylsulfonyl which may be substituted", "$C_{6-14}$ aryl-carbonyloxy which may be substituted" and "$C_{6-14}$ aryl-carbamoyloxy which may be substituted", those exemplified as the "substituents" in the above "$C_{7-19}$ aralkyl which may be substituted" can be mentioned. The number of the substituents is, for example, 1 to 5, preferably 1 to 3. When the number of substituents is 2 or more, each substituents can be the same or different.

Examples of the "heterocyclic groups" in the "heterocyclic groups which may be substituted" represented by $R^3$ or $R^{3a}$ include univalent groups formed by removing an optional one hydrogen atom from a 5- to 14-membered (monocyclic, bicyclic or tricyclic) heterocyclic ring containing 1 or 2 kinds of, 1 to 4 hetero atoms selected from nitrogen, sulfur and oxygen atom in addition to carbon atoms, preferably, (i) an aromatic heterocyclic ring, (ii) a 5- to 10-membered non-aromatic heterocyclic ring, or (iii) a 7- to 10-membered heterocyclic-bridge ring.

Here, examples of the "aromatic hetercyclic ring" include a 5- to 14-membered, preferably 5- to 10-membered, aromatic heterocyclic ring containing one or more hetero atoms (e.g. 1 to 4) selected from nitrogen, sulfur and oxygen atoms in addition to carbon atoms. Specific examples include aromatic heterocyclic rings such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, furazan, benzothiophene, benzofuran, benzimidazole, benzoxazole, benzothiazole, benzisothiazole, naphtho[2,3-b]thiophene, phenoxathiin, indole, isoindole, 1H-indazole, purine, 4H-quinolidine, isoquinoline, quinoline, phthalazine, naphthyridine, quinoxaline, quinazoline, cinnoline, carbazole, β-carboline, phenanthridine, acridine, phenazinephenothiadine, phenoxazine, phthalimide, etc.; or a ring formed by condensing these rings (preferably monocyclic rings) with one to multiple (preferably 1 or 2) aromatic rings (e.g. benzene ring, etc.), etc.

Examples of "5- to 10-membered non-aromatic heterocyclic rings" include 2- or 3-pyrroline, pyrrolidine, 2- or 3-imidazoline, 2-oxazoline, oxazolidine, 2- or 3-pyrazoline, pyrazolidine, 2-thiazoline, piperidine, piperazine, hexamethylenimine, morpholine, thiomorpholine, etc.

Examples of "7- to 10-membered heterocyclic-bridge rings" include quinuclidine, 7-azabicyclo[2.2.1]heptane, etc.

The "heterocyclic groups" are preferably 5- to 10-membered (monocyclic or bicyclic) heterocyclic groups containing 1 or 2 kinds of, preferably 1 to 4, hetero atoms selected from nitrogen, sulfur and oxygen atoms in addition to carbon atoms. Specific examples include aromatic heterocyclic groups such as 2- or 3-thienyl; 2-, 3- or 4-pyridyl; 2- or 3-furyl; 2-, 4- or 5-thiazolyl; 2-, 4- or 5-oxazolyl; 1-, 3- or 4-pyrazolyl; 2-pyrazinyl; 2-, 4- or 5-pyrimidinyl; 1-, 2- or 3-pyrrolyl; 1-, 2- or 4-imidazolyl; 3- or 4-pyridazinyl; 3-isothiazolyl; 3-isoxazolyl; 1,2,4-oxadiazol-5-yl; 1,2,4-oxadiazol-3-yl; 2-, 3-, 4-, 5- or 8-quinolyl; 1-, 3-, 4-, 5-, 6-, 7- or 8-isoquinolyl; 1-, 2-, 3-, 4-, 5-, 6- or 7-indolyl; 1-, 2-, 4- or 5-isoindolyl; 1-, 5- or 6-phthalazinyl; 2-, 3- or 5-quinoxalinyl; 2-, 3-, 4-, 5- or 6-benzofuranyl; 2-, 3-, 4-, 5- or 6-benzothienyl; 2-, 4-, 5- or 6-benzothiazolyl; 1-, 2-, 4-, 5- or 6-benzimidazolyl; etc.; and non-aromatic heterocyclic groups such as 1-, 2- or 3-pyrrolidinyl; 1-, 2-, 4- or 5-imidazolidinyl; 2- or 4-imidazolinyl; 2-, 3- or 4-pyrazolidinyl; piperidino; 2-, 3- or 4-piperidyl; 1- or 2-piperazinyl; morpholino; etc.

As the "substituents" in the "heterocyclic groups which may be substituted", those exemplified as the "substituents" in the above "5- to 10-membered aromatic heterocyclic groups which may be substituted" can be used. The number of substituents is, for example, 1 to 5, preferably 1 to 3. When the number of substituents is 2 or more, each substituents can be the same or different.

Examples of the "$C_{1-6}$ alkyl" represented by $R^4$ include methyl, ethyl, propyl, isopropyl, butyl, isobutyl, sec-butyl, tert-butyl, pentyl, hexyl, etc.

Examples of the "nitrogen-containing heterocyclic ring" in the "nitrogen-containing heterocyclic ring which may be substituted" formed by $R^3$ and $R^4$ together with the adjacent nitrogen atom include a 5- to 7-membered nitrogen-containing heterocyclic ring which contains at least one nitrogen atom in addition to carbon atoms and may contain 1 to 3 hetero atoms selected from nitrogen, sulfur and oxygen atoms. The "nitrogen-containing heterocyclic rings" are preferably piperidine, morpholine, thiomorpholine, piperazine, pyrrolidine, etc.

As the "substituents" in the "nitrogen-containing heterocyclic ring which may be substituted", those exemplified as the "substituents" in the above "5- to 10-membered aromatic heterocyclic groups which may be substituted" can be used. The number of substituents is, for example, 1 to 5, preferably 1 to 3. When the number of substituents is 2 or more, each substituents can be the same or different.

The "acyl" is preferably formyl, carboxy, carbamoyl, optionally halogenated $C_{1-6}$ alkyl-carbonyl (e.g. acetyl, etc.), $C_{1-6}$ alkoxy-carbonyl (e.g. methoxycarbonyl, ethoxycarbonyl, propoxycarbonyl, tert-butoxycarbonyl, etc.), $C_{6-14}$ aryl-carbonyl which may be substituted (e.g. benzoyl, 1-naphthoyl, 2-naphthoyl, etc.), $C_{6-14}$ aryloxy-carbonyl which may be substituted (e.g. phenyloxycarbonyl, 1-naphthyloxycarbonyl, 2-naphthyloxycarbonyl, etc.), $C_{7-19}$ aralkyloxy-carbonyl which may be substituted (e.g. benzyloxycarbonyl, phenethyloxycarbonyl, etc.), a 5- to 6-membered heterocyclic ring-carbonyl which may be substituted (e.g. nicotinoyl, etc.), mono-$C_{1-6}$ alkyl-carbamoyl (e.g. methylcarbamoyl, ethylcarbamoyl, etc.), di-$C_{1-6}$ alkyl-carbamoyl (e.g. dimethylcarbamoyl, diethylcarbamoyl, ethylmethylcarbamoyl, etc.), $C_{6-14}$ aryl-carbamoyl which may be substituted (e.g. phenylcarbamoyl, 4-methoxyphenylcarbamoyl, 3,4-dimethoxyphenylcarbamoyl, etc.), aromatic heterocyclic ring-carbamoyl which may be substituted (e.g. 2-pyridinylcarbamoyl, 2-quinolinylcarbamoyl, etc.), optionally halogenated $C_{1-6}$ alkylsulfonyl (e.g. methylsulfonyl, etc.), $C_{6-14}$ arylsulfonyl which may be substituted (e.g. phenylsulfonyl, etc.), etc.

Here, as the "optionally halogenated $C_{1-6}$ alkyl-carbonyl" and "optionally halogenated $C_{1-6}$ alkylsulfonyl", those exemplified as the "substituents" in the above "$C_{7-19}$ aralkyl which may be substituted" can be used, respectively.

As the "$C_{6-14}$ aryl-carbonyl which may be substituted", those exemplified as the "substituents" in the above "5- to 7-membered saturated cyclic amino which may be substituted" can be used.

As the "$C_{6-14}$ aryloxy-carbonyl which may be substituted", "$C_{7-19}$ aralkyloxy-carbonyl which may be substituted", "5- to 6-membered heterocyclic ring-carbonyl which may be substituted", "aromatic heterocyclic ring-carbamoyl which may be substituted" and "$C_{6-14}$ arylsulfonyl which may be substituted", those exemplified as the "substituents" in the above "hydrocarbon groups which may be substituted" can be used, respectively.

As the "$C_{6-14}$ aryl-carbamoyl which may be substituted", those exemplified as the "substituents" in the above "cyclic group which may be substituted" can be used.

Examples of the above "acylamino" include amino which is substituted by 1 or 2 of the above "acyl". Preferably, acylamino of the formulas: —$NR^5$—$COR^6$, —$NR^5$—$COOR^{6a}$, —$NR^5$—$SO_2R^{6a}$, —$NR^5$—$CONR^{6a}R^{6b}$, —PO(—$OR^5$)—$OR^6$, or —$PO_2$—$R^6$ wherein $R^5$ is hydrogen atom or $C_{1-6}$ alkyl; $R^6$ has the same meaning as the above $R^3$; $R^{6a}$ has the same meaning as the above $R^{3a}$; and $R^{6b}$ has the same meaning as $R^4$], etc., can be mentioned.

As the "$C_{1-6}$ alkyl" represented by $R^5$, the same one as the "$C_{1-6}$ alkyl" for the above $R^4$ can be mentioned.

The "acylamino" is preferably formylamino, optionally halogenated $C_{1-6}$ alkyl-carboxamide (e.g. methylcarboxamide, trifluoromethylcarboxamide, etc.), $C_{6-14}$ aryl-carboxamide which may be substituted (e.g. phenylcarboxamide, 2-methoxyphenylcarboxamide, 4-methoxyphenylcarboxamide, etc.), N—($C_{6-14}$ aryl-carbonyl which may be substituted)-N—$C_{1-6}$ alkylamino (e.g. N-4-methoxybenzoyl-N-methylamino, etc.), $C_{7-19}$ aralkyl-carboxamide which may be substituted (e.g. benzylcarboxamide, etc.), aromatic heterocyclic ring-carboxamide which may be substituted (e.g. benzothiophen-2-ylcarboxamide, etc.), optionally halogenated $C_{1-6}$ alkoxy-carboxamide (e.g. methoxycarboxamide, ethoxycarboxamide, propoxycarboxamide, butoxycarboxamide, etc.), $C_{6-14}$ arylaminocarbonylamino which may be substituted (e.g. phenylaminocarbonylamino, etc.), optionally halogenated $C_{1-6}$ alkylsulfonylamino (e.g. methylsulfonylamino, trifluoromethylsulfonylamino, ethylsulfonylamino, etc.), $C_{6-14}$ arylsulfonylamino which may be substituted (e.g. 4-methoxyphenylsulfonylamino, etc.), etc.

Here, as the "substituents" in the "$C_{6-14}$ aryl-carboxamide which may be substituted", "N—($C_{6-14}$ aryl-carbonyl which may be substituted)-N—$C_{1-6}$ arylkylamino", "$C_{7-19}$ aralkyl-carboxamide which may be substituted", "aromatic heterocyclic ring-carboxamide which may be substituted", "$C_{6-14}$ arylaminocarbonylamino which may be substituted" and "$C_{6-14}$ arylsulfonylamino which may be substituted", those exemplified as the "substituents" in the above "$C_{7-19}$ aralkyl which may be subsituted" can be mentioned. The number of substituents is, for example, 1 to 5, preferably 1 to 3. When the number of substituents is 2 or more, each substituents can be the same or different.

Examples of the above "acyloxy" include oxy substituted by one of the above "acyl". Preferably, acyloxy of the formulas: —O—$COR^7$, —O—$COOR^7$, —O—$CONHR^7$, —PO(OH)—$OR^7$ or —$PO_2$—$R^7$ wherein $R^7$ has the same meaning as the above $R^3$, etc., can be mentioned.

The "acyloxy" is preferably optionally halogenated $C_{1-6}$ alkyl-carbonyloxy (e.g. acetoxy, propanoyloxy, etc.), $C_{6-14}$ aryl-carbonyloxy which may be substituted (e.g. benzoyloxy, 4-methoxybenzoyloxy, etc.), optionally halogenated $C_{1-6}$ alkoxy-carbonyloxy (e.g. methoxycarbonyloxy, trifluoromethoxycarbonyloxy, ethoxycarbonyloxy, propoxycarbonyloxy, butoxycarbonyloxy, etc.), mono-$C_{1-6}$ alkyl-carbamoyloxy (e.g. methylcarbamoyloxy, ethylcarbamoyloxy, etc.), di-$C_{1-6}$ alkyl-carbamoyloxy (e.g. dimethylcarbamoyloxy, diethylcarbamoyloxy, etc.), $C_{6-14}$ aryl-carbamoyloxy which may be substituted (e.g. phenylcarbamoyloxy, naphthylcarbamoyloxy, etc.), nicotinoyloxy, etc.

As the "substituents" in "$C_{6-14}$ aryl-carbonyloxy which may be substituted" and "$C_{6-14}$ aryl-carbamoyloxy which may be substituted", those exemplified as the "substituents" in the above "$C_{7-19}$ aralkyl which may be substituted" can be mentioned. The number of substituents is, for example, 1 to 5, preferably 1 to 3. When the number of substituents is 2 or more, each substituents can be the same or different.

Examples of the "5- to 7-membered non-aromatic heterocyclic groups which may be substituted", which is the "substituents" in "cyclic group which may be substituted" represented by $Ar^1$, include 4,5-dihydro-1,3-oxazol-2-yl, 4,5-dihydro-1,3-thiazol-2-yl, 4,5-dihydro-1H-2-imidazolyl, etc. As the "substituents" in the "5- to 7-membered non-aromatic heterocyclic groups which may be substituted", those exemplified as the "substituents" in the above "5- to 7-membered saturated cyclic amino which may be substituted" can be used.

As the "acyl", "acyloxy" and "acylamino", which are the "substituents" in the "cyclic group which may be substituted" represented by $Ar^1$, those exemplified as the "substituents" in the above "5- to 10-membered aromatic heterocyclic groups which may be substituted" can be used.

The "substituents" in the "cyclic group which may be substituted" for $Ar^1$ are preferably halogen atom (preferably fluorine, chlorine and bromine, etc.); nitro; $C_{1-3}$ alkylenedioxy (preferably methylenedioxy, etc.); optionally halogenated $C_{1-6}$ alkyl (preferably, methyl, ethyl, propyl, trifluoromethyl, etc.); hydroxy-$C_{1-6}$ alkyl (preferably hydroxymethyl, etc.); optionally halogenated $C_{3-6}$ cycloalkyl (preferably cyclohexyl, etc.); optionally halogenated $C_{1-6}$ alkoxy (preferably methoxy, ethoxy, etc.); optionally halogenated $C_{1-6}$ alkylthio (preferably methylthio, etc.); hydroxy; $C_{7-19}$ aralkyloxy which may be substituted (preferably benzyloxy, 4-methoxybenzyloxy, 3-methoxybenzyloxy, 4-fluorobenzyloxy, 4-methylthiobenzyloxy, 4-ethylbenzyloxy, etc.); $C_{6-14}$ aryloxy which may be substituted (preferably phenyloxy, etc.); amino; mono-$C_{1-6}$ alkylamino (preferably methylamino, etc.); di-$C_{1-6}$ alkylamino (preferably dimethylamino, etc.); 5- to 7-membered saturated cyclic amino which may be substituted and may be condensed with a benzene ring (preferably 1,3-dioxo-1,3-dihydro-2H-isoindol-2-yl, methylpiperidino, oxopiperidino, etc.); 5- to 7-membered non-aromatic heterocyclic groups which may be substituted (preferably 4,5-dihydro-1,3-oxazol-2-yl, etc.); formyl; carboxy; $C_{6-14}$ aryl-carbonyl which may be substituted (preferably benzoyl, etc.); $C_{6-14}$ aryl-carbamoyl which may be substituted (preferably, phenylcarbamoyl, 4-methoxyphenylcarbamoyl, 3,4-dimethoxyphenylcarbamoyl, etc.); aromatic heterocyclic ring-carbamoyl which may be substituted (preferably 2-pyridinylcarbamoyl, 2-quinolinylcarbamoyl, etc.); $C_{1-6}$ alkoxy-carbonyl (preferably methoxycarbonyl, ethoxycarbonyl, etc.); optionally halogenated $C_{1-6}$ alkyl-carboxamide (preferably methylcarboxamide, trifluoromethylcarboxamide, etc.); $C_{6-14}$ aryl-carboxamide which may be substituted (preferably phenylcarboxamide, 2-methoxyphenylcarboxamide, 4-methoxyphenylcarboxamide, etc.); $C_{7-19}$ aralkyl-carboxamide which may be substituted (preferably benzylcarboxamide, etc.); aromatic heterocyclic ring-carboxamide which may be substituted (preferably benzothiophen-2-ylcarboxamide, etc.); N—($C_{6-14}$ aryl-carbonyl which may be substituted)-N—$C_{1-6}$ alkylamino (preferably N-4-methoxybenzoyl-N-methylamino, etc.); $C_{6-14}$ arylamino-carbonylamino which may be substituted (preferably phenylaminocarbonylamino, etc.); $C_{6-14}$ arylsulfonylamino which may be substituted (preferably 4-methoxyphenylsulfonylamino, etc.); $C_{6-14}$ arylcarbonyloxy which may be substituted (preferably 4-methoxybenzoyloxy, etc.); oxo; etc.

When the "cyclic group" in the "cyclic group which may be substituted" represented by $Ar^1$ is a non-aromatic cyclic hydrocarbon group or a non-aromatic heterocyclic group, $C_{6-14}$ aryl which may be substituted (preferably phenyl, 4-fluorophenyl, chlorophenyl, methylphenyl, methoxyphenyl), etc., can be used as a preferred substituent.

$Ar^1$ is preferably phenyl, biphenylyl (preferably 4-biphenylyl), phenyl-pyridyl (preferably 6-phenyl-3-pyridyl, 5-phenyl-2-pyridyl), phenyl-furyl (preferably 5-phenyl-2-furyl), phenyl-isoxazolyl (preferably 3-phenyl-isoxazol-5-yl), diphenyl-oxazolyl (preferably 2,4-diphenyl-1,3-oxazol-5-yl), pyridyl-phenyl (preferably 4-(4-pyridyl) phenyl), phenyl-pyrimidinyl (preferably 2-phenyl-5-pyrimidinyl), benzofuranyl-phenyl (preferably 4-(2-benzofuranyl)phenyl), or furyl-phenyl (preferably 4-(2-furyl)phenyl); each of which may have 1 to 3 (preferably 1 or 2) substituents selected from the group consisting of halogen atom (preferably fluorine, chlorine, bromine, etc.); nitro; $C_{1-3}$ alkylenedioxy (preferably methylenedioxy, etc.); optionally halogenated $C_{1-6}$ alkyl (preferably methyl, ethyl, propyl, trifluoromethyl, etc.); hydroxy-$C_{1-6}$ alkyl (preferably hydroxymethyl, etc.); optionally halogenated $C_{3-6}$ cycloalkyl (preferably cyclohexyl, etc.); optionally halogenated $C_{1-6}$ alkoxy (preferably methoxy, ethoxy, etc.); optionally halogenated $C_{1-6}$ alkythio (preferably methylthio, etc.); hydroxy; $C_{7-19}$ aralkyloxy which may be substituted (preferably benzyloxy, 4-methoxybenzyloxy, 3-methoxybenzyloxy, 4-fluorobenzyloxy, 4-methylthiobenzyloxy, 4-ethylbenzyloxy, etc.); $C_{6-14}$ aryloxy which may be substituted (preferably phenyloxy, etc.); amino; mono-$C_{1-6}$ alkylamino (preferably methylamino, etc.); di-$C_{1-6}$ alkylamino (preferably dimethylamino, etc.); 5- to 7-membered saturated cyclic amino which may be substituted and may be condensed with a benzene ring (preferably 1,3-dioxo-1,3-dihydro-2H-isoindol-2-yl, methylpiperidino, oxopiperidino, etc.); 5- to 7-membered non-aromatic heterocyclic groups which may be substituted (preferably 4,5-dihydro-1,3-oxazol-2-yl, etc.); formyl; carboxy; $C_{6-14}$ aryl-carbonyl which may be substituted (preferably benzoyl, etc.); $C_{6-14}$ aryl-carbamoyl which may be substituted (preferably phenylcarbamoyl, 4-methoxyphenylcarbamoyl, 3,4-dimethoxyphenylcarbamoyl, etc.); aromatic heterocyclic ring-carbamoyl which may be substituted (e.g. 2-piridinylcarbamoyl, 2-quinolinylcarbamoyl, etc.); $C_{1-6}$ alkoxy-carbonyl (preferably methoxycarbonyl, ethoxycarbonyl, etc.); optionally halogenated $C_{1-6}$ alkyl-carboxamide (preferably, methylcarboxamide, trifluoromethylcarboxamide, etc.); $C_{6-14}$ aryl-carboxamide which may be substituted (preferably phenylcarboxamide, 2-methoxyphenylcarboxamide, 4-methoxyphenylcarboxamide, etc.); $C_{7-19}$ aralkyl-carboxamide which may be substituted (preferably benzylcarboxamide, etc.); aromatic heterocyclic ring-carboxamide which may be substituted (preferably benzothiophen-2-ylcarboxamide, etc.); N—($C_{6-14}$ aryl-carbonyl which may be substituted)-N—$C_{1-6}$ alkylamino (preferably N-4-methoxybenzoyl-N-methylamino, etc.); $C_{6-14}$ arylamino-carbonylamino which may be substituted (preferably phenylaminocarbonylamino, etc.); $C_{6-14}$ arylsulfonylamino which may be substituted (preferably 4-methoxyphenylsulfonylamino, etc.); $C_{6-14}$ arylcarbonyloxy which may be substituted (preferably 4-methoxybenzoyloxy, etc.); oxo; etc.

Further, preferred examples of $Ar^1$ include piperidinyl (piperidino), piperazinyl, pyrrolidinyl, 1,3-dioxanyl, etc.; each of which may have 1 or 2 substituents selected from the group consisting of oxo and $C_{6-14}$ aryl which may be substituted (preferably phenyl, fluorophenyl, chlorophenyl, methylphenyl, methoxyphenyl).

$Ar^1$ is more preferably, (1) phenyl, biphenylyl (preferably 4-biphenylyl) or phenyl-pyridyl (preferably 6-phenyl-3-pyridyl, 5-phenyl-2-pyridyl); each of which may have 1 to 3 substituents selected from the group consisting of halogen atom (preferably fluorine, chlorine, bromine, etc.); optionally halogenated $C_{1-6}$ alkyl (preferably methyl, ethyl, propyl, trifluoromethyl, etc.); and optionally halogenated $C_{1-6}$ alkoxy (preferably methoxy, ethoxy, etc.); or (2) piperidinyl (piperidino) which may have 1 or 2 substituents selected from $C_{6-14}$ aryl (preferably phenyl, fluorophenyl, chlorophenyl, methylphenyl, methoxyphenyl) which may be substituted [preferably by 1 to 3 substituents selected from the group consisting of halogen atom (preferably fluorine, chlorine, bromine, etc.), optionally halogenated $C_{1-6}$ alkyl (preferably methyl, etc.) and optionally halogenated $C_{1-6}$ alkoxy (preferably methoxy, etc.)].

The "spacer having a main chain of 1 to 6 atoms" represented by X and Y means a space in which 1 to 6 atoms are linked. Here, the "number of atoms in the main chain" is counted so that the number of atoms in the main chain is minimum. For example, the number of atoms of 1,2-cyclopentylene is counted as 2, and the number of atoms of 1,3-cyclopentylene is counted as 3.

Examples of the "spacer having a main chain of 1 to 6 atoms" include a bivalent group consisting of 1 to 3 species selected from —O—, —S—, —CO—, —SO—, —SO$_2$—, —NR$^8$— (R$^8$ is hydrogen atom, optionally halogenated $C_{1-6}$ alkyl, optionally halogenated $C_{1-6}$ alkyl-carbonyl, optionally halogenated $C_{1-6}$ alkylsulfonyl), optionally halogenated bivalent $C_{1-6}$ non-cyclic hydrocarbon groups, and bivalent $C_{5-8}$ monocyclic non-aromatic hydrocarbon groups, and the like.

Here, as the "optionally halogenated $C_{1-6}$ alkyl", those exemplified as the "substituents" in the above "cyclic group which may be substituted" can be used.

As the "optionally halogenated $C_{1-6}$ alkyl-carbonyl" and "optionally halogenated $C_{1-6}$ alkylsulfonyl", those exemplified as the "substituents" in the above "$C_{7-19}$ aralkyl which may be substituted" can be used, respectively.

Examples of the "bivalent $C_{1-6}$ non-cyclic hydrocarbon groups" in the "optionally halogenated bivalent $C_{1-6}$ non-cyclic hydrocarbon groups" include (1) $C_{1-6}$ alkylene (e.g. —CH$_2$—, —(CH$_2$)$_2$—, —(CH$_2$)$_3$—, —(CH$_2$)$_4$—, —(CH$_2$)$_5$—, —(CH$_2$)$_6$—, —CH(CH$_3$)—, —C(CH$_3$)$_2$—, —CH(CF$_3$)—, —(CH(CH$_3$))$_2$—, —(CF$_2$)$_2$—, —(CH$_2$)$_2$C(CH$_3$)$_2$—, —(CH$_2$)$_3$C(CH$_3$)$_2$—, etc.);

(2) $C_{2-6}$ alkenylene (e.g. —CH=CH—, —CH$_2$—CH=CH—, —CH$_2$—CF=CH—, —C(CH$_3$)$_2$—CH=CH—, —CH$_2$—CH=CH—CH$_2$—, —CH$_2$—CH$_2$—CH=CH—CH=CH—CH=CH—, —CH=CH—CH$_2$—CH$_2$—CH$_2$—, etc.);

(3) $C_{2-6}$ alkynylene (e.g. —C≡C—, —CH$_2$—C≡C—, —CH$_2$—C≡C—CH$_2$—CH$_2$—, etc.), etc., each of which may have 1 to 5, preferably 1 to 3, halogen atoms (e.g. fluorine, chlorine, bromine, iodine, etc.).

As the "bivalent $C_{5-8}$ monocyclic non-aromatic hydrocarbon groups", for example, bivalent groups formed by removing optional two hydrogen atoms from $C_{5-8}$ cycloalkane or $C_{5-8}$ cycloalkene, can be mentioned. Specific examples include 1,2-cyclopentylene; 1,3-cyclopentylene; 1,2-cyclohexylene; 1,3-cyclohexylene; 1,4-cyclohexylene; 1,2-cycloheptylene; 1,3-cycloheptylene; 1,4-cycloheptylene; 3-cyclohxen-1,4-ylene; 3-cyclohexen-1,2-ylene; 2,5-cyclohexadien-1,4-ylene, etc. Especially, $C_{5-8}$ cycloalkylene is preferable.

The "spacer having a main chain of 1 to 6 atoms" represented by X and Y is preferably a bivalent group consisting of 1 to 3 species selected from —O—, —S—, —CO—, —SO—, —SO$_2$—, —NR$^8$— (R$^8$ is as defined above) and optionally halogenated bivalent $C_{1-6}$ non-cyclic hydrocarbon groups.

Preferred examples of the "spacer having a main chain of 1 to 6 atoms" include (1) $C_{1-6}$ alkylene (e.g. —CH$_2$—, —(CH$_2$)$_2$—, —(CH$_2$)$_3$—, —(CH$_2$)$_4$—, —(CH$_2$)$_5$—, —(CH$_2$)$_6$—, —CHCH$_3$—, —C(CH$_3$)$_2$—, —(CH(CH$_3$))$_2$—, —(CF$_2$)$_2$—, —(CH$_2$)$_2$C(CH$_3$)$_2$—, —(CH$_2$)$_3$C(CH$_3$)$_2$—, etc.);

(2) $C_{2-6}$ alkenylene (e.g. —CH=CH—, —CH$_2$—CH=CH—, —C(CH$_3$)$_2$—CH=CH—, —CH$_2$—CH=CH—CH$_2$—, —CH$_2$—CH$_2$—CH=CH—, —CH=CH—CH=CH—, —CH=CH—CH$_2$—CH$_2$—CH$_2$—, etc.);

(3) $C_{2-6}$ alkynylene (e.g. —C≡C—, —CH$_2$—C≡C—, —CH$_2$—C≡C—CH$_2$—CH$_2$—, etc.);

(4) —(CH$_2$)$_{w1}$O(CH$_2$)$_{w2}$—, —(CH$_2$)$_{w1}$S(CH$_2$)$_{w2}$—, —(CH$_2$)$_{w1}$CO(CH$_2$)$_{w2}$—, —(CH$_2$)$_{w1}$SO(CH$_2$)$_{w2}$—, —(CH$_2$)$_{w1}$SO$_2$(CH$_2$)$_{w2}$—, —(CH$_2$)$_{w1}$NR$^8$(CH$_2$)$_{w2}$—;

(5) —(CH$_2$)$_{w3}$CONR$^8$(CH$_2$)$_{w4}$—, —(CH$_2$)$_{w3}$NR$^8$CO(CH$_2$)$_{w4}$—, —(CH$_2$)$_{w3}$SO$_2$NR$^8$(CH$_2$)$_{w4}$—, —(CH$_2$)$_{w3}$NR$^8$SO$_2$(CH$_2$)$_{w4}$—, —(CH$_2$)$_{w3}$COO(CH$_2$)$_{w4}$—, —(CH$_2$)$_{w3}$OCO(CH$_2$)$_{w4}$—;

(6) —(CH$_2$)$_{w5}$NR$^8$CONR$^8$(CH$_2$)$_{w6}$—;

wherein R$^8$ is as defined above; R$^{8b}$ has the same meaning as R$^8$; w1 and w2 is an integer of 0 to 5, and w1+w2 is 0 to 5; w3 and w4 is an integer of 0 to 4, and w3+w4 is 0 to 4; w5 and w6 is an integer of 0 to 3, and w5+w6 is 0 to 3, etc.

More preferably, the "spacer having a main chain of 1 to 6 atoms" represented by X is —(CH$_2$)$_{w1}$O(CH$_2$)$_{w2}$—, —CONR—, —NR$^8$CO— (wherein the symbols are as defined above), —OCO—, —COO—, etc. Among these, —CONH—, —NHCO—, —COO—, etc. are preferred. In particular, —CONH— or —COO— are preferred.

More preferably, the "spacer having a main chain of 1 to 6 atoms" represented by Y is $C_{1-3}$ alkylene (e.g., —CH$_2$—, —(CH$_2$)$_2$—, —(CH$_2$)$_3$—, etc.), —(CH$_2$)$_{w3}$CONH(CH$_2$)$_{w4}$—, —(CH$_2$)$_{w3}$COO(CH$_2$)$_{w4}$— (wherein the symbols are as defined above), etc. In particular, $C_{1-3}$ alkylene (e.g. —CH$_2$—, —(CH$_2$)$_2$—, —(CH$_2$)$_3$—, etc.), etc., are preferred.

As the "condensed polycyclic aromatic rings" in "condensed polycyclic aromatic rings which may be substituted" represented by Ar, those exemplified as the "cyclic group" in the "cyclic group which may be substituted" represented by the above Ar$^1$ can be used.

The "condensed polycyclic aromatic rings" are preferably $C_{9-14}$ condensed polycyclic (bicyclic or tricyclic) aromatic hydrocarbons, or 10-membered condensed polycyclic aromatic heterocyclic rings.

More preferably, the "condensed polycyclic aromatic rings" are naphthalene, isoquinoline, quinoline, quinoxaline, phtharazine, naphthyridine, quinazoline, cinnoline, indole, etc. In particular, naphthlene, quinoline, etc. are preferred.

As the "substituents" in the "condensed polycyclic aromatic rings which may be substituted" represented by Ar, those exemplified as the "substituents" in the "cyclic group which may be substituted" represented by the above Ar$^1$ can be used.

The number of substituents is, for example, 1 to 5, preferably 1 to 3. When the number of substituents is 2 or more, each substituents can be the same or different.

Ar is especially preferably quinoline or naphthlene.

As the "hydrocarbon groups which may be substituted" represented by R$^1$ and R$^2$, those exemplified as the above R$^3$ can be used.

The "hydrocarbon groups which may be substituted" are preferably "$C_{1-6}$ alkyl which may be substituted" or phenyl.

Here, examples of the "$C_{1-6}$ alkyl", in the "$C_{1-6}$ alkyl which may be substituted" include methyl, ethyl, propyl, isopropyl, butyl, isobutyl, sec-butyl, tert-butyl, pentyl, hexyl, etc. Especially, methyl, ethyl, propyl, etc. are preferred.

Examples of the "substituents" in the "$C_{1-6}$ alkyl which may be substituted" include halogen atom (e.g. fluorine, chlorine, bromine, iodine, etc.), $C_{1-3}$ alkylenedioxy (e.g. methylenedioxy, ethylenedioxy etc.), nitro, cyano, optionally halogenated $C_{3-6}$ cycloalkyl, optionally halogenated $C_{1-6}$ alkoxy, optionally halogenated $C_{1-6}$ alkylthio, hydroxy, amino, mono-$C_{1-6}$ alkylamino (e.g. methylamino, ethylamino, propylamino, isopropylamino, butylamino, etc.), di-$C_{1-6}$ alkylamino (e.g. dimethylamino, diethylamino, dipropylamino, dibutylamino, ethylmethylamino, etc.), formyl, carboxy, carbamoyl, thiocarbamoyl, optionally halogenated $C_{1-6}$ alkyl-carbonyl, $C_{1-6}$ alkoxy-carbonyl (e.g. methoxycarbonyl, ethoxycarbonyl, propoxycarbonyl, tert-butoxycarbonyl, etc.), mono-$C_{1-6}$ alkyl-carbamoyl (e.g. methylcarbamoyl, ethylcarbamoyl, etc.), di-$C_{1-6}$ alkyl-carbamoyl (e.g. dimethylcarbamoyl, diethylcarbamoyl, ethylmethylcarbamoyl etc.), optionally halogenated $C_{1-6}$ alkylsulfonyl, formylamino, optionally halogenated $C_{1-6}$ alkyl-carboxamide, $C_{1-6}$ alkoxy-carboxamide (e.g. methoxycarboxamide, ethoxycarboxamide, propoxycarboxamide, butoxycarboxamide, etc.), $C_{1-6}$ alkylsulfonylamino (e.g. methylsulfonylamino, ethylsulfonylamino, etc.), $C_{1-6}$ alkyl-carbonyloxy (e.g. acetoxy, propanoyloxy, etc.), $C_{1-6}$-alkoxy-carbonyloxy (e.g. methoxycarbonyloxy, ethoxycarbonyloxy, propoxycarbonyloxy, butoxycarbonyloxy, etc.), mono-$C_{1-6}$ alkyl-carbamoyloxy (e.g. methylcarbamoyloxy, ethylcarbamoyloxy, etc.), di-$C_{1-6}$ alkyl-carbamoyloxy (e.g. dimethylcarbamoyloxy, diethylcarbamoyloxy, etc.), aromatic groups which may be substituted, etc. The number of substituents is, for example, 1 to 5, preferably 1 to 3. When the number of substituents is 2 or more, each substituents can be the same or different.

Here, as the "optionally halogenated $C_{3-6}$ cycloalkyl", "optionally halogenated $C_{1-6}$ alkoxy" and "optionally halogenated $C_{1-6}$ alkylthio", those exemplified as the "substituents" in the above "cyclic group which may be substituted" can be used.

As the "optionally halogenated $C_{1-6}$ alkyl-carbonyl", "optionally halogenated $C_{1-6}$ alkylsulfonyl" and "optionally halogenated $C_{1-6}$ alkyl-carboxamide", those exemplified as the "substituents" in the above "$C_{7-19}$ aralkyl which may be substituted" can be used.

As the "substituents" and "aromatic groups" in the "aromatic groups which may be substituted", those exemplified as the "substituents" and "aromatic groups" in the "cyclic group which may be substituted" represented by the above $Ar^1$ can be used. The number of substituents is, for example, 1 to 5, preferably 1 to 3. When the number of substituents is 2 or more, each substituents can be the same or different.

More preferably, "hydrocarbon group which may be substituted" represented by $R^1$ and $R^2$ is $C_{1-6}$ alkyl. In particular, methyl, ethyl, isopropyl, etc., are preferred.

Examples of the "nitrogen-containing heterocyclic rings" in the "nitrogen-containing heterocyclic rings which may be substituted" formed by $R^1$ and $R^2$ together with the adjacent nitrogen atom include 3- to 10-membered (preferably 3- to 8-membered) nitrogen-containing heterocyclic rings which contain at least one nitrogen atom in addition to carbon atoms, and which may further contain 1 to 3 hetero atoms selected from nitrogen, sulfur and oxygen atoms. Specific examples include aziridine, azetidine, morpholine, thiomorpholine, piperidine, piperazine, pyrrolidine, hexamethyleneimine, heptamethyleneimine, hexahydropyrimidine, 1,4-diazepan, thiazolidine, imidazolidine, heptahydroindole, decahydroquinoline, decahydroisoquinoline, and their unsaturated cyclic amines (e.g. 1,2,5,6-tetrahydropyridine, 1H-imidazole, 4,5-dihydro-1H-imidazole, 2,3-dihydroindole, 1,2,3,4-tetrahydroquinoline, 1,2,3,4-tetrahydroisoquinoline, etc.), etc. can be mentioned. Especially, morpholine, piperidine, piperazine, pyrrolidine, 1,3-thiazolidine, 1H-imidazole, 4,5-dihydro-1H-imidazole, 2,3-dihydroindole, 1,2,3,4-tetrahydroquinoline, 1,2,3,4-tetrahydroisoquinoline, etc., are preferred. In particular, morpholine, piperidine, piperazine, pyrrolidine, etc. are preferred.

As the "substituents" in the "nitrogen-containing heterocyclic rings which may be substituted", for example, those exemplified as the "substituents" in the above "5- to 7-membered saturated cyclic amino which may be substituted" can be used. The number of substituents is, for example, 1 to 5, preferably 1 to 3. When the number of substituents is 2 or more, each substituents can be the same or different.

The substituents are preferably optionally halogenated $C_{1-6}$ alkyl (preferably methyl); 5- to 10-membered aromatic heterocyclic groups (preferably pyridyl); $C_{6-14}$ aryl which may be substituted (preferably with $C_{1-6}$ alkyl)(preferably phenyl, methylphenyl); $C_{7-19}$ aralkyl (preferably benzyl); $C_{6-14}$ aryl-carbonyl which may be substituted (preferably with halogen atom) (preferably fluorobenzoyl, chlorobenzoyl); $C_{1-6}$ alkoxy-$C_{1-6}$ alkyl (preferably methoxymethyl); $C_{1-6}$ alkoxy-carbonyl (preferably tert-butoxycarbonyl), etc.

Preferably, $R^1$ and $R^2$, together with the adjacent nitrogen atom, form a nitrogen-containing heterocyclic ring which may be substituted.

In particular, $R^1$ and $R^2$, together with the adjacent nitrogen atom, form piperidino, pyrrolidin-1-yl, etc.

As the "nitrogen-containing heterocyclic rings which may be substituted" formed by $R^2$ together with the adjacent nitrogen atom and Y, those exemplified as the "nitrogen-containing heterocyclic rings which may be substituted" formed by the above $R^1$ and $R^2$ together with the adjacent nitrogen atom, can be mentioned.

As the "nitrogen-containing condensed heterocyclic rings" in the "nitrogen-containing condensed heterocyclic rings which may be substituted" formed by $R^2$ together with the adjacent nitrogen atom, Y and Ar, for example, 11- to 20-membered, preferably 11- or 18-membered condensed polycyclic (preferably tricyclic or tetracyclic) heterocyclic rings which contain at least one nitrogen atom and further contain one or more (for example, 1 to 4) hetero atoms selected from nitrogen, sulfur and oxygen atoms, in addition to carbon atoms, etc., can be mentioned. Specific examples include tetrahydrobenzo[g]isoquinoline, tetrahydrobenzo[b][1,6]naphthyridine, tetrahydrobenzo[b][1,7]naphthyridine, tetrahydropyrido[4,3-g]quinoline, tetrahydropyrido[3,4-g]quinoline, tetrahydropyrido[3,4-g]isoquinoline, tetrahydropyrido[3,4-g]quinoxaline, tetrahydropyrido[3,4-b]quinoxaline, tetrahydropyrido[4,3-b][1,5]naphthyridine, tetrahydropyrido[3,4-b][1,5]naphthyridine, tetrahydropyrido[3,4-g]quinazoline, tetrahydropyrido[3,4-g]phthalazine, tetrahydronaphtho[2,3-d]azepine, tetrahydroazepino[4,5-g]isoquinoline, tetrahydroazepino[4,5-b]quinoline, tetrahydroazepino[4,5-b]quinoxaline, tetrahydroazepino[4,5-g]quinoxaline, tetrahydroazepino[4,5-b][1,5]naphthyridine, tetrahydroazepino[4,5-g]phthalazine, hexahydronaphtho[2,3-d]azocine, hexhydroazocino[4,5-b]quinoline, tetrahydro-β-carboline, tetrahydropyrido[4,3-b]indole, tetrahydropyrrolo[3,2-g]isoquinoline, tetrahydropyrrolo[2,3-g]isoquinoline, tetrahydropyrido[3,4-b]acridine, tetrahydropyrido[3,4-b]phenazine, etc. In particular, tetrahydrobenzo[b][1,6]naphthyridine, etc. are preferred.

As the "substituents" in the "nitrogen-containing condensed heterocyclic rings which may be substituted", for example, those exemplified as the "substituents" in the above "5- to 7-membered saturated cyclic amino which may be substituted" can be used. The number of substituents is, for example, 1 to 5, preferably 1 to 3. When the number of substituents is 2 or more, each substituents can be the same or different.

The substituent is preferably optionally halogenated $C_{1-6}$ alkyl (preferably methyl).

Among the compounds represented by the formula (I), the compounds wherein X is $X^1$ [wherein $X^1$ is $CONR^8$, $NR^8CO$ (wherein $R^8$ is hydrogen atom, optionally halogenated $C_{1-6}$ alkyl, optionally halogenated $C_{1-6}$ alkyl-carbonyl or optionally halogenated $C_{1-6}$ alkylsulfonyl), OCO or COO] (provided that, when $X^1$ is CONR (wherein R is hydrogen atom or $C_{1-6}$ alkyl), Ar is not indole or benzoxazole which may have one or two halogen, hydroxy, $C_{1-6}$ alkyl or $C_{1-6}$ alkoxy; when $X^1$ is CONH, Ar is not 4-methyl-2-quinolone which may have a substituent selected from the group consisting of alkyl, alkoxy and halogen, or is not 2-benzoylamino-quinazoline; and, when $X^1$ is COO, $Ar^1$ is not an aromatic group which may be substituted), that is, the compounds represented by the formula (I') are novel compounds.

Among the compounds represented by the formula (I'), the compounds wherein $X^1$ is $CONR^8$ or $NR^8$ (wherein $R^8$ is hydrogen atom, optionally halogenated $C_{1-6}$ alkyl, optionally halogenated $C_{1-6}$ alkyl-carbonyl or optionally halogenated $C_{1-6}$ alkylsulfonyl) and Ar is quinoline or naphthalene, and the like are preferred.

Suitable examples of the compounds represented by the formula (I') include the following compounds:

4'-chloro-N-[6-[(N,N-dimethylamino)methyl]-2-naphthyl][1,1'-biphenyl]-4-carboxamide;
4'-chloro-N-[6-(1-pyrrolidinylmethyl)-2-naphthyl][1,1'-biphenyl]-4-carboxamide;
4'-chloro-N-[6-(1-piperidinylmethyl)-2-naphthyl][1,1'-biphenyl]-4-carboxamide;
N-(4-bromophenyl)-6-[(dimethylamino)methyl]-2-naphthamide;
N-(4'-chloro[1,1'-biphenyl]-4-yl)-6-[(N,N-dimethylamino)methyl]-2-naphthamide;
4'-chloro-N-[2-[(N,N-dimethylamino)methyl]-6-quinolinyl]-[1,1'-biphenyl]-4-carboxamide;
4'-fluoro-N-[2-(1-pyrrolidinylmethyl)-6-quinolinyl][1,1'-biphenyl]-4-carboxamide;
4'-chloro-N-[2-(1-pyrrolidinylmethyl)-6-quinolinyl][1,1'-biphenyl]-4-carboxamide;
4'-fluoro-N-[2-(1-piperidinylmethyl)-6-quinolinyl][1,1'-biphenyl]-4-carboxamide;
4'-chloro-N-[2-(1-piperidinylmethyl)-6-quinolinyl][1,1'-biphenyl]-4-carboxamide;
6-(4-fluorophenyl)-N-[6-(1-pyrrolidinylmethyl)-2-naphthyl]nicotinamide;
6-(4-chlorophenyl)-N-[6-(1-pyrrolidinylmethyl)-2-naphthyl]nicotinamide;
6-(4-methylphenyl)-N-[6-(1-pyrrolidinylmethyl)-2-naphthyl]nicotinamide;
6-(4-fluorophenyl)-N-[6-[(dimethylamino)methyl]-2-naphthyl]nicotinamide;
6-(4-chlorophenyl)-N-[6-[(dimethylamino)methyl]-2-naphthyl]nicotinamide;
6-(4-methylphenyl)-N-[6-[(dimethylamino)methyl]-2-naphthyl]nicotinamide;
4-(4-fluorophenyl)-N-[6-(1-pyrrolidinylmethyl)-2-naphthyl]-1-piperidinecarboxamide;
4-(4-methoxyphenyl)-N-[6-(1-pyrrolidinylmethyl)-2-naphthyl]-1-piperidinecarboxamide;
4-(4-methylphenyl)-N-[6-(1-pyrrolidinylmethyl)-2-naphthyl]-1-piperidinecarboxamide;
4-(4-methylphenyl)-N-[6-[(dimethylamino)methyl]-2-naphthyl]-1-piperidinecarboxamide;
6-(4-fluorophenyl)-N-[2-(1-pyrrolidinylmethyl)-6-quinolinyl]nicotinamide;
6-(4-chlorophenyl)-N-[2-(1-pyrrolidinylmethyl)-6-quinolinyl]nicotinamide;
6-(4-fluorophenyl)-N-[2-[(dimethylamino)methyl]-6-quinolinyl]nicotinamide;
6-(4-chlorophenyl)-N-[2-[(dimethylamino)methyl]-6-quinolinyl]nicotinamide;
4-(4-fluorophenyl)-N-[2-(1-pyrrolidinylmethyl)-6-quinolinyl]-1-piperidinecarboxamide;
4-(4-chlorophenyl)-N-[2-(1-pyrrolidinylmethyl)-6-quinolinyl]-1-piperidinecarboxamide;
4-(4-fluorophenyl)-N-[2-[(dimethylamino)methyl]-6-quinolinyl]-1-piperidinecarboxamide;
4-(4-chlorophenyl)-N-[2-[(dimethylamino)methyl]-6-quinolinyl]-1-piperidinecarboxamide;
6-(4-fluorophenyl)-N-[7-(1-pyrrolidinylmethyl)-3-quinolinyl]nicotinamide;
6-(4-chlorophenyl)-N-[7-[(dimethylamino)methyl]-3-quinolinyl]nicotinamide;
4-(4-fluorophenyl)-N-[7-(1-pyrrolidinylmethyl)-3-quinolinyl]-1-piperidinecarboxamide;
4-(4-chlorophenyl)-N-[7-[(dimethylamino)methyl]-3-quinolinyl]-1-piperidinecarboxamide;
4'-chloro-N-[7-[(dimethylamino)methyl]-3-quinolinyl][1,1'-biphenyl]-4-carboxamide;
4'-fluoro-N-[7-(1-pyrrolidinylmethyl)-3-quinolinyl][1,1'-biphenylyl]-4-carboxamide;
5-(4-chlorophenyl)-N-[6-[(dimethylamino)methyl]-2-naphthyl]-2-pyridinecarboxamide;
5-(4-fluorophenyl)-N-[6-(1-pyrrolidinylmethy)-2-naphthyl]-2-pyridinecarboxamide;
4'-fluoro-N-[6-[[4-(4-methoxyphenyl)-1-piperidinyl]methyl]-2-naphthyl][1,1'-biphenyl]-4-carboxamide;
4'-chloro-N-[6-[[4-(4-methoxyphenyl)-1-piperidinyl]methyl]-2-naphthyl][1,1'-biphenyl]-4-carboxamide;
4'-methoxy-N-[6-[[4-(4-methoxyphenyl)-1-piperidinyl]methyl]-2-naphthyl][1,1'-biphenyl]-4-carboxamide;
N-[6-[[4-(4-methoxyphenyl)-1-piperidinyl]methyl]-2-naphthyl]-4'-methyl[1,1'-biphenyl]-4-carboxamide;
4'-fluoro-N-[6-[[4-(4-fluorophenyl)-1-piperidinyl]methyl]-2-naphthyl][1,1'-biphenyl]-4-carboxamide;
4'-chloro-N-[6-[[4-(4-fluorophenyl)-1-piperidinyl]methyl]-2-naphthyl][1,1'-biphenyl]-4-carboxamide;
N-[6-[[4-(4-fluorophenyl)-1-piperidinyl]methyl]-2-naphthyl]-4'-methoxy[1,1'-biphenyl]-4-carboxamide;
N-[6-[[4-(4-fluorophenyl)-1-piperidinyl]methyl]-2-naphthyl]-4'-methyl[1,1'-biphenyl]-4-carboxamide;
4'-fluoro-N-[6-[[4-(4-methylphenyl)-1-piperidinyl]methyl]-2-naphthyl][1,1'-biphenyl]-4-carboxamide;
4'-chloro-N-[6-[[4-(4-methylphenyl)-1-piperidinyl]methyl]-2-naphthyl][1,1'-biphenyl]-4-carboxamide;
N-[6-[[4-(4-methylphenyl)-1-piperidinyl]methyl]-2-naphthyl]-4'-methoxy[1,1'-biphenyl]-4-carboxamide;
4'-methyl-N-[6-[[4-(4-methylphenyl)-1-piperidinyl]methyl]-2-naphthyl][1,1'-biphenyl]-4-carboxamide;
N-[6-[[4-(4-hydroxyphenyl)-1-piperidinyl]methyl]-2-naphthyl]-4'-methoxy[1,1'-biphenyl]-4-carboxamide;
N-[6-[[4-(4-aminophenyl)-1-piperidinyl]methyl]-2-naphthyl]-4'-methoxy[1,1'-biphenyl]-4-carboxamide;
4'-methoxy-N-[6-[[4-(4-nitrophenyl)-1-piperidinyl]methyl]-2-naphthyl][1,1'-biphenyl]-4-carboxamide;

N-[6-[[4-(4-chlorophenyl)-1-piperidinyl]methyl]-2-naphthyl]-4'-methoxy[1,1'-biphenyl]-4-carboxamide;
6-(4-fluorophenyl)-N-[6-[[4-(4-methoxyphenyl)-1-piperidinyl]methyl]-2-naphthyl]nicotinamide;
6-(4-chlorophenyl)-N-[6-[[4-(4-methoxyphenyl)-1-piperidinyl]methyl]-2-naphthyl]nicotinamide;
6-(4-methoxyphenyl)-N-[6-[[4-(4-methoxyphenyl)-1-piperidinyl]methyl]-2-naphthyl]nicotinamide;
N-[6-[[4-(4-methoxyphenyl)-1-piperidinyl]methyl]-2-naphthyl]-6-(4-methylphenyl) nicotinamide;
6-(4-fluorophenyl)-N-[6-[[4-(4-methylphenyl)-1-piperidinyl]methyl]-2-naphthyl]nicotinamide;
6-(4-chlorophenyl)-N-[6-[[4-(4-methylphenyl)-1-piperidinyl]methyl]-2-naphthyl]nicotinamide;
6-(4-methoxyphenyl)-N-[6-[[4-(4-methylphenyl)-1-piperidinyl]methyl]-2-naphthyl]nicotinamide;
6-(4-methylphenyl)-N-[6-[[4-(4-methylphenyl)-1-piperidinyl]methyl]-2-naphthyl]nicotinamide;
6-(4-fluorophenyl)-N-[6-[[4-(4-fluorophenyl)-1-piperidinyl]methyl]-2-naphthyl]nicotinamide;
6-(4-chlorophenyl)-N-[6-[[4-(4-fluorophenyl)-1-piperidinyl]methyl]-2-naphthyl]nicotinamide;
N-[6-[[4-(4-fluorophenyl)-1-piperidinyl]methyl]-2-naphthyl]-6-(4-methoxyphenyl) nicotinamide;
N-[6-[[4-(4-fluorophenyl)-1-piperidinyl]methyl]-2-naphthyl]-6-(4-methylphenyl) nicotinamide;
4-(4-fluorophenyl)-N-[6-[[4-(4-methoxyphenyl)-1-piperidinyl]methyl]-2-naphthyl]-1-piperidinecarboxamide;
4-(4-chlorophenyl)-N-[6-[[4-(4-methoxyphenyl)-1-piperidinyl]methyl]-2-naphthyl]-1-piperidinecarboxamide;
4-(4-methoxyphenyl)-N-[6-[[4-(4-methoxyphenyl)-1-piperidinyl]methyl]-2-naphthyl]-1-piperidinecarboxamide;
N-[6-[[4-(4-methoxyphenyl)-1-piperidinyl]methyl]-2-naphthyl]-4-(4-methylphenyl) -1-piperidinecarboxamide;
4-(4-fluorophenyl)-N-[6-[[4-(4-methylphenyl)-1-piperidinyl]methyl]-2-naphthyl]-1-piperidinecarboxamide;
4-(4-chlorophenyl)-N-[6-[[4-(4-methylphenyl)-1-piperidinyl]methyl]-2-naphthyl]-1-piperidinecarboxamide;
4-(4-methoxyphenyl)-N-[6-[[4-(4-methylphenyl)-1-piperidinyl]methyl]-2-naphthyl]-1-piperidinecarboxamide;
4-(4-methylphenyl)-N-[6-[[4-(4-methylphenyl)-1-piperidinyl]methyl]-2-naphthyl]-1-piperidinecarboxamide;
4-(4-fluorophenyl)-N-[6-[[4-(4-fluorophenyl)-1-piperidinyl]methyl]-2-naphthyl]-1-piperidinecarboxamide;
4-(4-chlorophenyl)-N-[6-[[4-(4-fluorophenyl)-1-piperidinyl]methyl]-2-naphthyl]-1-piperidinecarboxamide;
N-[6-[[4-(4-fluorophenyl)-1-piperidinyl]methyl]-2-naphthyl]-4-(4-methoxyphenyl) -1-piperidinecarboxamide;
N-[6-[[4-(4-fluorophenyl)-1-piperidinyl]methyl]-2-naphthyl]-4-(4-methylphenyl) -1-piperidinecarboxamide;
N-[6-[[4-(4-chlorophenyl)-1-piperidinyl]methyl]-2-naphthyl]-4-(4-fluorophenyl) -1-piperidinecarboxamide;
4-(4-chlorophenyl)-N-[6-[[4-(4-chlorophenyl)-1-piperidinyl]methyl]-2-naphthyl]-1-piperidinecarboxamide;
N-[6-[[4-(4-chlorophenyl)-1-piperidinyl]methyl]-2-naphthyl]-4-(4-methoxyphenyl)-1-piperidinecarboxamide;
N-[6-[[4-(4-chlorophenyl)-1-piperidinyl]methyl]-2-naphthyl]-4-(4-methylphenyl) -1-piperidinecarboxamide.

Examples of salts of compound (I) or (I') include salts with inorganic bases, ammonium salts, salts with organic bases, salts with inorganic acids, salts with organic acids, salts with basic or acidic amino acids, and the like.

Preferred examples of salts with inorganic bases include alkali metal salts such as sodium salts, potassium salts, etc.; alkaline earth metal salts such as calcium salts, magnesium salts, barium salts, etc.; aluminum salts; etc.

Preferred examples of salts with organic bases include salts with trimethylamine, triethylamine, pyridine, picoline, ethanolamine, diethanolamine, triethanolamine, dicyclohexylamine, N,N-dibenzylethylenediamine, etc.

Preferred examples of salts with inorganic acids include salts with hydrochloric acid, hydrobromic acid, nitric acid, sulfuric acid, phosphoric acid, etc.

Preferred examples of salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

Preferred examples of salts with basic amino acids include salts with arginine, lysine, ornithine, etc. Preferred examples of salts with acidic amino acids include salts with aspartic acid, glutamic acid, etc.

Among these salts, pharmaceutically acceptable salts are preferred. For example, when compound (I) or. (I') possesses an acidic functional group, it can form an inorganic salt such as an alkali metal salt (e.g., sodium salt, potassium salt, etc.), an alkaline earth metal salt (e.g. calcium salt, magnesium salt, barium salt, etc.), etc., an ammonium salt, etc. When compound (I) or (I') possesses a basic functional group, it can form an inorganic salt such as hydrochloride, sulfate, phosphate, hydrobromate, etc.; or an organic salt such as acetate, maleate, fumarate, succinate, methanesulfonate, p-toluenesulfonate, citrate, tartarate, etc.

Compounds (I) and (I') (hereinafter also abbreviated as the compound of the present invention) can be either anhydrides or hydrates. A hydrate may have 0.5 to 3 water molecules.

In addition, the compounds of the present invention can be labeled using isotopes (e.g. $^3H$, $^{14}C$, and $^{35}S$, etc.).

When the compound of the present invention contain optical isomers, stereoisomers, regio isomers, rotational isomers, these are also included as the compound of the present invention, and each of them can be obtained as a single substance by per se known synthesis methods and separation methods. For example, when optical isomers exist in the compound of the present invention, the optical isomers resolved from the compound are included in the compound of the present invention.

The optical isomers can be produced using per se known methods. Specifically, the optical isomer can be obtained by using an optically active synthetic intermediate, or subjecting a racemic mixture of the final product to optical resolution in accordance with common method.

Examples of optical resolution methods include per se known methods such as the fractional recrystallization method, chiral column method, diastereomer method, etc., which are described in detail below.

1) Fractional Recrystallization Method

The method which comprises allowing a racemate to form a salt with an optically active compound (e.g. (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.), separating the salt using a fractional recrystallization method, followed by, if desired, neutralizing process to obtain a free optical isomer.

2) Chiral Column Method

This method comprises subjecting a racemate or its salt to a column for separating an optical isomer (chiral column) for separation. For example, in the case of liquid chromatography, an optical isomer mixture is added to the chiral column such as ENANTIO-OVM [produced by Toso] or CHIRAL series [produced by Daicel], which is developed using water, various buffer solutions (e.g. phosphate buffer), organic solvents (e.g. ethanol, methanol, isopropanol, acetonitrile, trifluoroacetic acid, diethylamine, etc.) as single or mixed solutions, and the optical isomers are separated. Also, in the case of gas chromatography, for example, separation is conducted using a chiral column such as CP-Chirasil-DeX (produced by G.L. Science Co.).

3) Diastereomer Method

In this method, a racemic mixture is subjected to a chemical reaction with an optically active reagent to give a diastereomer mixture, which is separated into a single substance by an ordinary separation means (e.g. fractional recrystallization, chromatography method, etc.). This single substance is subjecting to removal of the optically active reagent part using chemical processing such as a hydrolysis reaction. For example, when a compound of the present invention possesses hydroxy or primary or secondary amino in its molecule, this compound is subjected to a condensation reaction with an optically active organic acid (e.g. MTPA [α-methoxy-α-(trifluoromethyl)phenylacetic acid], (–)-menthoxyacetic acid, etc.), to give the diastereomer in an ester form or an amide form, respectively. On the other hand, when a compound of the present invention possesses carboxylic acid group, this compound is subjected to a condensation reaction with an optically active amine or alcohol reagent, to give the diastereomer in an amide form or an ester form, respectively. The separated diastereomer can be converted to an optical isomer of the original compound, by applying acidic hydrolysis or basic hydrolysis.

A prodrug of compound (I') is a compound which is converted to compound (I') by reactions involving enzymes and gastric acid, etc. under physiological conditions in the living body; in other words, a compound that is changed into compound (I') by enzymatically-caused oxidation, reduction and hydrolysis, and a compound that is changed into compound (I') by hydrolysis caused by gastric acid. Examples of the prodrugs of compound (I') include compounds in which amino groups of compound (I') have been acylated, alkylated, or phosphorylated [e.g. compounds in which amino groups of compound (I') have been eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated, etc.]; compounds in which hydroxyl groups of compound (I') have been acylated, alkylated, phosphorylated, borated (e.g. compounds in which hydroxyl groups of compound (I') have been acetylated, palmitoylated, propanoylated, pivaloylated, succinylated, fumarilated, alanylated, dimethylaminomethylcarbonylated, etc.); compounds in which carboxyl groups of compound (I') have been esterified or amidated [e.g. compounds in which carboxyl groups of compound (I') have been ethylesterified, phenylesterified, carboxylmethylesterified, dimethylaminomethylesterified, pivaloyloxymethylesterified, ethoxycarbonyloxyethylesterified, phthalidylesterified, (5-methyl-2-oxo-1,3-dioxolen-4-yl)methylesterified, cyclohexyloxycarbonylethylesterified, or methylamidated, etc.]. These compounds can be produced from compound (I') using per se known methods.

Also, a prodrug of compound (I') can be a compound which is changed to compound (I') by physiological conditions, as described in pages 163 to 198 of Molecular Design, Volume 7, "Development of Drugs", published in 1990 by Hirokawa Shoten.

The compound of the present invention can be produced by [Production method 1] to [Production method 7] which are described in detail below, or analogous methods thereto.

Compounds (II) to (XIII), compound (IV'), compound (IIIa), compound (IIIb), compound (IIIc), compound (IIId), compound (IIIf), compound (IIIh) and compound (IIIi), used as raw materials, can be used in the form of salts, respectively. As such salts, those exemplified as salts of the above compound (I) or (I') can be used.

In the following [Production method 1] to [Production method 7], when an alkylation reaction, a hydrolysis reaction, an amination reaction, an esterification reaction, an amidation reaction, an esterification reaction, an etherification reaction, an oxidation reaction, a reduction reaction, etc. are carried out, these reactions are carried out in accordance with per se known methods. Examples of such methods include the methods described in Organic Functional Group Preparations, Second Edition, Academic Press, Inc., published in 1989; Comprehensive Organic Transformations, VCH Publishers Inc., published in 1989, etc.

[Production method 1]

Compound (Ia) having —$(CH_2)_{w3}CONR^{8a}(CH_2)_{w4}$— for X in the formula (I) is produced, for example, by the following amidation reaction.

(Amidation Reaction)

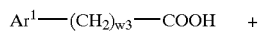
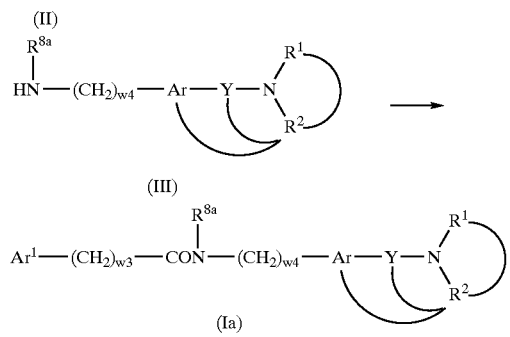

wherein $R^{8a}$ is hydrogen atom or an optionally halogenated $C_{1-6}$ alkyl; the other symbols are as defined above.

As the "optionally halogenated $C_{1-6}$ alkyl", those exemplified as "substituents" in the above "cyclic group which may be substituted" can be used.

The "amidation reaction" includes the following "method using a dehydration and condensation agent" and "method using a reactive derivative of carboxylic acid".

i) Method Using a Dehydration and Condensation Agent

Compound (III), 1 to 5 equivalents of compound (II), and 1 to 2 equivalents of a dehydration and condensation agent are reacted in an inert solvent. If necessary, the reaction can be carried out with the coexistence of 1 to 1.5 equivalents of 1-hydroxybenzotriazole (HOBT) and/or catalytic quantity to 5 equivalents of a base.

Examples of the "dehydrating and condensation agent" include dicyclohexylcarbodimide (DCC), 1-ethyl-3-(3-dimethylaminopropyl)carbodimide hydrochloride (WSC). WSC is particularly preferable.

Examples of the "inert solvent" include nitrile solvents (preferably acetonitrile), amide solvents (preferably DMF), halogenated hydrocarbon solvents (preferably dichloromethane), ether solvents (preferably THF). Two or more kinds of these can be mixed in an appropriate ratio for use.

Examples of the "base" include
1) strong bases exemplified by hydrides of alkali metals or alkaline earth metals (e.g. lithium hydride, sodium hydride, potassium hydride, calcium hydride, etc.), amides of alkali metals or alkaline earth metals (e.g. lithium amide, sodium amide, lithium diisopropylamide, lithium dicyclohexylamide, lithium hexamethyldisilazide, sodium hexamethyldisilazide, potassium hexamethyldisilazide, etc.), lower alkoxides of alkali metals or alkaline earth metals (e.g. sodium methoxide, sodium ethoxide, potassium tert-butoxide, etc.), etc.;
2) inorganic bases exemplified by hydroxides of alkali metals or alkaline earth metals (e.g. sodium hydroxide, potassium hydroxide, lithium hydroxide, barium hydroxide, etc.), carbonates of alkali metals or alkaline earth metals (e.g. sodium carbonate, potassium carbonate, cesium carbonate, etc.) and hydrogencarbonates of alkali metals or alkaline earth metals (e.g. sodium hydrogencarbonate, potassium hydrogencarbonate, etc.), etc.; and
3) organic bases exemplified by amines such as triethylamine, diisopropylethylamine, N-methylmorpholine, dimethylaminopyridine, DBU (1,8-diazabicyclo[5.4.0]undec-7-en), DBN (1,5-diazabicyclo[4.3.0]non-5-en), etc.; basic heterocyclic compounds such as pyridine, imidazole, 2,6-lutidine, etc.; and the like.

Among the above bases, triethylamine, 4-dimethylaminopyridine, etc., are preferable.

Reaction temperature is usually room temperature (0° C. to 30° C., hereafter the same). Reaction time is, for example, 10 to 24 hours.

ii) Method Using a Reactive Derivative of Carboxylic Acid

A reactive derivative of compound (II) and 1 to 5 equivalents (preferably 1 to 3 equivalents) of compound (III) are reacted in an inert solvent. If necessary, the reaction can be carried out with the coexistence of 1 to 10 equivalents, preferably 1 to 3 equivalents of a base. Examples of the "reactive derivative" of compound (II) include acid halides (e.g., acid chloride, acid bromide, etc.), mixed acid anhydrides (e.g. acid anhydrides with $C_{1-6}$ alkyl-carboxylic acid, $C_{6-10}$ aryl-carboxylic acid or $C_{1-6}$ alkylcarbonate), active esters (e.g. esters with phenol which may be substituted, 1-hydroxybenzotriazole or N-hydroxysuccinimide, etc.), etc.

Examples of the "substituents" in the "phenol which may be substituted" include halogen atom (e.g. fluorine, chlorine, bromine, iodine, etc.), nitro, optionally halogenated $C_{1-6}$ alkyl, optionally halogenated $C_{1-6}$ alkoxy. The number of substituents is, for example, 1 to 5.

As the "optionally halogenated $C_{1-6}$ alkyl" and "optionally halogenated $C_{1-6}$ alkoxy", those exemplified as "substituents" in the above "cyclic group which may be substituted" can be used.

Specific examples of "phenol which may be substituted" include phenol, pentachlorophenol, pentafluorophenol, p-nitrophenol, etc. The reactive derivative is, preferably, an acid halide.

Examples of the "inert solvent" include ether solvents, halogenated hydrocarbon solvents, aromatic solvents, nitrile solvents, amide solvents, ketone solvents, sulfoxide solvents, and water. Two or more kinds of these can be mixed in an appropriate ratio for use. Especially, acetonitrile, THF, dichloromethane, chloroform, etc. are preferable.

As the "base", the same as above are used. The base is preferably sodium hydride, potassium carbonate, sodium carbonate, sodium hydroxide, potassium hydroxide, sodium hydrogencarbonate, potassium hydrogencarbonate, triethylamine, pyridine, etc.

Reaction temperature is usually −20° C. to 50° C., preferably room temperature. Reaction time is usually 5 minutes to 40 hours, preferably 1 to 18 hours.

Compound (II) described above can be produced by per se known methods.

Compound (III) can be produced by subjecting the compound of the formula:

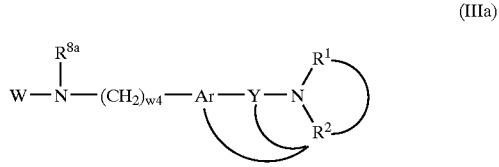

(IIIa)

wherein W is a protecting group for amino; and the other symbols are as defined above, to a deprotection reaction to remove W.

Examples of the protecting group for amino represented by W include formyl, $C_{1-6}$ alkyl-carbonyl (e.g. acetyl, propionyl, etc.), $C_{1-6}$ alkoxy-carbonyl (e.g. methoxycarbonyl, ethoxycarbonyl, tert-butoxycarbonyl, etc.), benzoyl, $C_{7-10}$ aralkyl-carbonyl (e.g. benzylcarbonyl, etc.), $C_{7-14}$ aralkyloxy-carbonyl (e.g. benzyloxycarbonyl, 9-fluorenylmethoxycarbonyl, etc.), trityl, phthaloyl, N,N-dimethylaminomethylene, silyl (e.g. trimethylsilyl, triethylsilyl, dimethylphenylsilyl, tert-butyldimethylsilyl, tert-butyldiethylsilyl, etc.), $C_{2-6}$ alkenyl (e.g. 1-allyl, etc.), etc. These groups may be substituted by 1 to 3 of halogen atom (e.g. fluorine, chlorine, bromine, iodine, etc.), $C_{1-6}$ alkoxy (e.g. methoxy, ethoxy, propoxy, etc.) or nitro, etc.

The deprotection reaction is carried out, for example, by maintaining compound (IIIa), preferably at 20° C. to 140° C., in an aqueous solution of an acid such as a mineral acid (e.g., hydrochloric acid, sulfuric acid, hydrobromic acid, iodic acid, periodic acid, etc.) etc., or a base such as an alkali metal hydroxide (e.g., sodium hydroxide, potassium hydroxide, lithium hydroxide, etc.) etc. The acid or base is usually used in an amount of 1 to 100 equivalents, preferably 1 to 40 equivalents based on compound (IIIa). Strength of the acid or base is usually 0.1 N to 18 N, preferably 1 N to 12 N. Reaction time is usually 0.5 hour to 48 hours, preferably 1 hour to 24 hours.

Further, when W is t-butoxycarbonyl group, etc., the deprotection reaction can also be carried out by dissolving compound (IIIa) in an organic acid (e.g., trifluoroacetic acid, formic acid, acetic acid, methanesulfonic acid, benzenesulfonic acid, trifluoromethanesulfonic acid, etc.) and maintaining the solution usually at −20° C. to 200° C., preferably 0° C. to 100° C. The organic acid is used in an amount of 1 to 100 equivalents, preferably 1 to 40 equivalents based on compound (IIIa).

The deprotection reaction can also be carried out by subjecting compound (IIIa) to catalytic reduction in an alcoholic solvent, for example, ethanol, etc., or a solvent such as acetic acid, etc., with a catalyst such as palladium, palladium-carbon, Raney nickel, Raney cobalt, platinum oxide, etc. at normal pressure or, if necessary, under pressure.

Compound (IIIa) can be produced by reacting a compound of the formula:

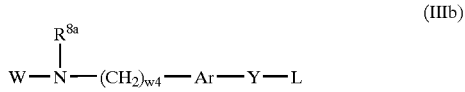

(IIIb)

wherein L is a leaving group and the other symbols are as defined above, with a compound of the formula:

(IIIi)

wherein the symbols are as defined above.

Examples of the "leaving group" represented by L include halogen atom (e.g. chlorine, bromine, iodine, etc.), optionally halogenated $C_{1-6}$ alkylsulfonyloxy (e.g. methanesulfonyloxy, ethanesulfonyloxy, trifluoromethanesulfonyloxy, etc.), $C_{6-10}$ arylsulfonyloxy which may be substituted, hydroxy, etc.

Examples of the "substituents" in the "$C_{6-10}$ arylsulfonyloxy which may be substituted" include halogen atom (e.g. chlorine, bromine, iodine, etc.), optionally halogenated $C_{1-6}$ alkyl, $C_{1-6}$ alkoxy, etc. The number of substituents is, for example, 1 to 3. Specific examples of the "$C_{6-10}$ arylsulfonyloxy which may be substituted" include benzenesulfonyloxy, p-toluenesulfonyloxy, 1-naphthalenesulfonyloxy, 2-naphthalenesulfonyloxy, etc.

The "leaving group" is preferably halogen atom (e.g. chlorine, bromine, iodine, etc.), methanesulfonyloxy, trifluoromethanesulfonyloxy, p-toluenesulfonyloxy, etc.

This reaction is usually carried out in an inert solvent.

Examples of the "inert solvent" include alcohol solvents, ether solvents, halogenated hydrocarbon solvents, aromatic solvents, nitrile solvents, amide solvents, ketone solvents, sulfoxide solvents, water, etc. Two or more kinds of these can be mixed in an appropriate ratio for use. Especially, acetonitrile, N,N-dimethylformamide (DMF), acetone, ethanol, pyridine, etc., are preferred.

Compound (IIIi) is used in an amount of 1 equivalent to 100 equivalents based on compound (IIIb). Further, compound (IIIi) can be used in an amount corresponding to a reaction solvent.

Reaction temperature is about −20° C. to 200° C., preferably room temperature to 100° C. Reaction time is, for example, 0.5 hour to 1 day.

This reaction can be carried out in the presence of a base. The base is preferably sodium hydride, potassium carbonate, sodium carbonate, sodium hydroxide, potassium hydroxide, sodium hydrogencarbonate, potassium hydrogencarbonate, triethylamine, pyridine, etc. The amount of the base is 0.1 to 100 equivalents, preferably 1 to 10 equivalents based on compound (IIIb).

Compound (IIIb) can be produced, for example, from the compound of the formula:

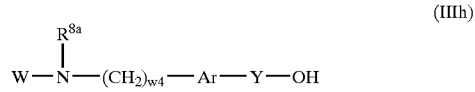

(IIIh)

wherein the symbols are as defined above.

In compound (IIIb), the compound wherein L is optionally halogenated $C_{1-6}$ alkylsulfonyloxy, or $C_{6-10}$ arylsulfonyloxy which may be substituted can be produced by subjecting compound (IIIh) to a known acylation reaction. This reaction is carried out, for example, by reacting compound (IIIh) with 1 to 5 equivalents of a corresponding sulfonyl halide in an inert solvent in the presence of a base. The base is preferably potassium carbonate, sodium hydrogen carbonate, triethylamine, N-methylmorpholine, pyridine, etc. The base is preferably used in an amount of 1 to 10 equivalents.

Examples of the "inert solvent" include ether solvents, halogenated hydrocarbon solvents, aromatic solvents, nitrile solvents, amide solvents, ketone solvents, sulfoxide solvents, etc.

Reaction temperature is −20° C. to 200° C., preferably 0° C. to 100° C. Reaction time is 0.1 hour to 48 hours, preferably 1 hour to 24 hours.

In compound. (IIIb), the compound wherein L is a halogen atom can be produced by subjecting compound (IIIh) to a known halogenation reaction.

This reaction is carried out by using a halogenating agent. Examples of the halogenating agent include an inorganic acid chloride such as thionyl chloride, thionyl bromide, phosphorus trichloride, phosphorus pentachloride, phosphorus oxychloride, etc.; a hydrogen halide acid such as hydrogen chloride acid, hydrobromic acid, etc., and the like.

Further, in compound (IIIb), the compound wherein L is a halogen atom can be produced by subjecting compound (IIIf) described hereinafter to the reaction described in Journal of Medicinal Chemistry, 35, 2761 (1992), etc. or a modification thereof. In this reaction, a halogenating agent such as bromine, N-bromosuccinimide, etc. and an additive such as benzoylperoxide, 2,2'-azobis(isobutyronitrile), etc. are used.

Compound (IIIh) can be produced by reducing an ester compound (IIId) described hereinafter by a known reduction method. As a reduction method, for example, there are a method using a reducing agent (e.g., a boron hydride reagent such as sodium borohydride, etc.; an aluminum hydride reagent such as lithium aluminum hydride, etc.), and the like.

Further, compound (IIIh) can be produced from the compound wherein Ar is 2-methylquinolines by N-oxide transfer according to a method described in a literature (e.g., Journal or Medicinal Chemistry 34, 3212 (1991); Journal of Medicinal Chemistry 35, 2761 (1992); etc.).

The above compound (IIIi) can be produced by a per se known method.

Compound (IIIa) can also be produced by reacting a compound of the formula:

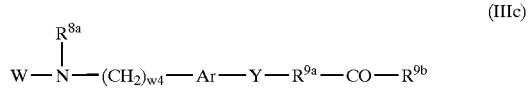

(IIIc)

wherein $R^{9a}$ is a bond or an optionally halogenated bivalent $C_{1-5}$ non-cyclic hydrocarbon group, $R^{9b}$ is hydrogen atom or an optionally halogenated $C_{1-5}$ alkyl group, and the other symbols are as defined above, with the above compound (IIIi).

Here, examples of the "optionally halogenated bivalent $C_{1-5}$ non-cyclic hydrocarbon group" include, among the "optionally halogenated bivalent $C_{1-6}$ non-cyclic hydrocarbon group" exemplified with respect to the above X and Y, the group having 1 to 5 carbon atoms.

Further, examples of the "optionally halogenated $C_{1-5}$ alkyl group" include, among the "optionally halogenated $C_{1-6}$ alkyl group" exemplified as the substituents of the above "cyclic group which may be substituted", the group having 1 to 5 carbon atoms.

This reaction can be carried out by reacting compound (IIIc) and, usually, 1 to 20 equivalents, preferably 1 to 5 equivalents of compound (IIIi) with a reducing agent in an inert solvent.

Examples of the "inert solvent" include alcohol solvents, ether solvents, halogenated hydrocarbon solvents, aromatic solvents, nitrile solvents, amide solvents, organic acid solvents, etc. Two or more kinds of these can be mixed in an appropriate ratio for use. Especially, methanol, ethanol, acetic acid, etc., are preferred.

Examples of the reducing agent include sodium borohydride, sodium triacetoxyborohydride, sodium cyanoborohydride, etc. The reducing agent is usually used in an amount of 1 to 20 equivalents, preferably 1 to 5 equivalents.

Reaction temperature is usually −20° C. to 150° C., preferably 20 to 100° C. Reaction time is usually 5 minutes to 40 hours, preferably 1 to 24 hours.

This reaction can also be carried out in the presence of an acid. Examples of the acid to be used include organic acids such as acetic acid, methanesulfonic acid, etc.; inorganic acid such as hydrochloric acid, sulfuric acid, etc.; and the like. The acid is used in an amount of 0.01 equivalent to 0.1 equivalent in case of an inorganic acid, and 0.01 equivalent to 100 equivalents or an amount corresponding to a solvent in case of an organic acid.

Compound (IIIc) can be produced by subjecting the above compound (IIIh) to a known oxidation reaction. The oxidation reaction can be carried out, for example, by using an oxidizing agent. As the oxidizing agent, there can be used, for example, manganese dioxide, chromic acid, lead tetraacetate, silver oxide, copper oxide, halogen acid, oxidation using dimethylsulfoxide (Swern oxidation), organic peracids, oxygen, electrode oxidation, etc.

Further, compound (IIIc) can also be produced from an ester compound (IIId) described hereinafter by a known method with an organic metal reagent such as Grignard reagent, lithium dialkylcopper, etc.

Compound (IIIa) can also be produced by subjecting a compound of the formula:

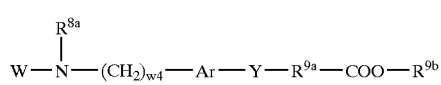

(IIId)

wherein the symbols are as defined above, and compound (IIII) to a per se known condensation reaction (for example, a method using the above dehydration condensation agent, a method using a reactive derivative of carboxy), and subjecting the resultant amide compound to a known reduction reaction. The reduction reaction is usually carried out by using a reducing agent. As the reducing agent, there can be used, for example, a borohydride reagent such as diborane, sodium borohydride, etc., an aluminum hydride reagent such as lithium aluminum hydride, etc., and the like.

Further, compound (IIIa) can also be produced by converting a compound of the formula:

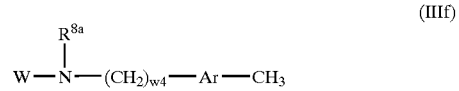

(IIIf)

wherein the symbols are as defined above into an enamine compound by a known method (for example, the method described in Heterocycles, 22, 195 (1984), etc.) and subjecting the resultant enamine compound to a known reduction reaction.

Here, the enamine compound is produced by using, for example, N,N-dimethylformamide dialkylacetal, etc.

The reduction reaction is usually carried out by using a reducing agent. As the reducing agent, there can be used sodium borohydride, sodium triacetoxyborohydride, sodium cyanoborohydride, or catalytic hydrogenation, etc.

This production method is also applicable to an active methylene group at an adjacent position of —CO— in case that, for example, Y is a divalent group consisting of —CO— and an alkylene in compound (IIIa).

The above compound (IIId) can be produced by a per se known method. For example, methyl 6-amino-2-naphthalene carboxylate and methyl 5-amino-2-naphthalene carboxylate can be produced according to the method described in WO98/43953, etc.

These aminonaphthalene carboxylic acids can also be produced by hydrolyzing corresponding naphthalene dicarboxylates according to, for example, the method described in JP 06107599, etc. to form monoesters and the resultant carboxylic acids are subjected to the reactions described in Journal of Organic Chemistry, 60, 4412 (1995); Chemical Pharmaceutical Bulletin, 35, 2698 (1987); etc.

The above compound (IIIf) can be produced by a per se known method. For example, 6-amino-2-methylquinoline can be produced by the methods described in Polymer Bulletin, 42, 175 (1999), Journal of Organic Chemistry, 28, 1753 (1963), Journal of Chemical Society C, 829 (1970), etc. or a modification thereof.

The above "method using a reactive derivative of carboxy" is also applicable to the production of the corresponding sulfonamide derivative and sulfinamide derivative from a sulfonic acid represented by the formula: $Ar^1$—$(CH_2)_{w3}$—$SO_2OH$ (wherein the symbols are as defined above) and a sulfinic acid of the formula: $Ar^1$—$(CH_2)_{w3}$—$SOOH$ (wherein the symbols are as defined above), respectively.

[Production Method 2]

Compound (Ib) having —$(CH_2)_{w3}$—COO$(CH_2)_{w4}$— for X in the formula (I), can be produced by the following esterification reaction.

(Esterification Reaction)

$Ar^1$—$(CH_2)_{w3}$—COOH +

(II)

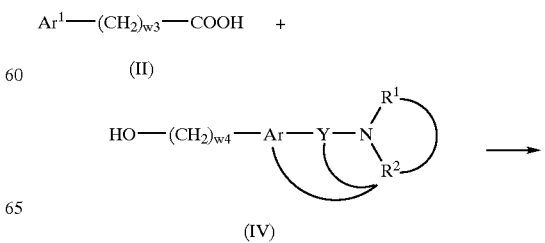

(IV)

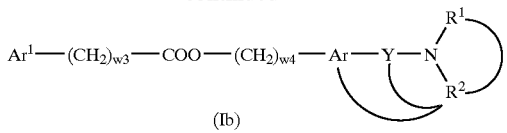

(Ib)

wherein the symbols are as defined above.

A reactive derivative of compound (II) and 1 to 5 equivalents (preferably 1 to 3 equivalents) of compound (IV) is reacted in an inert solvent. Usually, this reaction is carried out with the coexistence of 1 to 10 equivalents, preferably 1 to 3 equivalents of a base.

As the reactive derivative of compound (II), the same as above is used. Especially, an acid halide is preferable.

Examples of the "inert solvent" include ether solvents, halogenated hydrocarbon solvents, aromatic solvents, nitrile solvents, amide solvents, ketone solvents, sulfoxide solvents. Two or more kinds of these can be mixed in an appropriate ratio for use. Especially, acetonitrile, dichloromethane, chloroform, etc. are preferable.

As the "base", the same one as above can be used. The base is preferably sodium hydride, potassium carbonate, sodium carbonate, sodium hydroxide, potassium hydroxide, sodium hydrogencarbonate, potassium hydrogencarbonate, triethylamine, pyridine, etc.

Reaction temperature is usually -20° C. to 50° C., preferably room temperature. Reaction time is usually 5 minutes to 40 hours, preferably 1 to 18 hours.

Compound (IV) can be produced by a per se known method, for example the method described in WO9838156 or modification thereof.

[Production Method 3]

Compound (Ic) having —$(CH_2)_{w1}O(CH_2)_{w2}$— for X in the formula (I), can be produced by, for example, the following etherification reaction.

(Etherification Reaction)

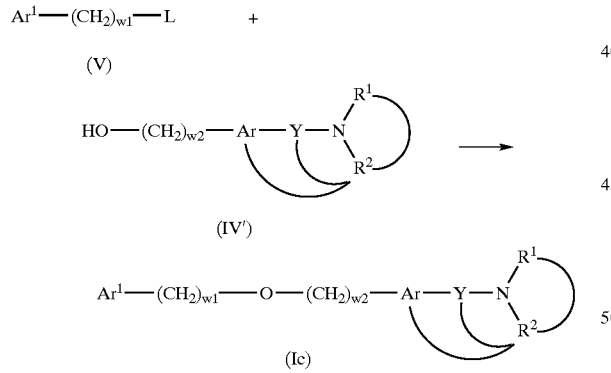

wherein the symbols are as defined above.

Compound (IV') and about 1 to 5 equivalents (preferably 1 to 2 equivalents) of compound (V) are reacted in inert solvent, with the coexistence of base.

As the "base", the same one as above can be used. The base is preferably potassium carbonate, sodium hydrogencarbonate, triethylamine, N-methylmorpholine, pyridine, etc. The amount of the base used is usually about 1 to 5 equivalents relative to compound (V).

Examples of the "inert solvent" include alcohol solvents, ether solvents, halogenated hydrocarbon solvents, aromatic solvents, nitrile solvents, amide solvents, ketone solvents, sulfoxide solvents, water. Two or more kinds of these can be mixed in an appropriate ratio for use. Especially, acetonitrile, N,N-dimethylformamide (DMF), acetone, ethanol, pyridine, etc., are preferable.

Reaction temperature is about -20° C. to 100° C., preferably room temperature to 80° C. Reaction time is, for example, about 0.5 hour to 1 day.

In the above production method, when the leaving group is hydroxy, Mitsunobu reaction can usually be used. In the Mitsunobu reaction, compound (V) and 0.5 to 5 equivalents (preferably 1 to 1.5 equivalents) of compound (IV') are reacted in inert solvent with the coexistence of 0.5 to 5 equivalents (preferably 1 to 1.5 equivalents) of ethyl acetyldicarboxylate.

Examples of the inert solvent include ether solvents, halogenated hydrocarbon solvents, aromatic solvents, nitrile solvents, amide solvents, ketone solvents, sulfoxide solvents. Two or more kinds of these can be mixed in an appropriate ratio for use. Especially, acetonitrile, dichloromethane, chloroform, etc. are preferable.

Reaction temperature is usually -20° C. to 50° C., preferably room temperature. Reaction time is usually 5 minutes to 40 hours, preferably 1 to 18 hours.

Compound (V) can be produced by a per se known method.

Compound (IV') can be produced by a per se known method, for example, the method described in WO9838156 or modification thereof.

[Production Method 4]

Compound (Id) having —$(CH_2)_{w3}NR^{8a}CO(CN_2)_{w4}$— for X in the formula (I), can be produced, for example, by the following amidation reaction.

(Amidation Reaction)

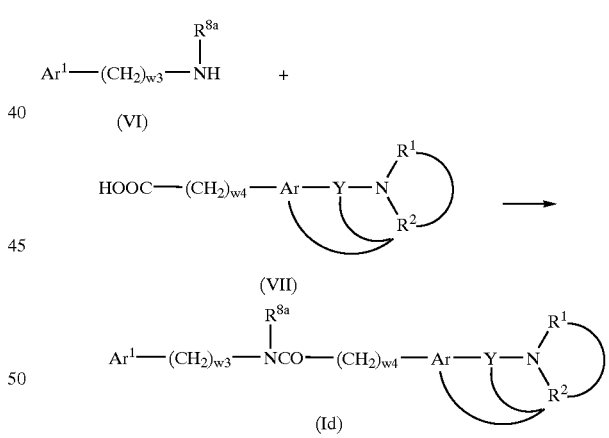

wherein the symbols are as defined above.

This production method is carried out in accordance with the above Production method 1.

Compound (VI) can be produced by a per se known method.

Compound (VII) can be produced by a per se known method, for example the method described in WO9838156 or modification thereof.

[Production Method 5]

Compound (Ie) having —$(CH_2)_{w5}NHCONR^{8a}(CH_2)_{w6}$— for X in the formula (I), can be produced, for example, by the following urea reaction.

(Urea Reaction)

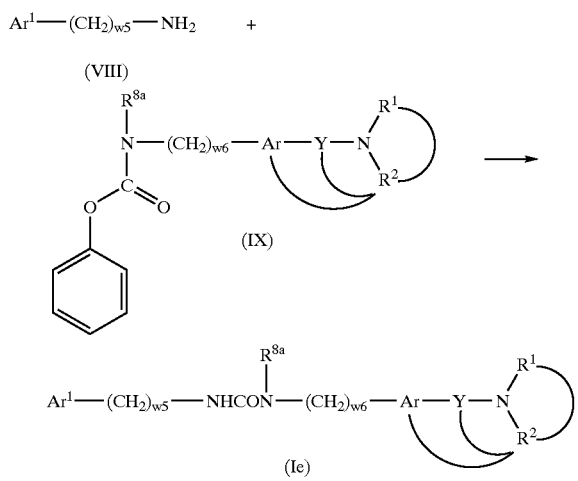

wherein the symbols are as defined above.

Compound (IX) and 1 to 5 equivalents (preferably 1 to 1.5 equivalents) of compound (VIII) is reacted in an inert solvent with the coexistence of a base.

As the "base", the same one as above can be used. The base is preferably potassium carbonate, sodium carbonate, sodium hydroxide, potassium hydroxide, sodium hydrogencarbonate, potassium hydrogencarbonate, triethylamine, pyridine, etc.

Examples of the "inert solvent" include alcohol solvents, ether solvents, halogenated hydrocarbon solvents, aromatic solvents, nitrile solvents, amide solvents, ketone solvents, sulfoxide solvents, water. Two or more kinds of these can be mixed in an appropriate ratio for use. Especially, acetonitrile, DMF, acetone, ethanol, pyridine, etc. are preferable.

Reaction temperature is usually −20° C. to 100° C., preferably room temperature to 80° C. Reaction time is, for example, 0.5 hour to 1 day.

Compound (VIII) and compound (IX) can be produced by a per se known method.

[Production Method 6]

Compound (If) having, for $Ar^1$, a ring assembly aromatic group ($Ar^2$—$Ar^3$) which may be substituted in the formula (I), can be produced by, for example, the following aryl-coupling reaction.

(Aryl-Coupling Reaction)

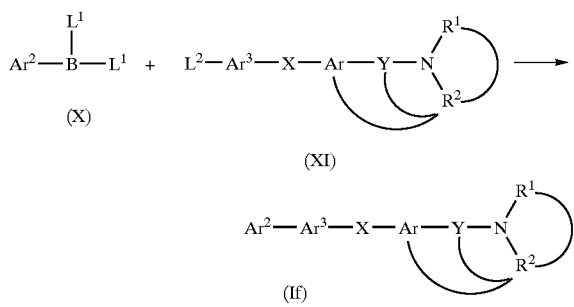

wherein $Ar^2$ and $Ar^3$ are monocyclic aromatic groups or condensed aromatic groups, each of which may be substituted; $L^1$ is hydroxy or $C_{1-6}$ alkyl; $L^2$ is halogen (preferably chlorine, bromine) or trifluoromethanesulfonyloxy; the other symbols are as defined above.

As "substituents", "monocyclic aromatic groups" and "condensed aromatic groups" in the "monocyclic aromatic groups or condensed aromatic groups, each of which may be substituted" for $Ar^2$ and $Ar^3$, those exemplified as the above $Ar^1$ can be used. Especially, it is preferable that both of $Ar^2$ and $Ar^3$ are phenyl groups which may be substituted, and $Ar^2$—$Ar^3$ is biphenylyl which may be substituted.

The aryl-coupling reaction can be carried out in accordance with per se known methods such as the method described in Acta. Chemica Scandinavia, pp. 221–230, 1993, or methods analogous thereto.

Compound (X) and 1 to 3 equivalents (preferably 1 to 1.5 equivalents) of compound (XI) are reacted in an inert solvent in the presence of a base and a transition metal catalyst.

As the base, the same one as above can be used. The base is preferably sodium carbonate, sodium hydrogencarbonate, etc.

The amount of the "base" used is, for example, about 1 to 10 equivalents relative to compound (XI).

Examples of the "transition metal catalyst" include palladium catalyst, nickel catalyst. Examples of the "palladium catalyst" include tetrakis(triphenylphosphine)palladium (O), palladium acetate, bis (triphenylphosphine) palladium (II) chloride, palladium-carbon. Examples of the "nickel catalyst" include tetrakis(triphenylphosphine) nickel (O).

The amount of the "transition metal catalyst" used is about 0.01 to 1 equivalent, preferably about 0.01 to 0.5 equivalent, relative to compound (XI).

Reaction temperature is room temperature to 150° C., preferably about 80° C. to 150° C. Reaction time is, for example, about 1 to 48 hours.

Examples of the "inert solvent" include water, alcohol solvents, aromatic solvents. Two or more kinds of these can be mixed in an appropriate ratio for use. Especially, a single solvent such as water, ethanol and toluene; or a mixed solvent of two or more kinds of these is preferred.

Compound (X) and compound (XI) can be produced by a per se known method.

Among compound (I), compound (I') can also be produced by the following [Production method 7].

[Production Method 7]

Compound (I') can also be produced by reacting a compound of the formula:

$$Ar^1—H \quad (XII)$$

wherein $Ar^1$ is as defined above, or a salt thereof with a compound of the formula:

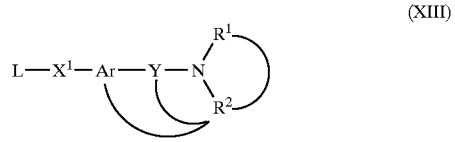

wherein the symbols are as defined above, or a salt thereof.

This production method can be carried out according to the above Production method 1.

Compound (XII) and compound (XIII) can be produced by a per se known method.

Examples of the above "alcohol solvents" include methanol, ethanol, isopropanol, tert-butanol, etc.

Examples of the above "ether solvents" include diethylether, tetrahydrofuran (THF), 1,4-dioxane, 1,2-dimethoxyethane, etc.

Examples of the above "halogenated hydrocarbon solvents" include dichloromethane, chloroform, 1,2-dichloroethane, carbon tetrachloride, etc.

Examples of the above "aromatic solvents" include benzene, toluene, xylene, pyridine, etc.

Examples of the above "hydrocarbon solvents" include hexane, pentane, cyclohexane, etc.

Examples of the above "amide solvents" include N,N-dimethylformamide (DMF), N,N-dimethylacetamide, N-methylpyrrolidone, etc.

Examples of the above "ketone solvent" include acetone, methylethylketone, etc.

Examples of the above "sulfoxide solvents" include dimethylsulfoxide (DMSO), etc.

Examples of the above "nitrile solvents" include acetonitrile, propionitrile, etc.

In a compound of the present invention thus obtained, the intramolecular functional group can be converted to a desired functional group by combining per se known chemical reactions. Examples of the chemical reactions include oxidation reaction, reduction reaction, alkylation reaction, hydrolysis reaction, amination reaction, esterification reaction, aryl-coupling reaction, deprotection reaction.

In each of the above reactions, when the starting material compounds possess amino, carboxy, hydroxy, and/or carbonyl as substituents, protecting groups which are generally used in peptide chemicals, etc., can be introduced into these groups, and the desired compound can be obtained by removing the protecting groups after the reaction if necessary.

Examples of the protecting group for amino include those exemplified with respect to the above W.

Examples of the protecting group for carboxy include $C_{1-6}$ alkyl (e.g. methyl, ethyl, propyl, isopropyl, butyl, tert-butyl, etc.), $C_{7-11}$ aralkyl (e.g. benzyl, etc.), phenyl, trityl, silyl (e.g. trimethylsilyl, triethylsilyl, dimethylphenylsilyl, tert-butyldimethylsilyl, tert-butyldiethylsilyl, etc.), $C_{2-6}$ alkenyl (e.g. 1-allyl, etc.). These groups may be substituted by 1 to 3 of halogen atom (e.g. fluorine, chlorine, bromine, iodine, etc.), $C_{1-6}$ alkoxy (e.g. methoxy, ethoxy, propoxy, etc.) or nitro.

Examples of the protecting group for hydroxy include $C_{1-6}$ alkyl (e.g. methyl, ethyl, propyl, isopropyl, butyl, tert-butyl, etc.), phenyl, trityl, $C_{7-10}$ aralkyl (e.g. benzyl, etc.), formyl, $C_{1-6}$ alkyl-carbonyl (e.g. acetyl, propionyl, etc.), benzoyl, $C_{7-10}$ aralkyl-carbonyl (e.g. benzylcarbonyl, etc.), 2-tetrahydropyranyl, 2-tetrahydrofuranyl, silyl (e.g. trimethylsilyl, triethylsilyl, dimethylphenylsilyl, tert-butyldimethylsilyl, tert-butyldiethylsilyl, etc.), $C_{2-6}$ alkenyl (e.g. 1-allyl, etc.). These groups may be substituted by 1 to 3 of halogen atom (e.g. fluorine, chlorine, bromine, iodine, etc.), $C_{1-6}$ alkyl (e.g. methyl, ethyl, n-propyl, etc.), $C_{1-6}$ alkoxy (e.g. methoxy, ethoxy, propoxy, etc.) or nitro, etc. can be substituted for these groups.

Examples of the protecting group for carbonyl include cyclic acetal (e.g. 1,3-dioxane, etc.), and non-cyclic acetal (e.g. di-$C_{1-6}$ alkylacetal, etc.).

Removal of the above protecting groups can be carried out in accordance with per se known methods such as those described in Protective Groups in Organic Synthesis, published by John Wiley and Sons (1980). For instance, the methods using acid, base, ultraviolet light, hydrazine, phenylhydrazine, sodium N-methyldithiocarbamate, tetrabutylammonium fluoride, palladium acetate, trialkylsilyl halide (e.g. trimethylsilyl iodide, trimethylsilyl bromide, etc.), and a reduction method, etc. can be used.

The compound of the present invention can be isolated and purified by per se known methods such as solvent extraction, changing of liquid properties, transdissolution, crystallization, recrystallization, chromatography, etc. It is also possible to isolate and purify the starting material compounds of the compound of the present invention, or their salts using the same known methods as above, but they can also be bemused as raw materials in the next process as a reaction mixture without being isolated.

The compound of the present invention possesses an excellent MCH receptor antagonistic action, therefore, it is useful as an agent for preventing or treating diseases caused by MCH. Also, the compound of the present invention is low in toxicity, and is excellent in oral absorbency and intracerebral transitivity.

Therefore, a melanin-concentrating hormone antagonist (hereafter, also abbreviated as "MCH antagonist") comprising a compound of the present invention can be safely administered to mammals (e.g. rats, mice, guinea pigs, rabbits, sheep, horses, swine, cattle, monkeys, humans, etc.) as an agent for preventing or treating diseases caused by MCH.

Here, examples of the diseases caused by MCH include obesity (e.g. malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity, etc.], hyperphagia, emotional disorders, reproductive function disorders, etc.

The compound of the present invention is also useful as an agent for preventing or treating lifestyle diseases such as diabetes, diabetic complications (e.g. diabetic retinopathy, diabetic neuropathy, diabetic nephropathy, etc.), arteriosclerosis, gonitis, etc.

Further, the compound of the present invention is useful as an anorectic agent.

The MCH antagonist and the pharmaceutical composition of the present invention can be used in combination with an alimentary therapy (e.g., alimentary therapy for diabetes) and exercise.

The MCH antagonist and the pharmaceutical composition of the present invention can be produced by subjecting compound (I) or compound (I') respectively, as it is, or together with a pharmacologically acceptable carrier, to pharmaceutical manufacturing process in accordance with a per se known means.

Here, examples of the pharmacologically acceptable carriers include various organic or inorganic carrier substances which are commonly used as materials for pharmaceutical preparations, such as excipients, lubricants, binders, and disintegrators in solid preparations; solvents, solubilizing agents, suspending agents, isotonizing agents, buffering agents, soothing agents, in liquid preparations; and the like. Also, in the pharmaceutical manufacturing process, additives such as antiseptics, antioxidants, coloring agents, sweeteners, absorbents, moistening agents, etc., can be used, if necessary.

Examples of the excipients include lactose, sucrose, D-mannitol, starch, cornstarch, crystalline cellulose, light anhydrous silicic acid, etc.

Examples of the lubricants include magnesium stearate, calcium stearate, talc, colloidal silica, etc.

Examples of the binders include crystalline cellulose, sucrose, D-mannitol, dextrin, hydroxypropylcellulose, hydroxypropylmethylcellulose, polyvinylpyrrolidone, starch, saccharose, gelatin, methylcellulose, carboxymethylcellulose sodium, etc.

Examples of the disintegrators include starch, carboxymethylcellulose, carboxymethylcellulose calcium, crosscarmellose sodium, carboxymethylstarch sodium, low-substituted hydroxypropylcellulose (L-HPC), etc.

Examples of the solvents include distilled water for injection, alcohol, propylene glycol, macrogol, sesame oil, corn oil, etc.

Examples of the solubilizing agents include polyethylene glycol, propylene glycol, D-mannitol, benzyl benzoate, ethanol, trisaminomethane, cholesterol, triethanolamine, sodium carbonate, sodium citrate, etc.

Examples of the suspending agents include surfactants such as stearyltriethanolamine, sodium lauryl sulfate, lauryl amino propionic acid, lecithin, benzalkonium chloride, benzethonium chloride, glyceryl monostearate; or hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose, etc.

Examples of the isotonizing agents include glucose, D-sorbitol, sodium chloride, glycerin, D-mannitol, etc.

Examples of the buffering agents include buffer solutions of phosphate, acetate, carbonate, citrate, etc.

Examples of the soothing agents include benzyl alcohol, etc.

Examples of the antiseptics include paraoxybenzoates, chlorobutanol, benzyl alcohol, phenethylalcohol, dehydroacetic acid, sorbic acid, etc.

Examples of the antioxidants include sulfite, ascorbic acid, etc.

The MCH antagonist and the pharmaceutical composition of the present invention can be safely administered orally or parenterally (e.g. by local, rectal and intravenous administration) in various dosage forms, for example, as oral drugs such as tablets (including sugar-coated tablets and film-coated tablets), powders, granules, capsules (including soft capsules), solutions; and parenteral preparations such as injectable preparations (e.g. preparations for subcutaneous injections, intravenous injections, intramuscular injections, intraperitoneal injections, etc.), external preparations (e.g. nasal preparations, percutaneous preparations, ointments, etc.), suppositories (e.g. rectal suppositories, vaginal suppositories, etc.), sustained-release preparations (e.g. sustained-release microcapsules, etc.), pellets, drip infusions, etc.

The content of compound (I) in the MCH antagonist of the present invention and the content of compound (I') in the pharmaceutical composition of the present invention are, for example, about 0.1 to 100% by weight based on the total weight of the MCH antagonist or pharmaceutical composition, respectively.

The dose of the MCH antagonist and the pharmaceutical composition of the present invention can be appropriately selected depending on the subject of administration, route of administration, disease, etc.

For example, the dose per day when the MCH antagonist or the pharmaceutical composition of the present invention is orally administered to an adult obesity patient (body weight: about 60 kg), is about 0.1 to about 500 mg, preferably about 1 to about 100 mg, more preferably about 5 to about 100 mg, in terms of compound (I) or compound (I'), each of which is an active ingredient. These amounts can be divided into one to several doses per day for administration.

The MCH antagonist and pharmaceutical composition of the present invention can be used in combination with other concomitant drugs which do not interfere with the MCH antagonist and pharmaceutical composition of the present invention, for the purpose of "strengthening of therapeutic effect against obesity", "reduction of dose of MCH antagonist", etc. Examples of the concomitant drugs include a "agents for treating diabetes", "agents for treating diabetic complications", "agents for treating obesity other than MCH antagonists", "agents for treating hypertension", "agents for treating hyperlipidemia (agents for treating arteriosclerosis)", "agents for treating arthritis", "antianxiety agents", "antidepressant", etc. Two or more kinds of these concomitant drugs can be combined in an appropriate ratio for use.

Examples of the above "agents for treating diabetes" include insulin sensitizers, insulin secretion enhancers, biguanides, insulins, α-glucosidase inhibitors, β3 adrenaline receptor agonists, etc.

Examples of the insulin sensitizers include pioglitazone or its salt (preferably hydrochloride), troglitazone, rosiglitazone or its salt (preferably maleate), JTT-501, GI-262570, MCC-555, YM-440, DRF-2593, BM-13-1258, KRP-297, R-119702, etc.

Examples of the insulin secretion enhancers include sulfonylureas. Specific examples of the sulfonylureas include tolbutamide, chlorpropamide, trazamide, acetohexamide, glyclopyramide and its ammonium salt, glibenclamide, gliclazide, glimepiride, etc.

Other than the above, examples of insulin secretion enhancers include repaglinide, nateglinide, mitiglinide (KAD-1229), JTT-608, etc.

Examples of biguamides include metformin, buformin, phenformin, etc.

Examples of insulins include animal insulins extracted from bovine or porcine pancreas; semi-synthetic human insulin which is enzymatically synthesized from insulin extracted from porcine pancreas; human insulin synthesized by genetic engineering, using *Escherichia coli* and yeast; etc. As insulin, also employed are insulin-zinc containing 0.45 to 0.9 (w/w)% of zinc; protamine-insulin-zinc produced from zinc chloride, protamine sulfate and insulin; etc. In addition, insulin can be an insulin fragment or derivative (e.g. INS-1, etc.).

Insulin can also include various types such as ultra immediate action type, immediate action type, two-phase type, intermediate type, prolonged action type, etc., and these can be selected depending on the pathological conditions of patients.

Examples of α-glucosidase inhibitors include acarbose, voglibose, miglitol, emiglitate, etc.

Examples of β3 adrenaline receptor agonists include AJ-9677, BMS-196085, SB-226552, AZ40140, etc.

Other than the above, examples of the "agents for treating diabetes" include ergoset, pramlintide, leptin, BAY-27-9955, etc.

Examples of the above "agents for treating diabetic complications" include aldose reductase inhibitors, glycation inhibitors, protein kinase C inhibitors, etc.

Examples of aldose reductase inhibitors include torulestat; eparlestat; imirestat; zenarestat; SNK-860; zopolrestat; AR1-509; AS-3201, etc.

Examples of glycation inhibitors include pimagedine. Examples of protein kinase C inhibitors include NGF, LY-333531, etc.

Other than the above, examples of "agents for treating diabetic complications" include alprostadil, thiapride hydrochloride, cilostazol, mexiletine hydrochloride, ethyl eicosapentate, memantine, pimagedline (ALT-711), etc.

Examples of the above "agents for treating obesity other than MCH antagonists" include lipase inhibitors and anorectics, etc.

Examples of lipase inhibitors include orlistat, etc.

Examples of anorectics include mazindol, dexfenfluramine, fluoxetine, sibutramine, baiamine, etc.

Other than the above, examples of "agents for treating obesity other than MCH antagonists" include lipstatin, etc.

Examples of the above "agents for treating hypertension" include angiotensin converting enzyme inhibitors, calcium antagonists, potassium channel openers, angiotensin II antagonists, etc.

Examples of angiotensin converting enzyme inhibitors include captopril, enarapril, alacepril, delapril (hydrochloride), lisinopril, imidapril, benazepril, cilazapril, temocapril, trandolapril, manidipine (hydrochloride), etc.

Examples of calcium antagonists include nifedipine, amlodipine, efonidipine, nicardipine, etc.

Examples of potassium channel openers include levcromakalim, L-27152, AL0671, NIP-121, etc.

Examples of angiotensin II antagonists include losartan, candesartan cilexetil, valsartan, irbesartan, CS-866, E4177, etc.

Examples of the above "agents for treating hyperlipidemia (agents for treating arteriosclerosis)" include HMG-CoA reductase inhibitors, fibrate compounds, etc.

Examples of HMG-CoA reductase inhibitors include pravastatin, simvastatin, lovastatin, atorvastatin, fluvastatin, lipantil, cerivastatin, itavastatin, ZD-4522, or their salts (e.g. sodium salts, etc.), etc.

Examples of fibrate compounds include bezafibrate, clinofibrate, clofibrate, simfibrate, etc.

Examples of the above "agents for treating arthritis" include ibuprofen, etc.

Examples of the above "antianxiety agents" include chlordiazepoxide, diazepam, oxozolam, medazepam, cloxazolam, bromazepam, lorazepam, alprazolam, fludiazepam, etc.

Examples of the above "antidepressants" include fluoxetine, fluvoxamine, imipramine, paroxetine, sertraline, etc.

The timing of administration of the above concomitant drugs is not limited. The MCH antagonist or pharmaceutical composition and the concomitant drugs can be administrated to the subject simultaneously or at staggered times.

The dosages of the concomitant drugs can be determined in accordance with clinically used dosages, and can be appropriately selected according to the subject of administration, route of administration, diseases and combinations of drugs, etc.

The administration forms for the concomitant drugs are not particularly limited as long as the MCH antagonist or the pharmaceutical composition are used in combination with a concomitant drugs at the time of administration. Examples of such administration forms includes 1) administration of a single preparation obtained by simultaneous preparation of MCH antagonist or pharmaceutical composition together with concomitant drugs, 2) simultaneous administration of two kinds of preparations obtained by separate preparation of MCH antagonist or pharmaceutical composition, and concomitant drugs, through the same route of administration, 3) staggered administration of two kinds of preparations obtained by separate preparation of MCH antagonist or pharmaceutical composition, and concomitant drugs, through the same route of administration, 4) simultaneous administration of two kinds of preparations obtained by separate preparation of MCH antagonist or pharmaceutical composition, and concomitant drugs, through different routes of administration, 5) staggered administration of two kinds of preparations obtained by separate preparation of MCH antagonist or pharmaceutical composition, and concomitant drugs, through different routes of administration (for example, administration of MCH antagonist or pharmaceutical composition; and concomitant drugs in this order; or administration in reverse order).

The ratio of combination of MCH antagonist or pharmaceutical composition with concomitant drugs can be appropriately selected in accordance with the subject of administration, route of administration and diseases, etc.

BEST MODE FOR CARRYING OUT THE INVENTION

The present invention will be explained further in detail by the following Reference Examples, Examples, Preparation Examples, and Experimental Examples. However, these do not limit the present invention, and they can be changed within the scope that does not deviate from the scope of the present invention.

In the following Reference Examples and Examples, "room temperature" means 0 to 30° C. Anhydrous magnesium sulfate or anhydrous sodium sulfate was used to dry the organic layer. "%" means percent by weight, unless otherwise specified.

Infrared absorption spectra were determined by the diffuse reflectance method, using fourier transform type infrared spectrophotometer.

FABMS (pos) is mass spectrum determined by the (+) method, in Fast Atom Bombardment Mass Spectrometry.

Other symbols used in the description have the following meanings.

s: singlet
d: doublet
t: triplet
q: quartet
m: multiplet
br: broad
J: coupling constant
Hz: Hertz
$CDCl_3$: Deuterated chloroform
DMSO-$d_6$: Deuterated dimethylsulfoxide
THF: tetrahydrofuran
DMF: N,N-dimethylformamide
DMSO: dimethylsulfoxide
WSCD: 1-ethyl-3-(3-dimethylaminopropyl) carbodimide
WSC: 1-ethyl-3-(3-dimethylaminopropyl) carbodimide hydrochloride
$^1$H-NMR: proton nuclear resonance
 (Free substances were usually measured in $CDCl_3$.)
IR: infrared absorption spectrum
Me: methyl
Et: ethyl
HOBt: 1-hydroxy-1H-benzotriazole
IPE: diisopropyl ether
DMAP: 4-dimethylaminopyridine In this specification and drawings, when bases and amino acids are shown by codes, these codes are based on those by the IUPAC-IUB Commission on Biochemical Nomenclature or common codes in the concerned fields. Examples of these codes are shown below. Also, where some optical isomers of amino acids can exist, the L form is shown unless otherwise specified.

DNA: deoxyribonucleic acid
cDNA: complementary deoxyribonucleic acid
A: adenine
T: thymine
G: guanine
C: cytosine
RNA: ribonucleic acid
mRNA: messenger ribonucleic acid DATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediamine tetraacetic acid
SDS: sodium dodecyl sulfate
EIA: enzyme immunoassay
Gly: glycine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Tro: tryptophan
Pro: proline
Asn: asparagine
Gln: glutamine
pGl: pyroglutamine
Me: methyl group
Et: ethyl group
Bu: butyl group
Ph: phenyl group
TC: thiazolidine-4(R)-carboxamide group Substituents, protecting groups and reagents frequently used in this specification, are shown by the following symbols.
Tos: p-toluenesulfonyl
CHO: formyl
Bzl: benzyl
Cl$_2$Bzl: 2,6-dichlorobenzyl
Bom: benzyloxymethyl
Z: benxyloxycarbonyl
Cl-Z: 2-chlorobenzyloxycarbonyl
Br-Z: 2-bromobenzyloxycarbonyl
Boc: t-butoxycarbonyl
DNP: dinitrophenol
Trt: trityl
Bum: t-butoxymethyl
Fmoc: N-9-fluorenylmethoxycarbonyl
HOBt: 1-hydroxybenztriazole
HOOBt: 3,4-dihydro-3-hydroxy-4-oxo-1,2,3-benzotriazine
HONB: 1-hydroxy-5-norbornene-2,3-dicarbodiimide
DCC: N,N'-dicyclohexylcarbodiimide
SEQ ID NO in the SEQUENCE LISTING in the specification of the present application shows the following sequences.
[SEQ ID NO: 1] shows a synthetic DNA used for screening of cDNA coding rat SLC-1.
[SEQ ID NO: 2] shows a synthetic DNA used for screening of cDNA coding rat SLC-1.
[SEQ ID NO: 3] shows an entire amino acid sequence of rat SLC-1.
[SEQ ID NO: 4] shows an entire base sequence of rat SLC-1cDNA wherein Sal I recognition sequence was added to the 5' side, and Spe I recognition sequence was added to the 3' side.
[SEQ ID NO: 5] shows riboprobe used to determine the quantity of SLC-1 mRNA expressed in each clone of rat SLC-1 expression. CHO cells.
[SEQ ID NO: 6] shows a synthetic DNA used to obtain cDNA for coding of human SLC-1.
[SEQ ID NO: 7] shows a primer used to make double-strand cDNA for coding human SLC-1.
[SEQ ID NO: 8] shows an entire base sequence of cDNA for coding human SLC-1.
[SEQ ID NO: 9] shows an entire amino acid sequence of human SLC-1.
[SEQ ID NO: 10] shows a synthetic DNA used for screening of cDNA for coding human SLC-1(S).
[SEQ ID NO: 11] shows a synthetic DNA used for screening of cDNA for coding human SLC-1(S).
[SEQ ID NO: 12] shows a synthetic DNA used for screening of cDNA for coding human SLC-1(L).
[SEQ ID NO: 13] shows a synthetic DNA used for screening of cDNA for coding human SLC-1(L).
[SEQ ID NO: 14] shows an entire base sequence of human SLC-1(S) cDNA wherein Sal I recognition sequence was added to the 5' side, and Spe I recognition sequence was added to the 3' side.
[SEQ ID NO: 15] shows an entire base sequence of human SLC-1(L) cDNA wherein Sal I recognition sequence was added to the 5' side, and Spe I recognition sequence was added to the 3' side.
[SEQ ID NO: 16] shows riboprobe used to determine the quantity of SLC-1 mRNA expressed in each clone of human SLC-1(S) expression CHO cells and SLC-1(L) expression CHO cells.

Transformant *Escherichia coli* DH10B/phSLC1L8 transformed by plasmid containing DNA which codes the base sequence shown by SEQ ID NO: 9, obtained in Reference Example 1-6, has been deposited with National Institute of Bioscience and Human-Technology (NIBH), Agency of Industrial Science and Technology, Ministry of International Trade and Industry, under accession of number FERM BP-6632 since Feb. 1, 1999; and with the Institute for Fermentation, Osaka, Japan (IFO), under accession number of IFO 16254 since Jan. 21, 1999.

EXAMPLES

Reference Example 1

Tert-butyl 6-[(N,N-dimethylamino)methyl]-2-naphthylcarbamate

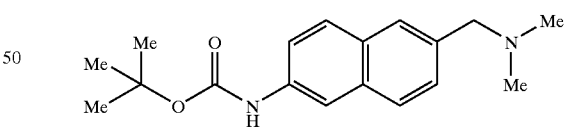

1) 2,6-naphthalenedicarboxylic acid dimethyl ester (26.0 g, 106 mmol) was dissolved in N,N-dimethylformamide (500 ml), and a 1N aqueous sodium hydroxide solution (106 ml) was added dropwise thereto at 100° C. over 30 minutes. After stirred for 3 hours, the solvent was distilled off under reduced pressure, water was added to the residue and the insolubles were filtered off. Concentrated hydrochloric acid (9 ml) was added to the filtrate, the precipitated crude product was filtered, washed with water, and recrystallized from hot methanol to obtain 6-(methoxycarbonyl)-2-naphthalenecarboxylic acid (14.6 g) as a white powder.

$^1$H-NMR (DMSO-d$_6$) δ: 3.94 (3H, s), 8.06 (2H, m), 8.24 (2H, m), 8.69 (2H, s).

2) The 6-(methoxycarbonyl)-2-naphthalenecarboxylic acid (5.00 g, 21.7 mmol) obtained in the above 1) and triethylamine (3.93 ml, 28.2 mmol) were dissolved in tert-butylalcohol (55 ml), diphenylphosphoryl azide (5.62 ml, 26.1 mmol) was added thereto, and the mixture was stirred at room temperature for 30 minutes and at 100° C. for 6 hours. To the reaction solution were added ethyl acetate and an aqueous saturated sodium bicarbonate solution, and the mixture was extracted with ethyl acetate. The extract was washed with a 10% aqueous citric acid solution and an aqueous saturated sodium chloride solution, dried over anhydrous sodium sulfate, and concentrated under reduced pressure. The resulting crude carbamate was dissolved in tetrahydrofuran (50 ml), lithium aluminum hydride (728 mg, 19.2 mmol) was added under ice-cooling, and the mixture was stirred at room temperature for 3 hours. To the reaction solution were added ethyl acetate and a 10% aqueous citric acid solution, the mixture was extracted, the organic layer was washed with an aqueous saturated sodium chloride solution, dried over anhydrous sodium sulfate, concentrated under reduced pressure, the residue was purified by silica gel column chromatography (developing solvent: toluene: ethyl acetate=10:1), and the eluent was crystallized from n-hexane to obtain tert-butyl 6-(hydroxymethyl)-2-naphthylcarbamate (2.26 g) as a white powder.

$^1$H-NMR (DMSO-$d_6$) δ: 1.51 (9H, s), 4.61 (2H, d, J=5.7 Hz), 5.24 (1H, t, J=5.7 Hz), 7.40 (1H, d, J=8.4 Hz), 7.49 (1H, m), 7.70–7.78 (3H, m), 8.07 (1H, s), 9.52 (1H, s). Elemental analysis for $C_{16}H_{19}NO_3$ Calcd: C, 70.31; H, 7.01; N, 5.12. Found: C, 70.36; H, 6.89; N, 5.14.

3) The tert-butyl 6-(hydroxymethyl)-2-naphthylcarbamate (1.00 g, 3.66 mmol) obtained in the above 2) was dissolved in dichloromethane (18 ml), manganese dioxide (1.59 g, 18.3 mmol) was added thereto, and the mixture was stirred at room temperature for 4 hours. The insolubles were filtered, the filtrate was concentrated under reduced pressure., and crystallized from diisopropyl ether to obtain tert-butyl 6-formyl-2-naphthylcarbamate (889 mg) as a white powder.

$^1$H-NMR (CDCl$_3$) δ: 1.57 (9H, s), 6.76 (1H, br), 7.44 (1H, m), 7.83 (1H, d, J=8.4 Hz), 7.92 (2H, m), 8.09 (1H, s), 8.25 (1H, s), 10.10 (1H, s).

4) The tert-butyl 6-formyl-2-naphthylcarbamate (300 mg, 1.11 mmol) obtained in the above 3) and dimethylamine hydrochloride (270 mg, 3.32 mmol) were dissolved in a mixed solution of methanol (2 ml) and tetrahydrofuran (2 ml), sodium cyanotrihydroborate (210 mg, 3.32 mmol) was added thereto, and the mixture was stirred at room temperature for 2 hours. To the reaction solution was added an aqueous potassium carbonate solution, and the mixture was extracted with ethyl acetate. The extract was washed with an aqueous saturated sodium chloride solution, dried over anhydrous sodium sulfate, and concentrated under reduced pressure. The residue was purified by silica gel column chromatography (developing solvent: ethyl acetate:methanol=10:1) to obtain the titled compound (242 mg) as a colorless oil.

$^1$H-NMR (CDCl$_3$) δ: 1.55 (9H, s), 2.27 (6H, s), 3.54 (2H, s), 6.75 (1H, s), 7.32 (1H, dd, J=3.1, 8.7 Hz), 7.42 (1H, d, J=8.4 Hz), 7.64 (1H, s), 7.71 (2H, d-like, J=8.7 Hz), 7.96 (1H, S).

Reference Example 2

Tert-butyl 6-(1-pyrrolidinylmethyl)-2-naphthylcarbamate

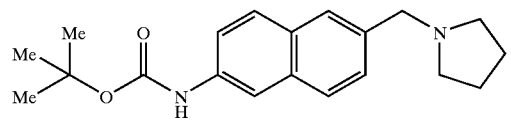

The tert-butyl 6-(hydroxymethyl)-2-naphthylcarbamate (500 mg, 1.83 mmol) obtained in 2) in Reference Example 1 and triethylamine (0.254 ml, 1.83 mmol) were dissolved in tetrahydrofuran (9 ml), methanesulfonyl chloride (0.142 ml, 1.83 mmol) was added under ice-cooling, and the mixture was stirred at room temperature for 30 minutes. The insolubles were filtered, and the filtrate was concentrated under reduced pressure to obtain a mesylate. The resulting mesylate was dissolved in acetonitrile (9 ml), potassium carbonate (758 mg, 5.49 mmol) and pyrrolidine (0.153 ml, 1.83 mmol) were added thereto, and the mixture was stirred at 60° C. for 3 hours. To the reaction solution were added ethyl acetate and water, the mixture was extracted, the organic layer was washed with an aqueous saturated sodium chloride solution, dried over anhydrous sodium sulfate, and concentrated under reduced pressure. The residue was purified by alumina column chromatography (developing solvent: ethyl acetate) to obtain tert-butyl 6-(1-pyrrolidinylmethyl)-2-naphthylcarbamate (388 mg) as a colorless oil.

$^1$H-NMR(CDCl$_3$) δ: 1.55 (9H, s), 1.80 (4H, m), 2.55 (4H, m), 3.74 (2H, s), 6.62 (1H, s), 7.30 (1H, m), 7.45 (1H, m), 7.69 (3H, m), 7.96 (1H, s).

Reference Example 3

Tert-butyl 6-(1-piperidinylmethyl)-2-naphthylcarbamate

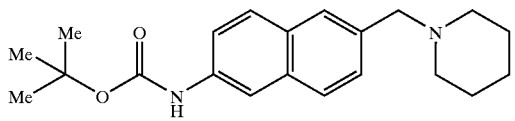

Using the tert-butyl 6-formyl-2-naphthylcarbamate (500 mg, 1.83 mmol) obtained in 3) of Reference Example 1 and piperidine (0.181 ml, 1.83 mmol), the same procedures as those of 4) of. Reference Example 1 were conducted to obtain the titled compound (305 mg) as a colorless oil.

$^1$H-NMR(CDCl$_3$) δ: 1.46 (2H, m), 1.55 (9H, s), 1.58 (4H, m), 2.42 (4H, m), 3.59 (2H, s), 6.60 (1H, s) 7.31 (1H, m), 7.43 (1H, m), 7.64 (1H, m), 7.71 (2H, m), 7.95 (1H, s).

Reference Example 4

N-(4-Bromophenyl)-6-(hydroxymethyl)-2-naphthamide

1) The 6-(methoxycarbonyl)-2-naphthalenecarboxylic acid (1.00 g, 4.34 mmol) obtained in 1) of Reference Example 1,4-bromoaniline (747 mg, 4.34 mmol) and dimethylaminopyridine.(531 mg, 4.34 mmol) were dissolved in N,N-dimethylformamide (10 ml), 1-ethyl-3-(3-dimethylaminopropyl)-carbodiimide hydrochloride (833 mg, 4.34 mmol) was added thereto under ice-cooling, and the mixture was stirred at room temperature for 1 hour and at 50° C. for 2 hours. To the reaction solution was added 1N hydrochloric acid, and the mixture was extracted with ethyl acetate. The extract was washed with a 1N aqueous sodium hydroxide solution and an aqueous saturated sodium chloride solution, dried over anhydrous sodium sulfate, and concentrated under reduced pressure. The residue was purified by alumina column chromatography (developing solvent: ethyl acetate), and the eluent was crystallized from ethyl acetate to obtain methyl 6-[(4-bromoanilino) carbonyl]-2-naphthoate (954 mg) as a white powder.

$^1$H-NMR (DMSO-$d_6$) δ: 3.95 (3H, s), 7.58 (2H, d, J=8.6 Hz), 7.82 (2H, d, J=8.6 Hz), 8.07 (2H, d, J=8.6 Hz), 8.22 (1H, d, J=8.6 Hz), 8.29 (1H, d, J=8.6 Hz), 8.63 (1H, s), 8.72 (1H, s), 10.64 (1H, s).

2) Methyl 6-[(4-bromoanilino)carbonyl]-2-naphthoate (900 mg, 2.34 mmol) obtained in the above 1) was dissolved in tetrahydrofuran (10 ml), lithium aluminum hydride (178 mg, 4.68 mmol) was added thereto under ice-cooling, and the mixture was stirred at room temperature for 2 hours. To the reaction solution were added ethyl acetate and 1N hydrochloric acid, and the mixture was extracted with ethyl acetate. The extract was washed with an aqueous saturated sodium bicarbonate solution and an aqueous saturated sodium chloride solution, dried over anhydrous sodium sulfate, and concentrated under reduced pressure. Chloroform was added to the residue to effect crystallization to obtain the titled compound (349 mg) as a white powder.

$^1$H-NMR (DMSO-$d_6$) δ: 4.71 (2H, d, J=5.6 Hz), 5.41(1H, t, J=5.6 Hz), 7.56 (3H, m), 7.82 (2H, d, J=8.4 Hz), 7.92 (1H, s), 8.02 (3H, m), 8.54 (1H, s), 10.53 (1H, s).

Reference Example 5

N-[2-(Hydroxymethyl)-6-quinolinyl]acetamide

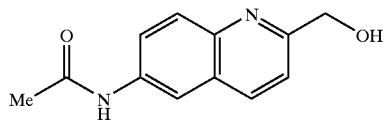

1) 6-amino-2-methylquinoline (1.02 g, 6.45 mmol) was dissolved in pyridine (30 ml), acetic anhydride (0.913 ml, 9.67 mmol) was added thereto, and the mixture was stirred at room temperature for 3 hours. The solvent was distilled off under reduced pressure, and diisopropyl ether was added thereto for crystallization, to obtain N-(2-methyl-6-quinolinyl)acetamide (1.20 g) as white powders.

$^1$H-NMR (CDCl$_3$) δ: 2.22 (3H, s), 2.71 (3H, s), 7.25 (1H, m), 7.52 (1H, m), 7.95 (2H, m), 8.10 (1H, s), 8.30 (1H, s).

2) The N-(2-methyl-6-quinolinyl)acetamide (1.20 g, 5.99 mmol) obtained in the above 1) was dissolved in chloroform (30 ml), m-chloroperbenzoic acid (2.48 g, 7.19 mmol) was added thereto, and the mixture was stirred at room temperature for 3 hours. The solvent was distilled off under reduced pressure, ethyl acetate was added to the residue, and the precipitated powders were filtered to obtain N-(2-methyl-1-oxide-6-quinolinyl)acetamide (1.06 g) as a white powder.

$^1$H-NMR (DMSO-$d_6$) δ: 2.12 (3H, s), 2.53 (3H, s), 7.51 (1H, d, J=8.4 Hz), 7.76 (2H, m), 8.40 (1H, s), 8.48 (1H, d, J=9.3 Hz), 10.36 (1H, s).

3) The N-(2-methyl-1-oxide-6-quinolinyl)acetamide (4.64 g, 21.5 mmol) obtained in the above 2) was dissolved in acetic anhydride (110 ml), and the solution was stirred at 80° C. for 4 hours. The solvent was distilled off under reduced pressure, and the residue was purified by alumina column chromatography (developing solvent: ethyl acetate) to obtain an oil. The resulting oil was dissolved in methanol (110 ml), a 1N aqueous sodium hydroxide solution (21.5 ml) was added thereto under ice-cooling, and the mixture was stirred at room temperature for 1 hour. The solvent was distilled off under reduced pressure. The resulting residue was purified by alumina column chromatography (developing solvent: ethyl acetate:methanol=5:1), and the eluate was crystallized from ethyl acetate-isopropyl ether (1:3) to obtain the titled compound (2.65 g) as white powders.

$^1$H-NMR (CD$_3$OD) δ: 2.23 (3H, s), 4.89 (2H, s), 7.68 (1H, d, J=8.7 Hz), 7.78 (1H, d, J=8.7 Hz), 7.95 (1H, d, J=8.7 Hz), 8.27 (1H, d, J=8.7 Hz), 8.33 (1H, s).

Reference Example 6

N-[2-(Chloromethyl)-6-quinolinyl]acetamide Hydrochloride

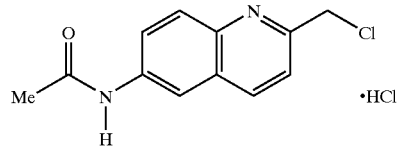

To the N-[2-(hydroxymethyl)-6-quinolinyl]acetamide (1.00 g, 4.62 mmol) obtained in Reference Example 5 was added thionyl chloride (23 ml) under ice-cooling, and the mixture was stirred for 2 hours. The reaction solution was concentrated under reduced pressure, and the resulting residue was washed with ethyl acetate to obtain the titled compound (900 mg) as a powder.

$^1$H-NMR (CD$_3$OD) δ: 2.23 (3H, s), 5.12 (2H, s), 8.08 (1H, d, J=8.4 Hz), 8.17 (2H, s-like), 8.74 (1H, s), 9.01 (1H, d, J=8.4 Hz).

Reference Example 7

2-(Chloromethyl)-6-quinolinylamine Dihydrochloride

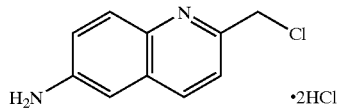

To the N-[2-(chloromethyl)-6-quinolinyl]acetamide hydrochloride (900 mg, 3.32 mmol) obtained in Reference Example 6 was added 5N hydrochloric acid (17 ml), and the mixture was stirred at 100° C. for 2 hours. The reaction solution was concentrated under reduced pressure, and the resulting residue was washed with tetrahydrofuran to obtain the titled compound (849 mg) as powders.

$^1$H-NMR (CD$_3$OD) δ: 5.07 (2H, s), 7.42 (1H, d, J=2.4 Hz), 7.71 (1H, dd, J=2.4, 9.0 Hz), 7.95 (1H, d, J=8.4 Hz), 8.06 (1H, d, J=9.0 Hz), 8.78 (1H, d, J=8.4 Hz).

Reference Example 8

4'-Chloro-N-[2-(chloromethyl)-6-quinolinyl][1,1'-biphenyl]-4-carboxamide

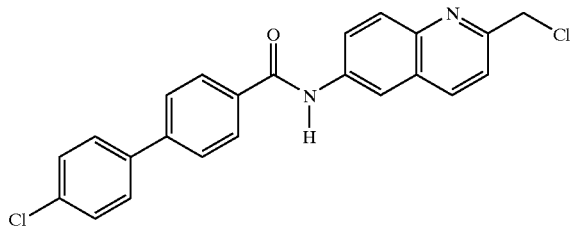

Using the 2-(chloromethyl)-6-quinolinylamine dihydrochloride obtained in Reference Example 7 and 4'-chloro[1,1'-biphenyl]-4-carboxylic acid, the same procedures as those for an amidation reaction using WSC of Example 1 were conducted to obtain the titled compound as powders.

$^1$H-NMR (DMSO-$d_6$) δ: 4.95 (2H, s), 7.58 (2H, d, J=8.4 Hz), 7.66 (1H, d, J=8.4 Hz), 7.82 (2H, d, J=8.4 Hz), 7.89 (2H, d, J=7.8 Hz), 8.01 (1H, d, J=9.0 Hz), 8.09 (1H, m), 8.13 (2H, d, J=7.8 Hz), 8.41 (1H, d, J=8.4 Hz), 8.61 (1H, s), 10.67 (1H, s).

Reference Example 9

2-(1-Pyrrolidinylmethyl)-6-quinolinylamine

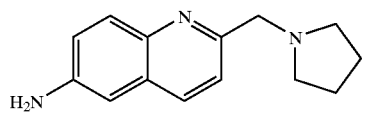

To the N-[2-(1-pyrrolidinylmethyl)-6-quinolinyl]acetamide (5.53 g, 20.5 mmol) obtained in 1) of Example 7 was added concentrated hydrochloric acid (100 ml), the mixture was stirred at 110° C. for 1 hour, and the solvent was distilled off under reduced pressure. To the resulting residue was added ethyl acetate, the mixture was washed with an aqueous potassium carbonate solution and an aqueous saturated sodium chloride solution, dried over anhydrous sodium sulfate, and the solvent was distilled off under reduced pressure to obtain the titled compound (4.56 g) as a powder from ethyl acetate-hexane.

$^1$H-NMR (PMSO-$d_6$) δ: 1.83 (4H, m), 2.62 (4H, m), 3.90 (2H, s), 3.92 (2H, br), 6.92 (1H, d, J=2.8 Hz), 7.15 (1H, dd, J=2.8, 8.6 Hz), 7.48 (1H, d, J=8.6 Hz), 7.88 (1H, d, J=2.8 Hz), 7.92 (1H, d, J=8.6 Hz). m.p.: 102–104° C.

Reference Example 10

N-[2-[(Diisopropylamino)methyl]-6-quinolinyl]acetamide

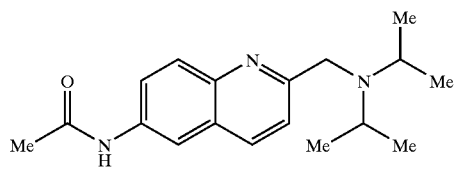

Using the N-[2-(hydroxymethyl)-6-quinolinyl]acetamide obtained in Reference Example 5, the same procedures as those of 1) of Example 6 were conducted to obtain the titled compound as a powder.

$^1$H-NMR (CDCl$_3$) δ: 1.05 (12H, d, J=6.3 Hz), 2.25 (3H, s), 2.95–3.16 (2H, m), 3.93 (2H, s), 7.40–7.64 (2H, m), 7.80 (1H, d, J=8.4 Hz), 7.95 (1H, d, J=8.4 Hz), 8.05 (1H, d, J=8.1 Hz), 8.28 (1H, br). m.p.: 147–148° C. (crystallization solvent: diethyl ether-hexane)

Reference Example 11

N-[2-[(cis-2,6-Dimethyl-1-piperidinyl)methyl]-6-quinolinyl]acetamide

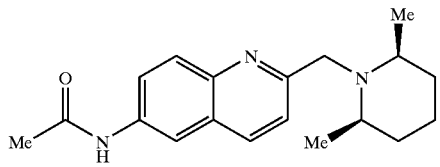

Using the N-[2-(hydroxymethyl)-6-quinolinyl]acetamide obtained in Reference Example 5, the same procedures as those of 1) of Example 6 were conducted to obtain the titled compound as powders.

$^1$H-NMR (CDCl$_3$) δ: 1.02 (6H, d, J=6.2 Hz), 1.25–1.76 (6H, m), 2.24 (3H, s), 2.50–2.70 (2H, m), 4.01 (2H, s), 7.52 (1H, dd, J=2.2 and 8.8 Hz), 7.73 (1H, br), 7.83 (1H, d, J=8.8 Hz), 7.94 (1H, d, J=8.4 Hz), 8.04 (1H, d, J=8.4 Hz), 8.29 (1H, d, J=2.2 Hz). Elemental analysis for $C_{19}H_{25}N_3O\cdot0.5H_2O$ Calcd: C, 71.22; H, 8.18; N, 13.11. Found: C, 71.01; H, 7.81; N, 12.90. m.p.: 120–122° C. (crystallization solvent: ethyl acetate-hexane)

Reference Example 12

2-(Diethylaminoethyl)-6-quinolineamine

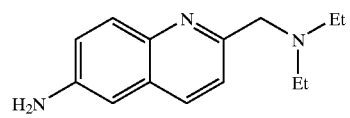

Using the N-[2-(hydroxymethyl)-6-quinolinyl]acetamide obtained in Reference Example 5, the same procedures as those of 1) of Example 6 and Reference Example 9 were conducted to obtain the titled compound as a powder.

$^1$H-NMR (CDCl$_3$) δ: 1.06 (6H, t, J=7.0 Hz), 2.60 (4H, q, J=7.0 Hz), 3.82 (2H, s), 3.91 (2H, br), 6.90 (1H, d, J=2.6 Hz), 7.12 (1H, dd, J=2.6 and 8.8 Hz), 7.54 (1H, d, J=8.4 Hz), 7.86 (2H, d, J=8.8 Hz). m.p.: 93–94° C. (crystallization solvent: diethyl ether-hexane)

Reference Example 13

N-[2-[(2,2,6,6-Tetramethyl-1-piperidinyl)methyl]-6-quinolinyl]acetamide

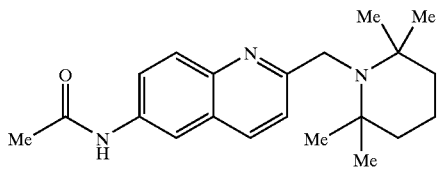

Using the N-[2-(hydroxymethyl)-6-quinolinyl]acetamide obtained in Reference Example 5, the same procedures as those of 1) of Example 6 were conducted to obtain the titled compound as powders.

¹H-NMR (CDCl₃) δ: 1.03 (12H, m), 1.50–1.73 (6H, m), 2.24 (3H, s), 4.07 (2H, s), 7.40–7.57 (2H, m), 7.93 (1H, d, J=8.8 Hz), 8.00 (1H, d, J=8.8 Hz), 8.06 (1H, d, J=8.8 Hz), 8.27 (1H, d, J=2.4 Hz).

Reference Example 14

2-(4-Chlorophenyl)-5-carboxy-1,3-dioxane

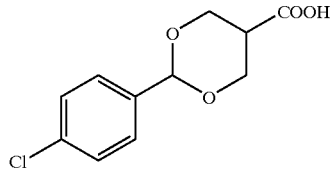

1) A solution of p-chlorobenzaldehyde (3.2 g, 22.7 mmol), diethyl bis(hydroxymethyl)malonate (5.0 g, 22.7 mmol) and p-toluenesulfonic acid monohydrate (0.44 g, 2.3 mmol) in toluene (70 ml) was heated to reflux for 2 hours in a 200 ml eggplant-shaped flask equipped with the Dean-Stark dehydrating apparatus. After the reaction solution was cooled, 100 ml of ethyl acetate was added thereto, the mixture was washed successively with a 1N aqueous sodium hydroxide solution (50 ml), water (50 ml) and an aqueous saturated sodium chloride solution (50 ml), and dried over magnesium sulfate. After the solvent was distilled off under reduced pressure, the residue was subjected to silica gel column chromatography (developing solvent: hexane-ethyl acetate= 4/1) to obtain 2-(4-chlorophenyl)-5,5'-dicarboethoxy-1,3-dioxane (5.9 g, 76%) as colorless crystals.

¹H-NMR (CDCl₃) δ: 1.27(3H, t, J=7.2 Hz), 1.31(3H, t, J=7.2 Hz), 4.13(2H, dd like), 4.20(2H, q, J=7.2 Hz), 4.33 (2H, q, J=7.2 Hz), 4.85(2H, dd like), 5.46(1H, s), 7.32(2H, d, J=10.2 Hz), 7.38(2H, d, J=10.2 Hz). m.p.: 54–55° C.

2) The 2-(4-chlorophenyl)-5,5'-dicarboethoxy-1,3-dioxane (5.8 g, 16.9 mmol) obtained in the above 1) was dissolved in 60 ml of 90% ethanol, potassium hydroxide (3.8 g, 67.7 mmol) was added thereto, and the mixture was heated to reflux for 3 hours. After the solvent was distilled off under reduced pressure, the resulting solid was suspended in diethyl ether (300 ml), and pH was adjusted to 2 with 2N hydrochloric acid under ice-cooling. The organic layer was separated, washed with an aqueous saturated sodium chloride solution (50 ml), and dried over magnesium sulfate. The solvent was distilled off under reduced pressure to obtain 2-(4-chlorophenyl)-5,5'-dicarboxy-1,3-dioxane (4.3 g, 82%) as a yellow solid.

¹H-NMR (CDCl₃) δ: 3.99(2H, d, J=12.2 Hz), 4.50(2H, dd J=4.6 Hz, 12.2 Hz), 5.42(1H, s), 7.35(2H, d, J=9.0 Hz), 7.42(2H, d, J=9.0 Hz). m.p.: 164–165° C.

3) A mixture of the 2-(4-chlorophenyl)-5,5'-dicarboxy-1,3-dioxane (4.3 g, 15 mmol) obtained in the above 2) and triethylamine (20 ml) was heated at 150° C. for 4 hours. After the reaction solution was concentrated under reduced pressure, the residue was dissolved in diethyl ether (200 ml), and pH was adjusted to 2 with 2N hydrochloric acid. The organic layer was washed with an aqueous saturated sodium chloride solution, dried over magnesium sulfate, and the solvent was distilled off under reduced pressure. The resulting solid was washed with a hexane-ethyl acetate solution to obtain the titled compound (3.09 g, 85%) as a pale yellow powder.

FAB(pos): 243[M+H]⁺ m.p.: 183–184° C.

Reference Example 15

6-(1-Piperidinylmethyl)naphthalene-2-amine

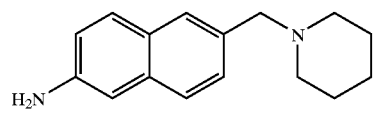

The tert-butyl 6-(1-piperidinylmethyl)-2-naphtylcarbamate (710 mg, 2.09 mmol) obtained in Reference Example 3 was dissolved in trifluoroacetic acid (10 ml), and the solution was stirred at room temperature for 1 hour. The reaction solution was concentrated under reduced pressure, ethyl acetate (50 ml) was added to the residue, the mixture was washed with an aqueous potassium carbonate solution (50 ml) and an aqueous saturated sodium chloride solution (50 ml), and concentrated under reduced pressure to obtain the titled compound (420 mg, 1.75 mmol) as pale orange crystals.

¹H-NMR (DMSO-d₆). δ: 1.38 (2H, m), 1.48 (4H, m), 2.32 (4H, br s), 3.44 (2H, s), 5.30 (2H, br s), 6.79 (1H, s), 6.90 (1H, dd, J=8.5 and 2.0 Hz), 7.23 (1H, d, J=8.3 Hz), 7.43(1H, d, J=8.5 Hz), 7.46 (1H, s), 7.54 (1H, d, J=8.5 Hz).

Reference Example 16

Tert-butyl 6-[(cis-2,6-dimethyl-1-piperidinyl)methyl]-2-naphthylcarbamate

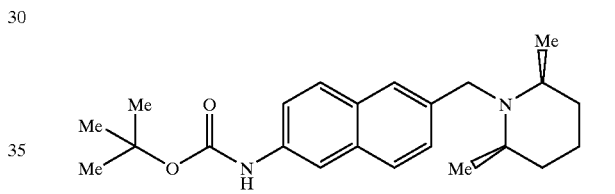

Using the tert-butyl 6-(hydroxymethyl)-2-naphthylcarbamate obtained in 2) of Reference Example 1, the same procedures as those of Reference Example 2 were conducted to obtain the titled compound as a pale yellow oil.

¹H-NMR (CDCl₃) δ: 1.08 (3H, s), 1.10 (3H, s), 1.34 (3H, m), 1.55 (12H, m), 2.53 (2H, m), 3.92 (2H, s), 6.58 (1H, brs), 7.30 (1H, dd, J=2.2 and 8.8 Hz), 7.45 (1H, dd, J=1.5 and 8.5 Hz), 7.71 (3H, m), 7.94 (1H, brs).

Reference Example 17

6-[(cis-2,6-Dimethyl-1-piperidinyl)methyl]naphthalene-2-amine

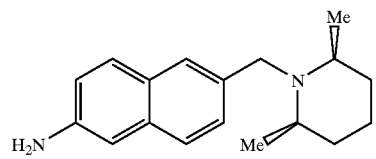

Using the tert-butyl 6-[(cis-2,6-diemthyl-1-piperidinyl) methyl)-2-naphthylcarbamate obtained in Reference Example 16, the same procedures as those of Reference Example 15 were conducted to obtain the titled compound as a pale yellow powder.

¹H-NMR (CDCl₃) δ: 1.11 (3H, s), 1.13 (3H, s), 1.32 (3H, m), 1.56 (3H, m), 2.52 (2H, m), 3.78(1H, brs), 3.91(2H, s), 6.92(1H, dd, J=2.4 and 8.7 Hz), 6.96(1H, m), 7.38(1H, dd, J=1.5 and 8.3 Hz), 7.51(1H, d, J=8.3 Hz), 7.63(1H, d, J=8.5 Hz), 7.68(1H, brs).

Reference Example 18

6-(1-Pyrrolidinylmethyl)naphthalene-2-amine

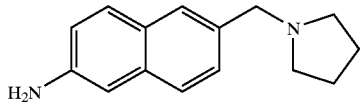

Using the tert-butyl 6-(1-pyrrolidinylmethyl)-1-naphthylcarbamate obtained in Reference Example 2, the same procedures as those of Reference Example 15 were conducted to obtain the titled compound as a colorless powder.

$^1$H-NMR (DMSO-$d_6$) δ: 1.81 (4H, m), 2.56 (4H, m), 3.74 (2H, s), 3.80 (2H, br), 6.93 (2H, dd, J=2.1, 8.4 Hz), 6.97 (1H, d, J=2.1 Hz), 7.38 (1H, dd, J=2.1, 8.4 Hz), 7.55 (1H, d, J=8.4 Hz), 7.61–7.64 (2H, m).

Reference Example 19

6-[(2,2,6,6-Tetramethyl-1-piperidinyl)methyl]-2-naphthaleneamine

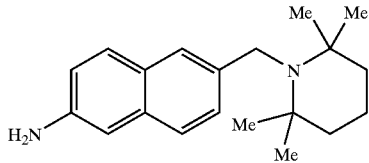

Using the tert-butyl 6-(hydroxymethyl)-2-naphthylcarbamate obtained in 2) of Reference Example 1, the same procedures as those of Reference Example 2 and Reference Example 15 were conducted to obtain the titled compound as a colorless powder.

$^1$H-NMR (DMSO-$d_6$) δ: 1.02 (12H, s), 1.57 (6H, m), 3.78 (2H, br), 3.89 (2H, s), 6.89–6.98 (2H, m), 7.41–7.54 (2H, m), 7.63 (1H, d, J=8.4 Hz), 7.76 (1H, s).

Reference Example 20

N-[6-[(Diisopropylamino)methyl]-2-naphthyl]-2-hydroxy-2-methylpropanamide

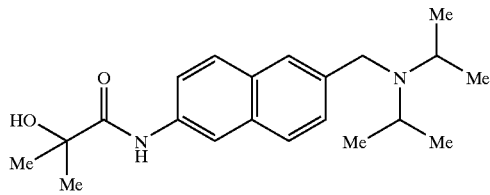

1) To a solution of 6-(hydroxymethyl)-2-naphthol (500 mg, 2.87 mmol) in dimethylacetamide (4 ml) was added sodium hydroxide (344 mg, 8.61 mmol), and the mixture was stirred for 1 hour. 2-bromo-2-methylpropanamide (1.43 g, 8.61 mmol) and potassium iodide (476 mg, 2.87 mmol) were added thereto, and the mixture was stirred at room temperature for 16 hours. To the reaction solution was added water, and the mixture was extracted with ethyl acetate. The extract was washed with a 1N aqueous sodium hydroxide solution and an aqueous saturated sodium chloride solution, and dried over anhydrous sodium sulfate. After the solvent was concentrated under reduced pressure, 2-[[6-(hydroxymethyl)-2-naphthyl]oxy]-2-methylpropanamide (506 mg) was obtained as a colorless powder from isopropyl ether.

$^1$H-NMR (CDCl$_3$) δ: 1.61 (6H, s), 1.85 (1H, t, J=6.0 Hz), 4.84 (2H, d, J=6.0 Hz), 5.57 (1H, br), 6.68 (1H, br), 7.16 (1H, dd, J=2.4, 8.7 Hz), 7.28 (1H, d, J=2.7 Hz), 7.47 (1H, dd, J=1.8, 8.7 Hz), 7.72–7.78 (3H, m).

2) To a solution of the 2-[[6-(hydroxymethyl)-2-naphthyl]oxy]-2-methylpropanamide (200 mg, 0.771 mmol) obtained in the above 1) in dimethylformamide (2.3 ml) and 1,3-dimethyl-3,4,5,6-tetrahydro-2 (1H)-pyrimidinone (0.23 ml) was added sodium hydride (68 mg, 1.70 mmol), and the mixture was stirred at 100° C. for 1 hour. The reaction solution was diluted with ethyl acetate, washed with an aqueous saturated sodium chloride solution, and dried over anhydrous sodium sulfate. After the solvent was concentrated under reduced pressure, the resulting residue was purified by alumina column chromatography (developing solvent: ethyl acetate) to obtain 2-hydroxy-N-[6-(hydroxymethyl)-2-naphthyl]-2-methylpropanamide (50 mg) as a colorless powder from isopropylether:hexane=1:1.

3) To a solution of the 2-hydroxy-N-[6-(hydroxymethyl)-2-naphthyl]-2-methylpropanamide (100 mg, 0.386 mmol) obtained in the above 2) and carbon tetrabromide (192 mg, 0.578 mmol) in dichloromethane (2.3 ml) was added triphenylphosphine (121 mg, 0.463 mmol), and the mixture was stirred at room temperature for 4 hours. The reaction solution was purified by alumina column chromatography (developing solvent: dichloromethane) to obtain an oil. To the resulting oil was added diisopropylamine (3 ml), and the mixture was stirred at 80° C. for 16 hours. The mixture was dissolved in 1N hydrochloric acid, washed with diethyl ether, and potassium carbonate was added to the aqueous layer to adjust to basic. This was extracted with ethyl acetate, washed with an aqueous saturated sodium chloride solution, and dried over anhydrous sodium sulfate. After the solvent was concentrated under reduced pressure, the resulting residue was purified by alumina column chromatography (developing solvent: ethyl acetate), and converted into a powder with hexane to obtain the titled compound (58 mg).

$^1$H NMR (CDCl$_3$) δ: 1.05 (12H, d, J=6.6 Hz), 1.60 (6H, s), 2.24 (1H, s), 3.05 (2H, m), 3.76 (2H, s), 7.50 (2H, m), 7.73 (3H, m), 8.25 (1H, d, J=2.2 Hz), 8.79 (1H, s).

Reference Example 21

1-[(6-Methoxy-2-naphthyl)methyl]pyrrolidine

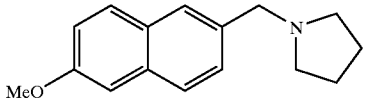

To a solution of 6-methoxy-2-naphthaldehyde (3.00 g, 16.1 mmol) and pyrrolidine (2.69 ml, 32.2 mmol) in tetrahydrofuran (32 ml) and acetic acid (16 ml) was added sodium triacetoxyhydroborate. (6.83 g, 32.2 mmol) at 0° C., and the mixture was stirred at room temperature for 7 hours. The solvent was distilled off under reduced pressure, 1N hydrochloric acid was added to the resulting oil, and the mixture was washed with diethyl ether. An 8N aqueous sodium hydroxide solution was added to the aqueous layer, followed by extraction with ethyl acetate. The extract was washed with an aqueous saturated sodium chloride solution, and dried over anhydrous sodium sulfate. The solvent was concentrated under reduced pressure to obtain the titled compound (3.89 g).

¹H-NMR (CDCl₃) δ: 1.80 (4H, m), 2.54 (4H, m), 3.74 (2H, s), 3.92 (3H, s), 7.13 (2H, m), 7.45 (1H, m), 7.68–7.73 (3H, m).

Reference Example 22

6-(1-Pyrrolidinylmethyl)-2-naphthol Hydrobromide

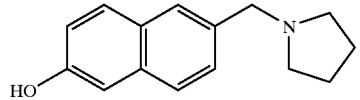

·HBr

A solution of the 1-[(6-methoxy-2-naphthyl)methyl]pyrrolidine (3.63 g, 15.0 mmol) obtained in Reference Example 21 in 48% hydrobromic acid (75 ml) was stirred at 100° C. for 6 hours. The reaction solution was diluted with water, the produced crystals were collected, and washed with water, tetrahydrofuran and diisopropyl ether to obtain the titled compound (2.45 g) as a colorless powder.

¹H-NMR (CDCl₃, free base) δ: 1.80 (4H, m), 2.71 (4H, m), 3.77 (2H, s), 5.20 (1H, br), 6.78 (1H, d, J=2.6 Hz), 7.85 (1H, dd, J=2.6, 8.8 Hz), 7.31 (2H, s-like), 8.43 (1H, d, J=8.8 Hz), 8.56 (1H, s).

Reference Example 23

2-Methyl-1,2,3,4-tetrahydrobenzo[b][1,4]naphthyridine-8-amine

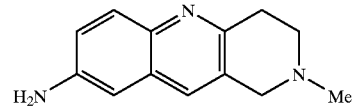

1) To a solution of 2-amino-5-nitrobenzaldehyde (1.00 g, 6.02 mmol) and 1-methyl-4-piperidinone (0.89 ml, 7.22 mmol) in ethanol (108 ml) was added a 4N aqueous sodium hydroxide solution (9.0 ml) at room temperature, and the mixture was stirred at 60° C. for 1 hour. The solvent was distilled off under reduced pressure, ethyl acetate was added to the resulting oil, the mixture was washed with an aqueous saturated sodium chloride solution, and dried over anhydrous sodium sulfate. After the solvent was concentrated under reduced pressure, the resulting residue was purified by alumina column chromatography (developing solvent: ethyl acetate), and converted into powders with diisopropyl ether to obtain 2-methyl-8-nitro-1,2,3,4-tetrahydrobenzo[b][1,6]naphthyridine (430 mg).

¹H-NMR (CDCl₃) δ: 2.55 (3H, s), 2.92 (2H, t, J=6.0 Hz), 3.32 (2H, t, J=6.0 Hz), 3.82 (2H, s), 7.96 (1H, s), 8.10 (1H, d, J=9.0 Hz), 8.40 (1H, dd, J=2.7, 9.0 Hz), 8.71 (1H, d, J=2.7 Hz).

2) A suspension of the 2-methyl-8-nitro-1,2,3,4-tetrahydrobenzo[b][1,6]naphthyridine (413 mg, 1.70 mmol) obtained in the above 1) and 10% palladium-carbon in methanol (9.5 ml) was stirred for 2 hours in the hydrogen atmosphere. After the catalyst was filtered, the filtrate was concentrated under reduced pressure, and converted into powders with diisopropyl ether, to obtain the titled compound (315 mg).

¹H-NMR (CDCl₃) δ: 2.51 (3H, s), 2.86 (2H, t, J=6.0 Hz), 3.20 (2H, t, J=6.0 Hz), 3.73 (2H, s), 3.88 (2H, br), 6.83 (1H, d, J=2.4 Hz), 7.09 (1H, dd, J=2.4, 9.0 Hz), 7.53 (1H, s), 7.80(1H, d, J=9.0 Hz).

Reference Example 24

[5-[(4-Bromobenzyl)oxy]-1H-indol-2-yl]methanol

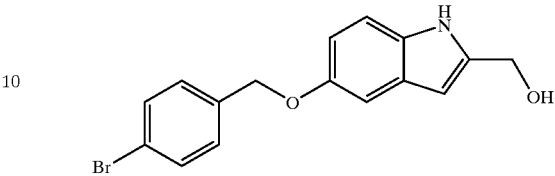

1) A solution of ethyl 5-hydroxy-1H-indole-2-carboxylate (508 mg, 2.48 mmol), 1-bromo-4-(bromomethyl)benzene (681 mg, 2.72 mmol) and potassium carbonate (684 mg, 4.95 mmol) in acetonitrile (12 ml) was stirred at 80° C. for 3 hours. The solvent was distilled off under reduced pressure, ethyl acetate was added to the resulting oil, the mixture was washed with an aqueous saturated sodium chloride solution, and dried over anhydrous sodium sulfate. After the solvent was concentrated under reduced pressure, the resulting residue was purified by alumina column chromatography (developing solvent: ethyl acetate), and converted into powders with isopropyl ether to obtain ethyl 5-[(4-bromobenzyl)oxy]-1H-indole-2-carboxylate (565 mg).

¹H-NMR (DMSO-d₆) δ: 1.33 (3H, t, J=6.9 Hz), 4.32 (2H, t, J=6.9 Hz), 5.08 (2H, s), 6.98–7.04 (2H, m), 7.18 (1H, d, J=2.4 Hz), 7.36 (1H, d, J=8.7 Hz), 7.43 (2H, d, J=8.4 Hz), 7.59 (2H, d, J=8.4 Hz), 11.77 (1H, s).

2) To a solution of the ethyl 5-[(4-bromobenzyl)oxy]-1H-indole-2-carboxylate (300 mg, 0.802 mmol) obtained in the above 1) in tetrahydrofuran (4 ml) was added lithium aluminum hydride (60.8 mg, 1.60 mmol) at 0° C., and the mixture was stirred for 1 hour. Ethyl acetate was added to the reaction solution, the mixture was washed with 1N hydrochloric acid and an aqueous saturated sodium chloride solution, and dried over anhydrous sodium sulfate. After the solvent was concentrated under reduced pressure, the resulting residue was purified by alumina column chromatography (developing solvent: ethyl acetate), and converted into powders with isopropyl ether and hexane to obtain the titled compound (219 mg).

¹H-NMR (DMSO-d₆) δ: 4.55 (2H, d, J=8.4 Hz), 5.05 (2H, s), 5.19 (1H, t, J=8.4 Hz), 6.16 (1H, s), 6.74 (1H, dd, J=8.8, 2.2 Hz), 7.03 (1H, d, J=2.2 Hz), 7.20 (1H, d, J=8.8 Hz), 7.41 (2H, d, J=8.4 Hz), 7.57 (2H, d, J=8.4 Hz), 10.84 (1H, s).

Example 1

4'-Chloro-N-[6-[(N,N-dimethylamino)methyl]-2-naphthyl][1,1'-biphenyl]-4-carboxamide

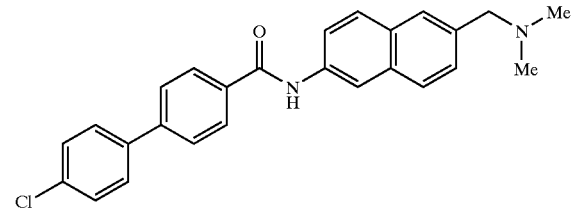

The tert-butyl 6-[(N,N-dimethylamino)methyl]-2-naphthylcarbamate (237 mg, 0.789 mmol) obtained in Reference Example 1 was dissolved in trifluoroacetic acid (4 ml), the solution was stirred at room temperature for 1 hour, and the solvent was concentrated under reduced pressure. To the residue were added ethyl acetate and an aqueous potassium carbonate solution, and the mixture was extracted with ethyl acetate. The extract was washed with an aqueous saturated sodium chloride solution, dried over anhydrous sodium sulfate and concentrated under reduced pressure. The resulting residue, 4'-chlorobiphenylcarboxylic acid (184 mg, 0.789 mmol) and dimethylaminopyridine (96.4 mg, 0.789 mmol) were dissolved in N,N-dimethylformamide (4 ml), 1-ethyl-3-(3-dimethylaminopropyl)carbodiimide hydrochloride (151 mg, 0.789 mmol) was added thereto under ice-cooling, and the mixture was stirred at room temperature for 16 hours. To the reaction solution were added ethyl acetate and an aqueous potassium carbonate solution, the mixture was extracted, the organic layer was washed with an aqueous saturated sodium chloride solution, dried over anhydrous sodium sulfate, and concentrated under reduced pressure. The residue was purified by alumina column chromatography (developing solvent: ethyl acetate), and the insolubles were crystallized from a mixed solution of ethyl acetate and diisopropyl ether (1:5) to obtain the titled compound (207 mg) as a white powder.

$^1$H-NMR (DMSO-d$_6$) δ: 2.19 (6H, s), 3.53 (2H, s), 7.45 (1H, d, J=8.4 Hz), 7.58 (2H, d, J=8.4 Hz), 7.73 (1H, s), 7.85 (7H, m), 8.12 (2H, d, J=8.4 Hz), 8.45 (1H, s), 10.49 (1H, s). FAB(pos): 415.2 [M+H]$^+$ m.p.: 230–231° C.

Example 2

4'-Chloro-N-[6-(1-pyrrolidinylmethyl)-2-naphthyl][1,1'-biphenyl]-4-carboxamide

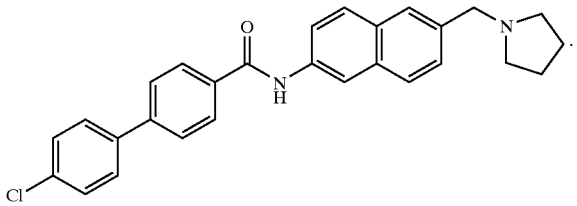

Using the tert-butyl 6-(1-pyrrolidinylmethyl)-2-naphthylcarbamate (0.387 mg, 1.19 mmol) obtained in Reference Example 2 and 4'-chlorobiphenylcarboxylic acid (112 mg, 0.482 mmol), the same procedures as those of Example 1 were conducted to obtain the titled compound (212 mg) as a white powder.

$^1$H-NMR (DMSO-d$_6$) δ: 1.71 (4H, m), 2.47 (4H, m), 3.71 (2H, s), 7.46 (1H, d, J=8.4 Hz), 7.57 (2H, d, J=8.4 Hz), 7.75–7.89 (8H, m), 8.12 (2H, d, J=8.7 Hz), 8.45 (1H, s), 10.48 (1H, s). FAB(pos): 441.1[M+H]$^+$ m.p.: 214–217° C. (crystallization solvent: ethyl acetate-diisopropyl ether)

Example 3

4'-Chloro-N-[6-(1-piperidinylmethyl)-2-naphthyl][1,1'-biphenyl]-4-carboxamide

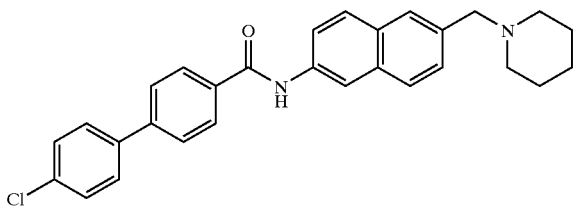

Using the tert-butyl 6-(1-piperidinylmethyl)-2-naphthylcarbamate (100 mg, 0.42 mmol) obtained in Reference Example 3 and 4'-chlorobiphenylcarboxylic acid (116 mg, 0.49 mmol), the same procedures as those of Example 1 were conducted to obtain the titled compound (103 mg) as a white powder.

$^1$H-NMR (DMSO-d$_6$) δ: 1.41–1.51 (6H, m), 2.37 (4H, m), 3.56 (2H, s), 7.46 (1H, d, J=8.4 Hz), 7.58 (2H, d, J=8.7 Hz), 7.72 (1H, s), 7.80 (7H, m), 8.12 (2H, d, J=8.7 Hz), 8.45 (1H, s), 10.48 (1H, s). m.p.: 220–222° C. (crystallization solvent: ethyl acetate-diisopropyl ether)

Example 4

N-(4-Bromophenyl)-6-[(dimethylamino)methyl]-2-naphthamide

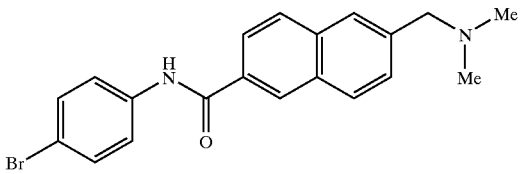

The N-(4-bromophenyl)-6-(hydroxymethyl)-2-naphthamide (349 mg, 0.980 mmol) obtained in Reference Example 4 and triethylamine (0.164 ml, 1.18 mmol) were dissolved in N,N-dimethylformamide (5 ml), methanesulfonyl chloride (0.091 ml, 18 mmol) was added thereto under ice-cooling, and the mixture was stirred for 30 minutes. To the reaction solution were added dimethylamine hydrochloride (160 mg, 96 mmol) and potassium carbonate (406 mg, 2.94 mmol), and the mixture was stirred at 60° C. for 16 hours. To the reaction solution were added ethyl acetate and water, and the mixture was extracted with ethyl acetate. The extract was washed with an aqueous saturated sodium chloride solution, dried over anhydrous sodium sulfate, and concentrated under reduced pressure. To the residue was added diisopropyl ether, followed by crystallization to obtain the titled compound (135 mg) as a white powder.

$^1$H-NMR (DMSO-d$_6$) δ: 2.19 (6H, s), 3.57 (2H, s), 7.57 (3H, m), 7.81 (2H, d, J=9.0 Hz), 7.87 (1H, s), 8.00 (3H, m), 8.54 (1H, s), 10.52 (1H, s).

Example 5

N-(4'-Chloro[1,1'-biphenyl]-4-yl)-6-[(N,N-dimethylamino)methyl]-2-naphthamide

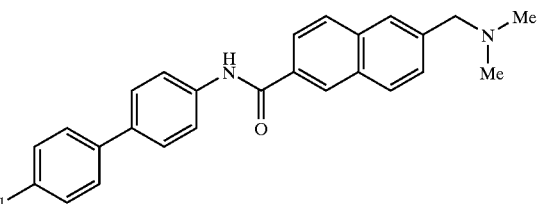

N-(4-Bromophenyl)-6-[(dimethylamino)methyl]-2-naphthamide (128 mg, 0.334 mmol) obtained in Example 4, 4-chlorophenylboronic acid (62.7 mg, 401 mmol) and a 2N aqueous sodium carbonate solution (0.668 ml, 1.34 mmol) were dissolved in a mixed solution of dimethoxyethane (3 ml) and tetrahydrofuran (0.3 ml), tetrakistriphenylphosphinepalladium (11.6 mg, 0.01 mol) was added thereto under the nitrogen atmosphere, and the mixture was stirred at 90° C. for 4 hours. To the reaction solution was added an aqueous saturated sodium chloride solution, and the mixture was extracted with ethyl acetate. The extract was dried over anhydrous sodium sulfate, and concentrated under reduced pressure. The residue was purified by alumina column chromatography (developing solvent: ethyl acetate), and the insolubles were crystallized from a mixed solution of ethyl acetate and diisopropyl ether (1:3) to obtain the titled compound (42 mg) as a white powder.

$^1$H-NMR (DMSO-d$_6$) δ: 2.21 (6H, s), 3.59 (2H, s), 7.51 (2H, d, J=8.7 Hz), 7.59 (1H, d, J=8.1 Hz), 7.72 (4H, m), 7.89 (1H, s), 7.95 (2H, d, J=8.7 Hz), 8.05 (3H, m), 8.58 (1H, s), 10.53 (1H, s). m.p.: 240–242° C.

Example 6

4'-Chloro-N-[2-[(N,N-dimethylamino)methyl]-6-quinolinyl][1,1'-biphenyl]-4-carboxamide

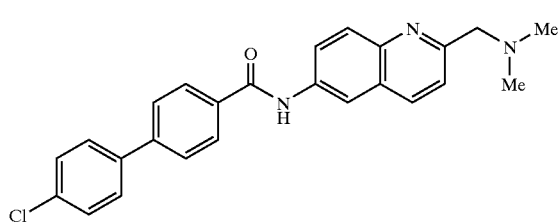

1) The N-[2-(hydroxymethyl)-6-quinolinyl]acetamide (92.3 mg, 0.427 mmol) obtained in Reference Example 5 and triethylamine (0.0712 ml, 0.512 mmol) were dissolved in N,N-dimethylformamide (2 ml), methanesulfonyl chloride (0.0396 ml, 0.512 mmol) was added under ice-cooling, and the mixture was stirred for 30 minutes. To the reaction solution were added dimethylamine hydrochloride (69.6 mg, 0.854 mmol) and potassium carbonate (177 mg, 1.28 mmol), and the mixture was stirred at 60° C. for 16 hours. To the reaction solution was added an aqueous potassium carbonate solution, followed by extraction with ethyl acetate. The extract was washed with an aqueous saturated sodium chloride solution, dried over anhydrous sodium sulfate, and concentrated under reduced pressure. The resulting residue was purified by alumina column chromatography (developing solvent: ethyl acetate) to obtain N-[2-[(N,N-dimethylamino)methyl]-6-quinolinyl]acetamide (71.9 mg) as an oil.

$^1$H-NMR (CDCl$_3$) δ: 2.25 (3H, s), 2.34 (6H, s), 3.76 (2H, s), 7.45–7.58 (3H, m), 8.02 (1H, d, J=9.0 Hz), 8.09 (1H, d, J=8.4 Hz), 8.31 (1H, s).

2) The N-[2-[(N,N-dimethylamino)methyl]-6-quinolinyl]acetamide (1.9 mg, 0.296 mmol) obtained in the above 1) was dissolved in concentrated hydrochloric acid (1.5 ml), and the solution was stirred at 110° C. for 2 hours. The solvent was distilled off under reduced pressure, an aqueous potassium carbonate solution was added to the residue, and the mixture was extracted with ethyl acetate. The extract was washed with an aqueous saturated sodium chloride solution, dried over anhydrous sodium sulfate, and concentrated under reduced pressure. The resulting residue, 4'-chlorobiphenylcarboxylic acid (68.8 mg, 0.296 mmol) and dimethylaminopyridine (36.1 mg, 0.296 mmol) were dissolved in N,N-dimethylformamide (1.5 ml), 1-ethyl-3-(3-dimethylaminopropyl)-carbodiimide hydrochloride (56.6 mg, 0.296 mmol) was added under ice-cooling, and the mixture was stirred at room temperature for 16 hours. To the reaction solution was added an aqueous potassium carbonate solution, and the mixture was extracted with ethyl acetate. The extract was washed with an aqueous saturated sodium chloride solution, dried over anhydrous sodium sulfate, and concentrated under reduced pressure. The resulting residue was purified by alumina column chromatography (developing solvent: ethyl acetate), and crystallized from ethyl acetate-diisopropyl ether (1:5) to obtain the titled compound (60.6 mg) as a white powder.

$^1$H-NMR (DMSO-d$_6$) δ: 2.23 (6H, s), 3.67 (2H, s), 7.58 (3H, m), 7.82 (2H, d, J=8.4 Hz), 7.89 (2H, d, J=8.4 Hz), 7.96 (1H, d, J=9.0 Hz), 8.04 (1H, dd, J=9.0, 2.1 Hz), 8.13 (2H, d, J=8.4 Hz), 8.29 (2H, d, J=8.4 Hz), 8.52 (1H, d, J=2.1 Hz), 10.60 (1H, s). FAB(pos): 416.1[M+H]$^+$ m.p.: 219–221° C.

Example 7

4'-Fluoro-N-[2-(1-pyrrolidinylmethyl)-6-quinolinyl][1,1'-biphenyl]-4-carboxamide

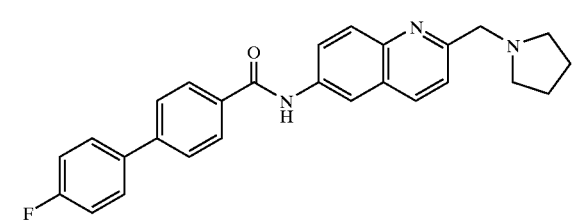

1) Using the N-[2-(hydroxymethyl)-6-quinolinyl]acetamide obtained in Reference Example 5 and pyrrolidine, the same procedures as those of 1) of Example 6 were conducted to obtain N-[2-(1-pyrrolidinylmethyl)-6-quinolinyl]acetamide as a white powder.

$^1$H-NMR (CDCl$_3$) δ: 1.85 (4H, m), 2.24 (3H, s), 2.70 (4H, m), 3.99 (2H, s), 7.58 (2H, m), 7.80 (1H, s), 7.98 (1H, d, J=9.0 Hz), 8.07 (1H, d, J=8.4 Hz), 8.29 (1H, s).

2) Using the N-[2-(hydroxymethyl)-6-quinolinyl]acetamide obtained in the above 1) and 4'-fluorobiphenylcarboxylic acid, the same procedures as those of 2) of Example 6 were conducted to obtain the titled compound as a white powder.

$^1$H-NMR (DMSO-d$_6$) δ: 1.76 (4H, m), 2.61 (4H, m), 3.94 (2H, s.), 7.36 (2H, m), 7.59 (1H, d, J=8.4 Hz), 7.87 (4H, m), 7.99–8.14 (4H, m), 8.30 (1H, d, J=8.4 Hz), 8.54 (1H, d, J=2.0 Hz), 10.61 (1H, s). FAB(pos): 426.1[M+H]$^+$ m.p.: 190–193° C. (crystallization solvent: ethyl acetate-diisopropyl ether)

Example 8

4'-Chloro-N-[2-(1-pyrrolidinylmethyl)-6-quinolinyl][1,1'-biphenyl]-4-carboxamide

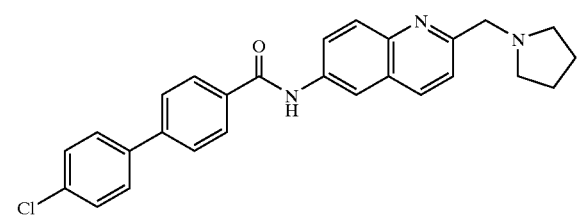

Using the N-[2-(1-pyrrolidinylmethyl)-6-quinolinyl]acetamide obtained in 1) of Example 7 and 4'-chlorobiphenylcarboxylic acid, the same procedures as those of 2) of Example 6 were conducted to obtain the titled compound as a white powder.

$^1$H-NMR (DMSO-d$_6$) δ: 1.77 (4H, m), 2.65 (4H, m), 3.98 (2H, s), 7.59 (3H, m), 7.59 (1H, d, J=8.4 Hz), 7.87 (4H, m), 7.99–8.14 (4H, m), 8.30 (1H, d, J=8.4 Hz), 8.54 (1H, d, J=2.0 Hz), 10.61 (1H, s). FAB(pos): 442.1[M+H]$^+$ m.p.: 200–202° C. (crystallization solvent: ethyl acetate-diisopropyl ether)

Example 9

4'-Fluoro-N-[2-(1-piperidinylmethyl)-6-quinolinyl][1,1'-biphenyl]-4-carboxamide

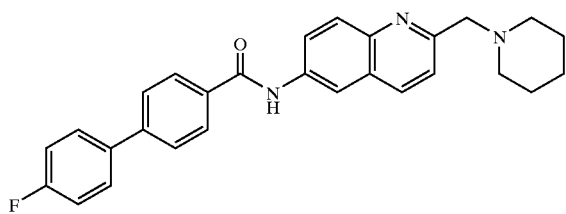

1) Using the N-[2-(hydroxymethyl)-6-quinolinyl] acetamide obtained in Reference Example 5 and piperidine, the same procedures as those of 1) of Example 6 were conducted to obtain N-[2-(1-piperidinylmethyl)-6-quinolinyl]acetamide as a white powder.

$^1$H-NMR (CDCl$_3$) δ: 1.47 (2H, m), 1.64 (4H, m), 2.25 (3H, s), 2.55 (4H, m), 3.83 (2H, s), 7.55 (1H, dd, J=2.4, 9.0 Hz), 7.60 (1H, s), 7.67 (1H, d, J=8.4 Hz), 7.98 (1H, d, J=9.0 Hz), 8.08 (1H, d, J=8.4 Hz), 8.30 (1H, d, J=2.4 Hz).

2) Using the N-[2-(1-piperidinylmethyl)-6-quinolinyl] acetamide obtained in the above 1) and 4'-fluorobiphenylcarboxylic acid, the same procedures as those of 2) of Example 6 were conducted to obtain the titled compound as a white powder.

$^1$H-NMR (DMSO-d$_6$) δ: 1.44 (2H, m), 1.56 (4H, m), 2.50 (4H, m), 3.77 (2H, s), 7.35 (2H, m), 7.60 (1H, d, J=8.7 Hz), 7.81–8.14 (8H, m), 8.30 (1H, d, J=8.4 Hz), 8.54 (1H, d, J=2.0 Hz), 10.61 (1H, s). FAB(pos): 440.2[M+H]$^+$ m.p.: 202–204° C. (crystallization solvent: ethyl acetate-diisopropyl ether)

Example 10

4'-Chloro-N-[2-(1-piperidinylmethyl)-6-quinolinyl][1,1'-biphenyl]-4-carboxamide

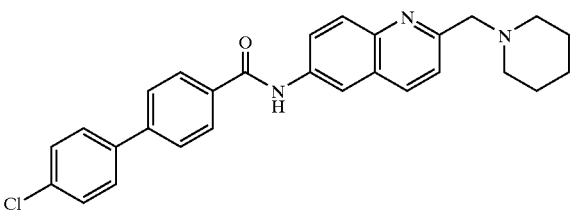

Using the N-[2-(1-piperidinylmethyl)-6-quinolinyl] acetamide obtained in 1) of Example 9 and 4'-chlorobiphenylcarboxylic acid, the same procedures as those of 2) of Example 6 were conducted to obtain the titled compound as a white powder.

$^1$H-NMR (DMSO-d$_6$) δ: 1.47 (2H, m), 1.61 (4H, m), 2.50 (4H, m), 3.33 (2H, s), 7.61 (3H, m), 7.81–7.90 (4H, m), 7.98–8.15 (4H, m), 8.34 (1H, d, J=8.4 Hz), 8.57 (1H, s), 10.65 (1H, s). FAB(pos): 456.1[M+H]$^+$ m.p.: 211–213° C. (crystallization solvent: ethyl acetate-diisopropyl ether)

Example 11

4'-Chloro-N-[2-(4-morpholinylmethyl)-6-quinolinyl][1,1'-biphenyl]-4-carboxamide

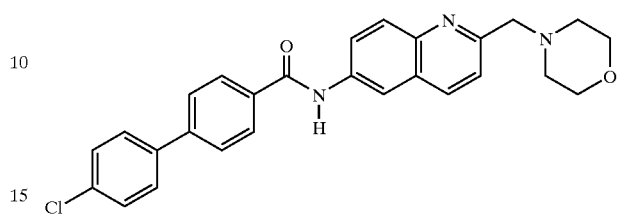

1) Using the N-[2-(hydroxymethyl)-6-quinolinyl] acetamide obtained in Reference Example 5 and piperidine, the same procedures as those of 1) of Example 6 were conducted to obtain N-[2-(4-morpholinylmethyl)-6-quinolinyl]acetamide as a powder.

$^1$H-NMR (CDCl$_3$) δ: 2.25 (3H, s), 2.55 (4H, t, J=4.5 Hz), 3.75 (4H, t, J=4.5 Hz), 3.81 (2H, s), 7.42 (1H, br), 7.51 (1H, dd, J=2.4, 9.0 Hz), 7.60 (1H, d, J=8.4 Hz), 8.01 (1H, d, J=9.0 Hz), 8.09 (1H, d, J=8.4 Hz), 8.32 (1H, d, J=2.4 Hz).

2) Using the N-[2-(4-morpholinylmethyl)-6-quinolinyl] acetamide obtained in the above 1), the same procedures as those of 2) of Example 6 were conducted to obtain the titled compound as a colorless powder.

$^1$H-NMR (DMSO-d$_6$) δ: 2.45 (4H, t, J=4.5 Hz), 3.61 (4H, t, J=4.5 Hz), 3.74 (2H, s), 7.59 (3H, m), 7.82 (2H, d, J=8.4 Hz), 7.88 (2H, d, J=8.4 Hz), 7.97 (1H, d, J=9.0), 8.04 (1H, dd, J=9.0, 2.1 Hz), 8.13 (2H, d, J=8.4 Hz), 8.30 (1H, d, J=8.4 Hz), 8.52 (1H, d, J=2.1 Hz), 10.60 (1H, s). Elemental analysis for $C_{27}H_{24}ClN_3O_2$ Calcd: C, 70.81; H, 5.28; N, 9.18. Found: C, 70.66; H, 5.31; N, 8.90. m.p.: 236–238° C. (crystallization solvent: ethyl acetate-diisopropyl ether)

Example 12

N-[2-(4-Morpholinylmethyl)-6-quinolinyl][1,1'-biphenyl]-4-carboxamide

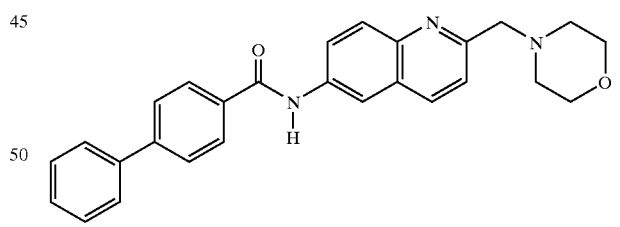

Using the N-[2-(4-morpholinylmethyl)-6-quinolinyl] acetamide obtained in 1) of Example 11, the same procedures as those of 2) of Example 6 were conducted to obtain the titled compound as a colorless powder.

$^1$H-NMR (DMSO-d$_6$) δ: 2.47 (4H, t, J=4.5 Hz), 3.61 (4H, t, J=4.5 Hz), 3.74 (2H, s), 7.44 (1H, m), 7.53 (2H, m), 7.61 (1H, d, J=8.4 Hz), 7.78 (2H, d, J=7.5), 7.88 (2H, d, J=8.4 Hz), 7.97 (1H, d, J=9.0 Hz), 8.04 (1H, dd, J=9.0, 2.1 Hz), 8.12 (1H, d, J=8.4 Hz), 8.30 (1H, d, J=8.4 Hz), 8.53 (1H, d, J=2.1 Hz), 10.59 (1H, s). Elemental analysis for $C_{27}H_{25}N_3O_2 \cdot 0.5H_2O$ Calcd: C, 74.98; H, 6.06; N, 9.72. Found: C, 75.08; H, 6.07; N, 9.80. m.p.: 214–215° C. (crystallization solvent: ethyl acetate-diisopropyl ether)

Example 13

4'-Fluoro-N-[2-(4-morpholinylmethyl)-6-quinolinyl][1,1'-biphenyl]-4-carboxamide

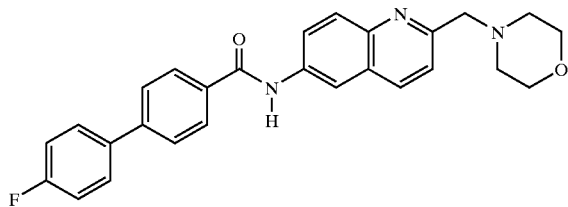

Using the N-[2-(4-morpholinylmethyl)-6-quinolinyl]acetamide obtained in 1) of Example 11, the same procedures as those of 2) of Example 6 were conducted to obtain the titled compound as a colorless powder.

$^1$H-NMR (DMSO-$d_6$) δ: 2.45 (4H, t, J=4.5 Hz), 3.61 (4H, t, J=4.5 Hz), 3.74 (2H, s), 7.35 (2H, m), 7.61 (1H, d, J=8.4 Hz), 7.84 (4H, m), 7.96 (1H, d, J=9.0 Hz), 8.04 (1H, dd, J=9.0, 2.4 Hz), 8.12 (2H, d, J=8.1 Hz), 8.30 (1H, d, J=8.4 Hz), 8.53 (1H, d, J=2.4 Hz), 10.59 (1H, s). Elemental analysis for $C_{27}H_{24}FN_3O_2$ Calcd: C, 73.45; H, 5.48; N, 9.52. Found: C, 73.37; H, 5.36; N, 9.52. m.p.: 211–212° C. (crystallization solvent: ethyl acetate-diisopropyl ether)

Example 14

6-(4-Methylphenyl)-N-[2-(4-morpholinylmethyl)-6-quinolinyl]nicotinamide

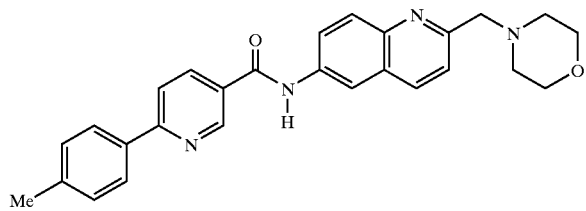

Using the N-[2-(4-morpholinylmethyl)-6-quinolinyl]acetamide obtained in 1) of Example 11, the same procedures as those of 2) of Example 6 were conducted to obtain the titled compound as a colorless powder.

$^1$H-NMR (DMSO-$d_6$) δ: 2.39 (3H, s), 2.45 (4H, t, J=4.5 Hz), 3.61 (4H, t, J=4.5 Hz), 3.75 (2H, s), 7.36 (2H, d, J=8.4 Hz), 7.62 (1H, d, J=8.4 Hz), 8.01 (2H, m), 8.12 (3H, m), 8.31 (1H, d, J=8.4 Hz), 8.42 (1H, dd, J=8.4, 2.4 Hz), 8.52 (1H, d, J=2.4 Hz), 9.23 (1H, d, J=2.4 Hz), 10.72 (1H, s). Elemental analysis for $C_{27}H_{26}N_4O_2 \cdot 0.5H_2O$ Calcd: C, 73.95; H, 5.98; N, 12.78. Found: C, 73.92; H, 5.92; N, 13.01. m.p.: 214–216° C. (crystallization solvent: ethyl acetate-diisopropyl ether)

Example 15

N-[2-[(Dimethylamino)methyl]-6-quinolinyl][1,1'-biphenyl]-4-carboxamide

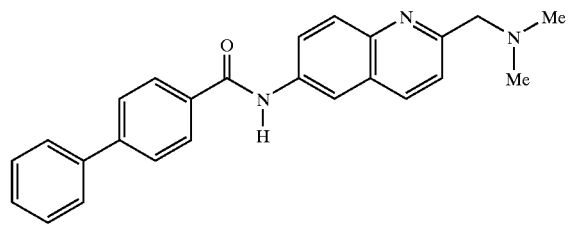

Using the N-[2-[(N,N-dimethylamino)methyl]-6-quinolinyl]acetamide obtained in 1) of Example 6, and biphenylcarboxylic acid, the same procedures as those of 2) of Example 6 were conducted to obtain the titled compound as a colorless powder.

$^1$H-NMR (DMSO-$d_6$) δ: 2.23 (6H, s), 3.66 (2H, s), 7.52 (4H, m), 7.78 (2H, d, J=7.8 Hz), 7.88 (2H, d, J=8.4 Hz), 7.96 (1H, d, J=9.0 Hz), 8.04 (1H, dd, J=9.0, 2.1 Hz), 8.12 (2H, d, J=8.1 Hz), 8.29 (1H, d, J=8.4 Hz), 8.53 (1H, d, J=2.1 Hz), 10.59 (1H, s). Elemental analysis for $C_{25}H_{23}N_3O$ Calcd: C, 78.71; H, 6.08; N, 11.02. Found: C, 78.44; H, 6.07; N, 11.01. m.p.: 191–194° C. (crystallization solvent: ethyl acetate-diisopropyl ether)

Example 16

N-[2-[(Dimethylamino)methyl]-6-quinolinyl]-4'-fluoro[1,1'-biphenyl]-4-carboxamide

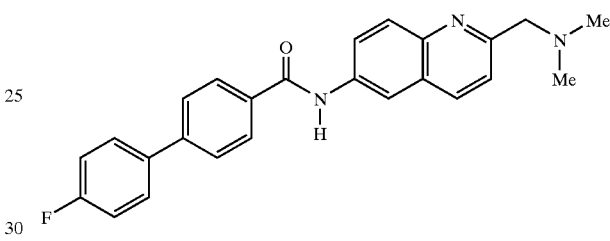

Using the N-[2-[(N,N-dimethylamino)methyl]-6-quinolinyl]acetamide obtained in 1) of Example 6, and 4'-fluorobiphenylcarboxylic acid, the same procedures as those of 2) of Example 6 were conducted to obtain the titled compound as a colorless powder.

$^1$H-NMR (DMSO-$d_6$) δ: 2.23 (6H, s), 3.67 (2H, s), 7.35 (2H, m), 7.58 (1H, d, J=8.4 Hz), 7.84 (4H, m), 7.96 (1H, d, J=9.0 Hz), 8.04 (1H, dd, J=9.0, 2.3 Hz), 8.12 (2H, d, J=8.4 Hz), 8.28 (1H, d, J=8.7 Hz), 8.52 (1H, d, J=2.3 Hz), 10.58 (1H, s). Elemental analysis for $C_{25}H_{22}FN_3O$ Calcd: C, 75.17; H, 5.55; N, 10.52. Found: C, 74.89; H, 5.60; N, 10.52. m.p.: 205–208° C. (crystallization solvent: ethyl acetate-diisopropyl ether)

Example 17

N-[2-[(Dimethylamino)methyl]-6-quinolinyl]-6-(4-methylphenyl)nicotinamide

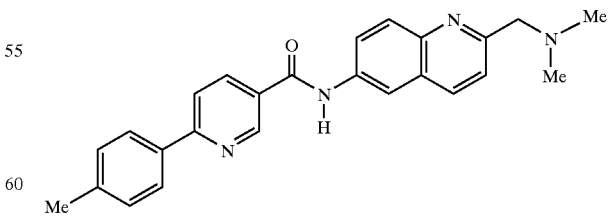

Using the N-[2-[(N,N-dimethylamino)methyl]-6-quinolinyl]acetamide obtained in 1) of Example 6, the same procedures as those of 2) of Example 6 were conducted to obtain the titled compound as a colorless powder.

$^1$H-NMR (DMSO-d$_6$) δ: 2.23 (6H, s), 2.39 (3H, s), 3.67 (2H, s), 7.36 (2H, d, J=8.1 Hz), 7.59 (1H, d, J=8.4 Hz), 8.02 (2H, m), 8.12 (3H, m), 8.30 (1H, d, J=8.7 Hz), 8.42 (1H, dd, J=8.4, 2.4 Hz), 8.51 (1H, s), 9.22 (1H, d, J=2.4 Hz), 10.72 (1H, s). Elemental analysis for C$_{25}$H$_{24}$N$_4$O Calcd: C, 75.73; H, 6.10; N, 14.13. Found: C, 75.44; H, 6.19; N, 14.12. m.p.: 220–222° C. (crystallization solvent: ethyl acetate-diisopropyl ether)

Example 18

4'-Chloro-N-[2-[(2,5-dimethyl-1-pyrrolidinyl)methyl]-6-quinolinyl][1,1'-biphenyl]-4-carboxamide

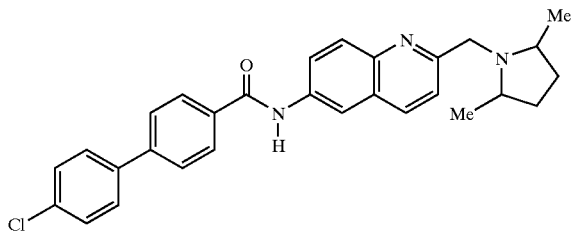

1) Using the N-[2-(hydroxymethyl)-6-quinolinyl]acetamide obtained in Reference Example 5 and piperidine, the same procedures as those of 1) of Example 6 were conducted to obtain N-[2-[(2,5-dimethyl-1-pyrrolidinyl)methyl]-6-quinolinyl]acetamide as a powder.

$^1$H-NMR (CDCl$_3$) δ: 0.99 (6H, d, 6.0 Hz), 1.86 (4H, m), 2.24 (3H, s), 2.72 (2H, m), 3.98 (2H, s), 7.53 (1H, dd, J=2.2, 9.0 Hz), 7.69 (1H, d, J=8.4 Hz), 7.80 (1H, br), 7.97 (1H, d, J=9.0 Hz), 8.03 (1H, d, J=8.4 Hz), 8.29 (1H, s).

2) Using the N-[2-[(2,5-dimethyl-1-pyrrolidinyl)methyl]-6-quinolinyl]acetamide obtained in the above 1), the same procedures as those of 1) of Example 6 were conducted to obtain the titled compound as a colorless powder.

FAB(pos): 470.2[M+H]$^+$

Example 19

N-[2-[(2,5-Dimethyl-1-pyrrolidinyl)methyl]-6-quinolinyl]-4'-fluoro[1,1'-biphenyl]-4-carboxamide

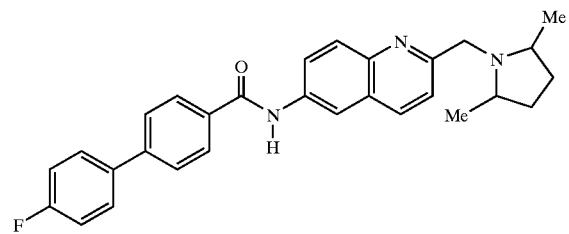

Using the N-[2-[(2,5-dimethyl-1-pyrrolidinyl)methyl]-6-quinolinyl]acetamide obtained in 1) of Example 18, the same procedures as those of 2) of Example 6 were conducted to obtain the titled compound as a colorless powder.

FAB(pos): 454.2[M+H]$^+$

Example 20

N-[2-[(2,5-Dimethyl-1-pyrrolidinyl)methyl]-6-quinolinyl][1,1'-biphenyl]-4-carboxamide

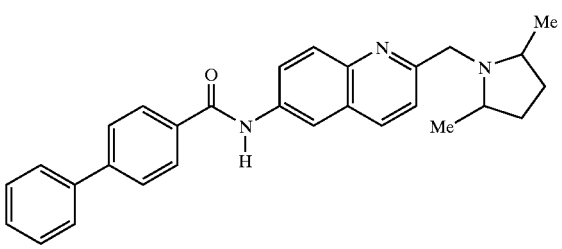

Using the N-[2-[(2,5-dimethyl-1-pyrrolidinyl)methyl]-6-quinolinyl]acetamide obtained in 1) of Example 18, the same procedures as those of 2) of Example 6 were conducted to obtain the titled compound as a colorless powder.

FAB(pos): 436.2[M+H]$^+$

Example 21

4-(4-Methyl-1-piperidinyl)-N-[2-(1-pyrrolidinylmethyl)-6-quinolinyl]benzamide

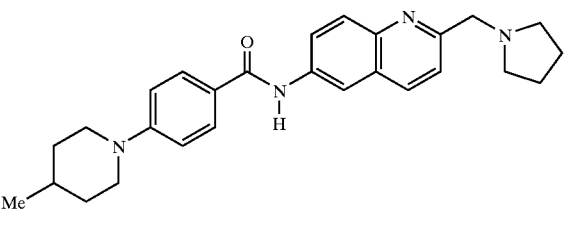

Using the N-[2-(1-pyrrolidinylmethyl)-6-quinolinyl]acetamide obtained in 1) of Example 7, the same procedures as those of 2) of Example 6 were conducted to obtain the titled compound as a colorless powder.

$^1$H-NMR (DMSO-d$_6$) δ: 0.98 (3H, d, J=6.4 Hz), 1.33 (2H, m), 1.59 (1H, m), 1.74 (2H, m), 1.80 (4H, m), 2.62 (4H, m), 2.86 (2H, m), 3.85 (2H, m), 3.94 (2H, s), 6.95 (2H, d, J=9.0 Hz), 7.57 (1H, d, J=8.7 Hz), 7.65 (1H, dd, J=2.4, 8.7 Hz), 7.81 (2H, d, J=9.0 Hz), 7.90 (1H, br), 8.05 (1H, d, J=8.7 Hz), 8.10 (1H, d, J=8.7 Hz), 8.45 (1H, d, J=2.4 Hz). FAB(pos): 429.3[M+H]$^+$ m.p.: 200–202° C. (crystallization solvent: ethyl acetate-diisopropyl ether)

Example 22

4-(2-Oxo-1-piperidinyl)-N-[2-(1-pyrrolidinylmethyl)-6-quinolinyl]benzamide

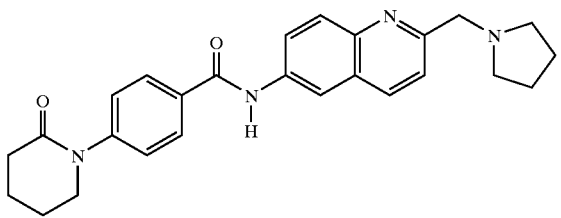

Using the N-[2-(1-pyrrolidinylmethyl)-6-quinolinyl]acetamide obtained in 1) of Example 7, the same procedures as those of 2) of Example 6 were conducted to obtain the titled compound as a colorless powder.

$^1$H-NMR (DMSO-d$_6$) δ: 1.84 (4H, m), 1.98 (4H, m), 2.62 (6H, m), 3.70 (2H, m), 3.94 (2H, s), 7.38 (2H, d, J=8.4 Hz), 7.59 (1H, d, J=8.4 Hz), 7.68 (1H, dd, J=2.3, 9.0 Hz), 7.90 (2H, d, J=8.4 Hz), 8.06 (1H, d, J=9.0 Hz), 8.11 (1H, d, J=8.4 Hz), 8.30 (1H, br), 8.45 (1H, d, J=2.3 Hz). FAB(pos): 429.2[M+H]$^+$ m.p.: 210–212° C. (crystallization solvent: ethyl acetate-diisopropyl ether)

Example 23

4'-Chloro-N-[2-[[(2R,6S)-2,6-dimethyl-1-piperidinyl]methyl]-6-quinolinyl][1,1'-biphenyl]-4-carboxamide

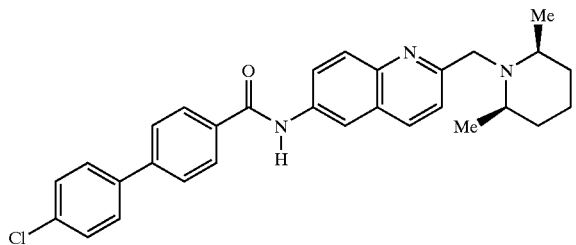

A solution of the 4'-chloro-N-[2-(chloromethyl)-6-quinolinyl][1,1'-biphenyl]-4-carboxamide (100 mg, 0.246 mmol) obtained in Reference Example 8, (2R,6S)-2,6-dimethylpiperidine (0.331 ml, 2.46 mmol) and potassium carbonate (67.9 mg, 0.491 mmol) in dimthylformamide (1.5 ml) was stirred at 80° C. for 3 hours. The reaction solution was concentrated under reduced pressure, and water was added thereto. The resulting precipitates were collected, and washed successively with water, ethanol and isopropyl ether to obtain the titled compound (65 mg) as a powder.

$^1$H-NMR (DMSO-d$_6$) δ: 1.01 (6H, d, J=6.0 Hz), 1.29 (2H, m), 1.61 (4H, m), 2.52 (2H, m), 3.96 (2H, s), 7.59 (2H, d, J=8.4 Hz), 7.75 (1H, d, J=8.4 Hz), 7.83 (2H, d, J=8.4 Hz), 7.90 (2H, d, J=8.4 Hz), 8.00 (2H, m), 8.14 (2H, d, J=8.4 Hz), 8.27 (1H, d, J=8.4 Hz), 8.53 (1H, s), 10.61 (1H, s). FAB (pos): 484[M+H]$^+$ Example 24

4'-Chloro-N-[2-[(4-methyl-1-piperazinyl)methyl]-6-quinolinyl][1,1'-biphenyl]-4-carboxamide

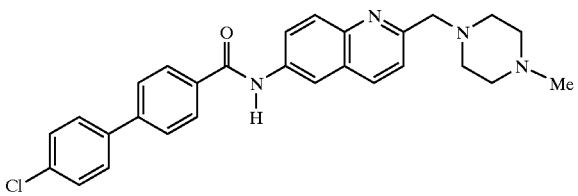

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

$^1$H-NMR (DMSO-d$_6$) δ:2.16 (3H, s), 2.35–2.50 (8H, m), 3.73 (2H, s), 7.58 (3H, m), 7.82 (2H, d, J=8.4 Hz), 7.89 (2H, d, J=8.4 Hz), 7.96 (1H, d, J=9.0 Hz), 8.04 (1H, m), 8.13 (2H, d, J=8.4 Hz), 8.29 (1H, d, J=8.7 Hz), 8.53 (1H, s), 10.61 (1H, s). FAB(pos): 471.2[M+H]$^+$ m.p.: 215° C. (decomposition) (crystallization solvent: ethyl acetate-diisopropyl ether)

Example 25

4'-Chloro-N-[2-[(2-methyl-4,5-dihydro-1H-imidazol-1-yl)methyl]-6-quinolinyl][1,1'-biphenyl]-4-carboxamide

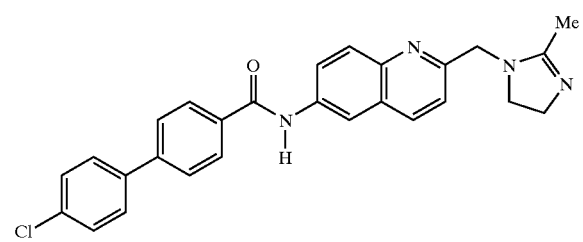

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as colorless a powder.

$^1$H-NMR (DMSO-d$_6$) δ: 1.97 (3H, s), 3.21 (2H, t, J=9.0 Hz), 3.52 (2H, t, J=9.0 Hz), 4.56 (2H, s), 7.46 (1H, d, J=8.4 Hz), 7.58 (2H, d, J=8.4 Hz), 7.82 (2H, d, J=8.4 Hz), 7.89 (2H, d, J=8.4 Hz), 7.97 (1H, d, J=9.0 Hz), 8.07 (1H, dd, J=9.0, 2.1 Hz), 8.13 (2H, d, J=8.4 Hz), 8.34 (1H, d, J=8.4 Hz), 8.56 (1H, d, J=2.1 Hz), 10.63 (1H, s). FAB(pos): 455[M+H]$^+$ Example 26

4'-Chloro-N-[2-(1,3-thiazolidin-3-ylmethyl)-6-quinolinyl][1,1'-biphenyl]-4-carboxamide

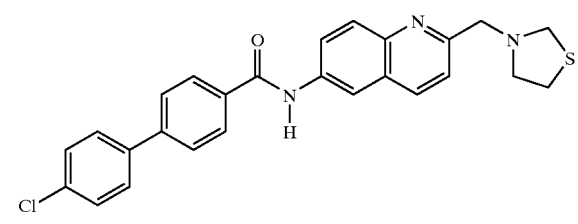

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

$^1$H-NMR (DMSO-d$_6$) δ: 2.94 (2H, t, J=6.0 Hz), 3.12 (2H, t, J=6.0 Hz), 3.78 (2H, s), 4.09 (2H, s), 7.58 (2H, d, J=8.6 Hz), 7.70 (1H, d, J=8.0 Hz), 7.83 (2H, d, J=8.4 Hz), 7.89 (2H, d, J=8.4 Hz), 8.00 (2H, m), 8.14 (2H, d, J=8.6 Hz), 8.34 (1H, d, J=8.8 Hz), 8.56 (1H, s), 10.63 (1H, s). FAB(pos): 460 [M+H]$^+$ Example 27

4'-Chloro-N-[2-[(2,2,6-tetramethyl-1-piperidinyl)methyl]-6-quinolinyl][1,1'-biphenyl]-4-carboxamide

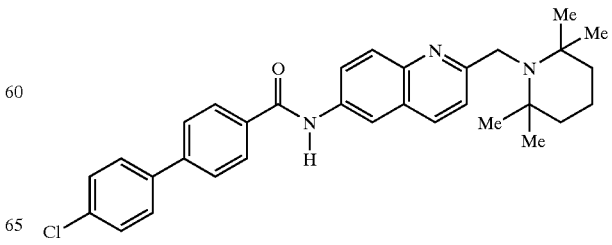

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

$^1$H-NMR (DMSO-d$_6$) δ: 1.02 (12H, s), 1.56 (6H, m), 4.01 (2H, s), 7.59 (2H, d, J=8.4 Hz), 7.90 (6H, m), 7.99 (1H, m), 8.13 (2H, d, J=8.0 Hz), 8.27 (1H, d, J=8.8 Hz), 8.51 (1H, s), 10.59 (1H, s). FAB(pos): 512 [M+H]$^+$ Example 28

4'-Chloro-N-[2-[[4-(2-pyridinyl)-1-piperazinyl]methyl]-6-quinolinyl][1,1'-biphenyl]-4-carboxamide

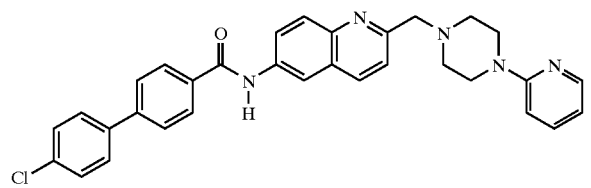

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

$^1$H-NMR (DMSO-d$_6$) δ: 2.36 (4H, m), 3.31 (4H, m), 3.60 (2H, s), 6.43 (1H, m), 6.61 (1H, d, J=8.8 Hz), 7.32–7.48 (4H, m), 7.60–7.71 (4H, m), 7.75–7.95 (5H, m), 8.11 (1H, d, J=8.4 Hz), 8.36 (1H, s), 10.42 (1H, s). FAB(pos): 534 [M+H]$^+$ Example 29

4'-Chloro-N-[2-[[4-(2-methylphenyl)-1-piperidinyl]methyl]-6-quinolinyl][1,1'-biphenyl]-4-carboxamide

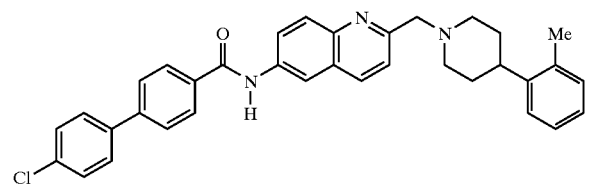

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

$^1$H-NMR (DMSO-d$_6$) δ: 1.71 (4H, m), 2.23 (3H, m), 2.31 (3H, s), 2.97 (2H, m), 3.80 (2H, s), 7.08–7.24 (4H, m), 7.59 (2H, d, J=8.4 Hz), 7.67 (1H, d, J=8.8 Hz), 7.83 (2H, d, J=8.4 Hz), 7.90 (2H, d, J=8.4 Hz), 8.03 (2H, m), 8.14 (2H, d, J=8.4 Hz), 8.32 (1H, d, J=8.4 Hz), 8.55 (1H, s), 10.63 (1H, s). FAB(pos): 546 [M+H]$^+$ Example 30

4'-Chloro-N-[2-[[4-(3-methylphenyl)-1-piperidinyl]methyl]-6-quinolinyl][1,1'-biphenyl]-4-carboxamide

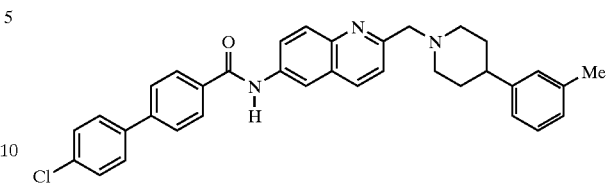

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

$^1$H-NMR (DMSO-d$_6$) δ: 1.71 (4H, m), 2.20 (3H, m), 2.27 (3H, s), 2.97 (2H, m), 3.57 (2H, s), 7.06 (4H, m), 7.59 (3H, m), 7.82 (4H, m), 8.02 (2H, m), 8.12 (2H, d, J=8.4 Hz), 8.35 (1H, m), 8.54 (1H, s), 10.61 (1H, s). FAB(pos): 546 [M+H]$^+$ Example 31

4'-Chloro-N-[2-[[4-(4-methylphenyl)-1-piperidinyl]methyl]-6-quinolinyl][1,1'-biphenyl]-4-carboxamide

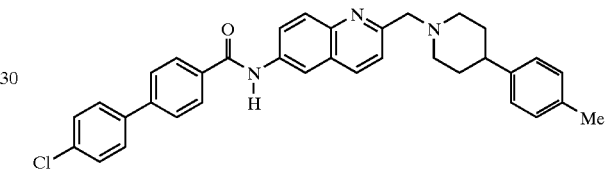

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

$^1$H-NMR (DMSO-d$_6$) δ: 1.71 (4H, m), 2.20 (3H, m), 2.26 (3H, s), 2.96 (2H, m), 3.78 (2H, s), 7.12 (4H, m), 7.61 (3H, m), 7.83 (2H, d, J=8.6 Hz), 7.90 (2H, d, J=8.6 Hz), 8.03 (2H, m), 8.14 (2H, d, J=8.2 Hz), 8.31 (1H, d, J=8.4 Hz), 8.55 (1H, s), 10.63 (1H, s). FAB(pos): 546 [M+H]$^+$ Example 32

4'-Chloro-N-[2-[(2-phenyl-4,5-dihydro-1H-imidazol-1-yl) methyl]-6-quinolinyl][1,1'-biphenyl]-4-carboxamide

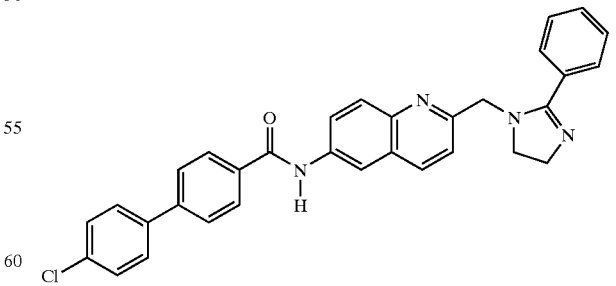

Using the 4'-chloro-N-[2-(chloromethyl)-6-quinolinyl][1,1-biphenyl]-4-carboxamide obtained in Reference Example 8, the same procedures as those of Example 23 were conducted to obtain the titled compound as a colorless powder.

¹H-NMR (DMSO-d₆) δ: 3.46 (2H, m), 3.82 (2H, m), 4.51 (2H, s), 7.48 (3H, m), 7.61 (4H, s), 7.79–8.16 (9H, m), 8.36 (1H, d, J=8.8 Hz), 8.58 (1H, d, J=1.8 Hz), 10.65 (1H, s). FAB(pos): 517[M+H]⁺

Example 33

4'-Chloro-N-[2-(3,4-dihydro-1(2H)-quinolinylmethyl)-6-quinolinyl][1,1'-biphenyl]-4-carboxamide

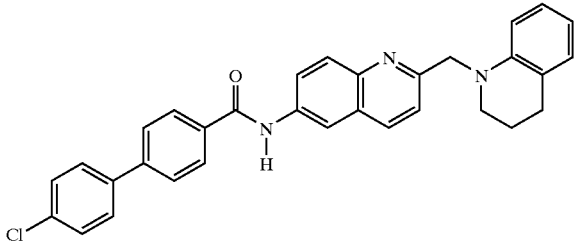

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

¹H-NMR (DMSO-d₆) δ: 2.00 (2H, m), 2.79 (2H, m), 3.55 (2H, m), 4.70 (2H, s), 6.47 (2H, m), 6.82–6.94 (2H, m), 7.38 (1H, d, J=8.4 Hz), 7.58 (2H, d, J=8.4 Hz), 7.83 (2H, d, J=8.4 Hz), 7.89 (2H, d, J=8.4 Hz), 8.01 (2H, m), 8.13 (2H, d, J=8.4 Hz), 8.27 (1H, d, J=8.4 Hz), 8.55 (1H, d, J=1.8 Hz), 10.63 (1H, s). FAB(pos): 504[M+H]⁺

Example 34

4'-Chloro-N-[2-(3,4-dihydro-2(1H)-isoquinolinylmethyl)-6-quinolinyl][1,1'-biphenyl]-4-carboxamide

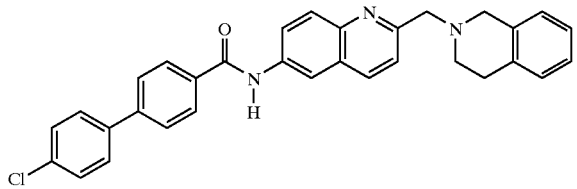

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

¹H-NMR (DMSO-d₆) δ: 2.77–2.83 (4H, m), 3.64 (2H, s), 3.93 (2H, s), 7.03–7.11 (4H, m), 7.57 (2H, d, J=8.8 Hz), 7.64 (1H, d, J=8.4 Hz), 7.82 (2H, d, J=8.8 Hz), 7.88 (2H, d, J=8.4 Hz), 8.01 (2H, m), 8.12 (2H, d, J=8.4 Hz), 8.30 (1H, d, J=8.4 Hz), 8.54 (1H, s), 10.62 (1H, s). FAB(pos): 504[M+H]⁺

Example 35

4'-Chloro-N-[2-(2,3-dihydro-1H-indol-1-ylmethyl)-6-quinolinyl][1,1'-biphenyl]-4-carboxamide

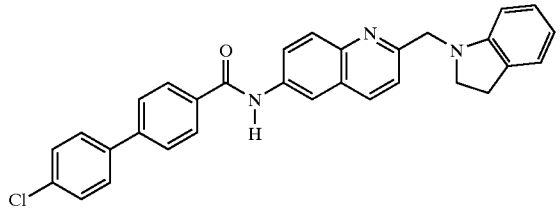

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

¹H-NMR (DMSO-d₆) δ: 2.96 (2H, m), 3.43 (2H, m), 4.53 (2H, s), 6.61 (2H, m), 6.95–7.09 (2H, m), 7.57 (3H, m), 7.83 (2H, d, J=8.8 Hz), 7.89 (2H, d, J=8.8 Hz), 8.02 (2H, m), 8.13 (2H, d, J=8.4 Hz), 8.32 (1H, d, J=8.8 Hz), 8.55 (1H, d, J=2.2 Hz), 10.63 (1H, s). FAB(pos): 490 [M+H]⁺

Example 36

4'-Chloro-N-[2-(1H-imidazol-1-ylmethyl)-6-quinolinyl][1,1'-biphenyl]-4-carboxamide

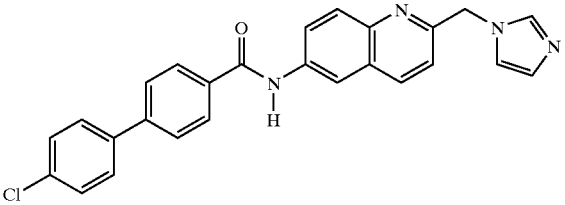

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

¹H-NMR (DMSO-d₆) δ: 5.49 (2H, s), 6.96 (1H, s), 7.28 (2H, m), 7.58 (3H, m), 7.82 (2H, d, J=8.4 Hz), 7.89 (2H, d, J=8.4 Hz), 8.01 (2H, m), 8.12 (2H, d, J=8.6 Hz), 8.35 (1H, d, J=8.4 Hz), 8.57 (1H, d, J=2.2 Hz), 10.65 (1H, s). FAB(pos): 439 [M+H]⁺

Example 37

4'-Chloro-N-[2-[(4-phenyl-1-piperazinyl)methyl]-6-quinolinyl][1,1'-biphenyl]-4-carboxamide

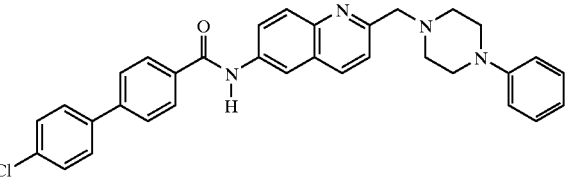

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

¹H-NMR (DMSO-d₆) δ: 2.62 (4H, m), 3.17 (4H, m), 3.82 (2H, s), 6.78 (1H, m), 6.93 (2H, d, J=7.8 Hz), 7.20 (2H, m), 7.58 (2H, d, J=8.8 Hz), 7.69 (1H, d, J=8.8 Hz), 7.83 (2H, d, J=8.8 Hz), 7.89 (2H, d, J=8.6 Hz), 8.01 (2H, m), 8.14 (2H, d, J=8.6 Hz), 8.32 (1H, d, J=8.6 Hz), 8.56 (1H, d, J=1.8 Hz), 10.63 (1H, s). FAB(pos): 533 [M+H]⁺

Example 38

4-(4-Fluorophenyl)-N-[2-(1-pyrrolidinylmethyl)-6-quinolinyl]-1-piperidinecarboxamide

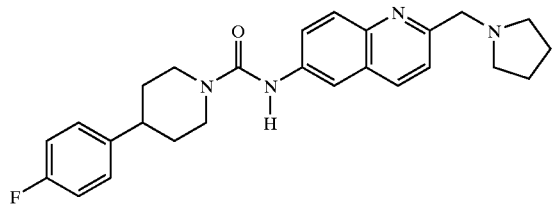

To a solution of the 2-(1-pyrrolidinylmethyl)-6-quinolinylamine (500 mg, 2.2 mmol) obtained in Reference Example 9 and pyridine (0.356 ml, 4.4 mmol) in tetrahydrofuran (11 ml) was added 4-nitrophenyl chloroformate (488 mg, 2.42 mmol) under ice-cooling. After stirred for 30 minutes, the reaction solution was concentrated, and dimethyl sulfoxide (11 ml) was added to the residue. 4-(4-Fluorophenyl)piperidine hydrochloride (569 mg, 2.64 mmol) and a 4N aqueous sodium hydroxide solution (0.66 ml) were added thereto at room temperature while stirring, and the mixture was stirred for 2 hours. Ethyl acetate and water were added, the mixture was extracted, the organic layer was washed with water, and concentrated, and the residue was purified by alumina column chromatography (developing solvent: ethyl acetate) to obtain the titled compound (612 mg) as a colorless powder from ethyl acetate-diisopropyl ether.

¹H-NMR (DMSO-d₆) δ: 1.57 (2H, m), 1.64 (4H, m), 1.82 (2H, m), 2.50 (4H, m), 2.79 (1H, m), 2.92 (2H, m), 3.81 (2H, s), 4.34 (2H, m), 7.12 (2H, m), 7.31 (2H, m), 7.51 (1H, d, J=8.4 Hz), 7.82 (2H, s-like), 8.07 (1H, s), 8.14 (1H, d, J=8.4 Hz), 8.83 (1H, s). FAB(pos): 433.2 [M+H]⁺ m.p.: 206–207° C. (crystallization solvent: ethyl acetate-diisopropyl ether)

Example 39

4-Phenyl-N-[2-(1-pyrrolidinylmethyl)-6-quinolinyl]-1-piperidinecarboxamide

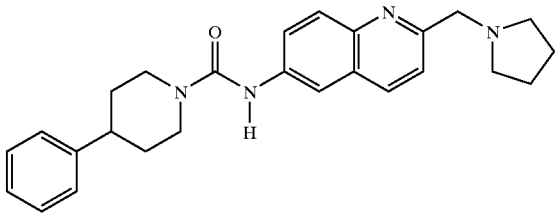

Using the 2-(1-pyrrolidinylmethyl)-6-quinolinylamine obtained in Reference Example 9, the same procedures as those of Example 38 were conducted to obtain the titled compound as a colorless powder.

¹H-NMR (DMSO-d₆) δ: 1.59–1.85 (8H, m), 2.50 (4H, m), 2.13 (1H, m), 2.89 (2H, m), 3.81 (2H, s), 4.33 (2H, m), 7.20–7.34 (5H, m), 7.51 (1H, d, J=8.4 Hz), 7.82 (2H, s-like), 8.07 (1H, s), 8.14 (1H, d, J=8.4 Hz), 8.83 (1H, s). FAB(pos): 415.3 [M+H]⁺ m.p.: 187–189° C. (crystallization solvent: ethyl acetate-diisopropyl ether)

Example 40

4-(4-Chlorophenyl)-N-[2-(1-pyrrolidinylmethyl)-6-quinolinyl]-1-piperidinecarboxamide

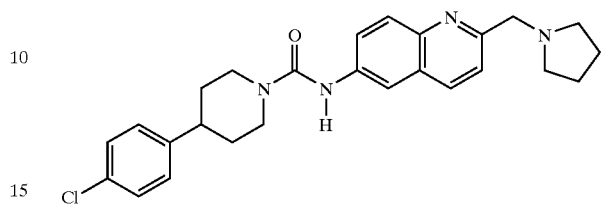

Using the 2-(1-pyrrolidinylmethyl)-6-quinolinylamine obtained in Reference Example 9, the same procedures as those of Example 38 were conducted to obtain the titled compound as a colorless powder.

¹H-NMR (DMSO-d₆) δ: 1.58 (2H, m), 1.72 (4H, m), 1.80 (2H, m), 2.50 (4H, m), 2.79 (1H, m), 2.92 (2H, m), 3.82 (2H, s), 4.33 (2H, m), 7.34 (4H, m), 7.51 (1H, d, J=8.4 Hz), 7.82 (2H, s-like), 8.07 (1H, s), 8.14 (1H, d, J=8.4 Hz), 8.85 (1H, s). FAB(pos): 449.9 [M+H]⁺ m.p.: 205° C. (decomposition) (crystallization solvent: ethyl acetate-diisopropyl ether)

Example 41

4-(4-Methylphenyl)-N-[2-(1-pyrrolidinylmethyl)-6-quinolinyl]-1-piperidinecarboxamide

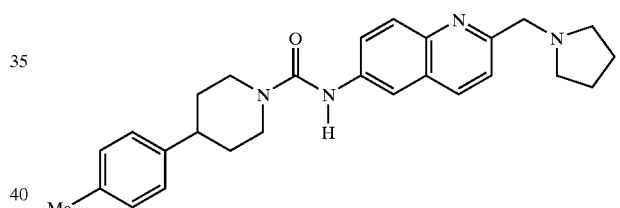

Using the 2-(1-pyrrolidinylmethyl)-6-quinolinylamine obtained in Reference Example 9, the same procedures as those of Example 38 were conducted to obtain the titled compound as a colorless powder.

¹H-NMR (DMSO-d₆) δ: 1.55 (2H, m), 1.72 (4H, m), 1.78 (2H, m), 2.27 (3H, s), 2.50 (4H, m), 2.72 (1H, m), 2.91 (2H, m), 3.81 (2H, s), 4.32 (2H, m), 7.13 (4H, m), 7.51 (1H, d, J=8.4 Hz), 7.82 (2H, s-like), 8.08 (1H, s), 8.14 (1H, d, J=8.4 Hz), 8.84 (1H, s). FAB(pos): 429.3 [M+H]⁺ m.p.: 214–216° C. (crystallization solvent: ethyl acetate-diisopropyl ether)

Example 42

6-(4-Methoxyphenyl)-N-[2-(1-pyrrolidinylmethyl)-6-quinolinyl]nicotinamide

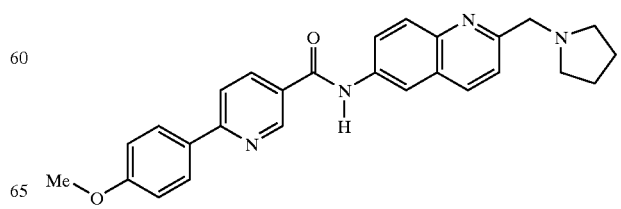

Using the N-[2-(1-pyrrolidinylmethyl)-6-quinolinyl] acetamide obtained in 1) of Example 7, the same procedures as those of 2) of Example 6 were conducted to obtain the titled compound as a colorless powder.

¹H-NMR (DMSO-d₆) δ: 1.73 (4H, m), 2.50 (4H, m), 3.85 (5H, s-like), 7.10 (2H, d, J=9.0 Hz), 7.59 (1H, d, J=8.7 Hz), 7.98 (2H, m), 8.11 (1H, d, J=8.4 Hz), 8.18 (2H, d, J=8.7 Hz), 8.29 (1H, d, J=9.0 Hz), 8.40 (1H, d, J=8.4 Hz), 8.51 (1H, s), 9.20 (1H, s), 10.71 (1H, s). FAB(pos): 439.2 [M+H]⁺ m.p.: 210° C. (decomposition)(crystallization solvent: ethyl acetate-diisopropyl ether)

Example 43

N-[2-(1-Pyrrolidinylmethyl)-6-quinolinyl][1,1'-biphenyl]-4-carboxamide

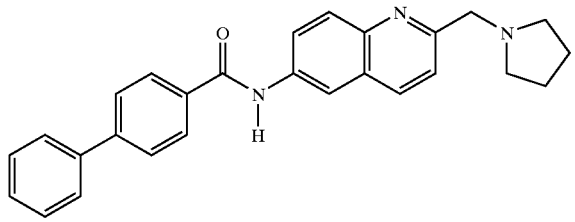

Using the N-[2-(1-pyrrolidinylmethyl)-6-quinolinyl] acetamide obtained in 1) of Example 7, the same procedures as those of 2) of Example 6 were conducted to obtain the titled compound as a colorless powder.

¹H-NMR (DMSO-d₆) δ: 1.73 (4H, m), 2.50 (4H, m), 3.85 (2H, s), 7.50 (4H, m), 7.78 (2H, d, J=8.1 Hz), 7.88 (2H, d, J=8.1 Hz), 8.02 (2H, m), 8.12 (2H, d, J=8.1 Hz), 8.28 (1H, d, J=8.7 Hz), 8.53 (1H, d, J=2.0 Hz), 10.60 (1H, s). FAB (pos): 408.2 [M+H]⁺ m.p.: 181–183° C. (crystallization solvent: ethyl acetate-diisopropyl ether)

Example 44

6-(4-Chlorophenyl)-N-[2-(1-pyrrolidinylmethyl)-6-quinolinyl]nicotinamide

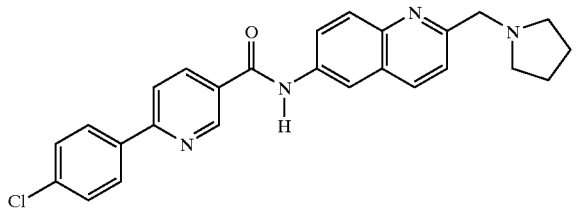

Using the N-[2-(1-pyrrolidinylmethyl)-6-quinolinyl] acetamide obtained in 1) of Example 7, the same procedures as those of 2) of Example 6 were conducted to obtain the titled compound as a colorless powder.

¹H-NMR (DMSO-d₆) δ: 1.73 (4H, m), 2.50 (4H, m), 3.85 (2H, s), 7.61 (3H, m), 8.01 (2H, m), 8.28 (4H, m), 8.48 (2H, m), 9.25 (1H, d, J=2.2 Hz), 10.76 (1H, s). FAB(pos): 443.2 [M+H]⁺ m.p.: 225–227° C. (crystallization solvent: ethyl acetate-diisopropyl ether)

Example 45

6-(4-Fluorophenyl)-N-[2-(1-pyrrolidinylmethyl)-6-quinolinyl]nicotinamide

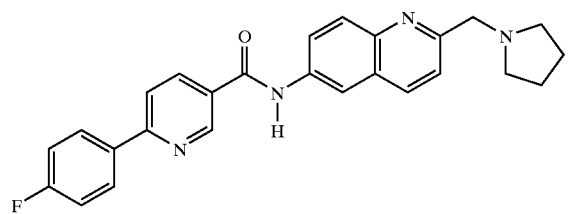

Using the N-[2-(1-pyrrolidinylmethyl)-6-quinolinyl] acetamide obtained in 1) of Example 7, the same procedures as those of 2) of Example 6 were conducted to obtain the titled compound as a colorless powder.

¹H-NMR (DMSO-d₆) δ: 1.73 (4H, m), 2.50 (4H, m), 3.86 (2H, s), 7.39 (2H, m), 7.60 (1H, d, J=8.4 Hz), 8.01 (2H, m), 8.19 (1H, d, J=8.4 Hz), 8.28 (3H, m), 8.45 (1H, dd, J=8.4, 2.1 Hz), 8.51 (1H, d, J=1.7 Hz), 9.24 (1H, d, J=2.0 Hz), 10.75 (1H, s). FAB(pos): 427.2[M+H]⁺ m.p.: 210° C. (crystallization solvent: ethyl acetate-diisopropyl ether)

Example 46

6-(4-Methylphenyl)-N-[2-(1-pyrrolidinylmethyl)-6-quinolinyl]nicotinamide

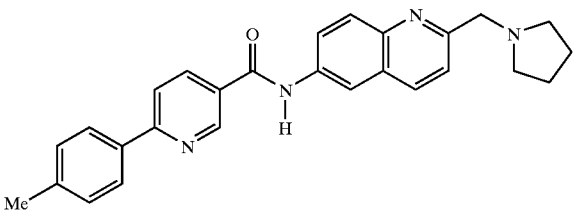

Using the N-[2-(1-pyrrolidinylmethyl)-6-quinolinyl] acetamide obtained in 1) of Example 7, the same procedures as those of 2)-of Example 6 were conducted to obtain the titled compound as a colorless powder.

¹H-NMR (DMSO-d₆) δ: 1.73 (4H, m), 2.39 (3H, s), 2.50 (4H, m), 3.86 (2H, s), 7.36 (2H, d, J=8.1 Hz), 7.59 (1H, d, J=8.4 Hz), 8.01 (2H, m), 8.13 (3H, m), 8.29 (1H, d, J=8.4 Hz), 8.42 (1H, dd, J=8.4, 2.2 Hz), 8.51 (1H, d, J=2.0 Hz), 9.22 (1H, d, J=2.2 Hz), 10.73 (1H, s). FAB(pos): 423.2[M+H]⁺ m.p.: 207–209° C. (crystallization solvent: ethyl acetate-diisopropyl ether)

Example 47

4'-Chloro-N-[2-[[4-(4-fluorobenzoyl)-1-piperidinyl]methyl]-6-quinolinyl][1,1'-biphenyl]-4-carboxamide

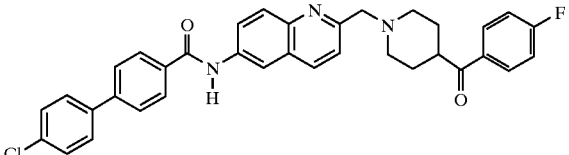

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

¹H-NMR (DMSO-d₆) δ: 1.76 (4H, m), 2.28 (2H, m), 2.89 (2H, m), 3.40 (1H, m), 3.79 (2H, s), 7.37 (2H, m), 7.62 (3H, m), 7.83 (2H, d, J=8.4 Hz), 7.90 (2H, d, J=8.4 Hz), 8.03–8.14 (6H, m), 8.31 (1H, d, J=8.6 Hz), 8.55 (1H, s), 10.63 (1H, s). FAB(pos): 578[M+H]⁺

Example 48

4'-Chloro-N-[2-[[4-(4-chlorobenzoyl)-1-piperidinyl]methyl]-6-quinolinyl][1,1'-biphenyl]-4-carboxamide

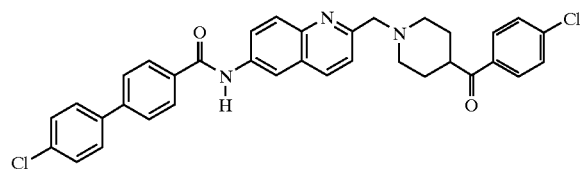

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

¹H-NMR (DMSO-d₆) δ: 1.77 (4H, m), 2.28 (2H, m), 2.90 (2H, m), 3.45 (1H, m), 3.79 (2H, s), 7.62 (5H, m), 7.83 (2H, d, J=8.4 Hz), 7.90 (2H, d, J=8.4 Hz), 8.03 (4H, m), 8.14 (2H, d, J=8.2 Hz), 8.31 (1H, d, J=8.4 Hz), 8.54 (1H, s), 10.63 (1H, s). FAB(pos): 594[M+H]⁺

Example 49

4'-Chloro-N-[2-[(methylanilino)methyl]-6-quinolinyl][1,1'-biphenyl]-4-carboxamide

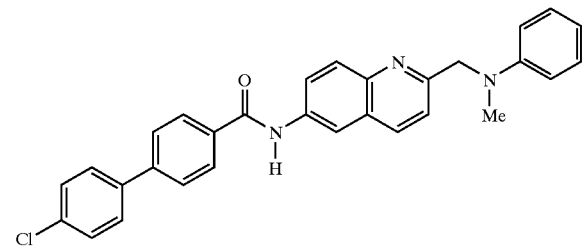

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

¹H-NMR (DMSO-d₆) δ: 3.17 (3H, s), 4.80 (2H, s), 6.62 (1H, m), 6.76 (2H, d, J=8.0 Hz), 7.15 (2H, m), 8.30 (1H, d, J=8.8 Hz), 7.59 (2H, d, J=8.4 Hz), 7.83 (2H, d, J=8.4 Hz), 7.90 (2H, d, J=8.4 Hz), 7.96 (2H, m), 8.13 (2H, d, J=8.4 Hz), 8.27 (1H, d, J=8.6 Hz), 8.55 (1H, s), 10.63 (1H, S). FAB(pos): 478[M+H]⁺

Example 50

4'-Chloro-N-[2-[[3-(4-fluorobenzoyl)-1-piperidinyl]methyl]-6-quinolinyl][1,1'-biphenyl]-4-carboxamide

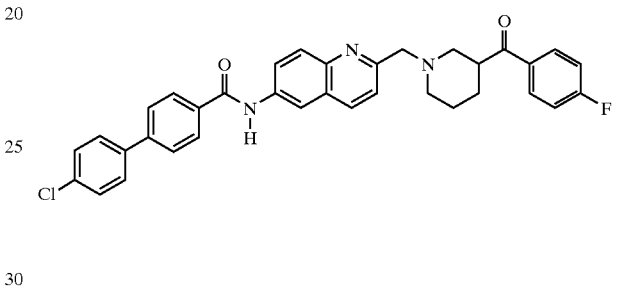

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

¹H-NMR (DMSO-d₆) δ: 1.39 (1H, s), 1.73 (3H, m), 2.23 (2H, m), 2.91 (2H, m), 3.63 (1H, m), 3.78 (2H, s), 7.31 (2H, m), 7.58 (3H, m), 7.86 (4H, m), 8.01 (4H, m), 8.13 (2H, d, J=8.4 Hz), 8.25 (1H, d, J=8.2 Hz), 8.54 (1H, s), 10.61 (1H, s). FAB(pos): 578[M+H]⁺

Example 51

4'-Chloro-N-[2-[(4-phenyl[-1-piperidinyl]methyl]-6-quinolinyl][1,1'-biphenyl]-4-carboxamide

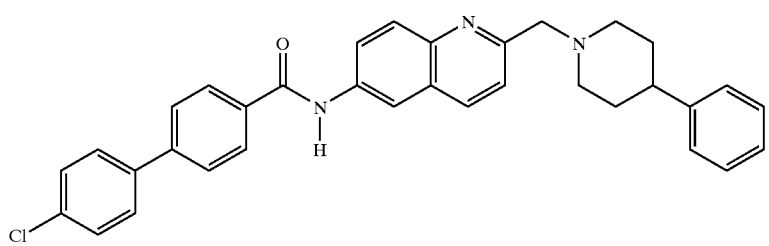

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

$^1$H-NMR (DMSO-d$_6$) δ: 1.74 (4H, m), 2.20 (2H, m), 2.52 (1H, m), 2.97 (2H, m), 3.79 (2H, s), 7.27 (5H, m), 7.58 (2H, d, J=8.4 Hz), 7.69 (1H, d, J=8.4 Hz), 7.83 (2H, d, J=8.8 Hz), 7.89 (2H, d, J=8.4 Hz), 8.00 (2H, m), 8.14 (2H, d, J=8.8 Hz), 8.31 (1H, d, J=8.4 Hz), 8.54 (1H, d, J=1.8 Hz), 10.62 (1H, s). FAB(pos): 532[M+H]$^+$ Example 52

1-(4-Chlorophenyl)-N-[2-(1-pyrrolidinylmethyl)-6-quinolinyl]-4-piperidinecarboxamide

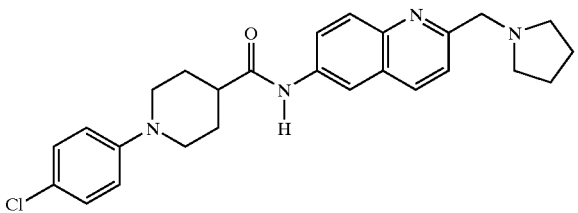

Using the N-[2-(1-pyrrolidinylmethyl)-6-quinolinyl]acetamide obtained in 1) of Example 7, the same procedures as those of 2) of Example 6 were conducted to obtain the titled compound as a colorless powder.

$^1$H-NMR (DMSO-d$_6$) δ: 1.73 (4H, m), 1.89 (4H, m), 2.50 (5H, m), 2.75 (2H, m), 3.76 (2H, m), 3.83 (2H, s), 6.99 (2H, d, J=9.0 Hz), 7.24 (2H, d, J=9.0 Hz), 7.55 (1H, d, J=8.8 Hz), 7.77 (1H, dd, J=8.8, 2.2 Hz), 7.90 (1H, d, J=8.8 Hz), 8.21 (1H, d, J=8.8 Hz), 8.38 (1H, d, J=2.2 Hz), 10.26 (1H, s). FAB(pos): 449[M+H]$^+$ m.p.: 204–206° C. (crystallization solvent: ethyl acetate-diisopropyl ether)

Example 53

N-[2-[(2-Benzyl-4,5-dihydro-1H-imidazol-1-yl)methyl]-6-quinolinyl]-4'-chloro[1,1'-biphenyl]-4-carboxamide

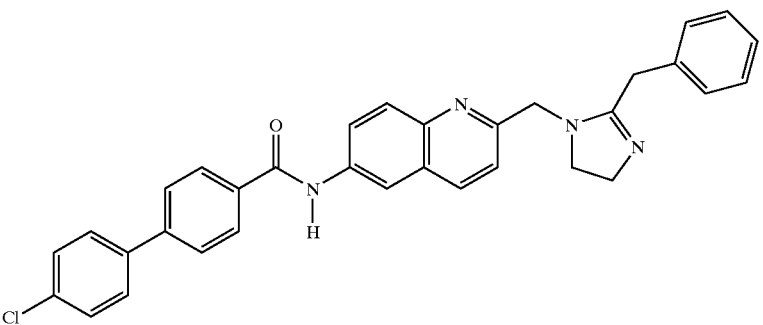

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

$^1$H-NMR (DMSO-d$_6$) δ: 3.22 (2H, m), 3.60 (2H, m), 3.75 (2H, s), 4.51 (2H, s), 7.17–7.33 (6H, m), 7.57 (2H, d, J=8.4 Hz), 7.82 (2H, d, J=8.4 Hz), 7.88 (2H, d, J=8.4 Hz), 7.99 (2H, m), 8.12 (2H, d, J=8.4 Hz), 8.25 (1H, d, J=9.0 Hz), 8.53 (1H, s), 10.62 (1H, s). FAB(pos): 531[M+H]$^+$ Example 54

N-[2-(1-Piperidinylmethyl)-6-quinolinyl][1,1'-biphenyl]-4-carboxamide

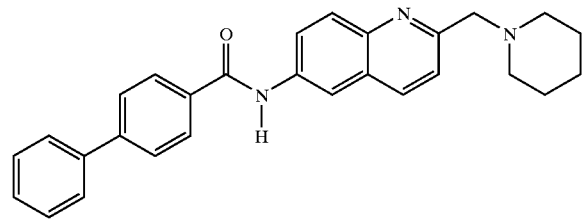

1) Using the N-[2-(hydroxymethyl)-6-quinolinyl]acetamide obtained in Reference Example 5 and piperidine, the same procedures as those of 1) of Example 6 were conducted to obtain N-[2-(1-piperidinylmethyl)-6-quinolinyl]acetamide.

$^1$H-NMR (CDCl$_3$) δ: 1.38–1.70 (6H, m), 2.24 (3H, s), 2.38–2.53 (4H, m), 3.76 (2H, s), 7.52 (1H, dd, J=2.6, 9.2 Hz), 7.63 (1H, d, J=8.4 Hz), 7.67 (1H, br), 7.99 (1H, d, J=9.2 Hz), 8.07 (1H, d, J=8.4 Hz), 8.31 (1H, d, J=2.6 Hz). Elemental analysis for C$_{17}$H$_{21}$N$_3$O.0.25H$_2$O Calcd: C, 70.93; H, 7.53; N, 14.60. Found: C, 71.06; H, 7.37; N, 14.62. m.p.: 182–184° C. (crystallization solvent: ethyl acetate-n-hexane)

2) The N-[2-(1-piperidinylmethyl)-6-quinolinyl]acetamide (4.5 g, 16 mmol) obtained in the above 1) and concentrated hydrochloric acid (70 ml) were stirred at 110° C. for 1 hour. The solvent was distilled off under reduced pressure, an aqueous sodium hydroxide solution was added to the residue, and the mixture was extracted with ethyl acetate. The extract was washed with an aqueous saturated sodium chloride solution, dried over anhydrous sodium sulfate, and concentrated under reduced pressure. The resulting residue was purified by alumina column chromatography (developing solvent: ethyl acetate) to obtain 6-amino-2-(1-pipelidinylmethyl)quinoline (3.4 g) as an oil.

$^1$H-NMR (CDCl$_3$) δ: 1.37–1.68 (6H, m), 2.39–2.55 (4H, m), 3.72 (2H, s), 3.91 (2H, br), 6.89 (1H, d, J=2.6 Hz), 7.12 (1H, dd, J=2.6 and 8.8 Hz), 7.51 (1H, d, J=8.4 Hz), 7.86 (1H, d, J=8.4 Hz), 7.87 (1H, d, J=8.8 Hz).

3) The 6-amino-2-(1-piperidinylmethyl)quinoline (250 mg, 1 mmol) obtained in the above 2), biphenylcarboxylic acid (220 mg, 1.1 mmol) and dimethylaminopyridine (150 mg, 1.2 mmol) were dissolved in N,N-dimethylformamide (8 ml), WSC (230 mg, 1.2 mmol) was added thereto under ice-cooling, and the mixture was stirred at room temperature for 18 hours. To the reaction solution was added an aqueous potassium carbonate solution, and the mixture was extracted with ethyl acetate. The extract was washed with an aqueous saturated sodium chloride solution, dried over anhydrous sodium sulfate, and concentrated under reduced pressure. The resulting residue was purified by alumina column chromatography (developing solvent: ethyl acetate), and crystallized from acetic acid to obtain the titled compound (335 mg) having a melting point of 186–188° C. as colorless needle crystals.

$^1$H-NMR (CDCl$_3$) δ: 1.38–1.76 (6H, m), 2.43–2.56 (4H, m), 3.78 (2H, s), 7.38–7.56 (3H, m), 7.59–7.81 (6H, m), 7.96–8.18 (5H, m), 8.49 (1H, d, J=2.2 Hz). Elemental analysis for C$_{28}$H$_{27}$N$_3$O.0.5H$_2$O Calcd: C, 78.11; H, 6.56; N, 9.76. Found: C, 78.48; H, 6.31; N, 10.00.

Example 55

4'-Methyl-N-[2-(1-piperidinylmethyl)-6-quinolinyl][1,1'-biphenyl]-4-carboxamide

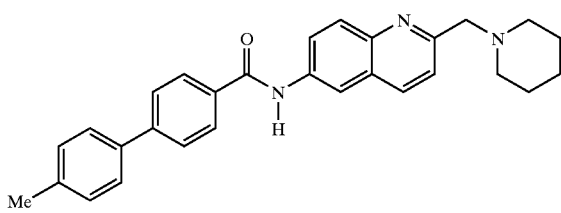

Using the 6-amino-2-(1-pipelidinylmethyl)quinoline obtained in 2) of Example 54, the same procedures as those of 3) of Example 54 were conducted to obtain the titled compound as a colorless powder.

$^1$H-NMR (CDCl$_3$) δ: 1.38–1.70 (6H, m), 2.39–2.56 (7H, m), 3.79 (2H, s), 7.30 (2H, d, J=0.6 Hz), 7.56 (2H, d, J=7.6 Hz), 7.63–7.78 (4H, m), 7.95–8.07 (5H, m), 8.49 (1H, d, J=1.8 Hz). Elemental analysis for C$_{29}$H$_{29}$N$_3$O.0.25H$_2$O Calcd: C, 79.15; H, 6.76; N, 9.55. Found: C, 79.38; H, 6.88; N, 9.73. m.p.: 198–200° C. (crystallization solvent: ethyl acetate)

Example 56

4'-Methoxy-N-[2-(1-piperidinylmethyl)-6-quinolinyl][1,1'-biphenyl]-4-carboxamide

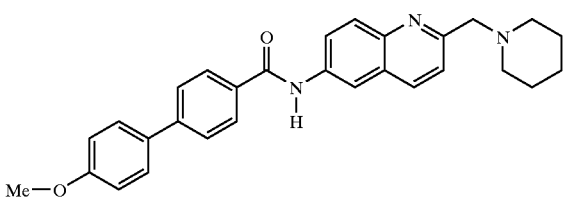

Using the 6-amino-2-(1-pipelidinylmethyl)quinoline obtained in 2) of Example 54, the same procedures as those of 3) of Example 54 were conducted to obtain the titled compound as a colorless powder.

$^1$H-NMR (CDCl$_3$) δ: 1.38–1.85 (6H, m), 2.41–2.56 (4H, m), 3.78 (2H, s), 3.88 (3H, s), 7.02(2H, d, J=8.8 Hz), 7.54–7.66 (6H, m), 7.93–8.20 (5H, m), 8.49 (1H, d, J=2.2 Hz). Elemental analysis for C$_{29}$H$_{29}$N$_3$O$_2$.0.25H$_2$O Calcd: C, 76.38; H, 6.52; N, 9.21. Found: C, 76.21; H, 6.38; N, 9.32. m.p.: 192–194° C. (crystallization solvent: ethyl acetate)

Example 57

6-(4-Chlorophenyl)-N-[2-(1-piperidinylmethyl)-6-quinolinyl]nicotinamide

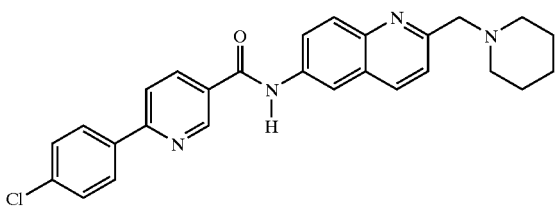

Using the 6-amino-2-(1-pipelidinylmethyl)quinoline obtained in 2) of Example 54, the same procedures as those of 3) of Example 54 were conducted to obtain the titled compound as a colorless powder.

$^1$H-NMR (CDCl$_3$) δ: 1.38–1.80 (6H, m), 2.38–2.58 (4H, m), 3.78 (2H, s), 7.48 (2H, d, J=8.4 Hz), 7.62–7.75 (2H, m), 7.84 (1H, d, J=8.0 Hz), 7.96–8.18 (4H, m), 8.24 (1H, br), 8.31 (1H, dd, J=2.2, 8.4 Hz), 8.45 (1H, d, J=2.2 Hz), 9.20 (1H, d, J=1.4 Hz). Elemental analysis for C$_{27}$H$_{25}$ClN$_4$O.0.5H$_2$O Calcd: C, 69.59; H, 5.62; N, 12.02. Found: C, 69.33; H, 5.52; N, 12.08. m.p.: 215–218° C. (decomposition) (crystallization solvent: ethyl acetate)

Example 58

6-(4-Methylphenyl)-N-[2-(1-piperidinylmethyl)-6-quinolinyl]nicotinamide

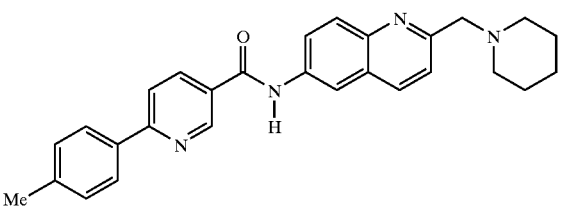

Using the 6-amino-2-(1-pipelidinylmethyl)quinoline obtained in 2) of Example 54, the same procedures as those of 3) of Example 54 were conducted to obtain the titled compound as a colorless powder.

$^1$H-NMR (CDCl$_3$) δ: 1.38–1.80 (6H, m), 2.40–2.56 (7H, m), 3.79 (2H, s), 7.33 (2H, d, J=8.4 Hz), 7.63–7.74 (2H, m), 7.86 (1H, d, J=8.0 Hz), 7.93–8.19 (5H, m), 8.29 (1H, dd, J=2.2, 8.4 Hz), 8.46 (1H, d, J=2.2 Hz), 9.19 (1H, d, J=2.2 Hz). m.p.: 206–207° C. (decomposition) (crystallization solvent: ethyl acetate) FAB(pos): 437[M+H]$^+$ Example 59

6-(4-Fluorophenyl)-N-[2-(1-piperidinylmethyl)-6-quinolinyl]nicotinamide

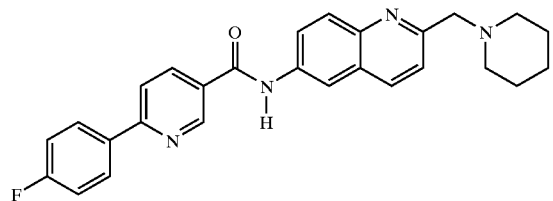

Using the 6-amino-2-(1-pipelidinylmethyl)quinoline obtained in 2) of Example 54, the same procedures as those of 3) of Example 54 were conducted to obtain the titled compound as a colorless powder.

¹H-NMR (CDCl₃) δ: 1.38–1.74 (6H, m), 2.42–2.56 (4H, m), 3.78 (2H, s), 7.20 (2H, dd, J=8.4 and 8.8 Hz), 7.63–7.76 (2H, m), 7.84 (1H, d, J=8.0 Hz), 8.02–8.18 (5H, m), 8.31 (1H, dd, J=2.2, 8.4 Hz), 8.46 (1H, d, J=2.2 Hz), 9.19 (1H, d, J=1.8 Hz). Elemental analysis for $C_{27}H_{25}FN_4O \cdot 0.25H_2O$ Calcd: C, 72.87; H, 5.78; N, 12.59. Found: C, 72.91; H, 5.45; N, 12.75. m.p.: 209–210° C. (decomposition) (crystallization solvent: ethyl acetate)

Example 60

6-(4-Methoxyphenyl)-N-[2-(1-piperidinylmethyl)-6-quinolinyl]nicotinamide

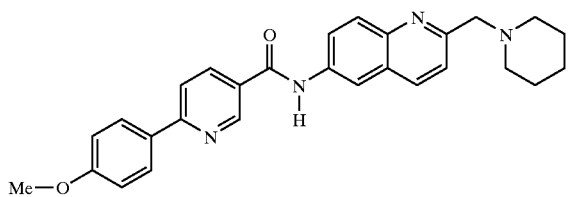

Using the 6-amino-2-(1-piperidinylmethyl)quinoline obtained in 2) of Example 54, the same procedures as those of 3) of Example 54 were conducted to obtain the titled compound as a colorless powder.

¹H-NMR (CDCl₃) δ: 1.38–1.71 (6H, m), 2.43–2.56 (4H, m), 3.80 (2H, s), 3.90 (3H, s), 7.04 (2H, d, J=9.0 Hz), 7.64–7.73 (2H, m), 7.83 (1H, d, J=8.4 Hz), 8.00–8.18 (5H, m), 8.28 (1H, dd, J=2.6, 8.4 Hz), 8.46 (1H, d, J=2.6 Hz), 9.17 (1H, d, J=1.8 Hz). Elemental analysis for $C_{28}H_{28}N_4O_2 \cdot 0.25H_2O$ Calcd: C, 73.58; H, 6.28; N, 12.26. Found: C, 73.56; H, 6.16; N, 12.24. m.p.: 210–211° C. (decomposition) (crystallization solvent: ethyl acetate)

Example 61

4'-Methyl-N-[2-(1-pyrrolidinylmethyl)-6-quinolinyl][1,1'-biphenyl]-4-carboxamide

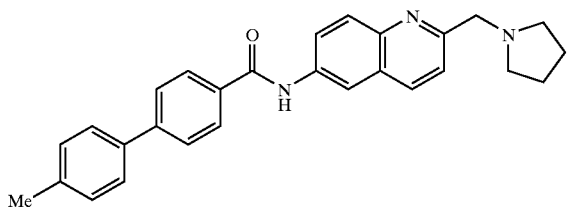

Using the N-[2-(1-pyrrolidinylmethyl)-6-quinolinyl] acetamide obtained in 1) of Example 7, the same procedures as those of 2) of Example 6 were conducted to obtain the titled compound as a colorless powder.

¹H-NMR (DMSO-d₆) δ: 1.73 (4H, m), 2.37 (3H, s), 2.50 (4H, m), 3.85 (2H, s), 7.33 (2H, d, J=8.1 Hz), 7.58 (1H, d, J=8.4 Hz), 7.68 (2H, d, J=8.1 Hz), 7.85 (2H, d, J=8.4 Hz), 7.95 (1H, d, J=9.0 Hz), 8.04 (1H, dd, J=2.4, 9.0 Hz), 8.10 (2H, d, J=8.4 Hz), 8.27 (1H, d, J=8.4 Hz), 8.52 (1H, d, J=2.4 Hz). FAB(pos) 422.3[M+H]⁺ m.p.: 192–193° C. (crystallization solvent: ethyl acetate-diisopropyl ether)

Example 62

4'-Methoxy-N-[2-(1-pyrrolidinylmethyl)-6-quinolinyl][1,1'-biphenyl]-4-carboxamide

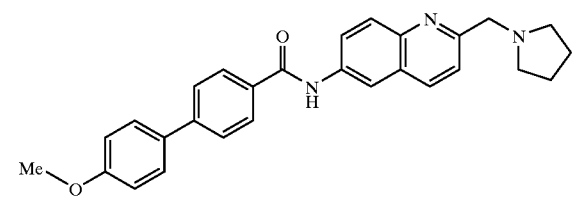

Using the N-[2-(1-pyrrolidinymethyl)-6-quinolinyl] acetamide obtained in 1) of Example 7, the same procedures as those of 2) of Example 6 were conducted to obtain the titled compound as a colorless powder.

¹H-NMR (DMSO-d₆) δ: 1.73 (4H, m), 2.50 (4H, m), 3.83 (3H, s), 3.85 (2H, s), 7.08 (2H, d, J=8.7 Hz), 7.58 (1H, d, J=8.4 Hz), 7.74 (2H, d, J=8.7 Hz), 7.83 (2H, d, J=8.4 Hz), 7.95 (1H, d, J=9.0 Hz), 8.03 (1H, dd, J=2.1, 9.0 Hz), 8.09 (2H, d, J=8.4 Hz), 8.27 (1H, d, J=8.4 Hz), 8.52 (1H, d, J=2.1 Hz). FAB(pos) 438.3[M+H]⁺ m.p.: 197–199° C. (crystallization solvent: ethyl acetate-diisopropyl ether)

Example 63

4-(4-Chlorophenyl)-N-[2-(1-piperidinylmethyl)-6-quinolinyl]-1-piperidinecarboxamide

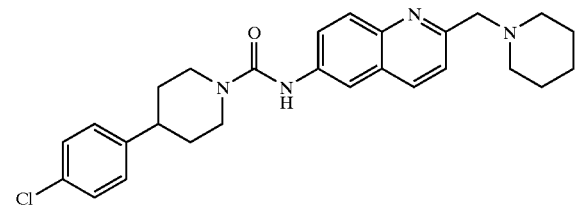

Using the 6-amino-2-(1-piperidinylmethyl)quinoline obtained in 2) of Example 54, the same procedures as those of Example 38 were conducted to obtain the titled compound as a colorless powder.

¹H-NMR (CDCl₃) δ: 1.37–2.02 (10H, m), 2.38–2.54 (4H, m), 2.63–2.84 (1H, m), 2.94–3.14 (2H, m), 3.76 (2H, s), 4.20–4.36 (2H, m), 6.65 (1H, br), 7.15 (2H, d, J=8.4 Hz), 7.30 (2H, d, J=8.4 Hz), 7.49 (1H, dd, J=2.2 and 9.2 Hz), 7.60 (1H, d, J=8.4 Hz), 7.93–8.10 (3H, m). Elemental analysis for $C_{27}H_{31}ClN_4O \cdot 1.5H_2O$ Calcd: C, 66.18; H, 6.99; N, 11.43. Found: C, 66.32; H, 6.75; N, 11.74. m.p.: 214–217° C. (dec.) (crystallization solvent: ethyl acetate-diethyl ether)

Example 64

4-(4-Methylphenyl)-N-[2-(1-piperidinylmethyl)-6-quinolinyl]-1-piperidinecarboxamide

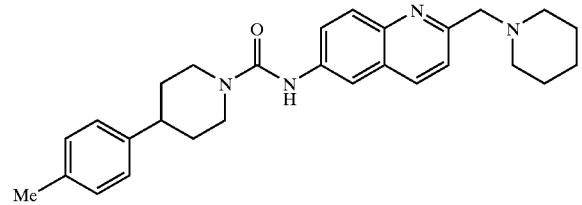

Using the 6-amino-2-(1-piperidinylmethyl)quinoline obtained in 2) of Example 54, the same procedures as those of Example 38 were conducted to obtain the titled compound as a colorless powder.

¹H-NMR (CDCl₃) δ: 1.40–2.02 (10H, m), 2.34 (3H, s), 2.47–2.83 (5H, m), 2.95–3.15 (2H, m), 3.82 (2H, s), 4.20–4.36 (2H, m), 6.70 (1H, br), 7.14 (4H, br), 7.53 (1H, dd, J=2.2 and 8.8 Hz), 7.64 (1H, d, J=8.4 Hz), 7.93–8.10 (3H, m). Elemental analysis for $C_{28}H_{34}N_4O \cdot H_2O$ Calcd: C, 73.01; H, 7.88; N, 12.16. Found: C, 72.68; H, 7.57; N, 12.20. m.p.: 204–205° C. (decomposition) (crystallization solvent: ethyl acetate-diethyl ether)

Example 65

4-(4-Fluorophenyl)-N-[2-(1-piperidinylmethyl)-6-quinolinyl]-1-piperidinecarboxamide

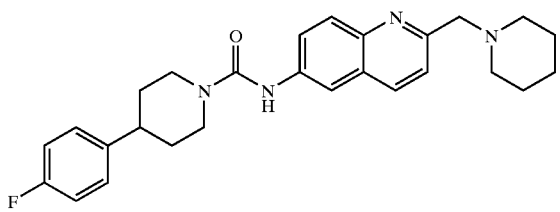

Using the 6-amino-2-(1-piperidinylmethyl)quinoline obtained in 2) of Example 54, the same procedures as those of Example 38 were conducted to obtain the titled compound as a colorless powder.

¹H-NMR (CDCl₃) δ: 1.36–2.02 (10H, m), 2.37–2.55 (4H, m), 2.63–2.85 (1H, m), 2.94–3.14 (2H, m), 3.76 (2H, s), 4.10–4.36 (2H, m), 6.66 (1H, br), 7.01 (2H, dd, J=8.4 and 8.8 Hz), 7.11–7.24 (2H, m), 7.50 (1H, dd, J=2.2 and 8.8 Hz), 7.60 (1H, d, J=8.4 Hz), 7.92–8.10 (3H, m). Elemental analysis for $C_{27}H_{31}FN_4O \cdot 0.5H_2O$ Calcd: C, 71.18; H, 7.08; N, 12.30. Found: C, 71.13; H, 6.94; N, 12.52. m.p.: 203–204° C. (decomposition) (crystallization solvent: ethyl acetate-diethyl ether)

Example 66

4-(4-Methoxyphenyl)-N-[2-(1-piperidinylmethyl)-6-quinolinyl]-1-piperidinecarboxamide

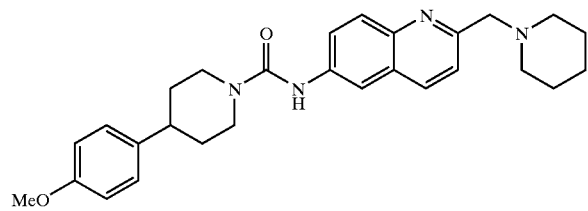

Using the 6-amino-2-(1-piperidinylmethyl)quinoline obtained in 2) of Example 54, the same procedures as those of Example 38 were conducted to obtain the titled compound as a colorless powder.

¹H-NMR (CDCl₃) δ: 1.37–2.02 (10H, m), 2.42–2.57 (4H, m), 2.60–2.80 (1H, m), 2.94–3.14 (2H, m), 3.78 (2H, s), 3.80 (3H, s), 4.19–4.36 (2H, m), 6.66 (1H, br), 6.87 (2H, d, J=8.4 Hz), 7.15 (2H, d, J=8.4 Hz), 7.50 (1H, dd, J=2.6 and 9.2 Hz), 7.61 (1H, d, J=8.4 Hz), 7.93–8.10 (3H, m). m.p.: 197–198° C. (decomposition) (crystallization solvent: ethyl acetate-diethyl ether)

Example 67

2'-Fluoro-N-[2-(1-piperidinylmethyl)-6-quinolinyl][1,1'-biphenyl]-4-carboxamide

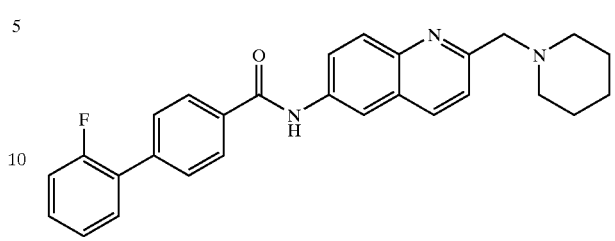

Using the 6-amino-2-(1-piperidinylmethyl)quinoline obtained in 2) of Example 54, the same procedures as those of 3) of Example 54 were conducted to obtain the titled compound as a colorless powder.

¹H-NMR (CDCl₃) δ: 1.40–1.77 (6H, m), 2.47–2.65 (4H, m), 3.86 (2H, s), 7.12–7.54 (4H, m), 7.63–7.78 (4H, m), 7.96–8.22 (5H, m), 8.48 (1H, d, J=2.6 Hz). m.p.: 163–164° C. (crystallization solvent: ethyl acetate)

Example 68

2',4'-Difluoro-N-[2-(1-piperidinylmethyl)-6-quinolinyl][1,1'-biphenyl]-4-carboxamide

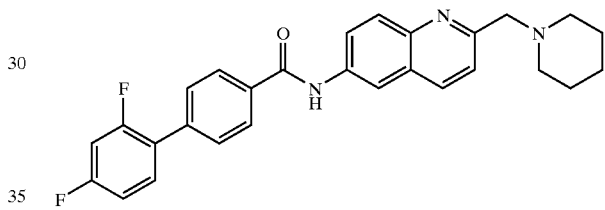

Using the 6-amino-2-(1-piperidinylmethyl)quinoline obtained in 2) of Example 54, the same procedures as those of 3) of Example 54 were conducted to obtain the titled compound as a colorless powder.

¹H-NMR (CDCl₃) δ: 1.40–1.78 (6H, m), 2.50–2.67 (4H, m), 3.87 (2H, s), 6.89–7.08 (2H, m), 7.38–7.54 (1H, m), 7.59–7.80 (4H, m), 7.96–8.23 (5H, m), 8.47 (1H, br). Elemental analysis for $C_{28}H_{25}F_2N_3O \cdot 0.5H_2O$ Calcd: C, 72.09; H, 5.62; N, 9.01. Found: C, 71.79; H, 5.59; N, 8.75. m.p.: 181–182° C. (crystallization solvent: ethyl acetate)

Example 69

6-(2,4-Difluorophenyl)-N-[2-(1-piperidinylmethyl)-6-quinolinyl]nicotinamide

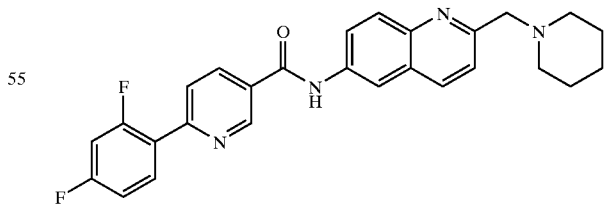

Using the 6-amino-2-(1-piperidinylmethyl)quinoline obtained in 2) of Example 54, the same procedures as those of 3) of Example 54 were conducted to obtain the titled compound as a colorless powder.

¹H-NMR (CDCl₃) δ: 1.41–1.77 (6H, m), 2.47–2.68 (4H, m), 3.86 (2H, s), 6.88–7.13 (2H, m), 7.73 (2H, d, J=8.4 Hz), 7.90–8.00 (1H, m), 8.02–8.25 (4H, m), 8.32 (1H, dd, J=2.2 and 8.4 Hz), 8.46 (1H, d, J=1.8 Hz), 9.24 (1H, d, J=1.8 Hz). Elemental analysis for $C_{27}H_{24}F_2N_4O \cdot 0.5H_2O$ Calcd: C, 69.37; H, 5.39; N, 11.98. Found: C, 69.14; H, 5.21; N, 12.04. m.p.: 182–183° C. (crystallization solvent: ethyl acetate)

Example 70

2',4'-Dichloro-N-[2-(1-piperidinylmethyl)-6-quinolinyl][1,1'-biphenyl]-4-carboxamide

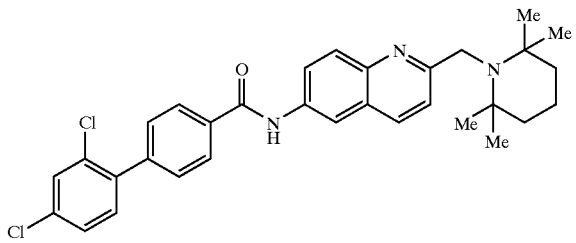

Using the N-[2-[(2,2,6,6-tetramethyl-1-piperidinyl)methyl]-6-quinolinyl]acetamide obtained in Reference Example 13, the same procedures as those of 2) of Example 6 were conducted to obtain the titled compound as a colorless powder.

$^1$H-NMR (CDCl$_3$) δ: 1.40–1.76 (6H, m), 2.48–2.63 (4H, m), 3.84 (2H, s), 7.22–7.40 (2H, m), 7.52–7.78 (5H, m), 7.96–8.19 (5H, m), 8.47 (1H, d, J=2.2 Hz). Elemental analysis for $C_{28}H_{25}Cl_2N_3O \cdot 0.5H_2O$ Calcd: C, 67.34; H, 5.25; N, 8.41. Found: C, 67.46; H, 5.20; N, 8.47. m.p.: 210–212° C. (decomposition)(crystallization solvent: ethyl acetate)

Example 71

4'-Fluoro-N-[2-[(2,2,6,6-tetramethyl-1-piperidinyl)methyl]-6-quinolinyl][1,1'-biphenyl]-4-carboxamide

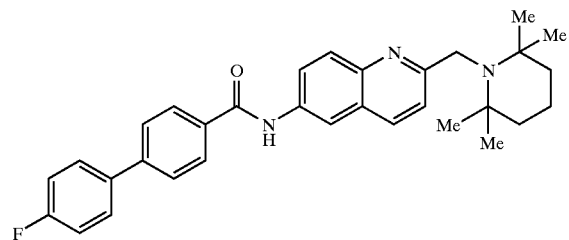

Using the N-[2-[(2,2,6,6-tetramethyl-1-piperidinyl)methyl]-6-quinolinyl]acetamide obtained in Reference Example 13, the same procedures as those of 2) of Example 6 were conducted to obtain the titled compound as a colorless powder.

$^1$H-NMR (CDCl$_3$) δ: 1.05 (12H, s), 1.60 (6H, br), 4.10 (2H, s), 7.17 (2H, t, J=8.8 Hz), 7.56–7.76 (5H, m), 7.96–8.17 (6H, m), 8.46 (1H, d, J=2.6 Hz). m.p.: 229–231° C. (decomposition)(crystallization solvent: ethyl acetate)

Example 72

6-(4-Chlorophenyl)-N-[2-[(2,2,6,6-tetramethyl-1-piperidinyl)methyl]-6-quinolinyl]nicotinamide

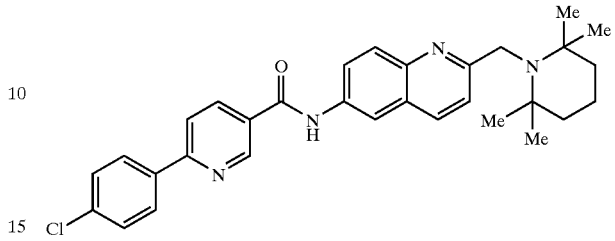

Using the N-[2-[(2,2,6,6-tetramethyl-1-piperidinyl)methyl]-6-quinolinyl]acetamide obtained in Reference Example 13, the same procedures as those of 2) of Example 6 were conducted to obtain the titled compound as a colorless powder.

$^1$H-NMR (CDCl$_3$) δ: 1.05 (12H, s), 1.60 (6H, br), 4.10 (2H, s), 7.49 (2H, d, J=8.8 Hz), 7.64–7.74 (1H, m), 7.81–7.90 (1H, m), 7.96–8.18 (6H, m), 8.27–8.38 (1H, m), 8.44 (1H, d, J=2.2 Hz), 9.20 (1H, d, J=1.8 Hz). Elemental analysis for $C_{31}H_{33}ClN_4O \cdot H_2O$ Calcd: C, 70.11; H, 6.64; N. 10.55. Found: C, 70.16; H, 6.59; N, 10.62. m.p.: 258–259° C. (crystallization solvent: ethyl acetate)

Example 73

6-(4-Methylphenyl)-N-[2-[(2,2,6,6-tetramethyl-1-piperidinyl)methyl]-6-quinolinyl]nicotinamide

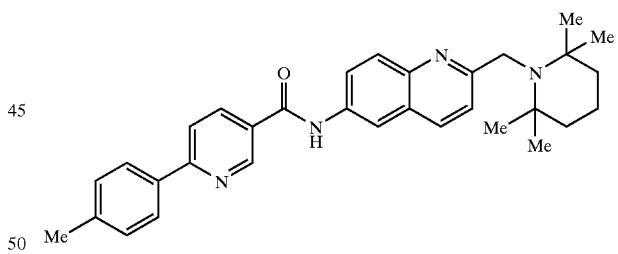

Using the N-[2-[(2,2,6,6-tetramethyl-1-piperidinyl)methyl]-6-quinolinyl]acetamide obtained in Reference Example 13, the same procedures as those of 2) of Example 6 were conducted to obtain the titled compound as a colorless powder.

$^1$H-NMR (CDCl$_3$) δ: 1.05 (12H, s), 1.60 (6H, br), 2.44 (3H, s), 4.10 (2H, s), 7.33 (2H, d, J=8.2 Hz), 7.63–7.74 (1H, m), 7.87 (1H, d, J=8.4 Hz), 7.94–8.16 (6H, m), 8.25–8.35 (1H, m), 8.44 (1H, d, J=2.6 Hz), 9.19 (1H, d, J=1.8 Hz). Elemental analysis for $C_{32}H_{36}N_4O \cdot H_2O$ Calcd: C, 75.26; H, 7.50; N, 10.97. Found: C, 74.98; H, 7.44; N, 11.07. m.p.: 246–247° C. (crystallization solvent: ethyl acetate)

Example 74

4-(4-Chlorophenyl)-N-[2-[(2,2,6,6-tetramethyl-1-piperidinyl)methyl]-6-quinolinyl]-1-piperidinecarboxamide

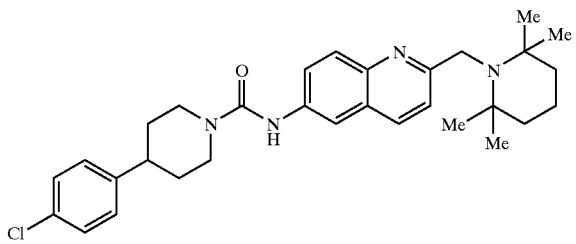

Using the N-[2-[(2,2,6,6-tetramethyl-1-piperidinyl)methyl]-6-quinolinyl]acetamide obtained in Reference Example 13, the same procedures as those of 2) of Example 54 and Example 38 were conducted to obtain the titled compound as a colorless powder.

$^1$H-NMR (CDCl$_3$) δ: 1.03 (12H, s), 1.46–2.01 (10H, m), 2.63-2.84 (1H, m), 2.95–3.15 (2H, m), 4.07 (2H, s), 4.20–4.37 (2H, m), 6.62 (1H, br), 7.15 (2H, d, J=8.4 Hz), 7.30 (2H, d, J=8.4 Hz), 7.49 (1H, dd, J=2.6 and 8.8 Hz), 7.81–8.11 (4H, m). FAB(pos): 519[MH]$^+$Elemental analysis for C$_{31}$H$_{39}$ClN$_4$O.0.5H$_2$O Calcd: C, 70.50; H, 7.63; N, 10.61. Found: C, 70.88; H, 7.79; N, 11.14. m.p.: 203–204° C. (crystallization solvent: ethyl acetate-diethyl ether)

Example 75

4-(4-Methylphenyl)-N-[2-[(2,2,6,6-tetramethyl-1-piperidinyl)methyl]-6-quinolinyl]-1-piperidinecarboxamide

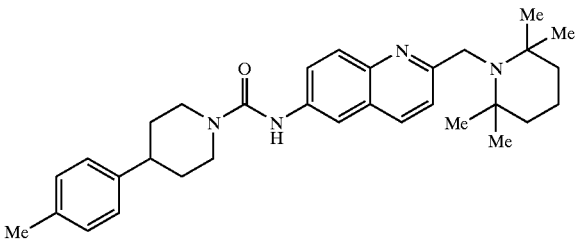

Using the N-[2-[(2,2,6,6-tetramethyl-1-piperidinyl)methyl]-6-quinolinyl]acetamide obtained in Reference Example 13, the same procedures as those of 2) of Example 54 and Example 38 were conducted to obtain the titled compound as a colorless powder.

$^1$H-NMR (CDCl$_3$) δ: 1.04 (12H, s), 1.50–2.02 (10H, m), 2.34 (3H, s), 2.63–2.84 (1H, m), 2.94–3.13 (2H, m), 4.07 (2H, s), 4.20–4.34 (2H, m), 6.59 (1H, br), 7.14 (4H, s), 7.48 (1H, dd, J=2.2 and 9.2 Hz), 7.86–8.09 (4H, m). Elemental analysis for C$_{32}$H$_{42}$N$_4$O.0.5H$_2$O Calcd: C, 75.70; H, 8.54; N, 11.04. Found: C, 75.57; H, 8.30; N, 11.16. m.p.: 200–202° C. (crystallization solvent: ethyl acetate-diethyl ether)

Example 76

N-[2-[(2,2,6,6-Tetramethyl-1-piperidinyl)methyl]-6-quinolinyl][1,1'-biphenyl]-4-carboxamide

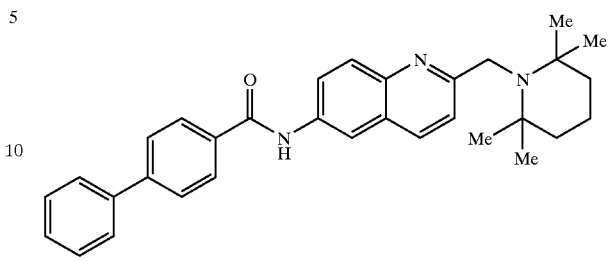

Using the N-[2-[(2,2,6,6-tetramethyl-1-piperidinyl)methyl]-6-quinolinyl]acetamide obtained in Reference Example 13, the same procedures as those of 2) of Example 6 were conducted to obtain the titled compound as a colorless powder.

$^1$H-NMR (CDCl$_3$) δ: 1.05 (12H, s), 1.60 (6H, br), 4.10 (2H, s), 7.40–7.56 (3H, m), 7.60–7.80 (6H, m), 7.96–8.16 (5H, m), 8.47 (1H, d, J=2.4 Hz). m.p.: 200–201° C. (crystallization solvent: ethyl acetate)

Example 77

4'-Methyl-N-[2-[(2,2,6,6-tetramethyl-1-piperidinyl)methyl]-6-quinolinyl][1,1'-biphenyl]-4-carboxamide

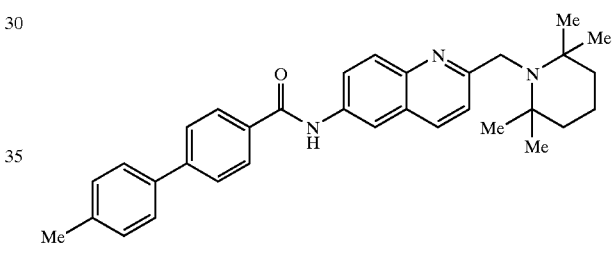

Using the N-[2-[(2,2,6,6-tetramethyl-1-piperidinyl)methyl]-6-quinolinyl]acetamide obtained in Reference Example 13, the same procedures as those of 2) of Example 6 were conducted to obtain the titled compound as a colorless powder.

$^1$H-NMR (CDCl$_3$) δ: 1.04 (12H, s), 1.59 (6H, br), 2.42 (3H, s), 4.09 (2H, s), 7.30 (2H, d, J=8.2 Hz), 7.55 (2H, d, J=8.2 Hz), 7.63–7.77 (4H, m), 7.95–8.16 (5H, m), 8.46 (1H, d, J=2.6 Hz). Elemental analysis for C$_{33}$H$_3$N$_3$O.0.5H$_2$O Calcd: C, 79.16; H, 7.65; N, 8.39. Found: C, 79.21, H, 7.66; N, 8.41. m.p.: 242–243° C. (crystallization solvent: ethyl acetate)

Example 78

4'-Methoxy-N-[2-[(2,2,6,6-tetramethyl-1-piperidinyl)methyl]-6-quinolinyl][1,1'-biphenyl]-4-carboxamide

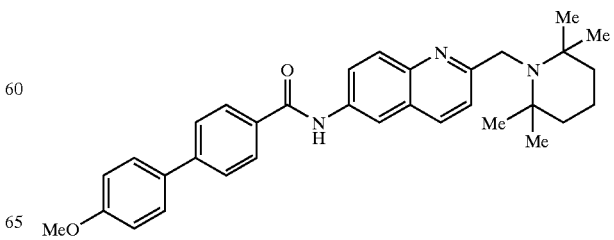

Using the N-[2-[(2,2,6,6-tetramethyl-1-piperidinyl)methyl]-6-quinolinyl]acetamide obtained in Reference Example 13, the same procedures as those of 2) of Example 6 were conducted to obtain the titled compound as a colorless powder.

$^1$H-NMR (CDCl$_3$) δ: 1.04 (12H, s), 1.59 (6H, br), 3.88 (3H, s), 4.10 (2H, s), 7.02 (2H, d, J=8.8 Hz), 7.55–7.76 (5H, m), 7.94–8.16 (6H, m), 8.46 (1H, d, J=2.6 Hz). m.p.: 210–211° C. (crystallization solvent: ethyl acetate)

Example 79

4'-Fluoro-N-[2-[(cis-2,6-dimethyl-1-piperidinyl)methyl]-6-quinolinyl][1,1'-biphenyl]-4-carboxamide

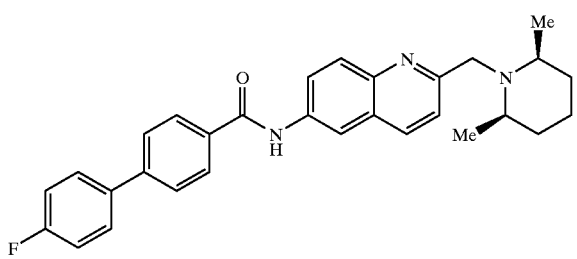

Using the N-[2-[(cis-2,6-dimethyl-1-piperidinyl)methyl]-6-quinolinyl]acetamide obtained in Reference Example 11, the same procedures as those of 2) of Example 6 were conducted to obtain the titled compound as a colorless powder.

$^1$H-NMR (CDCl$_3$) δ: 1.05 (6H, d, J=6.2 Hz), 1.28–1.80 (6H, m), 2.51–2.73 (2H, m), 4.04 (2H, s), 7.17 (2H, t, J=8.8 Hz), 7.54–7.76 (5H, m), 7.86 (1H, d, J=8.4 Hz), 7.96–8.17 (5H, m), 8.46 (1H, d, J=2.2 Hz). Elemental analysis for C$_{30}$H$_{30}$FN$_3$O.0.5H$_2$O Calcd: C, 75.60; H, 6.56; N, 8.82. Found: C, 75.72; H, 6.31; N, 8.72. m.p.: 187–188° C. (crystallization solvent: ethyl acetate)

Example 80

N-[2-[(cis-2,6-Dimethyl-1-piperidinyl)methyl]-6-quinolinyl][1,1'-biphenyl]-4-carboxamide

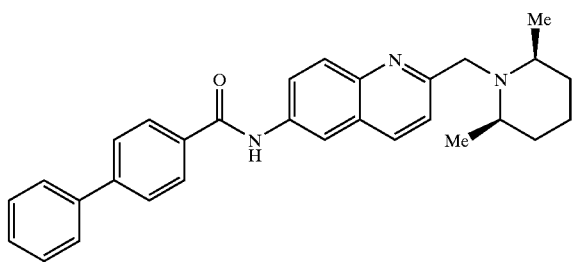

Using the N-[2-[(cis-2,6-dimethyl-1-piperidinyl)methyl]-6-quinolinyl]acetamide obtained in Reference Example 11, the same procedures as those of 2) of Example 6 were conducted to obtain the titled compound as a colorless powder.

$^1$H-NMR (CDCl$_3$) δ: 1.05 (6H, d, J=6.2 Hz), 1.28–1.77 (6H, m), 2.52–2.72 (2H, m), 4.04 (2H, s), 7.40–7.57 (3H, m), 7.60–7.80 (5H, m), 7.86 (1H, d, J=8.4 Hz), 7.96–8.16 (5H, m), 8.47 (1H, d, J=2.2 Hz). Elemental analysis for C$_{30}$H$_{31}$N$_3$O.0.5H$_2$O Calcd: C, 78.57; H, 7.03; N, 9.16. Found: C, 78.36, H, 6.64; N, 9.12. m.p.: 180–181° C. (crystallization solvent: ethyl acetate)

Example 81

4'-Methyl-N-[2-[(cis-2,6-dimethyl-1-piperidinyl)methyl]-6-quinolinyl][1,1'-biphenyl]-4-carboxamide

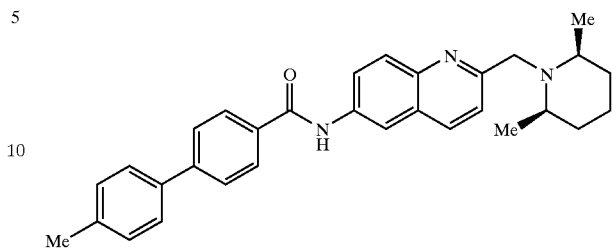

Using the N-[2-[(cis-2,6-dimethyl-1-piperidinyl)methyl]-6-quinolinyl]acetamide obtained in Reference Example 11, the same procedures as those of 2) of Example 6 were conducted to obtain the titled compound as a colorless powder.

$^1$H-NMR (CDCl$_3$) δ: 1.05 (6H, d, J=6.2 Hz), 1.28–1.80 (6H, m), 2.43 (3H, s), 2.52–2.73 (2H, m), 4.04 (2H, s), 7.30 (2H, d, J=8.2 Hz), 7.55 (2H, d, J=8.2 Hz), 7.63–7.78 (3H, m), 7.85 (1H, d, J=8.4 Hz), 7.94–8.17 (5H, m), 8.46 (1H, d, J=2.2 Hz). Elemental analysis for C$_{31}$H$_{33}$N$_3$O.0.5H$_2$O Calcd: C, 78.78; H, 7.25; N, 8.89. Found: C, 78.87; H, 7.08; N, 8.82. m.p.: 198–199° C. (dec.) (crystallization solvent: ethyl acetate)

Example 82

4'-Methoxy-N-[2-[(cis-2,6-dimethyl-1-piperidinyl)methyl]-6-quinolinyl][1,1'-biphenyl]-4-carboxamide

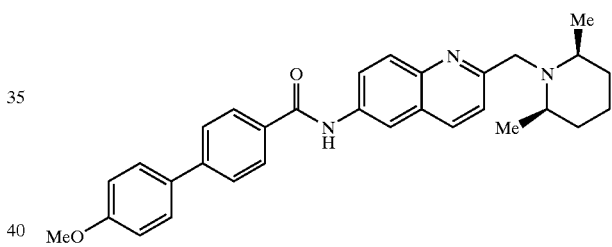

Using the N-[2-[(cis-2,6-dimethyl-1-piperidinyl)methyl]-6-quinolinyl]acetamide obtained in Reference Example 11, the same procedures as those of 2) of Example 6 were conducted to obtain the titled compound as a colorless powder.

$^1$H-NMR (CDCl$_3$) δ: 1.04 (6H, d, J=6.0 Hz), 1.23–1.85 (6H, m), 2.50–2.72 (2H, m), 3.87 (3H, s), 4.03 (2H, s), 7.01 (2H, d, J=8.8 Hz), 7.50–7.77 (5H, m), 7.85 (1H, d, J=8.4 Hz), 7.90–8.20 (5H, m), 8.46 (1H, br). m.p.: 194–196° C. (dec.) (crystallization solvent: ethyl acetate)

Example 83

6-(4-Chlorophenyl)-N-[2-[(cis-2,6-dimethyl-1-piperidinyl)methyl]-6-quinolinyl]nicotinamide

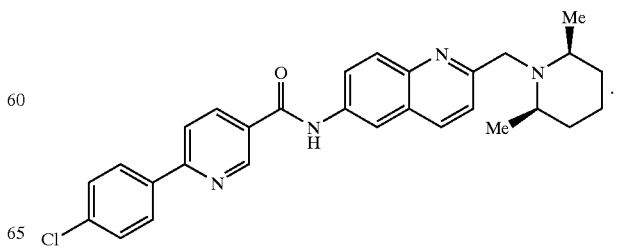

Using the N-[2-[(cis-2,6-dimethyl-1-piperidinyl)methyl]-6-quinolinyl]acetamide obtained in Reference Example 11, the same procedures as those of 2) of Example 6 were conducted to obtain the titled compound as a colorless powder.

$^1$H-NMR (CDCl$_3$) δ: 1.04 (6H, d, J=6.2 Hz), 1.27–1.76 (6H, m), 2.51–2.76 (2H, m), 4.03 (2H, s), 7.47 (2H, d, J=8.4 Hz), 7.70 (1H, dd, J=2.2 and 8.8 Hz), 7.76–7.92 (2H, m), 7.94–8.13 (4H, m), 8.23–8.36 (2H, m), 8.42 (1H, d, J=2.2 Hz), 9.19 (1H, d, J=2.2 Hz). Elemental analysis for C$_{29}$H$_{29}$ClN$_4$O.0.5H$_2$O Calcd: C, 70.50; H, 6.12; N, 11.34. Found: C, 70.58; H, 6.06; N, 11.14. m.p.: 217–219° C. (dec.) (crystallization solvent: ethyl acetate)

Example 84

6-(4-Methylphenyl)-N-[2-[(cis-2,6-dimethyl-1-piperidinyl)methyl]-6-quinolinyl]nicotinamide

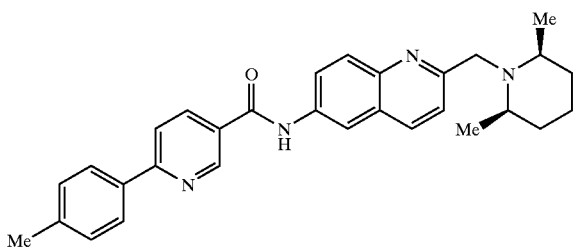

Using the N-[2-[(cis-2,6-dimethyl-1-piperidinyl)methyl]-6-quinolinyl]acetamide obtained in Reference Example 11, the same procedures as those of 2) of Example 6 were conducted to obtain the titled compound as a colorless powder.

$^1$H-NMR (CDCl$_3$) δ: 1.04 (6H, d, J=6.2 Hz), 1.28–1.80 (6H, m), 2.43 (3H, s), 2.51–2.72 (2H, m), 4.04 (2H, s), 7.32 (2H, d, J=8.0 Hz), 7.69 (1H, dd, J=2.2 and 8.8 Hz), 7.80–8.20 (7H, m), 8.28 (1H, dd, J=2.2 and 8.4 Hz), 8.43 (1H, d, J=2.2 Hz), 9.18 (1H, d, J=2.2 Hz). m.p.: 225–226° C. (dec.) (crystallization solvent: ethyl acetate)

Example 85

4-(4-Chlorophenyl)-N-[2-[(cis-2,6-dimethyl-1-piperidinyl)methyl]-6-quinolinyl]-1-piperidinecarboxamide

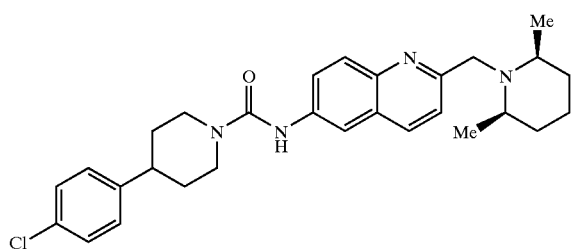

Using the N-[2-[(cis-2,6-dimethyl-1-piperidinyl)methyl]-6-quinolinyl]acetamide obtained in Reference Example 11, the same procedures as those of Example 54 and Example 38 were conducted to obtain the titled compound as a colorless powder.

$^1$H-NMR (CDCl$_3$) δ: 1.04 (6H, d, J=6.2 Hz), 1.23–2.02 (10H, m), 2.50–2.83 (3H, m), 2.94–3.15 (2H, m), 4.02 (2H, s), 4.20–4.37 (2H, m), 6.64 (1H, br), 7.15 (2H, d, J=8.4 Hz), 7.30 (2H, d, J=8.4 Hz), 7.50 (1H, dd, J=2.2 and 8.8 Hz), 7.79 (1H, d, j=8.8 Hz), 7.88–8.08 (3H, m). m.p.: 196–198° C. (dec.) (crystallization solvent: ethyl acetate-diethyl ether)

Example 86

4-(4-Methylphenyl)-N-[2-[(cis-2,6-dimethyl-1-piperidinyl)methyl]-6-quinolinyl]-1-piperidinecarboxamide

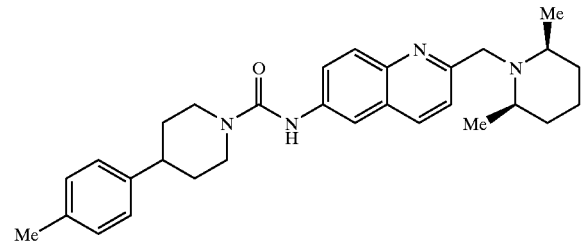

Using the N-[2-[(cis-2,6-dimethyl-1-piperidinyl)methyl]-6-quinolinyl]acetamide obtained in Reference Example 11, the same procedures as those of 2) of Example 54 and Example 38 were conducted to obtain the titled compound as a colorless powder.

$^1$H-NMR (CDCl$_3$) δ: 1.04 (6H, d, J=6.0 Hz), 1.20–2.03 (10H, m), 2.33 (3H, s), 2.50–2.82 (3H, m), 2.90–3.15 (2H, m), 4.02 (2H, s), 4.17–4.39 (2H, m), 6.70 (1H, br), 7.13 (4H, br), 7.51 (1H, d, J=8.8 Hz), 7.78 (1H, d, J=8.8 Hz), 7.95–8.15 (3H, m). Elemental analysis for C$_{30}$H$_{38}$N$_4$O.H$_2$O Calcd: C, 73.74; H, 8.25; N, 11.47. Found: C, 74.12; H, 8.05; N, 11.82. m.p.: 177–178° C. (dec.) (crystallization solvent: ethyl acetate-diethyl ether)

Example 87

4-(4-Fluorophenyl)-N-[2-[(cis-2,6-dimethyl-1-piperidinyl)methyl]-6-quinolinyl]-1-piperidinecarboxamide

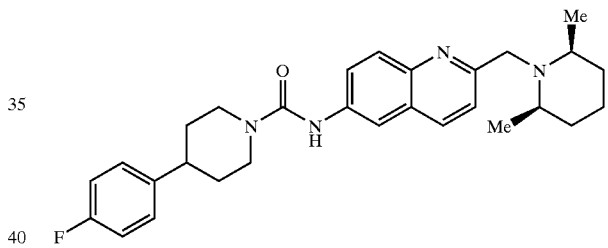

Using the N-[2-[(cis-2,6-dimethyl-1-piperidinyl)methyl]-6-quinolinyl]acetamide obtained in Reference Example 11, the same procedures as those of 2) of Example 54 and Example 38 were conducted to obtain the titled compound as colorless amorphous powders.

$^1$H-NMR (CDCl$_3$) δ: 1.04 (6H, d, J=6.2 Hz), 1.22–2.02 (10H, m), 2.50–2.82 (3H, m), 2.94–3.14 (2H, m), 4.01 (2H, s), 4.10–4.36 (2H, m), 6.66 (1H, br), 7.01 (2H, dd, J=8.4 and 8.8 Hz), 7.11–7.24 (2H, m), 7.50 (1H, dd, J=2.2 and 8.8 Hz), 7.60 (1H, d, J=8.4 Hz), 7.92–8.10 (3H, m).

FAB(pos): 475[MH]$^+$

Example 88

4-(4-Methoxy)-N-[2-[(cis-2,6-dimethyl-1-piperidinyl)methyl]-6-quinolinyl]-1-piperidinecarboxamide

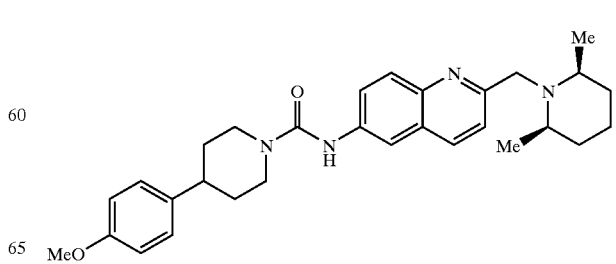

Using the N-[2-[(cis-2,6-dimethyl-1-piperidinyl)methyl]-6-quinolinyl]acetamide obtained in Reference Example 11, the same procedures as those of 2) of Example 54 and Example 38 were conducted to obtain the titled compound as colorless amorphous powders.

$^1$H-NMR (CDCl$_3$) δ: 1.04 (6H, d, J=6.2 Hz), 1.23–2.02 (10H, m), 2.50–2.83 (3H, m), 2.94–3.14 (2H, m), 3.80 (3H, s), 4.01 (2H, s), 4.19–4.36 (2H, m), 6.66 (1H, br), 6.87 (2H, d, J=8.4 Hz), 7.15 (2H, d, J=8.4 Hz), 7.50 (1H, dd, J=2.6 and 9.2 Hz), 7.61 (1H, d, J=8.4 Hz), 7.93–8.10 (3H, m). FAB (pos): 487[MH]$^+$

Example 89

2',4-Difluoro-N-[2-[(cis-2,6-dimethyl-1-piperidinyl)methyl]-6-quinolinyl][1,1'-biphenyl]-4-carboxamide

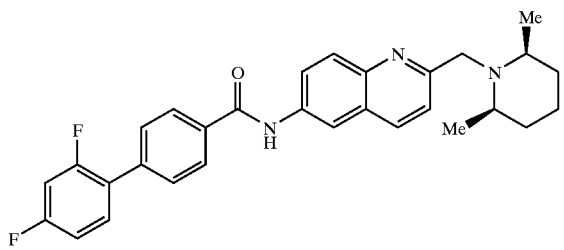

Using the N-[2-[(cis-2,6-dimethyl-1-piperidinyl)methyl]-6-quinolinyl]acetamide obtained in Reference Example 11, the same procedures as those of 2) of Example 6 were conducted to obtain the titled compound as colorless amorphous powders.

$^1$H-NMR (CDCl$_3$) δ: 1.05 (6H, d, J=6.2 Hz), 1.28–1.83 (6H, m), 2.51–2.82 (2H, m), 4.04 (2H, s), 6.88–7.08 (2H, m), 7.37–7.53 (1H, m), 7.60–7.74 (3H, m), 7.86 (1H, d, J=8.4 Hz), 7.95–8.18 (5H, m), 8.46 (1H, d, J=2.2 Hz). FAB(pos): 486[MH]$^+$

Example 90

2',4-Dichloro-N-[2-[(cis-2,6-dimethyl-1-piperidinyl)methyl]-6-quinolinyl][1,1'-biphenyl]-4-carboxamide

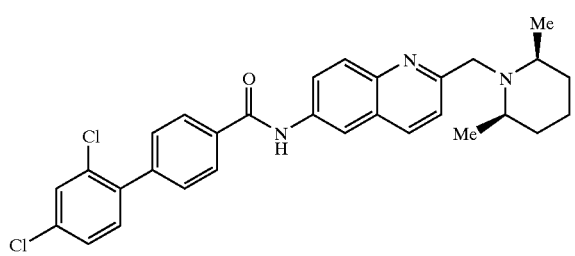

Using the N-[2-[(cis-2,6-dimethyl-1-piperidinyl)methyl]-6-quinolinyl]acetamide obtained in Reference Example 11, the same procedures as those of 2) of Example 6 were conducted to obtain the titled compound as a colorless powder.

$^1$H-NMR (CDCl$_3$) δ: 1.04 (6H, d, J=6.3 Hz), 1.27–1.80 (6H, m), 2.52–2.70 (2H, m), 4.03 (2H, s), 7.23–7.40 (2H, m), 7.46–7.60 (3H, m), 7.68 (1H, dd, J=2.1 and 9.0 Hz), 7.86 (1H, d, J=8.4 Hz), 7.93–8.05 (3H, m), 8.09 (1H, d, J=8.4 Hz), 8.16 (1H, br), 8.46 (1H, d, J=2.4 Hz).

m.p.: 162–164° C. (crystallization solvent: ethyl acetate)

Example 91

4'-Chloro-N-[2-[(diisopropylamino)methyl]-6-quinolinyl][1,1'-biphenyl]-4-carboxamide

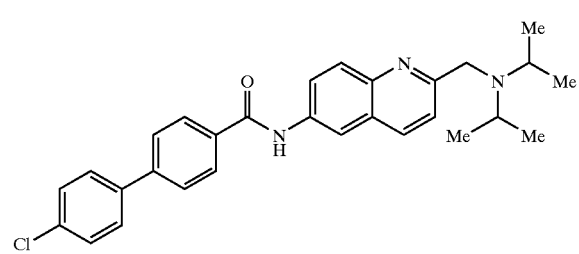

Using the N-[2-[(diisopropylamino)methyl]-6-quinolinyl]acetamide obtained in Reference Example 10, the same procedures as those of 2) of Example 6 were conducted to obtain the titled compound as a colorless powder.

$^1$H-NMR (CDCl$_3$) δ: 1.06 (12H, d, J=6.6 Hz), 2.96–3.19 (2H, m), 3.94 (2H, s), 7.45 (2H, d, J=8.8 Hz), 7.56 (2H, d, J=8.8 Hz), 7.63–7.73 (3H, m), 7.83 (1H, d, J=8.8 Hz), 7.94–8.19 (5H, m), 8.46 (1H, d, J=2.2 Hz). m.p.: 201–202° C. (dec.)(crystallization solvent: ethyl acetate)

Example 92

4'-Chloro-N-[2-[(diethylamino)methyl]-6-quinolinyl][1,1'-biphenyl]-4-carboxamide

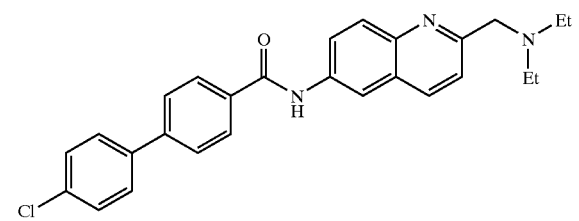

Using the 2-(diethylaminomethyl)-6-quinolinamine obtained in Reference Example 12, the same procedures as those of 3) of Example 54 were conducted to obtain the titled compound as a colorless powder.

$^1$H-NMR (CDCl$_3$) δ: 1.09 (6H, t, J=7.2 Hz), 2.64 (4H, q, J=7.2 Hz), 3.89 (2H, s), 7.45 (2H, d, J=8.4 Hz), 7.57 (2H, d, J=8.4 Hz), 7.62–7.78 (4H, m), 7.94–8.19 (5H, m), 8.47 (1H, d, J=2.2 Hz). m.p.: 196–198° C. (decomposition) (crystallization solvent: ethyl acetate-diethyl ether)

Example 93

N-[2-[(2-Methyl-4,5-dihydro-1H-imidazol-1-yl)methyl]-6-quinolinyl][1,1'-biphenyl]-4-carboxamide

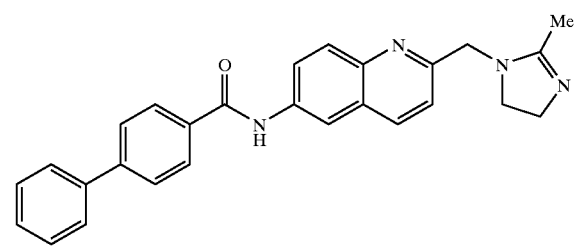

Using the 2-(chloromethyl)-6-quinolinylamine dihydrochloride obtained in Reference Example 7, the same procedures as those of Reference Example 8 and Example 23 were conducted to obtain the titled compound as a powder.

¹H-NMR (DMSO-d$_6$) δ: 2.20 (3H, s), 3.36–3.96 (4H, m), 4.70 (2H, s), 7.34–7.56 (5H, m), 7.58–7.82 (3H, m), 7.91–8.26 (5H, m), 8.61 (1H, d, J=2.2 Hz), 10.40 (1H, br).

FAB(pos): 421 [MH]$^+$ m.p.: 212–220° C. (decomposition) (crystallization solvent: ethyl acetate)

Example 94

N-[2-[(2-Phenyl-4,5-dihydro-1H-imidazol-1-yl)methyl]-6-quinolinyl][1,1'-biphenyl]-4-carboxamide

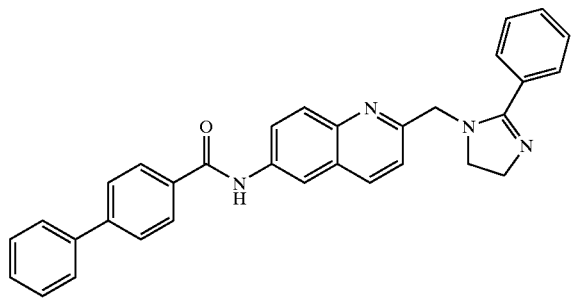

Using the 2-(chloromethyl)-6-quinolinylamine dihydrochloride obtained in Reference Example 7, the same procedures as those of Reference Example 8 and Example 23 were conducted to obtain the titled compound as a powder.

¹H-NMR (CDCl$_3$) δ: 3.54 (2H, t, J=9.8 Hz), 3.98 (2H, t, J=9.8 Hz), 4.59 (2H, s), 7.30–7.80 (15H, m), 8.01 (2H, d, J=8.0 Hz), 8.17 (1H, d, J=8.4 Hz), 8.39 (1H, s), 8.55 (1H, d, J=1.8 Hz). FAB(pos): 483[MH]$^+$ m.p.: 212–216° C. (decomposition)(crystallization solvent: ethyl acetate)

Example 95

4'-Fluoro-N-[2-[(2-methyl-4,5-dihydro-1H-imidazol-1-yl)methyl]-6-quinolinyl][1,1'-biphenyl]-4-carboxamide

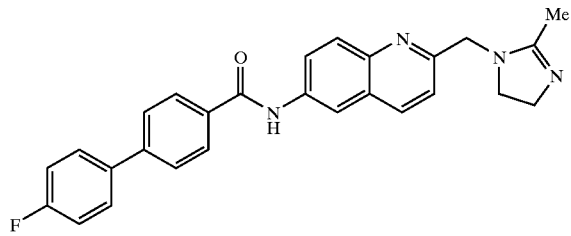

Using the 2-(chloromethyl)-6-quinolinylamine dihydrochloride obtained in Reference Example 7, the same procedures as those of Reference Example 8 and Example 23 were conducted to obtain the titled compound as a pale brown powder.

¹H-NMR (DMSO-d$_6$) δ: 1.99 (3H, s), 3.3 (2H, br m), 3.5 (2H, br m), 4.58 (2H, s), 7.3–7.5 (3H, br m), 7.8–8.1 (9H, br m), 8.35 (1H, br d), 8.56 (1H, br s). m.p.: 240–242° C. (decomposition) (crystallization solvent: ethyl acetate)

Example 96

4'-Fluoro-N-[2-[(2-phenyl-4,5-dihydro-1H-imidazol-1-yl)methyl]-6-quinolinyl][1,1'-biphenyl]-4-carboxamide

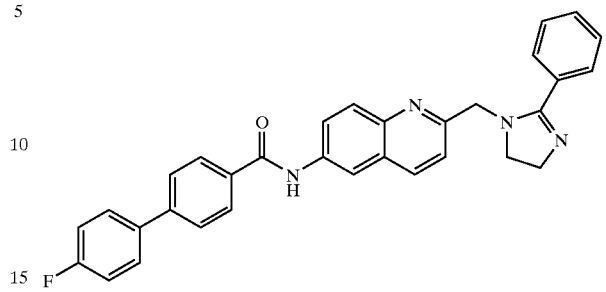

Using the 2-(chloromethyl)-6-quinolinylamine dihydrochloride obtained in Reference Example 7, the same procedures as those of Reference Example 8 and Example 23 were conducted to obtain the titled compound as a pale brown powder.

¹H-NMR (DMSO-d$_6$) δ: 3.45 (2H, t, J=10.0 Hz), 3.82 (2H, t, J=10.0 Hz), 4.50 (2H, s), 7.31–7.66 (8H, m), 7.80–8.15 (9H, m), 8.35 (1H, d, J=8.8 Hz), 8.57 (1H, d, J=2.2 Hz). m.p.: 209–210° C. (crystallization solvent: ethyl acetate)

Example 97

N-[2-[(2-Benzyl-4,5-dihydro-1H-imidazol-1-yl)methyl]-6-quinolinyl]-4'-fluoro-[1,1'-biphenyl]-4-carboxamide

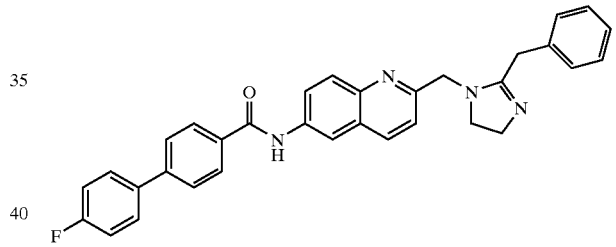

Using the 2-(chloromethyl)-6-quinolinylamine dihydrochloride obtained in Reference Example 7, the same procedures as those of Reference Example 8 and Example 23 were conducted to obtain the titled compound as a pale brown powder.

¹H-NMR (DMSO-d$_6$) δ: 3.22 (2H, t, J=9.8 Hz), 3.60 (2H, t, J=9.8 Hz), 3.75 (2H, s), 4.52 (2H, s), 7.17–7.40 (8H, m), 7.80–8.14 (9H, m), 8.25 (1H, d, J=8.4 Hz), 8.54 (1H, d, J=1.8 Hz). m.p.: 200–202° C. (crystallization solvent: ethyl acetate)

Example 98

Trans-2-(4-chlorophenyl)-N-[2-(1-pyrrolidinylmethyl)-6-quinolinyl]-1,3-dioxane-5-carboxamide

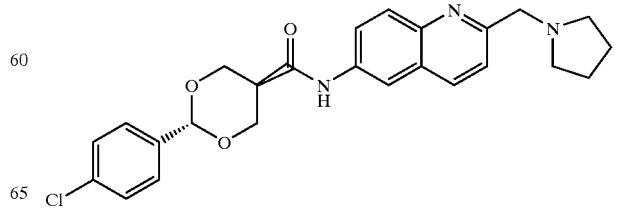

Using the 2-(1-pyrrolidinylmethyl)-6-quinolinylamine obtained in Reference Example 9 and 2-(4-chlorophenyl)-5-carboxy-1,3-dioxane obtained in Reference Example 14, the same procedures as those of 3) of Example 54 were conducted to obtain the titled compound as a colorless powder.

$^1$H-NMR (CDCl$_3$) δ: 1.82 (4H, m), 2.62 (4H, m), 3.10 (1H, m), 3.94 (2H, s), 4.27 (2H, t like), 4.46 (2H, dd like), 5.57 (1H, s), 7.35–7.62 (7H, m), 8.06 (2H, t, J=12.6 Hz), 8.29 (1H, d, J=2.7 Hz). m.p.: 244–246° C. (crystallization solvent: ethyl acetate)

Example 99

4-(4-Fluorophenyl)-N-[6-(1-pyrrolidinylmethyl)-2-naphthyl]-1-piperidinecarboxamide

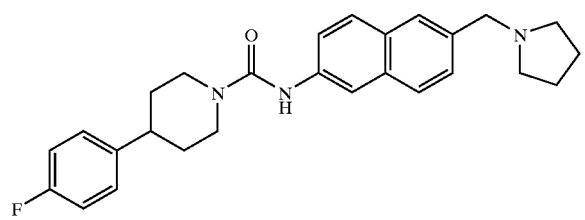

Using the 6-(1-pyrrolidinylmethyl)naphthalene-2-amine obtained in Reference Example 18, the same procedures as those of Example 38 were conducted to obtain the titled compound as a colorless powder.

$^1$H-NMR (DMSO-d$_6$) δ: 1.57 (2H, m), 1.69 (4H, m), 1.80 (2H, m), 2.45 (4H, m), 2.77 (1H, m), 2.90 (2H, m), 3.68 (2H, s), 4.32 (2H, m), 7.13 (2H, m), 7.34 (2H, m), 7.38 (1H, m), 7.60 (1H, m), 7.66–7.76 (3H, m), 8.00 (1H, d, J=2.1 Hz), 8.71 (1H, s). FAB(pos): 432[M+H]$^+$ m.p.: 209–211° C. (crystallization solvent: ethyl acetate-diisopropyl ether)

Example 100

4-(4-Methoxyphenyl)-N-[6-(1-pyrrolidinylmethyl)-2-naphthyl]-1-piperidinecarboxamide

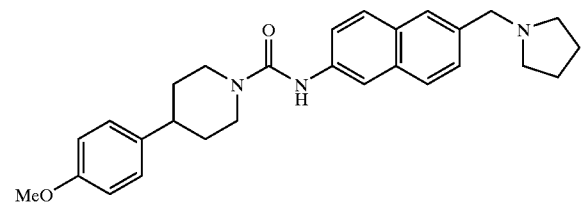

Using the 6-(1-pyrrolidinylmethyl)naphthalene-2-amine obtained in Reference Example 18, the same procedures as those of Example 38 were conducted to obtain the titled compound as a colorless powder.

$^1$H-NMR (CDCl$_3$) δ: 1.70–1.95 (8H, m), 2.55 (4H, m), 2.70 (1H, m), 3.02 (2H, m), 3.74 (2H, s), 3.80 (3H, s), 4.26 (2H, m), 6.56 (1H, s), 6.87 (2H, d, J=8.4 Hz), 7.15 (2H, d, J=8.8 Hz), 7.38 (2H, m), 7.69–7.76 (3H, m), 7.92 (1H, m). FAB(pos): 444[M+H]$^+$ m.p.: 194–196° C. (crystallization solvent: ethyl acetate-diisopropyl ether)

Example 101

4-(4-Chlorophenyl)-N-[6-(1-pyrrolidinylmethyl)-2-naphthyl]-1-piperidinecarboxamide

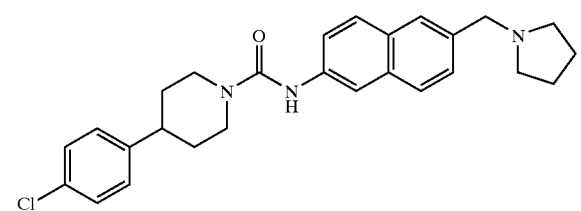

Using the 6-(1-pyrrolidinylmethyl)naphthalene-2-amine obtained in Reference Example 18, the same procedures as those of Example 38 were conducted to obtain the titled compound as a colorless powder.

$^1$H-NMR (DMSO-d$_6$) δ: 1.55 (2H, m), 1.68 (4H, m), 1.78 (2H, m), 2.43 (4H, m), 2.76 (1H, m), 2.88 (2H, m), 3.65 (2H, s), 4.30 (2H, m), 7.33 (5H, m), 7.57 (1H, m), 7.64–7.74 (3H, m), 7.98 (1H, d, J=2.5 Hz), 8.69 (1H, s). FAB(pos): 432 [M+H]$^+$ m.p.: 209–211° C. (crystallization solvent: ethyl acetate-diisopropyl ether)

Example 102

4-Phenyl-N-[6-(1-pyrrolidinylmethyl)-2-naphthyl]-1-piperidinecarboxamide

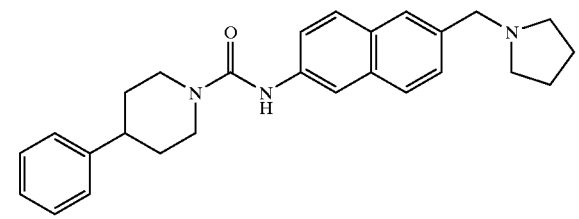

Using the 6-(1-pyrrolidinylmethyl)naphthalene-2-amine obtained in Reference Example 18, the same procedures as those of Example 38 were conducted to obtain the titled compound as a colorless powder.

$^1$H-NMR (DMSO-d$_6$) δ: 1.60 (2H, m), 1.76 (4H, m), 1.82 (2H, m), 2.46 (4H, m), 2.76 (1H, m), 2.91 (2H, m), 3.68 (2H, s), 4.32 (2H, m), 7.18–7.34 (5H, m), 7.39 (1H, m), 7.60 (1H, m), 7.69–7.76 (3H, m), 8.00 (1H, d, J=1.8 Hz), 8.71 (1H, s). FAB(pos): 414[M+H]$^+$ m.p.: 193–195° C. (crystallization solvent: ethyl acetate-diisopropyl ether)

Example 103

4-Methylphenyl-N-[6-(1-pyrrolidinylmethyl)-2-naphthyl]-1-piperidinecarboxamide

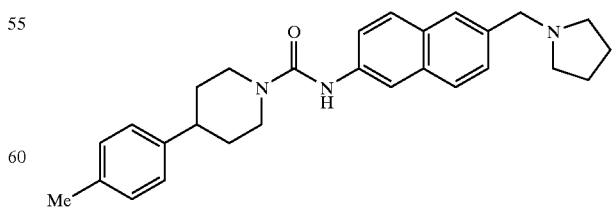

Using the 6-(1-pyrrolidinylmethyl)naphthalene-2-amine obtained in Reference Example 18, the same procedures as those of Example 38 were conducted to obtain the titled compound as a colorless powder.

$^1$H-NMR (DMSO-d$_6$) δ: 1.55 (2H, m), 1.70 (4H, m), 1.80 (2H, m), 2.26 (3H, s), 2.46 (4H, m), 2.71 (1H, m), 2.90 (2H, m), 3.68 (2H, s), 4.31 (2H, m), 7.12 (4H, m), 7.39 (1H, m), 7.60 (1H, m), 7.66–7.76 (3H, m), 8.00 (1H, d, J=1.8 Hz), 8.70 (1H, s). FAB(pos): 428[M+H]$^+$ m.p.: 210–212° C. (crystallization solvent: ethyl acetate-diisopropyl ether)

Example 104

6-(4-Fluorophenyl)-N-[6-(1-piperidinylmethyl)-2-naphthyl]nicotinamide

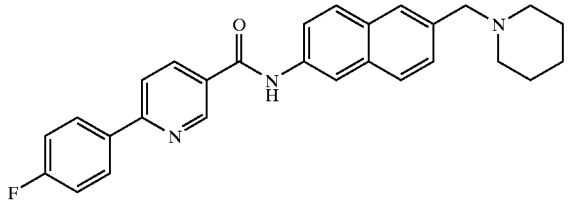

Using the 6-(1-piperidinylmethyl)naphthalene-2-amine obtained in Reference Example 15, the same procedures as those of 3) of Example 54 were conducted to obtain the titled compound as a colorless powder.

$^1$H-NMR (DMSO-d$_6$): 1.41 (2H, m), 1.51 (4H, m), 2.36 (4H, brs), 3.56 (2H, s), 7.38 (2H, dd, J=8.3 and 8.8 Hz), 7.47 (1H, d, J=8.3 Hz), 7.73 (1H, s), 7.83 (2H, m), 7.89 (1H, d, J=9.0 Hz), 8.18 (1H, d, J=8.3 Hz), 8.27 (2H, m), 8.44 (2H, m), 9.24 (1H, m), 10.64 (1H, brs). m.p.: 218–219° C. (crystallization solvent: ethyl acetate-diisopropyl ether)

Example 105

6-(4-Methoxyphenyl)-N-[6-(1-piperidinylmethyl)-2-naphthyl]nicotinamide

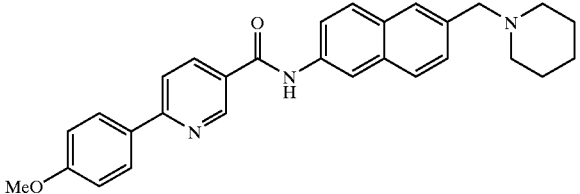

Using the 6-(1-piperidinylmethyl)naphthalene-2-amine obtained in Reference Example 15, the same procedures as those of 3) of Example 54 were conducted to obtain the titled compound as a colorless powder.

$^1$H-NMR (DMSO-d$_6$): 1.40 (2H, m), 1.51 (4H, m), 2.37 (4H, brs), 3.57 (2H, s), 3.84 (3H, s), 7.09 (2H, d, J=8.3 Hz), 7.46 (1H, d, J=8.1 Hz), 7.73 (1H, s), 7.81 (2H, m), 7.89 (1H, d, J=9.0 Hz), 8.10 (1H, d, J=8.1 Hz), 8.17 (2H, d, J=8.3 Hz), 8.39 (1H, d, J=8.3 Hz), 8.43 (1H, s), 9.2 (1H, brs). m.p.: 263–264° C. (crystallization solvent: ethyl acetate-diisopropyl ether)

Example 106

6-(4-Chlorophenyl)-N-[6-(1-piperidinylmethyl)-2-naphthyl]nicotinamide

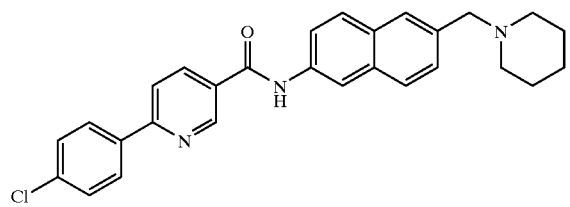

Using the 6-(1-piperidinylmethyl)naphthalene-2-amine obtained in Reference Example 15, the same procedures as those of 3) of Example 54 were conducted to obtain the titled compound as a colorless powder.

$^1$H-NMR (DMSO-d$_6$): 1.41 (2H, m), 1.51 (4H, m), 2.36 (4H, brs), 3.56 (2H, s), 7.38 (2H, dd, J=8.3 and 8.8 Hz), 7.47 (1H, d, J=8.3 Hz), 7.73 (1H, s), 7.83 (2H, m), 7.89 (1H, d, J=9.0 Hz), 8.18 (1H, d, J=8.3 Hz), 8.27 (2H, m), 8.44 (2H, m), 9.24 (1H, m), 10.64 (1H, brs). m.p.: 228–229° C. (crystallization solvent: ethyl acetate-acetone)

Example 107

4-(4-Fluorophenyl)-N-[6-(1-piperidinylmethyl)-2-naphthyl]-1-piperidinecarboxamide

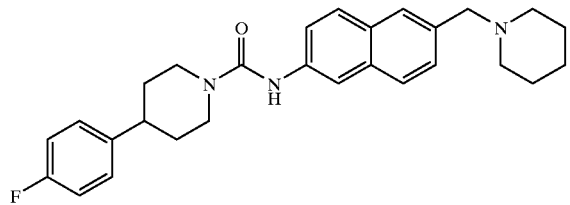

Using the 6-(1-piperidinylmethyl)naphthalene-2-amine obtained in Reference Example 15, the same procedures as those of Example 38 were conducted to obtain the titled compound as a colorless powder.

$^1$H-NMR (DMSO-d$_6$): 1.40 (2H, m), 1.48–1.61 (6H, m), 1.80 (2H, d, J=12.0 Hz), 2.34 (4H, brs), 2.77 (1H, m), 2.90 (2H, dd, J=12.0 and 12.2 Hz), 3.52 (2H, s), 4.32 (2H, d, J=13.2 Hz), 7.12 (2H, t, J=8.5 Hz), 7.30 (1H, d, J=5.9 Hz), 7.32 (1H, d, J=5.6 Hz), 7.38 (1H, d, J=8.3 Hz), 7.62 (2H, m), 7.68 (1H, d, J=8.3 Hz), 7.74 (1H, d, J=8.8 Hz), 8.00 (1H, s), 8.71 (1H, brs). m.p.: 209–211° C. (crystallization solvent: ethyl acetate-diisopropyl ether)

Example 108

4-(4-Chlorophenyl)-N-[6-(1-piperidinylmethyl)-2-naphthyl]-1-piperidinecarboxamide

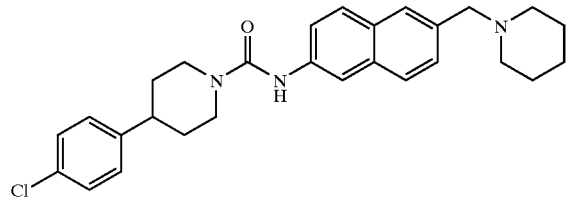

Using the 6-(1-piperidinylmethyl)naphthalene-2-amine obtained in Reference Example 15, the same procedures as those of Example 38 were conducted to obtain the titled compound as a colorless powder.

¹H-NMR (DMSO-d₆): 1.39 (2H, m), 1.48–1.61 (6H, m), 1.81 (2H, m), 2.35 (4H, brs), 2.78 (1H, m), 2.90 (2H, dd, J=11.5 and 12.7 Hz), 3.52 (2H, s), 4.32 (2H, d, J=13.7 Hz), 7.30–7.39 (5H, m), 7.59–7.75 (4H, m), 8.01 (1H, s), 8.71 (1H, brs). m.p.: 231–232° C., (crystallization solvent: ethyl acetate-diisopropyl ether)

Example 109

4-(4-Methylphenyl)-N-[6-(1-piperidinylmethyl)-2-naphthyl]-1-piperidinecarboxamide

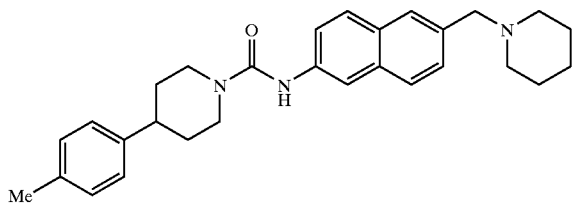

Using the 6-(1-piperidinylmethyl)naphthalene-2-amine obtained in Reference Example 15, the same procedures as those of Example 38 were conducted to obtain the titled compound as a colorless powder.

¹H-NMR (DMSO-d₆): 1.40 (2H, m), 1.48–1.61 (6H, m), 1.80 (2H, d, J=12.4 Hz), 2.26 (3H, s), 2.34 (4H, brs), 2.71 (1H, m), 2.89 (2H, dd, J=12.4 and 11.5 Hz), 3.52 (2H, s), 4.31 (2H, d, J=12.9 Hz), 7.10–7.16 (4H, m), 7.38 (1H, d, J=8.0 Hz), 7.61 (2H, m), 7.68 (1H, d, J=8.5 Hz), 7.74 (1H, d, J=8.8 Hz), 8.00 (1H, s), 8.70 (1H, brs). m.p.: 227–228° C. (crystallization solvent: ethyl acetate-diisopropyl ether)

Example 110

4-(4-Chlorophenyl)-N-[6-[(cis-2,6-dimethyl-1-piperidinyl)methyl]-2-naphthyl]-1-piperidinecarboxamide

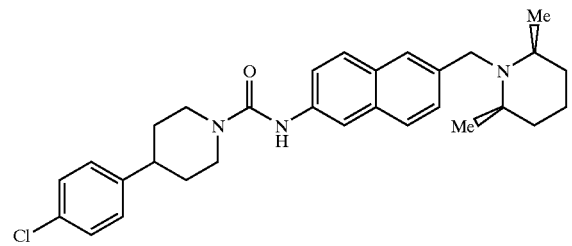

Using the 6-[(cis-2,6-dimethyl-1-piperidinyl)methyl] naphthalene-2-amine obtained in Reference Example 17, the same procedures as those of Example 38 were conducted to obtain the titled compound as a colorless powder.

¹H-NMR (DMSO-d₆): 0.98 (3H, s), 1.00 (3H, s), 1.28 (3H, m), 1.58 (3H, m), 1.81 (2H, m), 2.78 (1H, m), 2.90 (2H, m), 3.82 (2H, s), 4.31 (2H, m), 7.33 (4H, m), 7.43 (1H, m), 7.65 (1H, m), 7.72 (2H, m), 7.98 (1H, brs), 8.68 (1H, brs). m.p.: 199–200° C. (crystallization solvent: ethyl acetate-diisopropyl ether)

Example 111

N-[6-[(cis-2,6-Dimethyl-1-piperidinyl)methyl]-2-naphthyl]piperidine-4-(4-methoxyphenyl)-1-carboxamide

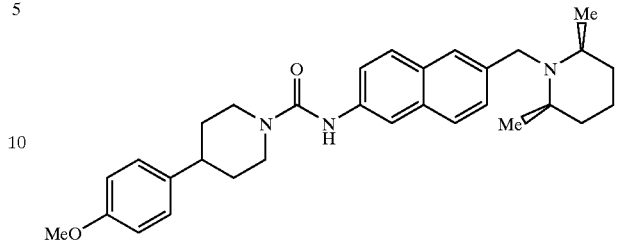

Using the 6-[(cis-2,6-dimethyl-1-piperidinyl)methyl] naphthalene-2-amine obtained in Reference Example 17, the same procedures as those of Example 38 were conducted to obtain the titled compound as a colorless powder.

¹H-NMR (DMSO-d₆): 0.98 (3H, s), 1.00 (3H, s), 1.27 (3H, m), 1.57 (3H, m), 1.78 (2H, m), 2.69 (1H, m), 2.89 (2H, m), 3.72 (3H, s), 3.82 (2H, s), 4.31 (2H, m), 6.86 (2H, d, J=8.5 Hz), 7.18 (2H, d, J=8.5 Hz), 7.43 (1H, d, J=8.5 Hz), 7.58 (1H, d, J=8.8 Hz), 7.65 (1H, d, J=8.5 Hz), 7.72 (2H, m), 7.98 (1H, brs), 8.67 (1H, brs). m.p.: 170–171° C. (crystallization solvent: ethyl acetate-diisopropyl ether)

Example 112

N-[6-[(cis-2,6-Dimethyl-1-piperidinyl)methyl]-2-naphthyl]piperidine-4-(4-fluorophenyl)-1-carboxamide

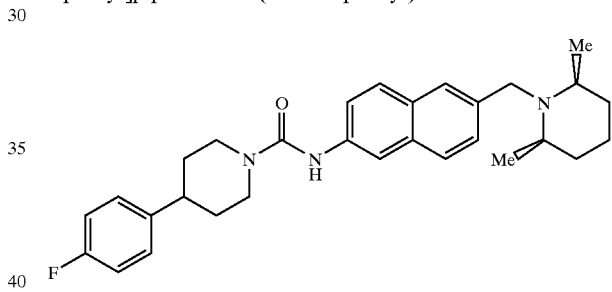

Using the 6-[(cis-2,6-dimethyl-1-piperidinyl)methyl] naphthalene-2-amine obtained in Reference Example 17, the same procedures as those of Example 38 were conducted to obtain the titled compound as a colorless powder.

¹H-NMR (DMSO-d₆): 0.98 (3H, s), 1.00 (3H, s), 1.28 (3H, m), 1.58 (3H, m), 1.81 (2H, m), 2.78 (1H, m), 2.90 (2H, m), 3.82 (2H, s), 4.31 (2H, m), 7.33 (4H, m), 7.43 (1H, m), 7.65 (1H, m), 7.72 (2H, m), 7.98 (1H, brs), 8.68 (1H, brs). m.p.: 219–222° C. (crystallization solvent: ethyl acetate-diisopropyl ether)

Example 113

6-(4-Chlorophenyl)-N-[6-[(cis-2,6-dimethyl-1-piperidinyl)methyl]-2-naphthyl]nicotinamide

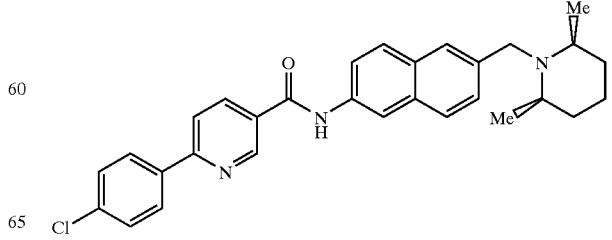

Using the 6-[(cis-2,6-dimethyl-1-piperidinyl)methyl]naphthalene-2-amine obtained in Reference Example 17, the same procedures as those of 3) of Example 54 were conducted to obtain the titled compound as a colorless powder.

$^1$H-NMR (DMSO-d$_6$): 0.99 (3H, s), 1.01 (3H, s), 1.29 (3H, m), 1.58 (3H, m), 3.85 (2H, s), 7.52 (1H, d, J=8.3 Hz), 7.61 (2H, d, J=8.3 Hz), 7.79 (2H, d, J=8.5 Hz), 7.87 (2H, m), 8.20 (1H, m), 8.24 (2H, d, J=8.5 Hz), 8.42 (1H, brs), 8.46 (1H, dd, J=2.2 and 8.3 Hz), 9.25 (1H, d, J=2.0 Hz), 10.63 (1H, brs). m.p.: 229–230° C. (crystallization solvent: ethyl acetate-diisopropyl ether)

Example 114

N-[6-[(cis-2,6-Dimethyl-1-piperidinyl)methyl]-2-naphthyl]-4'-methoxy[1,1'-biphenyl]-4-carboxamide

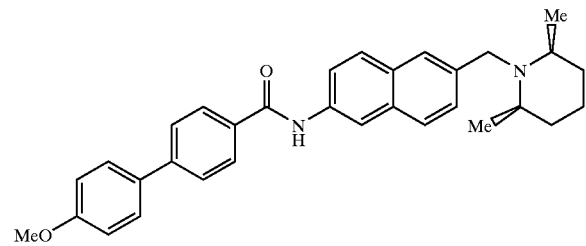

Using the 6-[(cis-2,6-dimethyl-1-piperidinyl)methyl]naphthalene-2-amine obtained in Reference Example 17, the same procedures as those of 3) of Example 54 were conducted to obtain the titled compound as a colorless powder.

$^1$H-NMR (DMSO-d$_6$): 0.99 (3H, s), 1.01 (3H, s), 1.29 (3H, m), 1.58 (3H, m), 3.82 (3H, s), 3.85 (2H, s), 7.07 (2H, d, J=8.7 Hz), 7.51 (1H, d, J=8.7 Hz), 7.73 (2H, d, J=8.5 Hz), 7.82 (6H, m), 8.08 (2H, d, J=8.3 Hz), 8.42 (1H, brs), 10.41 (1H, brs). m.p.: 199–200° C. (crystallization solvent: ethyl acetate-diisopropyl ether)

Example 115

4'-Chloro-N-[6-[(cis-2,6-dimethyl-1-piperidinyl)-methyl]-2-naphthyl][1,1'-biphenyl]-4-carboxamide

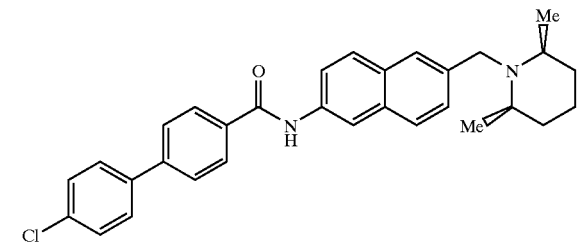

Using the 6-[(cis-2,6-dimethyl-1-piperidinyl)methyl]naphthalene-2-amine obtained in Reference Example 17, the same procedures as those of 3) of Example 54 were conducted to obtain the titled compound as a colorless powder.

$^1$H-NMR (DMSO-d$_6$): 0.99 (3H, s), 1.01 (3H, s), 1.29 (3H, m), 1.58 (3H, m), 3.85 (2H, s), 7.51 (1H, d, J=8.3 Hz), 7.57 (2H, d, J=8.5 Hz), 7.82 (8H, m), 8.12 (2H, d, J=8.1 Hz), 8.43 (1H, brs), 10.47 (1H, brs). m.p.: 220–222° C. (crystallization solvent: ethyl acetate-diisopropyl ether)

Example 116

4'-Chloro-N-[2-[[2-(3-pyridinyl)-1-piperidinyl]-methyl]-6-quinolinyl][1,1'-biphenyl]-4-carboxamide

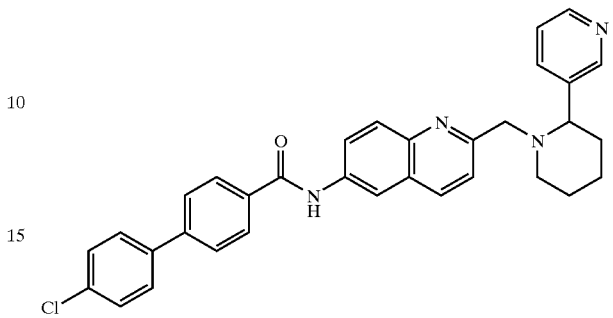

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

$^1$H-NMR (DMSO-d$_6$) δ: 1.63–1.75 (6H, m), 2.16 (1H, m), 2.87 (1H, m), 3.27 (2H, m), 3.73 (2H, m), 7.40 (1H, m), 7.59 (3H, m), 7.82–8.00 (7H, m), 8.13 (2H, d, J=8.4 Hz), 8.30 (1H, d, J=8.4 Hz), 8.47–8.54 (2H, m), 8.69 (1H, s). FAB (pos): 533[M+H]$^+$ m.p.: 124–126° C. (dec.)(crystallization solvent: ethyl acetate-diisopropyl ether)

Example 117

4'-Chloro-N-[2-[[(2S)-2-(methoxymethyl)pyrrolidinyl]-methyl]-6-quinolinyl][1,1'-biphenyl]-4-carboxamide

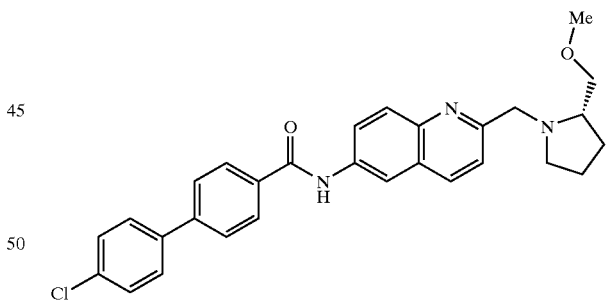

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

$^1$H-NMR (DMSO-d$_6$) δ: 1.68 (3H, m), 1.95 (1H, m), 2.33 (1H, m), 2.84 (2H, m), 3.25–3.44 (5H, m), 3.64–3.71 (1H, m), 4.28–4.35 (1H, m), 7.59 (3H, m), 7.82–8.08 (6H, m), 8.14 (2H, d, J=8.4 Hz), 8.29 (1H, d, J=8.4 Hz), 8.53 (1H, s), 10.62 (1H, s). FAB(pos): 486[M+H]$^+$ m.p.: 172–174° C. (crystallization solvent: ethyl acetate-diisopropyl ether)

Example 118

Tert-butyl (2S)-1-[[6-[[(4'-chloro[1,1'-biphenyl]-4-yl)carbonyl]amino]-2-quinolinyl]methyl]-2-pyrrolidinecarboxylate

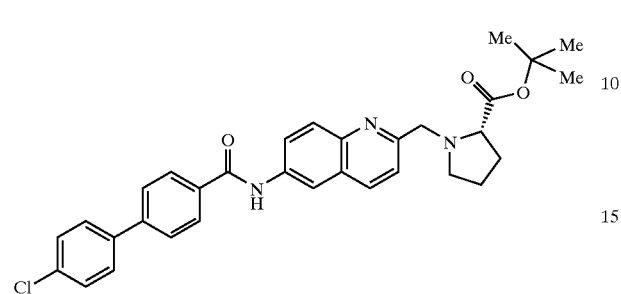

Using the 4'-chloro-N-[2-(chloromethyl)-6-quinolinyl][1,1'-biphenyl]-4-carboxamide obtained in Reference Example 8, the same procedures as those of Example 23 were conducted to obtain the titled compound as a colorless powder.

$^1$H-NMR (DMSO-d$_6$) δ: 1.38 (9H, s), 1.80 (3H, m), 2.05 (1H, m), 2.92 (1H, m), 3.35 (2H, m), 3.82–4.17 (2H, m), 7.62 (3H, m), 7.82–8.08 (6H, m), 8.14 (2H, d, J=8.8 Hz), 8.30 (1H, d, J =8.4 Hz), 8.53 (1H, s), 10.63 (1H, s). FAB(pos): 542[M+H]$^+$ m.p.: 163–166° C. (crystallization solvent: ethyl acetate-diisopropyl ether)

Example 119

4-(4-Methoxyphenyl)-N-[6-[(2,2,6,6-tetramethyl-1-piperidinyl)methyl]-2-naphthyl]-1-piperidinecarboxamide

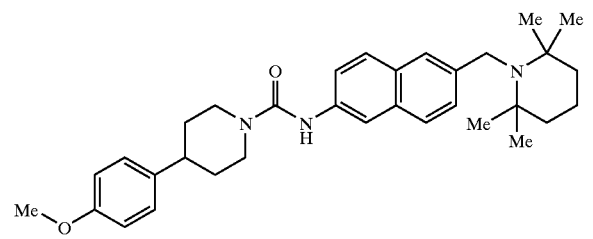

Using the 6-[(2,2,6,6-tetramethyl-1-piperidinyl)methyl]-2-naphthaleneamine obtained in Reference Example 19, the same procedures as those of Example 38 were conducted to obtain the titled compound as a colorless powder.

$^1$H-NMR (DMSO-d$_6$) δ: 1.00 (12H, s), 1.53–1.81 (10H, m), 2.71 (1H, m), 2.88 (2H, m), 3.72 (3H, s), 3.90 (2H, s), 4.30 (2H, m), 6.86 (2H, d, J=8.8 Hz), 7.18 (2H, d, J=8.8 Hz), 7.52–7.79 (5H, m), 7.97 (1H, s), 8.66 (1H, s). FAB(pos): 514[M+H]$^+$ m.p.: 164–166° C. (crystallization solvent: ethyl acetate-diisopropyl ether)

Example 120

4'-Methoxy-N-[6-[(2,2,6,6-tetramethyl-1-piperidinyl)methyl]-2-naphthyl][1,1'-biphenyl]-4-carboxamide

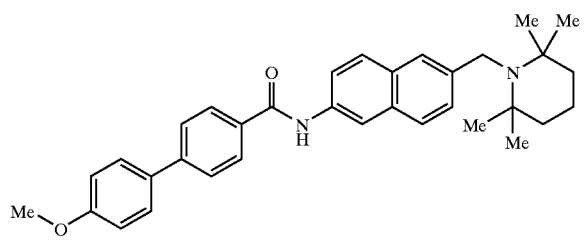

Using the 6-[(2,2,6,6-tetramethyl-1-piperidinyl)methyl]-2-naphthaleneamine obtained in Reference Example 19, the same procedures as those of 3) of Example 54 were conducted to obtain the titled compound as a colorless powder.

$^1$H-NMR (DMSO-d$_6$) δ: 1.01 (12H, s), 1.55 (6H, m), 3.82 (3H, s), 3.93 (2H, s), 7.06 (2H, d, J=9.2 Hz), 7.57 (1H, d, J=9.6 Hz), 7.71–7.87 (8H, m), 8.08 (2H, d, J=8.4 Hz), 8.41 (1H, s), 10.40 (1H, s). FAB(pos): 507[M+H]$^+$ m.p.: 212–214° C. (crystallization solvent: ethyl acetate-diisopropyl ether)

Example 121

4'-Fluoro-N-[6-[(2,2,6,6-tetramethyl-1-piperidinyl)methyl]-2-naphthyl][1,1'-biphenyl]-4-carboxamide

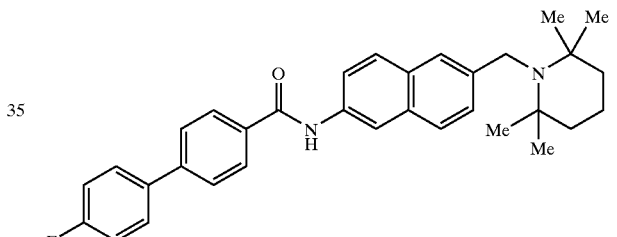

Using the 6-[(2,2,6,6-tetramethyl-1-piperidinyl)methyl]-2-naphthaleneamine obtained in Reference Example 19, the same procedures as those of 3) of Example 54 were conducted to obtain the titled compound as a colorless powder.

$^1$H-NMR (DMSO-d$_6$) δ: 1.01 (12H, s), 1.54 (6H, m), 3.93 (2H, s), 7.35 (2H, m), 7.74–7.87 (8H, m), 8.11 (2H, d, J=8.4 Hz), 8.41 (1H, s), 10.43 (1H, s). FAB(pos): 495[M+H]$^+$ m.p.: 238–241° C. (crystallization solvent: ethyl acetate-diisopropyl ether)

Example 122

4'-Methyl-N-[6-[(2,2,6,6-tetramethyl-1-piperidinyl)methyl]-2-naphthyl][1,1'-biphenyl]-4-carboxamide

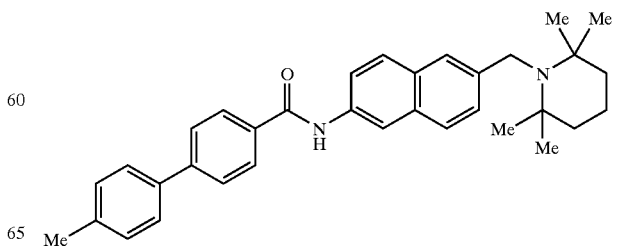

Using the 6-[(2,2,6,6-tetramethyl-1-piperidinyl)methyl]-2-naphthaleneamine obtained in Reference Example 19, the same procedures as those of 3) of Example 54 were conducted to obtain the titled compound as a colorless powder.

¹H-NMR (DMSO-d₆) δ: 1.01 (12H, s), 1.55 (6H, m), 2.37 (3H, s), 3.93 (2H, s), 7.32 (2H, d, J=8.2 Hz), 7.57 (1H, d, J=9.6 Hz), 7.66–7.87 (8H, m), 8.10 (2H, d, J=8.6 Hz), 8.41 (1H, s), 10.41 (0.1H, s). FAB(pos): 491[M+H]⁺ m.p.: 235–237° C. (crystallization solvent: ethyl acetate-diisopropyl ether)

Example 123

4'-Chloro-N-[6-[(2,2,6,6-tetramethyl-1-piperidinyl)methyl]-2-naphthyl][1,1'-biphenyl]-4-carboxamide

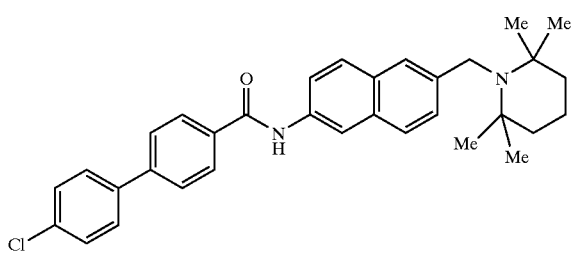

Using the 6-[(2,2,6,6-tetramethyl-1-piperidinyl)methyl]-2-naphthaleneamine obtained in Reference Example 19, the same procedures as those of 3) of Example 54 were conducted to obtain the titled compound as a colorless powder.

¹H-NMR (DMSO-d₆) δ: 1.01 (12H, s), 1.54 (6H, m), 3.93 (2H, s), 7.57 (3H, m), 7.74–7.89 (8H, m), 8.12 (2H, d, J=8.6 Hz), 8.41 (1H, s), 10.45 (1H, s). FAB(pos): 511[M+H]⁺ m.p.: 244–246° C. (crystallization solvent: ethyl acetate-diisopropyl ether)

Example 124

4'-Chloro-N-[6-[(diisopropylamino)methyl]-2-naphthyl][1,1'-biphenyl]-4-carboxamide

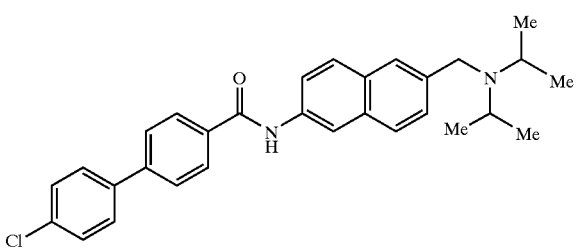

Using the N-6-[(diisopropylamino)methyl]-2-naphthyl]-2-hydroxy-2-methylpropanamide obtained in Reference Example 20, the same procedures as those of 2) of Example 6 were conducted to obtain the titled compound as a colorless powder.

¹H-NMR (DMSO-d₆) δ: 1.03 (12H, d, J=6.6 Hz), 3.01 (2H, m), 3.75 (2H, s), 7.52 (1H, d, J=8.7 Hz), 7.57 (2H, d, J=8.7 Hz), 7.76–7.89 (8H, m), 8.12 (2H, d, J=8.4 Hz), 8.43 (1H, s), 10.47 (1H, s). FAB(pos): 471[M+H]⁺ m.p.: 246–250° C. (crystallization solvent: ethyl acetate-diisopropyl ether)

Example 125

6-(1-Pyrrolidinylmethyl)-2-naphthyl 4-(4-chlorophenyl)-1-piperidinecarboxylate

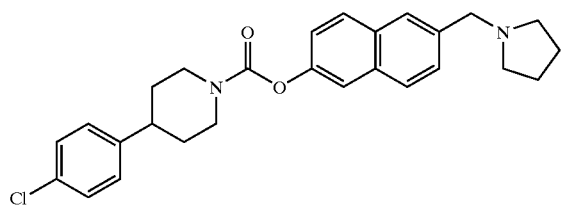

Using the 6-(1-pyrrolidinylmethyl)-2-naphthol hydrobromide obtained in Reference Example 22, the same procedures as those of Example 38 were conducted to obtain the titled compound as a colorless powder.

¹H-NMR (CDCl₃) δ: 1.68–1.83 (6H, m), 1.90–1.95 (2H, m), 2.55 (4H, m), 2.74 (1H, m), 2.97–3.12 (2H, m), 3.77 (2H, s), 4.49 (2H, m), 7.17 (2H, m), 7.26–7.33 (3H, m), 7.49 (1H, m), 7.55 (1H, d, J=2.4 Hz), 7.73–7.76 (2H, m), 7.81 (1H, d, J=9.3 Hz). FAB(pos): 449[M+H]⁺ m.p.: 121–123° C. (crystallization solvent: ethyl acetate-diisopropyl ether)

Example 126

6-(1-Pyrrolidinylmethyl)-2-naphthyl 4-(4-methoxyphenyl)-1-piperidinecarboxylate

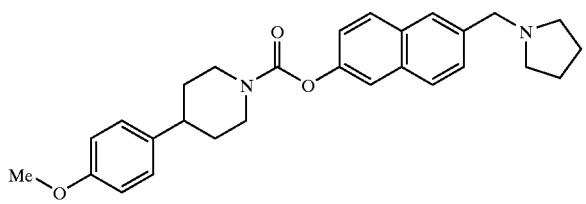

Using the 6-(1-pyrrolidinylmethyl)-2-naphthol hydrobromide obtained in Reference Example 22, the same procedures as those of Example 38 were conducted to obtain the titled compound as a colorless powder.

¹H-NMR (DMSO-d₆) δ: 1.71–1.80 (8H, m), 2.50 (4H, m), 2.75 (1H, m), 2.99–3.15 (2H, m), 3.72 (5H, s-like), 4.14–4.32 (2H, m), 6.88 (2H, m), 7.20–7.33 (3H, m), 7.50 (1H, m), 7.65 (1H, s), 7.82–7.93(3H, m). FAB(pos): 445 [M+H]⁺ m.p.: 127–129 C (crystallization solvent: ethyl acetate-diisopropyl ether)

Example 127

6-(1-Pyrrolidinylmethyl)-2-naphthyl 4-(4-methylphenyl)-1-piperidinecarboxylate

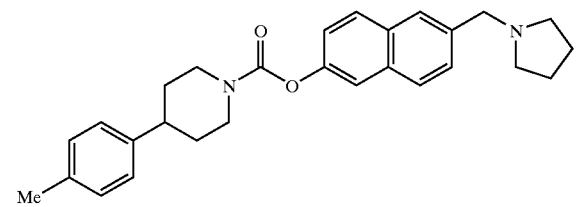

Using the 6-(1-pyrrolidinylmethyl)-2-naphthol hydrobromide obtained in Reference Example 22, the same procedures as those of Example 38 were conducted to obtain the titled compound as a colorless powder.

¹H-NMR (DMSO-d₆) δ: 1.72–2.00 (8H, m), 2.28 (3H, s), 2.51 (4H, m), 2.68–3.15 (3H, m), 3.54 (2H, s), 4.30 (2H, m), 7.15–8.01 (10H, m). FAB(pos): 429[M+H]⁺ m.p.: 238–240° C. (crystallization solvent: ethyl acetate-diisopropyl ether)

Example 128

6-(1-Pyrrolidinylmethyl)-2-naphthyl 4-(4-fluorophenyl)-1-piperidinecarboxylate

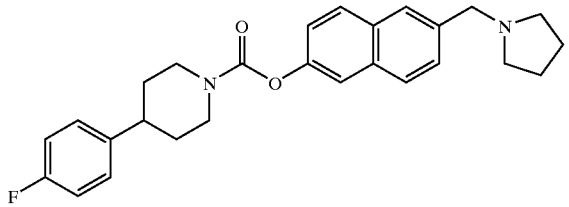

Using the 6-(1-pyrrolidinylmethyl)-2-naphthol hydrobromide obtained in Reference Example 22, the same procedures as those of Example 38 were conducted to obtain the titled compound as a colorless powder.

¹H-NMR (DMSO-d₆) δ: 1.73–1.91 (8H, m), 2.51 (4H, m), 2.71–3.15 (3H, m), 3.76 (2H, s), 4.23 (2H, m), 7.15 (2H, m), 7.35 (3H, m), 7.52 (1H, m), 7.66 (1H, m), 7.90 (3H, m). FAB(pos): 433[M+H]⁺ m.p.: 106–108° C. (crystallization solvent: ethyl acetate-diisopropyl ether)

Example 129

6-(1-Pyrrolidinylmethyl)-2-naphthyl 4-(4-phenyl-1-piperidinecarboxylate hydrochloride

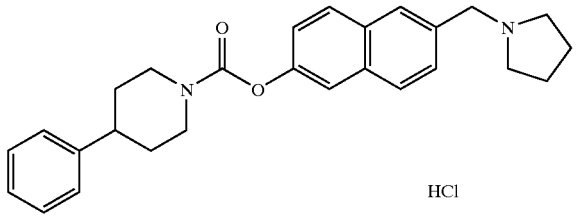

Using the 6-(1-pyrrolidinylmethyl)-2-naphthol hydrobromide obtained in Reference Example 22, the same procedures as those of Example 38 were conducted to obtain the titled compound as a colorless powder.

¹H-NMR (DMSO-d₆) δ: 1.69 (2H, m), 1.90 (4H, m), 2.00 (2H, m), 2.82 (1H, m), 3.12 (2H, m), 3.22 (4H, m), 4.21–4.49 (4H, m), 7.16–7.44 (5H, m), 7.75 (3H, m), 7.93–8.12 (3H, m), 10.69 (1H, br). FAB(pos): 415[M+H]⁺ m.p.: 213–215° C. (crystallization solvent: ethyl acetate-diisopropyl ether)

Example 130

N-(2-Methyl-1,2,3,4-tetrahydrobenzo[b][1,6]naphthyridin-8-yl)[1-1'-biphenyl]-4-carboxamide

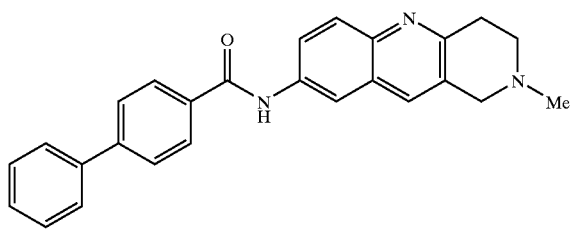

Using the 2-methyl-1,2,3,4-tetrahydrobenzo[b][1,6]naphtyridine-8-amine obtained in Reference Example 23, the same procedures as those of 3) of Example 54 were conducted to obtain the titled compound as a colorless powder.

¹H-NMR (DMSO-d₆) δ: 2.42 (3H, s), 2.80 (2H, m), 3.10 (2H, m), 3.71 (2H, s), 7.53 (3H, m), 7.78 (2H, d, J=8.4 Hz), 7.83 (3H, m), 8.00 (2H, m), 8.12 (2H, d, J=8.4 Hz), 8.47 (1H, d, J=2.2 Hz), 10.56 (1H, s). m.p.: 236–238° C. (crystallization solvent: ethyl acetate-diisopropyl ether)

Example 131

4'-Fluoro-N-(2-methyl-1,2,3,4-tetrahydrobenzo[b][1,6]naphthyridin-8-yl)[1-1'-biphenyl]-4-carboxamide

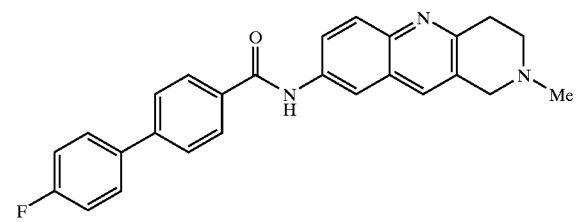

Using the 2-methyl-1,2,3,4-tetrahydrobenzo[b][1,6]naphtyridine-8-amine obtained in Reference Example 23, the same procedures as those of 3) of Example 54 were conducted to obtain the titled compound as a colorless powder.

¹H-NMR (DMSO-d₆) δ: 2.42 (3H, s), 2.80 (2H, m), 3.10 (2H, m), 3.71 (2H, s), 7.36 (2H, m), 7.88 (5H, m), 7.99 (2H, m), 8.11 (2H, d, J=8.4 Hz), 8.46 (1H, d, J=2.2 Hz), 10.56 (1H, s). m.p.: 230–232° C. (crystallization solvent: ethyl acetate-diisopropyl ether)

Example 132

4'-Chloro-N-(2-methyl-1,2,3,4-tetrahydrobenzo[b][1,6]naphthyridin-8-yl)[1-1'-biphenyl]-4-carboxamide

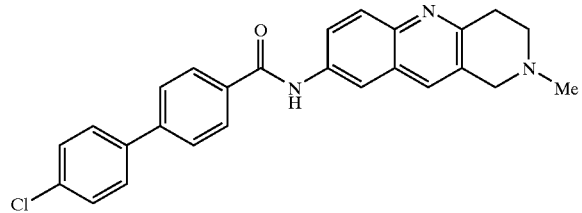

Using the 2-methyl-1,2,3,4-tetrahydrobenzo[b][1,6]naphtyridine-8-amine obtained in Reference Example 23, the same procedures as those of 3) of Example 54 were conducted to obtain the titled compound as a colorless powder.

¹H-NMR (DMSO-d₆) δ: 2.42 (3H, s), 2.80 (2H, m), 3.07 (2H, m), 3.71 (2H, s), 7.58 (2H, d, J=8.4 Hz), 7.80–7.99 (7H, m), 8.12 (2H, d, J=8.4 Hz), 8.46 (1H, d, J=2.0 Hz), 10.57 (1H, s). m.p.: 238–240° C. (crystallization solvent: ethyl acetate-diisopropyl ether)

Example 133

N-[2-[(Diisopropylamino)methyl]-6-quinolinyl][1-1'-biphenyl]-4-carboxamide

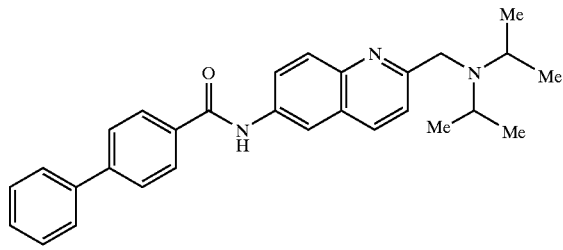

Using the N-[2-[(diisopropylamino)methyl]-6-quinolinyl]acetamide obtained in Reference Example 10, the same procedures as those of 2) of Example 6 were conducted to obtain the titled compound as a colorless powder.

$^1$H-NMR (DMSO-$d_6$) δ: 1.03 (12H, d, J=6.6 Hz), 3.02 (2H, m), 3.86 (2H, s), 7.43–7.56 (3H, m), 7.69 (1H, d, J=8.4 Hz), 7.67–8.05 (6H, m), 8.12 (2H, d, J=8.4 Hz), 8.26 (1H, d, J=8.4 Hz), 8.51 (1H, d, J=2.2 Hz), 10.58 (1H, s). FAB (pos) 438[M+H]$^+$ m.p.: 208–209° C. (crystallization solvent: ethyl acetate-diisopropyl ether)

Example 134

N-[2-[(Diisopropylamino)methyl]-6-quinolinyl]-4'-methoxy[1-1'-biphenyl]-4-carboxamide

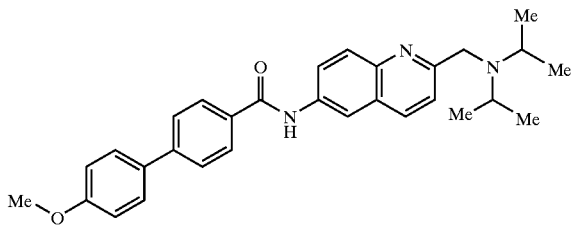

Using the N-[2-[(diisopropylamino)methyl]-6-quinolinyl]acetamide obtained in Reference Example 10, the same procedures as those of 2) of Example 6 were conducted to obtain the titled compound as a colorless powder.

$^1$H-NMR (DMSO-$d_6$) δ: 1.02 (12H, d, J=6.6 Hz), 3.02 (2H, m), 3.82(3H, s), 3.85 (2H, s), 7.07 (2H, d, J=9.2 Hz), 7.72 (3H, m), 7.82 (2H, d, J=8.4 Hz), 7.96 (2H, m), 8.08 (2H, d, J=8.8 Hz), 8.25 (1H, d, J=8.4 Hz), 8.50 (1H, s), 10.55 (1H, s). FAB(pos) 468[M+H]$^+$ m.p.: 223–225° C. (crystallization solvent: ethyl acetate-diisopropyl ether)

Example 135

N-[2-[(Diisopropylamino)methyl]-6-quinolinyl]-4'-fluoro[1-1'-biphenyl]-4-carboxamide

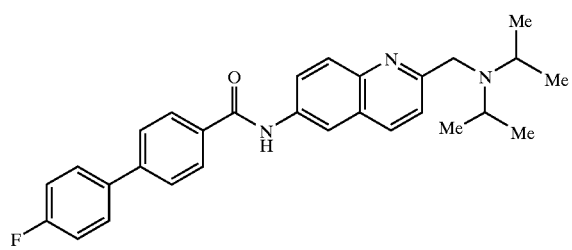

Using the N-[2-[(diisopropylamino)methyl]-6-quinolinyl]acetamide obtained in Reference Example 10, the same procedures as those of 2) of Example 6 were conducted to obtain the titled compound as a colorless powder.

$^1$H-NMR (DMSO-$d_6$) δ: 1.02 (12H, d, J=6.6 Hz), 3.02 (2H, m), 3.86 (2H, s), 7.35 (2H, m), 7.69 (1H, d, J=8.4 Hz), 7.80–7.88 (4H, m), 7.96 (2H, m), 8.11 (2H, d, J=8.4 Hz), 8.25 (1H, d, J=8.4 Hz), 8.51 (1H, d, J=2.2 Hz), 10.58 (1H, s). FAB(pos) 456[M+H]$^+$ m.p.: 207–209° C. (crystallization solvent: ethyl acetate-diisopropyl ether)

Example 136

N-[2-[(Diisopropylamino)methyl]-6-quinolinyl]-4'-methyl [1-1'-biphenyl]-4-carboxamide

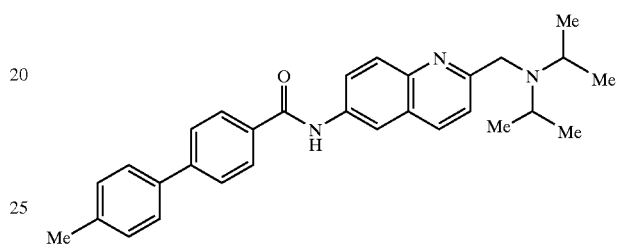

Using the N-[2-[(diisopropylamino)methyl]-6-quinolinyl]acetamide obtained in Reference Example 10, the same procedures as those of 2) of Example 6 were conducted to obtain the titled compound as a colorless powder.

$^1$H-NMR (DMSO-$d_6$) δ: 1.02 (12H, d, J=6.6 Hz), 2.37 (3H, s), 3.02 (2H, m), 3.85 (2H, s), 7.32 (2H, d, J=8.2 Hz), 7.69 (3H, m), 7.84 (2H, d, J=8.4 Hz), 7.96 (2H, m), 8.10 (2H, d, J=8.2 Hz), 8.25 (1H, d, J=8.8 Hz), 8.51 (1H, d, J=2.2 Hz), 10.56 (1H, s). FAB(pos) 452[M+H]$^+$ m.p.: 225–227° C. (crystallization solvent: ethyl acetate-diisopropyl ether)

Example 137

N-[2-[(Diisopropylamino)methyl]-6-quinolinyl]-6-(4-methylphenyl)nicotinamide

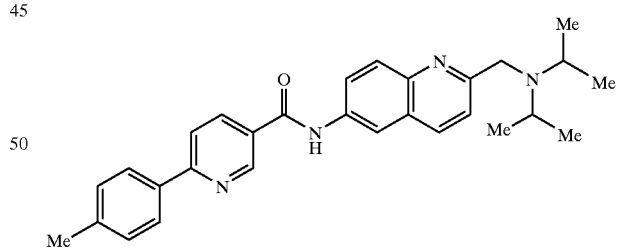

Using the N-[2-[(diisopropylamino)methyl]-6-quinolinyl]acetamide obtained in Reference Example 10, the same procedures as those of 2) of Example 6 were conducted to obtain the titled compound as a colorless powder.

$^1$H-NMR (DMSO-$d_6$) δ: 1.02 (12H, d, J=6.6 Hz), 2.39 (3H, s), 3.02 (2H, m), 3.86 (2H, s), 7.36 (2H, d, J=8.4 Hz), 7.70 (1H, d, J=8.4 Hz), 7.97 (2H, m), 8.13 (3H, m), 8.27 (1H, d, J=8.4 Hz), 8.42 (1H, m), 8.50 (1H, d, J=2.4 Hz), 9.22 (1H, d, J=2.4 Hz), 10.70 (1H, s). FAB(pos) 453[M+H]+ m.p.: 211–213° C. (crystallization solvent: ethyl acetate-diisopropyl ether)

Example 138

6-(4-Chlorophenyl)-N-[2-[(diisopropylamino)methyl]-6-quinolinyl]nicotinamide

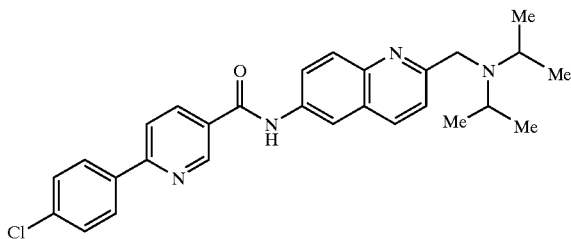

Using the N-[2-[(diisopropylamino)methyl]-6-quinolinyl]acetamide obtained in Reference Example 10, the same procedures as those of 2) of Example 6 were conducted to obtain the titled compound as a colorless powder.

$^1$H-NMR (DMSO-d$_6$) δ: 1.02 (12H, d, J=6.6 Hz), 3.02 (2H, m), 3.86(2H, s), 7.61 (2H, m), 7.70 (1H, d, J=8.1 Hz), 7.93 (2H, m), 8.23 (4H, m), 8.48 (2H, m), 9.25 (1H, m), 10.74 (1H, s). FAB(pos) 473[M+H]+ m.p.: 201–203° C. (crystallization solvent: ethyl acetate-diisopropyl ether).

Example 139

N-[2-[(Diisopropylamino)methyl]-6-quinolinyl]-4-(4-methylphenyl)-1-piperidinecarboxamide

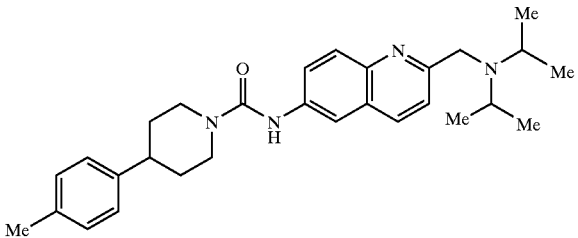

Using the N-[2-[(diisopropylamino)methyl]-6-quinolinyl]acetamide obtained in Reference Example 10, the same procedures as those of 2) of Example 54 and Example 38 were conducted to obtain the titled compound as a colorless powder.

$^1$H-NMR (DMSO-d$_6$) δ: 1.02 (12H, d, J=6.9 Hz), 1.60–1.77 (4H, m), 2.26 (3H, s), 2.85–3.03 (5H, m), 3.82 (2H, s), 4.43 (2H, m), 7.1–2 (4H, m), 7.62 (1H, d, J=8.4 Hz), 7.79 (2H, s-like), 8.05 (1H, s), 8.12 (1H, d, J=8.8 Hz), 8.81 (1H, s). FAB(pos) 459[M+H]+ m.p.: 184–186° C. (crystallization solvent: ethyl acetate-diisopropyl ether

Example 140

4-(4-Chlorophenyl)-N-[2-[(diisopropylamino)methyl]-6-quinolinyl]-1-piperidinecarboxamide

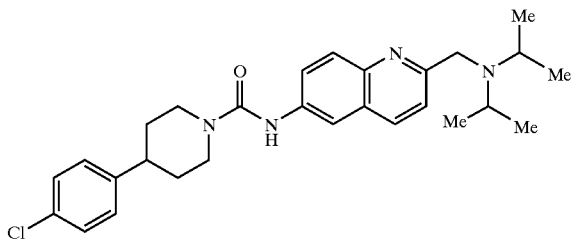

Using the N-[2-[(diisopropylamino)methyl]-6-quinolinyl]acetamide obtained in Reference Example 10, the same procedures as those of 2) of Example 54 and Example 38 were conducted to obtain the titled compound as a colorless powder.

$^1$H-NMR (DMSO-d$_6$) δ: 1.01 (12H, d, J=6.3 Hz), 1.59 (2H, m), 1.81 (2H, s), 2.78–3.00 (5H, m), 3.82 (2H, s), 4.32 (2H, m), 7.32 (4H, m), 7.62 (1H, d, J=8.1 Hz), 7.79 (2H, s-like), 8.05 (1H, s), 8.12 (1H, d, J=9.0 Hz), 8.81 (1H, s). FAB(pos) 479[M+H]+ m.p.: 201–203° C. (crystallization solvent: ethyl acetate-diisopropyl ether

Example 141

5-[(4-Bromobenzyl)oxy]-2-(1-pyrrolidinylmethyl)-1H-indole

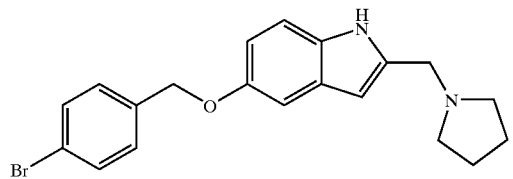

To a solution of [5-[(4-bromobenzyl)oxy]-1H-indol-2-yl] methanol (100 mg, 0.301 mmol) obtained in Reference Example 24 and triethylamine (0.050 ml, 0.361 mmol) in tetrahydrofuran (3 ml) was added methanesulfonyl chloride (0.0256 ml, 0.331 mmol) at 0° C., and the mixture was stirred for 15 minutes. To the reaction solution was added pyrrolidine (0.3 ml), the mixture was stirred for 1 hour, and 1N hydrochloric acid was added, followed by washing with diethyl ether. Potassium carbonate was added to the aqueous layer to adjust to basic, the mixture was extracted with ethyl acetate, washed with an aqueous saturated sodium chloride solution, and dried over anhydrous sodium sulfate. The solvent was concentrated under reduced pressure, the resulting residue was purified by alumina column chromatography (developing solvent: ethyl acetate), and converted into powders by isopropyl ether to obtain the titled compound (1.8 mg)

$^1$H-NMR (CDCl$_3$) δ: 1.83 (4H, m), 2.62 (4H, m), 3.80 (2H, s), 5.04 (2H, s), 6.27 (1H, s), 6.85 (1H, dd, J=2.4, 8.4 Hz), 7.05(1H, d, J=2.4 Hz), 7.19 (1H, d, J=8.4 Hz), 7.33 (2H, d, J=8.6 Hz), 7.49 (2H, d, J=8.6 Hz), 8.95 (1H, s).

Example 142

6-Phenyl-N-[6-(1-pyrrolidinylmethyl)-2-naphthyl]nicotinamide

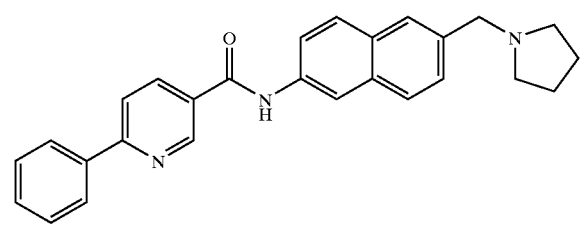

Using the 6-(1-pyrrolidinylmethyl)naphehalene-2-amine obtained in Reference Example 18, the same procedures as those of 3) of Example 54 were conducted to obtain the titled compound as a colorless powder.

$^1$H-NMR (DMSO-d$_6$) δ: 1.73 (4H, m), 2.50 (4H, m), 3.75 (2H, s), 7.47–7.59 (4H, m), 7.77–7.92 (4H, m), 8.20 (3H, m), 8.44 (2H, m), 9.25 (1H, m), 10.63 (1H, s). m.p.: 212–214° C. (crystallization solvent: ethyl acetate-diisopropyl ether)

Example 143

6-(4-Methoxyphenyl)-N-[6-(1-pyrrolidinylmethyl)-2-naphthyl]nicotinamide

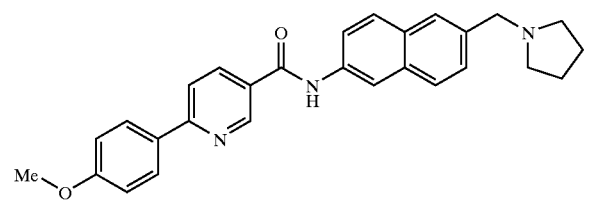

Using the 6-(1-pyrrolidinylmethyl)naphehalene-2-amine obtained in Reference Example 18, the same procedures as those of 3) of Example 54 were conducted to obtain the titled compound as a colorless powder.

$^1$H-NMR (DMSO-d$_6$) δ: 1.72 (4H, m), 2.50 (4H, m), 3.73 (2H, s), 3.85 (3H, s), 7.09 (2H, d, J=9.0 Hz), 7.47 (1H, dd, J=1.5, 8.4 Hz), 7.76–7.91 (4H, m), 8.10 (1H, d, J=8.4 Hz), 8.18 (2H, d, J=9.0 Hz), 8.38–8.44 (2H, m), 9.20 (1H, m), 10.59 (1H, s). m.p.: 261–263° C. (crystallization solvent: ethyl acetate-diisopropyl ether)

Example 144

6-(4-Fluorophenyl)-N-[6-(1-pyrrolidinylmethyl)-2-naphthyl]nicotinamide

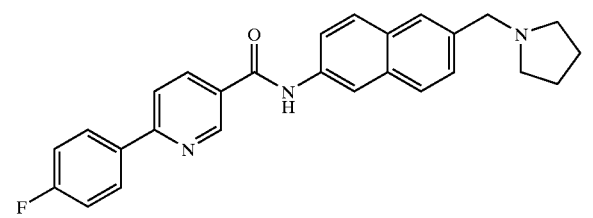

Using the 6-(1-pyrrolidinylmethyl)naphehalene-2-amine obtained in Reference Example 18, the same procedures as those of 3) of Example 54 were conducted to obtain the titled compound as a colorless powder.

$^1$H-NMR (DMSO-d$_6$) δ: 1.71 (4H, m), 2.47 (4H, m), 3.72 (2H, s), 7.41 (2H, m), 7.48 (1H, d, J=9.6 Hz), 7.76–7.91 (4H, m), 8.18 (1H, d, J=8.4 Hz), 8.28 (2H, m), 8.45 (2H, m), 9.24 (1H, d, J=2.4 Hz), 10.63 (1H, s). m.p.: 238–240° C. (crystallization solvent: ethyl acetate-diisopropyl ether)

Example 145

6-(4-Methylphenyl)-N-[6-(1-pyrrolidinylmethyl)-2-naphthyl]nicotinamide

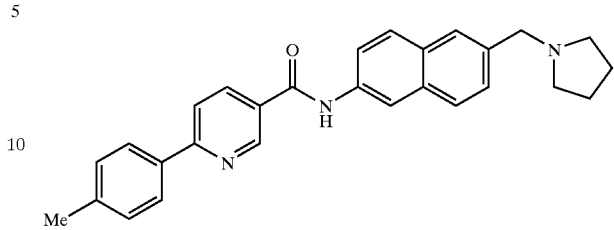

Using the 6-(1-pyrrolidinylmethyl)naphehalene-2-amine obtained in Reference Example 18, the same procedures as those of 3) of Example 54 were conducted to obtain the titled compound as a colorless powder.

$^1$H-NMR (DMSO-d$_6$) δ: 1.71 (4H, m), 2.39 (3H, s), 2.47 (4H, m), 3.71 (2H, s), 7.35 (2H, d, J=7.8 Hz), 7.45 (1H, dd, J=1.8, 8.4 Hz), 7.74–7.89 (4H, m), 8.12 (3H, m), 8.44 (2H, m), 9.23 (1H, m), 10.62 (1H, br). m.p.: 260–262° C. (crystallization solvent: ethyl acetate-diisopropyl ether)

Example 146

6-(4-Chlorophenyl)-N-[6-(1-pyrrolidinylmethyl)-2-naphthyl]nicotinamide

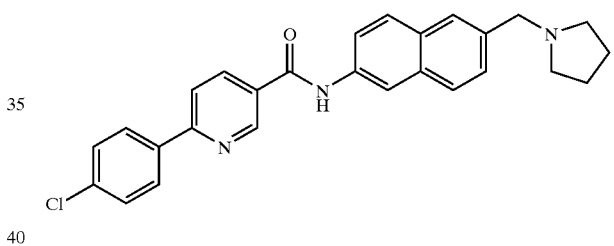

Using the 6-(1-pyrrolidinylmethyl)naphehalene-2-amine obtained in Reference Example 18, the same procedures as those of 3) of Example 54 were conducted to obtain the titled compound as a colorless powder.

$^1$H-NMR (DMSO-d$_6$) δ: 1.71 (4H, m), 2.47(4H, m), 3.71 (2H, s), 7.47 (1H, dd, J=1.8, 8.4 Hz), 7.61 (2H, d, J=8.4 Hz), 7.76–7.88 (4H, m), 8.23 (3H, m), 8.45 (2H, m), 9.24 (1H, d, J=1.5 Hz), 10.68 (1H, br). m.p.: 270–274° C. (crystallization solvent: ethyl acetate-diisopropyl ether)

Preparation Example 1

| | | |
|---|---|---|
| (1) | Compound obtained in Example 1 | 50 mg |
| (2) | Lactose | 34 mg |
| (3) | Corn starch | 10.6 mg |
| (4) | Corn starch (paste) | 5 mg |
| (5) | Magnesium stearate | 0.4 mg |
| (6) | Carboxymethylcellulose calcium | 20 mg |
| | Total | 120 mg |

In accordance with a conventional manner, the above (1) to (6) are admixed and tableted using a tableting machine to give tablets.

Reference Example 1—1
Amplification of Rat SLC-1 Receptor cDNA by PCR Method Using Rat-Brain-Originated cDNA Reverse transcription reaction was carried out using random primer, with rat-brain-originated poly (A)⁺RNA (Clone Tech Co.) as a template. The reagent from the TaKaRa RNA PCR ver. 2 kit was used for the reverse transcription reaction. Next, using this reverse transcription product as a template, amplification was carried out by a PCR method using synthetic DNA primers with SEQ ID NOS: 1 and 2. Synthetic DNA primers were constructed to amplify genes in the domain where genes were translated into the receptor protein. At that time, individual restriction enzyme recognition sequences were also added to the 5' side and 3' side of the gene so as to add a nucleotide sequence recognizing the restriction enzyme Sal I to the 5' side of the gene, and to add a nucleotide sequence recognizing the restriction enzyme Spe I to the 3' side of the gene. The reaction mixture was composed of 0.5 µl of cDNA template, 0.4 µM of respective synthetic DNA primer, 0.25 mM of dNTPs, 0.5 µl of Pfu (StrataGene Co.) DNA polymerase, and buffers attached to enzymes, with setting total reaction quantity at 50 µl.

A thermal cycler (Parkin Elmer Co.) was used to produce cycles for amplification. After heating at 94° C. for 60 seconds, the cycle consisting of 94° C. for 60 seconds, 60° C. for 30 seconds, and 72° C. for 150 seconds, was repeated 35 times, and finally reaction was conducted at 72° C. for 10 minutes. After 0.8% agarose gel electrophoresis, the amplified products were confirmed by ethidium bromide dying.

Reference Example 1-2
Subcloning of PCR Products Into Plasmid Vector, and Confirmation of an Amplified cDNA Sequence by Decoding of a Nucleotide Sequence in an Inserted cDNA Portion The reaction product after PCR conducted in Reference Example 1—1 was separated using 0.8% low-melting point agarose gel. After the band section was cut out using a razor, DNA was recovered by conducting fragmentation, phenol extraction, phenol-chloroform extraction and ethanol precipitation. The recovered DNA was subcloned on plasmid vector PCR-Script Amp SK(⁺) in accordance with prescription of the PCR-Script™ Amp SK(+) cloning kit (Stratagene Co.). After this was introduced into *Escherichia coli* XL-1 Blue (Stratagene Co.) by transformation, the clones with fragments of inserted cDNA were selected in LB agar culture medium containing ampicillin and X-gal. Only clones showing white color were separated using a sterilized toothpick, and transformant *E. coli* XL-1 Blue/rat SLC-1 was obtained.

Each clone was cultured overnight in LB culture medium containing ampicillin, and plasmid DNA was prepared using QIA prep8 mini prep (Qiagen). A portion of the prepared DNA was digested with Sal I and Spe I, and the size of the inserted receptor cDNA fragment was confirmed. Reactions to determine nucleotide sequences were carried out using a DyeDeoxy Terminator Cycle Sequence Kit (Parkin Elmer Co.), and decoded using a fluorescent light automatic sequencer. The sequences of the 3 clones obtained were analyzed, and it was confirmed that all of them match the reported gene sequence (SEQ ID NO: 4) in which the Sal I recognition sequence was added to the 5' side and the Spe I recognition sequence was added to the 3' side of the cDNA sequence (Lakaye, B., et al., Biochim. Biophys. Acta, Vol. 1401, pp. 216–220 (1998), accession No. AF08650) coding rat SLC-1 protein (SEQ ID NO: 3).

Reference Example 1-3
Preparation of CHO Cells for Rat SLC-1 Expression

The full-length amino acid sequence of rat brain originated SLC-1, which was confirmed in Reference Example 1–2, was coded, and plasmid was prepared using a plasmid Midi Kit (Qiagen) from the *E. coli* transformed by the plasmid, to which the gene with Sal I recognition sequence added to the 5' side and Spe I recognition sequence added to the 3' side, had been introduced. Then, the insert section was cut out by digesting with Sal I and Spe I. The insert DNA was cut out with a razor from the agarose gel after electrophoresis.

Next, fragmentation, phenol extraction, phenol-chloroform extraction, and ethanol precipitation, were conducted and the DNA was recovered. This insert DNA was added to vector plasmid pAKKO-111H (the same vector plasmid as pAKKO1.11H described in Hinuma, S., et al., Biochim. Biophys. Acta, Vol. 1219, pp. 251–259 (1994)) for animal cell expression which was digested with Sal I and Spe I, and ligation was conducted using T4 ligase (TaKaRa Shuzo), to construct pAKKO-SLC-1 plasmid for protein expression.

After *E. coli* DH5 (TOYOBO) transformed by pAKKO-SLC-1 was cultured, pAKKO-SLC-1 plasmid DNA was prepared using a Plasmid Midi Kit (Qiagen). This was introduced into CHO dhfr⁻ cells in accordance with the attached protocol, using a CellPhect Transfection Kit (Amersham Pharmacia Biotech Co.). A coprecipitating suspension of 10 µg of DNA and calcium phosphate was prepared, and this suspension was added to 10 cm Petri dishes in which 5×10⁵ or 1×10⁶ of CHO dhfr⁻ cells had been seeded 24 hours previously. After these cells were cultured for 1 day in MEMα culture medium containing 10% fetal bovine serum, subculture was conducted, and cultivation was conducted in selective culture medium, MEMα culture medium containing no nucleic acid but containing 10% dialyzed fetal bovine serum. 56 Clones of colonies of the transformed CHO cells expressing SLC-1, proliferated in the selective culture medium, were selected.

Reference Example 1-4
Selection of CHO/SLC-1 Cell Strain Expressing a Large Quantity of Full-Length Rat SLC-1 Receptor Protein mRNA The quantity of expressed full-length rat SLC-1 receptor protein mRNA of 56 clones of the CHO/SLC-1 strains established in Reference Example 1-3, was measured using a Cytostar T Plate (Amersham Pharmacia Biotech Co.) as shown below according to the attached protocol. Each well of the Cytostar T Plate was seeded with each clone of the CHO/SLC-1 strain by 2.5×10⁴, and cultured for 24 hours, then the cells were fixed using 10% formalin. After 0.25% Triton X-100 was added to each well to increase cell permeability, ³⁵S-labeled riboprobes with SEQ ID NO: 5 were added and hybridized. 20 mg/ml of RNaseA was added to each well to digest free riboprobes. After the plate was thoroughly washed, the radioactivity of the hybridized riboprobes was determined using a Topcounter. Strains with high radioactivity showed large amounts of mRNA expression. In particular, mainly used was Clone number 44 among 3 clones which showed large amounts of mRNA expression.

Reference Example 1-5
Isolation of Plasmid Containing Human SLC-1 cDNA

After nicks were inserted into the DNA of Human fetal brain originated cDNA library (SUPERSCRIPT™ cDNA Library; GIBCOBRL Co.) according to the manual of the Genetrapper cDNA positive selection system (GIBCOBRL Co.), using pharge F1 endonuclease, single stranded human fetal brain originated cDNA library was prepared by digesting the above-mentioned library with *Escherichia coli* exonuclease III.

Biotin-14-dCTP was added to the 3' end of synthetic oligonucleotide (equivalent to 1434–1451 of accession No. U71092) of SEQ ID NO: 6 which was prepared according to the report by Kolakowski Jr., et al. (Kolakowski Jr., et al. (1996) FEBS Lett. Vol. 398, pp. 253–258) using Terminal Deoxynucleotidyl Transferase, and biotinated oligonucleotide was prepared. The above manual was followed regarding composition of a reaction mixture and reaction time.

After 4 μg of single stranded human fetal brain originated cDNA library was kept at 95° C. for 1 minute, the library was rapidly cooled on ice. 20 ng of Biotinated oligonucleotide was added, which was hybridized using the attached hybridization buffer at 37° C. for 1 hour. Streptoavidin beads were added to the mixture, then single stranded human fetal brain originated cDNA hybridized by biotinated oligonucleotide, was isolated using a MAGNA-SEP Magnetic Particle Separator (GIBCOBRL Co.). The complementary strand was synthesized according to the manual, using as primer 50 ng of synthetic oligonucleotide (equivalent to 1011–1028 of accession No. U71092) of SEQ ID NO: 7, prepared based on the report by Kolakowski Jr., et al (Kolakowski Jr., et al. (1996) FEBS Lett. Vol. 398, pp. 253–258), to give the double stranded plasmid.

Reference Example 1-6
Determination of Nucleotide Sequence of Plasmid Containing Isolated Human SLC-1 cDNA After the plasmid obtained in Reference Example 1-5 was introduced into ELECTROMAX™DH10B™ Cells by the electroporation method, clones with cDNA inserted fragments were selected in LB agar culture medium containing ampicillin and X-gal. Using a sterilized toothpick, only the clones showing white color were separated to give transformant *E. coli* DH10B/hSLC-1. Individual clones were cultured overnight in LB culture medium containing ampicillin, and the plasmid DNA was refined using QIA prep8 mini prep (Qiagen). The reactions to determine nucleotide sequence were conducted using a DyeDeoxy Terminator Cycle Sequence Kit (Parkin Elmer Co.), and the nucleotide sequence was decoded using a fluorescent light automatic sequencer.

As the results, obtained was the sequence shown in SEQ ID NO: 8. The amino acid sequence (SEQ ID NO: 9) coded by the nucleotide sequence obtained here, differs from the human SLC-1 amino acid sequence predicted as the sequence analogized from rat SLC-1 based on human chromosome DNA sequence (accession number: Z86090) containing human SLC-1 sequence, in the report by Lakaye, et al. (Lakaye, B., et al. (1998) Biochem. Biophys. Acta. Vol. 1401, pp. 216–220). This shows the presence of ATG, the initiation codon, on mRNA, in the 69 and 64 amino acids upstream from the estimated sequence. *Escherichia coli* DH10B/phSLC1L8, the transformant produced by the plasmid containing DNA coding this sequence was deposited at IFO and NIBH.

Reference Example 1-7
Amplification of Human SLC-1 cDNA by PCR Method Using Human Fetal Brain Originated cDNA Amplification by the PCR method was conducted using as the template plasmid containing human SLC-1 DNA sequence cloned by the gene trap method, and using synthetic DNA primers of SEQ ID NO: 10 and SEQ ID NO: 11, and synthetic DNA primers of SEQ ID NO: 12 and SEQ ID NO: 13, respectively. The former amplified DNA and the latter amplified DNA were named as "human SLC-1(S)" and "human SLC-1(L)", respectively. The synthetic DNA primer was constructed so that the genes in the domain translated to the receptor protein were amplified. At that time, a recognition sequence for each restriction enzyme was added to the 5' side and 3' side, so that the nucleotide sequence recognized by restriction enzyme Sal I would be added to the 5' side of the gene, and the nucleotide sequence recognized by restriction enzyme Spe I would be added to the 3' side. The composition of the reaction mixture for human SLC-1(S) amplification was: 5 μl of plasmid template containing human SLC-1 DNA sequence, 0.4 μM of respective synthetic DNA primers, 0.2 mM of dNTPs and 0.5 μl of Pfu DNA polymerase and buffers attached to the enzyme, with setting total quantity for reaction at 50 μl. A thermal cycler (Parkin Elmer Co.) was used for the cycles for amplification. After heating at 94° C. for 60 seconds, the cycle consisting of 94° C. for 60 seconds, 57° C. for 60 seconds, and 72° C. for 150 seconds, was repeated 25 times, and finally the temperature of the reactant was maintained at 72° C. for 10 minutes. The composition of the reaction mixture for human SLC-1(L) amplification was 5 μl of plasmid template containing human SLC-1 DNA sequence, 0.4 μM of respective synthetic DNA primers, 0.2 mM of dNTPs, 0.5 μl of Pfu DNA polymerase and buffers attached to the enzymes, with setting total quantity for reaction at 50 μl. A thermal cycler (Parkin Elmer Co.) was used for the cycles for amplification. After heating at 94° C. for 60 seconds, the cycle consisting of 94° C. for 60 seconds, 60° C. for 60 seconds, and 72° C. for 3 minutes, was repeated 25 times, and finally the temperature of the reactant was maintained at 72° C. for 10 minutes. After 0.8% agarose gel electrophoresis, confirmation of amplified products was conducted by ethidium bromide dying.

Reference Example 1-8
Subcloning of PCR Product into Plasmid Vector and Confirmation of Amplified cDNA Sequence by Decoding of Nucleotide Sequence of Inserted cDNA Section The reaction product after PCR in Reference Example 1-7 was separated using 0.8% low-melting point agarose gel, and the band section was cut out using a razor. After that, fragmentation, phenol extraction, phenol-chloroform extraction, and ethanol precipitation were conducted, and the DNA was recovered. The recovered DNA was subcloned into pCR-Script Amp SK(+) plasmid vector, as prescribed by the PCR-Script™ Amp SK(+) cloning kit (Stratagene Co.). After this was introduced into *Escherichia coli* DH5 a competent cells (TOYOBO) and transformed, the clones with cDNA inserted fragments were selected in LB agar culture medium containing ampicillin and X-gal. Using a sterilized toothpick, only clones showing white color were separated to give *E. coli* DH5α/hSLC-1(S), which is a transformant of human SLC-1 (S), and *E. coli* DH5α/hSLC-1(L), which is a transformant of human SLC-1 (L). Each clone was cultured overnight in LB culture medium containing ampicillin, and plasmid DNA was prepared using QIA prep8 mini prep (Qiagen). Some of the prepared DNA was digested with Sal I and Spe I restriction enzymes, and the size of the receptor cDNA fragments inserted was confirmed. The reactions to determine nucleotide sequence were conducted using a DyeDeoxy Terminator Cycle Sequence Kit (Parkin Elmer Co.) and the nucleotide sequence was decoded using a fluorescent light automatic sequencer. The sequence of the obtained clones respectively matched the DNA sequence (SEQ ID NO: 14) which should be amplified by synthetic DNA primers of SEQ ID NO: 10 and SEQ ID NO: 11 using human SLC-1 gene as a template, and the DNA sequence (SEQ ID NO: 15) which should be amplified by synthetic DNA primers of SEQ ID NO: 12 and SEQ ID NO: 13 using human SLC-1 gene as a template.

Reference Example 1-9
Preparation of CHO Cells for Expression of Human SLC-1(S), and CHO Cells for Expression of Human SLC-1(L)

Plasmid was prepared from the E. coli clones transformed by the plasmid wherein inserted were human SLC-1(S) and human SLC-1(L) whose sequences were confirmed in Reference Example 1-8, using a Plasmid Midi Kit (Qiagen), and the insert section was cut out using Sal I and Spe I restriction enzymes. After electrophoresis was conducted, the insert DNA was cut out from agarose gel using a razor. Next, fragmentation, phenol extraction, phenol-chloroform extraction, and ethanol precipitation were conducted, and the insert DNA was recovered.

This insert DNA was added to pAKKO-111H vector plasmid for animal cell expression, digested with Sal I and Spe I (the same vector plasmid as the pAKKO1.11H described in Hinuma, S., et al., Biochim. Biophys. Acta, Vol. 1219, pp. 251–259 (1994)), and ligation was conducted by adding T4 ligase (TaKaRa Shuzo), to construct pAKKO-hSLC-1(S) and pAKKO-hSLC-1(L) plasmids for protein expression.

After E. coli DH5α (TOYOBO) transformed by pAKKO-hSLC-1(S) and pAKKO-hSLC-1(L) was cultured, pAKKO-hSLC-1(S) and pAKKO-hSLC-1(L) plasmid DNAs were prepared using a Plasmid Midi Kit (Qiagen). These were introduced into CHO dhfr⁻ cells in accordance with the attached protocol, using a CellPhect Transfection Kit (Amersham Pharmacia Biotech Co.). A coprecipitative suspension of 10 μg of DNA with calcium phosphate was made, which was added to 10 cm Petri dishes seeded 24 hours in advance with $5 \times 10^5$ or $1 \times 10^6$ CHO dhfr⁻ cells. After the above was cultured for 1 day in MEMα culture medium containing 10% fetal bovine serum, subculture was conducted, and then cultivation was conducted in MEMα culture medium containing no nucleic acid but containing 10% dialyzed fetal bovine serum, which is a selective culture medium. 56 clones of colonies of transformed cells which are human SLC-1(S) gene introduced CHO cells, and 61 clones of colonies of transformed cells which are human SLC-1(L) gene introduced CHO cells, both of which proliferated in the selective culture medium, were selected.

Reference Example 1-10
Selection of Cell Colonies into which Genes with Large Quantities of Human SLC-1(S) and Human SLC-1 (L) mRNA Expression have been Introduced The quantities of expressed mRNA of 56 clones of CHO/hSLC-1(S) colonies and 61 clones of CHO/hSLC-1(L) colonies, both of which were established in Reference Example 1-9, were measured in accordance with the attached protocol using a Cytostar T Plate (Amersham Pharmacia Biotech Co.) as shown below.

After each well of the Cytostar T Plate was seeded with each clone of CHO/hSLC-1(S) colonies and CHO/hSLC-1 (L) colonies by $2.5 \times 10^4$, and cultured for 24 hours, the cells were fixed using 10% formalin.

After 0.25% Triton X-100 was added to each well to increase cell permeability, $^{35}$S-labeled riboprobe of SEQ ID NO: 16 was added and hybridization was conducted.

20 mg/ml of RNaseA was added to each well to digest free riboprobe. After the plate was washed well, the radioactivity of the hybridized riboprobe was determined. Colonies showing high radioactivity expressed large quantities of mRNA. Of the 7 clones which expressed large quantities of mRNA, mainly used was Clone number 57.

Experimental Example 1
Determination of Antagonist Activity Using GTPYS Binding Assay of Test Compound Membrane fraction was prepared by the following method, using the human SLC-1 expressing CHO cell clone 57 obtained in Reference Example 1-10, and the rat SLC-1 expressing CHO cell clone 44 obtained in Reference Example 1-4.

The human and rat SLC-1 expressing CHO cells ($1 \times 10^8$) were scraped in buffer saline phosphate (pH 7.4) to which 5 mM EDTA (ethylenediaminetetraacetic acid) had been added, and centrifuged. 10 ml of homogenized buffer (10 mM NaHCO$_3$, 5 mM EDTA, pH 7.5) was added to the cell pellets, and they were homogenized using a Polytron homogenizer. The supernatant obtained by centrifugation at 400×g for 15 minutes was further centrifuged at 100,000×g for 1 hour, to obtain the membrane fraction precipitate. This precipitate was suspended in 2 ml of assay buffer [50 mM Tris-HCl (pH 7.5), 1 mM EDTA, 0.1% BSA (bovine serum albumin), 10 mM MgCl$_2$, 100 mM NaCl, 1 μM GDP (guanosine 5'-diphosphate), 0.25 mM PMSF (phenylmethylsulfonyl fluoride), 1 mg/ml pepstatin, 20 mg/ml leupeptin, 10 mg/ml phosphoramidon], which was centrifuged at 100,000×g for 1 hour. The membrane fraction recovered as precipitate was suspended again in 2 ml of assay buffer, and after the suspension was divided, individual portions were preserved at −80° C. and thawed before every use.

Determination of antagonist activity of the test compound was conducted as shown below. After 171 μl of SLC-1 expressing CHO cell membrane fractions diluted with assay buffer was poured into each well of a 96-well polypropylene plate, 2 μl of $3 \times 10^{-10}$M MCH diluted with DMSO solution, 2 μl of test compound solution diluted to various concentrations, and 25 μl of [$^{35}$S]-Guanosine 5'-(γ-thio) triphosphate (produced by Daiichi Kagaku Yakuhin) were added respectively. (Final concentration of cell membrane: 20 μg/ml, final concentration of [$^{35}$S]-Guanosine 5'-(γ-thio) triphosphate: 0.33 nM).

After this reaction mixture was allowed to react for 1 hour under stirring, it was filtered under vacuum using a glass filter (GF-C), then the filter was washed 3 times with 300 μl of washing solution (50 mM Tris-HCl buffer solution pH 7.5). 50 ml of liquid scintillator was added to the glass filter, and residual radioactivity was determined using a liquid scintillation counter.

The IC$_{50}$ value of the compound was calculated from the binding inhibition rate (%), based on the definition that the binding inhibition rate (%)=(radioactivity when compound and MCH were added−radioactivity when DMSO solution was added)/(radioactivity when MCH was added−radioactivity when DMSO solution was added)×100.

The results were shown below.

| Compound Number | Inhibition Activity (IC$_{50}$ value: nM) |
|---|---|
| Example 1 | 5 |

INDUSTRIAL APPLICABILITY

Compounds (I), (I') and salts thereof possess excellent MCH receptor antagonistic activities, and are useful as an agent for preventing or treating obesity, etc.

What is claimed is:

1. A compound of the formula:

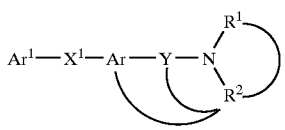

(I')

wherein $Ar^1$ is a cyclic group which may be substituted; $X^1$ is $CONR^8$, $NR^8CO$ (wherein $R^8$ is hydrogen atom, optionally halogenated $C_{1-6}$ alkyl, optionally halogenated $C_{1-6}$ alkyl-carbonyl or optionally halogenated $C_{1-6}$ alkylsulfonyl), OCO or COO;
Y is —$CH_2$—;
Ar is a quinoline ring which may be substituted;
$R^1$ and $R^2$ are the same or different and are hydrogen atom or a hydrocarbon group which may be substituted; or $R^1$ and $R^2$, together with the adjacent nitrogen atom, may form a pyrrolidine ring which may be substituted; provided that, when $X^1$ is CONH, Ar is not 4-methyl-2-quinolone which may have a substituent selected from the group consisting of alkyl, alkoxy and halogen; and, when $X^1$ is COO, $Ar^1$ is not an aromatic group which may be substituted; or a salt thereof.

2. The compound according to claim 1, wherein $X^1$ is $CONR^8$ or $NR^8CO$ (wherein $R^8$ is hydrogen atom, optionally halogenated $C_{1-6}$ alkyl, optionally halogenated $C_{1-6}$ alkyl-carbonyl or optionally halogenated $C_{1-6}$ alkylsulfonyl).

3. The compound according to claim 1, wherein the cyclic group represented by $Ar^1$ is an aromatic group.

4. The compound according to claim 3, wherein the aromatic group is formed by removing an optional one hydrogen atom from an aromatic ring assembly formed by 2 or 3 members selected from $C_{6-14}$ monocyclic or condensed polycyclic aromatic hydrocarbon and 5- to 10-membered aromatic heterocyclic ring.

5. The compound according to claim 1, wherein $Ar^1$ is phenyl, biphenylyl or phenyl-pyridyl, each of which may be substituted with 1 to 3 substituents selected from halogen, optionally halogenated $C_{1-6}$ alkyl and optionally halogenated $C_{1-6}$ alkoxy.

6. The compound according to claim 1, wherein $Ar^1$ is piperidinyl which may be substituted with $C_{6-14}$ aryl which may be substituted.

7. The compound according to claim 1, wherein $X^1$ is CONH or COO.

8. The compound according to claim 1, wherein $R^1$ and $R^2$ together with the adjacent nitrogen atom, form a pyrrolidine ring which may be substituted.

9. A pharmaceutical composition comprising the compound according to claim 1, or a salt thereof.

10. The compound according to claim 1 which is:

4'-fluoro-N-[2-(1-pyrrolidinylmethyl)-6-quinolinyl][1,1'-biphenyl]-4-carboxamide;

4(4chlorophenyl)-N-[2-(1-pyrrolidinylmethyl)-6-quinolinyl]-1-piperidinecarboxamide;

N-[2-(1-pyrrolidinylmethyl)-6quinolinyl][1,1'-biphenyl]-4-carboxamide;

6-(4-methylphenyl)-N-[2-(1-pyrrolidinymethyl)-6-quinolinyl]nicotinamide;

or a salt thereof.

11. A process for producing a compound of the formula:

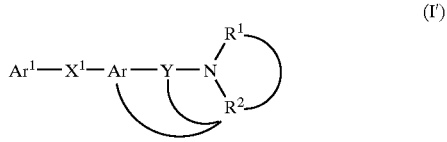

(I')

wherein each symbol is as defined in claim 1, a salt thereof, which comprises reacting a compound of the formula:

$Ar^1$—H (XII)

wherein $Ar^1$ is as defined in claim 1, or a salt thereof with a compound of the formula:

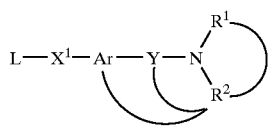

(XIII)

wherein L is a leaving group and the other symbols are as defined above, or a salt thereof.

12. A method for preventing or treating obesity in a mammal in need thereof, which comprises administering to said mammal an effective amount of the compound according to claim 1.

13. A method for making a pharmaceutical for preventing or treating obesity comprising combining the compound according to claim 1 with a pharmaceutically acceptable carrier, diluent or excipient.

* * * * *

UNITED STATES PATENT AND TRADEMARK OFFICE
CERTIFICATE OF CORRECTION

PATENT NO. : 6,930,185 B2  Page 1 of 4
APPLICATION NO. : 10/258492
DATED : August 16, 2005
INVENTOR(S) : Yuji Ishihara, Nobuhiro Suzuki and Shiro Takekawa It is certified that error appears in the above-identified patent and that said Letters Patent is hereby corrected as shown below:

Col. 141, lines 26-32, in Claim 1, please replace the chemical structure

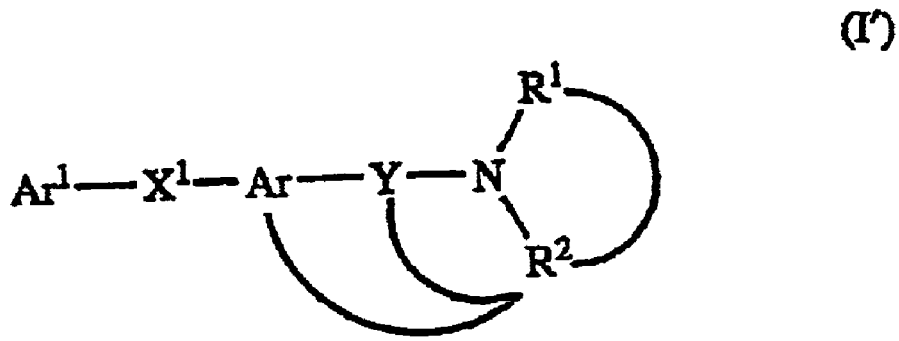

with the following:

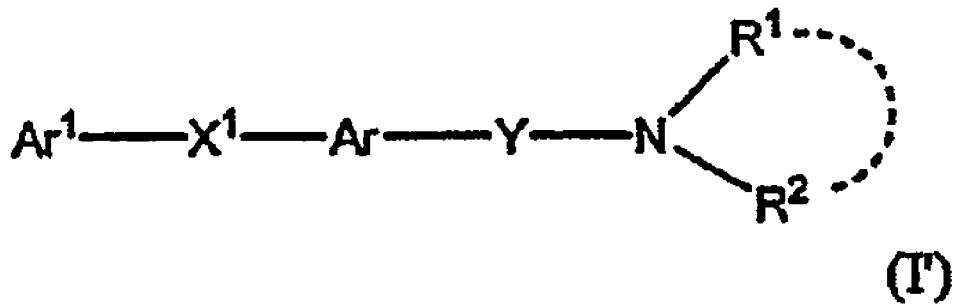

UNITED STATES PATENT AND TRADEMARK OFFICE
CERTIFICATE OF CORRECTION

| | |
|---|---|
| PATENT NO. | : 6,930,185 B2 |
| APPLICATION NO. | : 10/258492 |
| DATED | : August 16, 2005 |
| INVENTOR(S) | : Yuji Ishihara, Nobuhiro Suzuki and Shiro Takekawa |

It is certified that error appears in the above-identified patent and that said Letters Patent is hereby corrected as shown below:

Col. 142, lines 39-43, in Claim 10, please delete

"4(4chlorophenyl)-N-[2-(1-pyrrolidinylmethyl)-6-quinolinyl]-1-piperidinecarboxamide; N-[2-(1-pyrrolidinylmethyl)-6quinolinyl][1,1'-biphenyl]-4-carboxamide; and insert -- 4-(4-chlorophenyl)-N-[2-(1-pyrrolidinylmethyl)-6-quinolinyl]-1-piperidinecarboxamide; N-[2-(1-pyrrolidinylmethyl)-6-quinolinyl][1,1'-biphenyl]-4-carboxamide;--:

UNITED STATES PATENT AND TRADEMARK OFFICE
CERTIFICATE OF CORRECTION

PATENT NO. : 6,930,185 B2  Page 3 of 4
APPLICATION NO. : 10/258492
DATED : August 16, 2005
INVENTOR(S) : Yuji Ishihara, Nobuhiro Suzuki and Shiro Takekawa It is certified that error appears in the above-identified patent and that said Letters Patent is hereby corrected as shown below:

Col. 142, in Claim 11, please replace the chemical structure

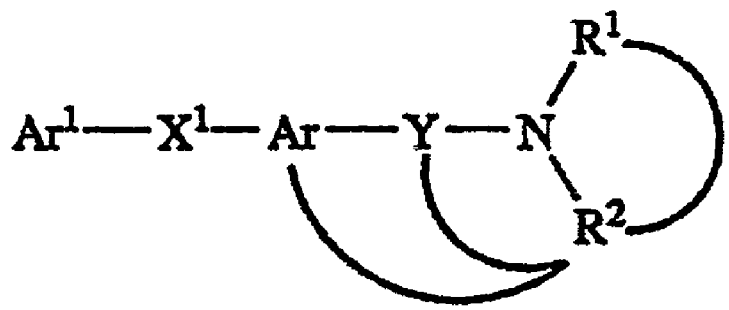

with the following:

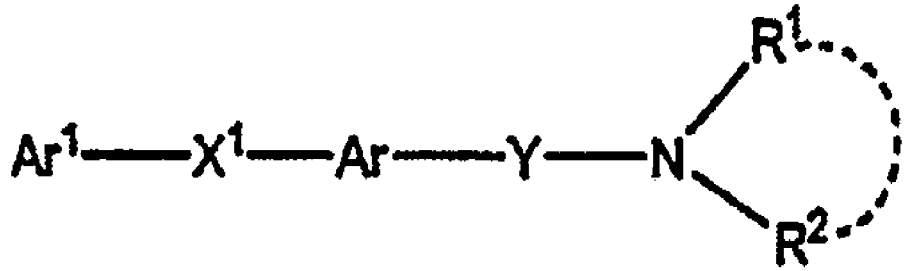

UNITED STATES PATENT AND TRADEMARK OFFICE
CERTIFICATE OF CORRECTION

PATENT NO. : 6,930,185 B2
APPLICATION NO. : 10/258492
DATED : August 16, 2005
INVENTOR(S) : Yuji Ishihara, Nobuhiro Suzuki and Shiro Takekawa It is certified that error appears in the above-identified patent and that said Letters Patent is hereby corrected as shown below:

Col. 142, line 58, in Claim 11, please delete

"wherein each symbol is as defined in claim 1, a salt thereof," and insert --wherein each symbol is as defined in claim 1, or a salt thereof,--

Col. 143, in Claim 11, please replace the chemical structure

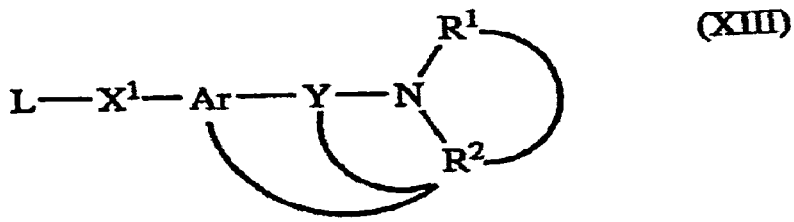

with the following:

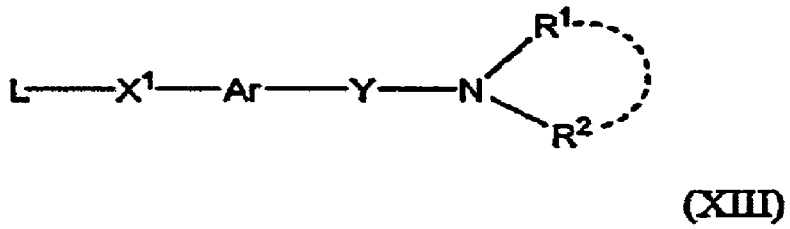

Signed and Sealed this

Fifth Day of December, 2006

JON W. DUDAS
*Director of the United States Patent and Trademark Office*